(12) United States Patent
Oestergaard et al.

(10) Patent No.: US 9,085,637 B2
(45) Date of Patent: Jul. 21, 2015

(54) SELECTIVE PYY COMPOUNDS AND USES THEREOF

(71) Applicant: Novo Nordisk A/S, Bagsvaerd (DK)

(72) Inventors: Soeren Oestergaard, Broenshoej (DK); Kilian Waldemar Conde Frieboes, Maeloev (DK); Birgit Wieczorek, Copenhagen (DK); Jens Kaalby Thomsen, Hellerup (DK); Birgitte Schjellerup Wulff, Virum (DK); Carsten Jessen, Birkeroed (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/540,474

(22) Filed: Nov. 13, 2014

(65) Prior Publication Data

US 2015/0152150 A1 Jun. 4, 2015

Related U.S. Application Data

(60) Provisional application No. 61/906,020, filed on Nov. 19, 2013.

(30) Foreign Application Priority Data

Nov. 15, 2013 (EP) .................................... 13193082
Jul. 11, 2014 (EP) .................................... 14176725

(51) Int. Cl.
  *C07K 14/47* (2006.01)
  *A61K 38/17* (2006.01)
  *A61K 45/06* (2006.01)

(52) U.S. Cl.
  CPC ............. *C07K 14/47* (2013.01); *A61K 38/1709* (2013.01); *A61K 45/06* (2013.01)

(58) Field of Classification Search
  CPC ................................................ C12N 2501/835
  See application file for complete search history.

(56) References Cited

U.S. PATENT DOCUMENTS

| 6,046,167 A | 4/2000 | Balasubramaniam |
| 2006/0135747 A1 | 6/2006 | Levy et al. |
| 2006/0211610 A1 | 9/2006 | Dong |
| 2007/0135351 A1 | 6/2007 | Conde-Knape et al. |
| 2007/0203058 A1 | 8/2007 | Lau et al. |
| 2008/0269114 A1 | 10/2008 | Schwartz |
| 2009/0111730 A1 | 4/2009 | Dorwald et al. |
| 2009/0186811 A1 | 7/2009 | Schwartz |
| 2009/0215682 A1 | 8/2009 | Moore et al. |
| 2010/0069307 A1 | 3/2010 | Danho et al. |
| 2011/0275559 A1 | 11/2011 | Ostergaard et al. |
| 2013/0096055 A1 | 4/2013 | Kofoed et al. |

FOREIGN PATENT DOCUMENTS

| CN | 1867360 A | 11/2006 |
| CN | 101005857 A | 7/2007 |
| EP | 0908515 A2 | 4/1999 |
| RU | 2275207 C2 | 4/2006 |
| WO | 9614854 A1 | 5/1996 |
| WO | 9964394 A1 | 12/1999 |
| WO | 03/002158 A1 | 1/2003 |
| WO | 2004066966 A2 | 8/2004 |
| WO | 2005/005667 A2 | 1/2005 |
| WO | 2005/027978 A2 | 3/2005 |
| WO | 2005/028516 A2 | 3/2005 |
| WO | 2005/058958 A2 | 6/2005 |
| WO | 2005/077094 A2 | 8/2005 |
| WO | 2005/089786 A2 | 9/2005 |
| WO | 2005/089789 A2 | 9/2005 |
| WO | 2005/089790 A2 | 9/2005 |
| WO | 2005/117984 A2 | 12/2005 |
| WO | 2006/005667 A2 | 1/2006 |
| WO | 2006020207 A2 | 2/2006 |
| WO | 2006/049681 A2 | 5/2006 |
| WO | 2006/077035 A1 | 7/2006 |
| WO | 2007/009894 A2 | 1/2007 |
| WO | 2007/038943 A1 | 4/2007 |
| WO | 2007038942 A1 | 4/2007 |
| WO | 2007/068718 A1 | 6/2007 |
| WO | 2007065808 A2 | 6/2007 |
| WO | 2007109354 A2 | 9/2007 |
| WO | 2008/003947 A1 | 1/2008 |
| WO | 2008/053360 A2 | 5/2008 |
| WO | 2008/087186 A2 | 7/2008 |
| WO | 2008/087190 A2 | 7/2008 |
| WO | 2008132435 A1 | 11/2008 |

(Continued)

OTHER PUBLICATIONS

Ito T et al, Effects of peripheral administration of PYY3-36 on feed intake and; plasma acyl-ghrelin levels in pigs, Journal of Endocrinology, Year 2006, vol. 191, pp. 113-119.
Ortiz A. et al, A Novel Long-Acting Selective Neuropeptide Y2 Receptor Polyethylene Glycol-Conjugated Peptide Agonist Reduces Food Intake and Body Weight and Improves Glucose Metabolism in Rodents , The Journal of Pharmacology and Experimental Therapeutics (2007), vol. 323, No. 2, pp. 692-700.
Roger Reidelberger et al., Effects of Glycine-Extended and Serine13-Phosphorylated Forms of Peptide YY on Food Intake in Rats, Peptides, Year 2011; vol. 32, No .4, pp. 770-775.
Soren L. Pedersen et al., Peptide hormone isoforms: N-terminally branched PYY3-36 isoforms give improved lipid and fat-cell metabolism in diet-induced obese mice, Journal of Peptide Science, Year 2010, vol. 16, Issue 11, pp. 664-673.

(Continued)

*Primary Examiner* — Karlheinz R Skowronek
*Assistant Examiner* — Lianko Garyu
(74) *Attorney, Agent, or Firm* — Rosemarie R. Wilk-Orescan

(57) ABSTRACT

The invention relates to PYY compounds having the amino acid in the position corresponding to position 30 of hPYY(1-36) substituted with tryptophan and derivatives thereof with a modifying group attached to the position corresponding to position 7 of hPYY(1-36). The compounds of the invention are selective Y2 receptor agonists. The invention also relates to pharmaceutical compositions comprising such PYY compounds and pharmaceutically acceptable excipients, as well as the medical use of the PYY compounds.

20 Claims, No Drawings

(56) References Cited

FOREIGN PATENT DOCUMENTS

| WO | 2009007714 A2 | 1/2009 |
| WO | 2009/030771 A1 | 3/2009 |
| WO | 2009033710 A1 | 3/2009 |
| WO | 2009/042922 A2 | 4/2009 |
| WO | 2009042922 A2 | 4/2009 |
| WO | 2009/138511 A1 | 11/2009 |
| WO | 2010031521 A2 | 3/2010 |
| WO | 2010031707 A1 | 3/2010 |
| WO | 2010052144 A2 | 5/2010 |
| WO | 2011033068 A1 | 3/2011 |
| WO | 2011045232 A2 | 4/2011 |
| WO | 2011058165 A1 | 5/2011 |
| WO | 2011131646 A1 | 10/2011 |

OTHER PUBLICATIONS van den Hoek A. et al., Chronic PYY3-36 treatment promotes fat oxidation and ameliorates insulin resistance in C57BL6 mice, American Journal of Physiology-Endocrinology and Metabolism, Year 2007, 292, pp. E238-E245.

Adrian et al., Gut, 1978, vol. 19, No. 10, pp. 907-909 Pharmacokinetics of pancreatic polypeptide in man.

Heizmann et al, Peptide Research, "Synthesis of an N-3-guanidinopropylglycine (Narg) Derivative as a Versatile Building Block for Solid-Phase Peptide and Peptoid Synthesis", 1994, vol. 7, No. 6, pp. 328-332.

Batterham, R.L. et al., "Gut Hormone PYY3-36 Physiologically Inhibits Food Intake", Nature, 2002, vol. 418, pp. 650-654.

Bowie et al. (Science, 1990, 247:1300-1310) "Deciphering the Message in Protein Sequences: Tolerance to Amino Acid Substitutions".

Burgess et al. (J. Cell Biol. 111:2129-2138, 1990) "Possible Dissociation of the Heparin-binding and Mitogenic Activities of Heparin-binding (Acidic Fibroblast) Growth Factor-1 from Its Recepetor-binding Activites by Site-directed Mutagenesis of a Single Lysine Residue".

Lazar et al. (Mol. Cel. Biol., 8:1247-1252, 1988) "Transforming Growth Factor α: Mutation of Aspartic Acid 47 and Leucine 48 Results in Different Biological Activities".

Bork (Genome Research, 2000, 10:398-400) "Powers and Pitfalls in Sequence Analysis: the 70% Hurdle".

T.W. Schwartz., "Pancreatic Polypeptide: A Hormone Under Vagal Control", Gastroenterology. 1983, vol. 85, pp. 1411-1425.

Whitcomb. Am. J. Physiol. "Characterization of saturable binding sites for circulating pancreatic polypeptide in rat brain." 1990 vol. 259 G687-G691.

Jorgensen, J. Ch. et al. Euro. J. Pharmacol. "Structure-function studies on neuropeptide Y and pancreatic polypeptide—evidence for two PP-fold receptors in vas deferens" 1990 vol. 186: 105-114.

Cooke, D et al. Nature Reviews. "The obesity pipeline: current srategies in the development of anti-obesity drugs" 2006 vol. 5: 919-931.

Kamiji, M.M et al. Current Topics in Medical Chemistry "NPY Y2 and Y4 receptors selective ligands: promising anti-obesity drugs?" vol. 7: 1734-1742, 2007; abstract only.

Sainsbury, A. et al. Mol Nad Cell Biol "Synergistic Effects of Y2 and Y4 Receptors on Adiposity and Bone Mass Revealed in Double Knockout Mice" vol. 23: 5225-5233, 2003.

Sampson, W.R. J. Pep. Sci. "The Synthesis of 'Difficult' Peptides Using 2-Hydroxy-4-Methoxybenzyl or Pseudoproline Amino Acid Building Blocks: a Comparative Study" 1999 vol. 5: 403-409.

Knudsen et al. J Med Chem. "Potent Derivatives of Glucagon-Like Peptide-1 with Pharmacokinetic Properties Suitable for Once Daily Administration" 2000. vol. 43(9). p. 1664-1669.

Boggiano, M.M. et al, "PYY3-36 as an anti-obesity drug target", Obesity Reviews. 2005 vol. 6: 307-322.

Kojima S et al. A role for pancreatic polypeptide in feeding and body weight regulation, "Peptides", Year 2007, vol. 28, No. 2, pp. 459-463.

Lin Shu et al. Critical Role of Arcuate Y4 Receptors and the Melanocortin System in Pancreatic Polypeptide-Induced Reduction in Food Intake in Mice, "PLOS ONE" Year 2009, vol. 4, No. 12, pp. e8488-e8488.

US 9,085,637 B2

SELECTIVE PYY COMPOUNDS AND USES THEREOF

CROSS-REFERENCE TO RELATED APPLICATIONS

This application claims priority under 35 U.S.C. §119 of U.S. Provisional Application 61/906,020, filed Nov. 19, 2013; this application further claims priority of European Application 13193082.8, filed Nov. 15, 2013, and European Application 14176725.1, filed Jul. 11, 2014; the contents of all above-named applications are incorporated herein by reference.

TECHNICAL FIELD

The present invention relates to analogues and/or derivatives of Peptide YY (PYY), and their pharmaceutical use.

INCORPORATION-BY-REFERENCE OF THE SEQUENCE LISTING

The instant application contains a Sequence Listing which has been submitted in ASCII format via EFS-Web and is hereby incorporated by reference in its entirety. Said ASCII copy, created on Nov. 13, 2014, is named 130009US02_SeqListing and is 34 kilobytes in size.

BACKGROUND OF THE INVENTION

PYY is released during a meal from L-cells in the distal small intestine and the colon. PYY is known to have peripheral effects in the gastrointestinal (GI) tract and also act centrally as a satiety signal. PYY is naturally secreted as a 36 amino acid peptide (PYY(1-36)) with a C-terminal amide but is cleaved to PYY(3-36) which constitutes approximately 50% of the circulating PYY. The enzyme responsible for the degradation is dipeptidyl peptidase IV (DPPIV). PYY(3-36) is rapidly eliminated by proteases and other clearance mechanisms. The half-life of PYY(3-36) has been reported to be <30 minutes in pigs. Thus, PYY displays suboptimal pharmacokinetic properties, meaning that the peptide has to be administered at least twice daily.

Whereas PYY(1-36) activates Y1, Y2 and Y5 receptors with very little selectivity and the Y4 receptor slightly less, the DPP IV processed PYY(3-36) displays increased selectivity for the Y2 receptor over Y1, Y4 and Y5 receptors, albeit some Y1 and Y5 affinity is retained. Y2 receptor activation is known to decrease appetite and food intake whereas Y1 and Y5 receptor activation leads to an increase in appetite and food intake. Furthermore, Y1 and Y5 receptor activation may lead to an increase in blood pressure.

PYY(3-36) has been suggested for use in the treatment of obesity and associated diseases based on the demonstrated effects of certain of these peptides in animal models and in man, and on the fact that obese people have low basal levels of PYY as well as lower meal responses of this peptide. Furthermore, Y2 agonists have been demonstrated to have anti-secretory and pro-absorptive effects in the gastro-intestinal (GI) tract. The potential use of Y2 agonists in the treatment of a number of gastro-intestinal disorders has been suggested.

Based on demonstrated effects in e.g. Zucker rats and Diet-Induced Obese (DIO) mice Y2 selective PYY(3-36) analogues have a positive effect on glucose metabolism and are thus suggested to be used for the treatment of diabetes.

WO 2009/138511 A1 relates to long-acting Y2 and/or Y4 receptor agonists. WO 2011/033068 A1 relates to PYY analogues stabilised against C-terminal proteolytic breakdown. WO 2011/058165 A1 relates to Y2 receptor agonists with protracted pharmacokinetic properties.

For the treatment of conditions responsive to Y receptor modulation such as obesity and diabetes it would be attractive to use PYY analogues which are specific for the Y receptor subtype Y2 and importantly also display protracted pharmacokinetic properties and as such can be used in a dosing regimen with lower frequency of administration than PYY or PYY(3-36).

SUMMARY

The invention relates to PYY compounds. The PYY compounds of the present invention may comprise up to 10 amino acid modifications as compared to human PYY(3-36) (hPYY(3-36), SEQ ID NO:2), and have the amino acid in the position corresponding to position 30 of human PYY(1-36) (hPYY(1-36), SEQ ID NO:1) substituted with tryptophan.

In one aspect, the PYY compounds further comprise N(alpha)-methylarginine in the position corresponding to position 35 of hPYY(1-36).

Also or alternatively, in one aspect, the PYY compounds further comprise a lysine in the position corresponding to position 7 of hPYY(1-36), and a modifying group attached to the epsilon amino group of this lysine.

In one aspect, the invention also relates to pharmaceutical compositions comprising such PYY compounds and pharmaceutically acceptable excipients, as well as the medical use of the PYY compounds.

Also or alternatively, in one aspect, the invention relates to PYY compounds being Y2 receptor agonists.

Also or alternatively, in one aspect, the invention relates to PYY compounds displaying selectivity towards the Y receptor subtype Y2 as compared to Y receptor subtypes Y1, Y4 and Y5.

Also or alternatively, in one aspect, the invention relates to PYY compounds with longer half-life than the half-life of hPYY(3-36). Also or alternatively, in one aspect, the invention relates to PYY compounds with longer half-life than the half-life of hPYY(1-36).

DESCRIPTION OF THE INVENTION

The invention relates to PYY compounds. The PYY compounds of the present invention may comprise up to 10 amino acid modifications as compared to hPYY(3-36), and have the amino acid in the position that corresponds to position 30 of hPYY(1-36) substituted with tryptophan.

Also, in one aspect, the arginine residue in the position corresponding to position 35 of hPYY(1-36) has a methyl group added to the α-amino group, meaning that the residue in the position corresponding to position 35 of hPYY(1-36) is thus N(alpha)-methylarginine.

Also or alternatively, in one aspect, the PYY compounds further comprise a lysine in the position corresponding to position 7 of hPYY(1-36), and a modifying group attached to the epsilon amino group of this lysine.

Also or alternatively, in one aspect, the invention relates to PYY compounds being Y receptor subtype Y2 agonists.

Also or alternatively, in one aspect, the invention relates to PYY compounds displaying selectivity towards the Y receptor subtype Y2 as compared to Y receptor subtypes Y1, Y4 and Y5.

In one aspect peptides being "selective" for specific receptors over other receptors refers to peptides that display at least 10 fold, such as at least 20 fold, at least 50 fold, or at least 100 fold higher potency for one Y receptor over other Y receptors as measured in vitro in an assay for receptor function, such as an Actone functional potency assay, and compared by EC50 values, or a Scintillation Proximity Assay (SPA) measuring receptor binding affinity, and compared by Ki values.

In what follows, Greek letters may be represented by their symbol or the corresponding written name, for example: α=alpha; β=beta; ϵ=epsilon; γ=gamma; ω=omega; etc.

PYY Compounds

The term "hPYY(1-36)" as used herein refers to the human Peptide YY, the sequence of which is included in the sequence listing as SEQ ID NO:1. The peptide having the sequence of SEQ ID NO:1 may also be designated native hPYY.

The term "PYY compound" as used herein refers to a peptide, or a compound, which is a variant of hPYY(1-36). The term "PYY compound" as used herein may also refer to a peptide, or a compound, which is a variant of hPYY(3-36) (SEQ ID NO:2).

The term "PYY compound" as used herein may also refer to a peptide, or a compound, which is a variant of hPYY(4-36).

The C-terminal of the PYY compounds of the present invention is an amide, as is the C-terminal of native hPYY(1-36) (SEQ ID NO:1) and hPYY(3-36) (SEQ ID NO:2), respectively.

The PYY compounds of the present invention can be PYY analogues and/or derivatives thereof.

The term "PYY analogue" is used for PYY compounds, where at least one amino acid modification in the backbone is present.

The term "PYY derivative" is used for PYY compounds comprising at least one non-amino acid substituent covalently attached.

A derivative of a PYY analogue is thus a PYY compound comprising at least one amino acid modification and at least one non-amino acid substituent covalently attached.

The PYY compounds of the present invention may comprise up to 10 amino acid modifications as compared to hPYY (3-36).

The term "amino acid modification" used throughout this application is used in the meaning of a modification to an amino acid as compared to hPYY(3-36). This modification can be the result of a deletion of an amino acid, addition of an amino acid, substitution of one amino acid with another or a substituent covalently attached to an amino acid of the peptide.

The PYY compounds of the invention comprises a tryptophan at the position corresponding to position 30 of hPYY (1-36), meaning that the PYY compounds of the invention may comprise up to 9 amino acid modifications as compared to hPYY(3-36) in addition to this modification in the position corresponding to position 30 of hPYY(1-36).

As an example, [Lys7, Gln18, Trp30, NMeArg35]hPYY (3-36) comprises 4 amino acid substitutions as compared to hPYY(3-36).

As another example, [Arg4, Lys7, Gln18, Trp30, NMeArg35]hPYY(4-36) comprises 5 amino acid substitutions and 1 deletion as compared to hPYY(3-36), meaning that this compound has 6 amino acid modifications as compared to hPYY(3-36).

In yet another aspect, the PYY peptides of the invention may exhibit at least 70%, 75% or 80% sequence identity to hPYY(3-36). As an example of a method for determination of the sequence identity between two analogues the two peptides [NMeArg35]hPYY(3-36) and hPYY(3-36) are aligned. The sequence identity of the [NMeArg35]hPYY(3-36) analogue relative to hPYY(3-36) is given by the total number of aligned residues minus the number of different residues (i.e. the number of aligned identical residues) divided by the total number of residues in hPYY(3-36). Accordingly, in said example the sequence identity is (34-1)/34.

PYY compounds or PYY analogues of the invention may be described by reference to i) the number of the amino acid residue in hPYY(1-36) which corresponds to the amino acid residue which is changed (i.e., the corresponding position in hPYY(1-36), and to ii) the actual change.

The following is a non-limiting example of suitable analogue nomenclature. [NMeArg35]hPYY(3-36) designates an analogue of the human PYY(1-36), wherein the naturally occurring arginine in position 35 has been substituted with N(alpha)-methylarginine (the arginine residue in the position corresponding to position 35 of hPYY(1-36) has a methyl group added to the alpha-amino group) and the naturally occurring tyrosine and proline in position 1 and 2, respectively, have been deleted.

Likewise, [Trp30]hPYY(3-36) designates an analogue of human PYY(3-36), wherein the naturally occurring leucine in position 30 of human PYY(1-36) has been substituted with tryptophan.

The following is a non-limiting example of suitable nomenclature for a derivative of a PYY analogue. 7-N{Epsilon}-[2-[2-[2-[[2-[2-[2-[[(4S)-4-carboxy-4-(17-carboxyheptadecanoylamino)butanoyl]amino]ethoxy] ethoxy]acetyl]amino]ethoxy]-ethoxy]acetyl]-[Lys7, Gln18, Trp30, NMeArg35]hPYY(3-36) designates a derivative of an analogue of hPYY(3-36) (SEQ ID NO:2), wherein [Lys7, Gln18, Trp30, NMeArg35] designate the amino acid changes as compared to human PYY(3-36) with the numbers referring to the corresponding positions of PYY(1-36), and wherein the substituent [2-[2-[2-[[2-[2-[2-[[(4S)-4-carboxy-4-(17-carboxyheptadecanoylamino)-butanoyl]amino]ethoxy]ethoxy] acetyl]amino]ethoxy]ethoxy]acetyl]- is attached to the epsilon amino group of the lysine in the position corresponding to position 7 in hPYY(1-36).

The expressions "a position equivalent to" or "corresponding position" are used to characterise the site of change in a variant PYY sequence by reference to hPYY(1-36).

In general throughout the application, when referring to a particular position of a PYY analogue, the position referred to is the position of the PYY analogue corresponding to that particular position of hPYY(1-36).

The expression used throughout this application, that a PYY compound comprises a particular amino acid at a position corresponding to a certain position of hPYY(1-36), means that the native amino acid in that position has been replaced with that particular amino acid.

Amino acid residues may be identified by their full name, their one-letter code, and/or their three-letter code. These three ways are fully equivalent.

Analogues "comprising" certain specified changes may comprise further changes, when compared to hPYY(1-36). In one aspect, the analogue "has" the specified changes.

PYY Analogues

A PYY analogue is a PYY peptide in which a number of amino acid residues have been modified when compared to hPYY(1-36). These modifications include substitutions, insertions, and/or deletions, alone or in combination.

In a specific aspect, the PYY analogues of the invention include one or more modifications of a "non-essential" amino acid residue. In the context of the invention, a "non-essential" amino acid residue is a residue that can be altered, i.e., deleted or substituted in the human PYY amino acid sequence without abolishing or substantially reducing the activity of the PYY analogue towards the Y2 receptor.

Substitutions.

In one aspect amino acids may be substituted by conservative substitution. The term "conservative substitution" as used herein denotes that one or more amino acids are replaced by another, biologically similar residue. Examples include substitution of amino acid residues with similar characteristics, e.g. small amino acids, acidic amino acids, polar amino acids, basic amino acids, hydrophobic amino acids and aromatic amino acids.

In one aspect, the PYY analogues of the invention may comprise substitutions of one or more unnatural and/or non-amino acids, e.g., amino acid mimetics, into the sequence of PYY.

Deletions and Truncations.

In one aspect, the PYY analogues of the invention may have one or more amino acid residues deleted from the amino acid sequence of human PYY, alone or in combination with one or more insertions or substitutions.

Insertions.

In one aspect, the PYY analogues of the invention may have one or more amino acid residues inserted into the amino acid sequence of human PYY, alone or in combination with one or more deletions and/or substitutions.

In one aspect, the PYY analogues of the invention may include insertions of one or more unnatural amino acids and/or non-amino acids into the sequence of PYY.

The PYY peptide may be derived from vertebrates, such as human, mouse, sheep, goat, cow, or horse. The term "vertebrate" means members of the subphylum Vertebrata, a primary division of the phylum Chordata that includes the fish, amphibians, reptiles, birds, and mammals, all of which are characterized by a segmented spinal column and a distinct well-differentiated head. The term "mammal" means humans as well as all other warm-blooded members of the animal kingdom possessed of a homeostatic mechanism in the class Mammalia, e.g., companion mammals, zoo mammals, and food-source mammals. Some examples of companion mammals are canines (e.g., dogs), felines (e.g., cats) and horses; some examples of food-source mammals are pigs, cattle, sheep, and the like. In one aspect the mammal is a human or a companion mammal. In one aspect the mammal is a human, male or female.

The term "peptide", as e.g. used in the context of the PYY compounds of the invention, refers to a compound which comprises a series of amino acids interconnected by amide (or peptide) bonds.

The PYY peptides of the invention comprise at least 24 constituent amino acids connected by peptide bonds. In particular embodiments the PYY peptides comprise at least 33 amino acids. In particular embodiments the PYY peptides comprise at least 34 amino acids.

Amino acids are molecules containing an amine group and a carboxylic acid group, and, optionally, one or more additional groups, often referred to as a side chain.

The term "amino acid" includes proteinogenic (or coded or natural) amino acids (amongst the 20 standard amino acids), as well as non-proteinogenic (or non-coded or non-natural) amino acids. Proteinogenic amino acids are those which are naturally incorporated into proteins. The standard amino acids are those encoded by the genetic code. Non-proteinogenic amino acids are either not found in proteins, or not produced by standard cellular machinery (e.g., they may have been subject to post-translational modification). Non-limiting examples of non-proteinogenic amino acids are Aib (α-aminoisobutyric acid), N(alpha)-methylarginine, as well as the D-isomers of the proteinogenic amino acids. One example of a D-isomer of a proteinogenic amino acid is the D-isomer of aspartic acid, which can also be written as D-Asp.

In what follows, all amino acids of the PYY compound for which the optical isomer is not stated is to be understood to mean the L-isomer (unless otherwise specified).

PYY Derivatives

The term "derivative" as used herein in the context of a PYY peptide or analogue means a chemically modified PYY peptide, in which one or more substituents have been covalently attached to the peptide.

In one aspect of the invention, the substituent may be an N-terminal substituent.

Also or alternatively, in one aspect, the substituent may be a modifying group or alternatively, referred to as a protracting moiety.

N-Terminal Substituent

In one aspect of the invention, the PYY compound comprises a substituent covalently attached to the alpha-amino group in the amino acid residue in the N-terminus of the PYY compound. In one aspect, the amino acid residues in the positions corresponding to positions 1-3 of hPYY(1-36) are absent, and the N-terminal substituent is covalently attached to the amino acid residue in the position corresponding to position 4 of hPYY(1-36).

In one aspect, the N-terminal substituent is an alkoxy group. In one aspect, the N-terminal substituent is an alkoxy group comprising up to 12 carbon atoms. In another aspect, the N-terminal substituent is an alkoxy group comprising up to 6 carbon atoms.

Modifying Group/Protracting Moiety

In one aspect, the PYY compound comprises a substituent or modifying group covalently attached to the amino acid residue in the position corresponding to position 7 of hPYY (1-36). In one further aspect, the substituent or modifying group is capable of forming non-covalent conjugates with proteins, thereby promoting the circulation of the derivative with the blood stream, and also having the effect of protracting the time of action of the derivative, due to the fact that the conjugate of the PYY derivative and albumin is only slowly removed by renal clearance. Thus, the substituent, or modifying group, as a whole may also be referred to as a protracting moiety.

The modifying group may be covalently attached to a lysine residue of the PYY peptide by acylation, i.e., via an amide bond formed between a carboxylic acid group of the modifying group and the epsilon amino group of the lysine residue. The amino group of lysine could also be coupled to an aldehyde of the modifying group by reductive amination. In another aspect the thiol group of cysteine could by coupled to a maleiimido group of the modifying group by Michael addition or coupled to the chloro- or iodoacetyl group of the modifying group by nucleophilic substitution.

In one aspect, the modifying group may be covalently attached to a lysine residue in a position corresponding to position 7 of hPYY(1-36) by acylation, i.e., via an amide bond formed between a carboxylic acid group of the modifying group and the epsilon amino group of the lysine residue.

The derivatives of the invention may exist in different stereoisomeric forms having the same molecular formula and sequence of bonded atoms, but differing only in the three-dimensional orientation of their atoms in space. The stereoisomerism of the exemplified derivatives of the invention is indicated in the experimental section, in the names as well as the structures, using standard nomenclature. Unless otherwise stated the invention relates to all stereoisomeric forms of the claimed derivative.

Herein, all amino acids of the PYY compound for which the optical isomer is not stated are to be understood to mean the L-isomer (unless otherwise specified).

Pharmaceutically Acceptable Salts

The PYY compounds of the invention may be in the form of a pharmaceutically acceptable salt.

Salts are e.g. formed by a chemical reaction between a base and an acid, e.g.: $2NH_3+H_2SO_4 \rightarrow (NH_4)_2SO_4$.

The salt may be a basic salt, an acidic salt, or it may be neither nor (i.e. a neutral salt). Basic salts produce hydroxide ions and acid salts hydronium ions in water.

The salts of the derivatives of the invention may be formed with added cations or anions between anionic or cationic groups, respectively. These groups may be situated in the peptide moiety, and/or in the side chain of the derivatives of the invention.

Non-limiting examples of anionic groups of the derivatives of the invention include free carboxylic groups in the side chain, if any, as well as in the peptide moiety. The peptide moiety often includes free carboxylic groups at internal acid amino acid residues such as Asp and Glu.

Non-limiting examples of cationic groups in the peptide moiety include the free amino group at the N-terminus, if present, as well as any free amino group of internal basic amino acid residues such as His, Arg, and Lys.

Functional Properties

In a first functional aspect, the PYY compounds of the invention have a good Y2 receptor potency. Also, or alternatively, in a second aspect, they bind very well to the Y2 receptor. Preferably they are full Y2 receptor agonists as is reflected by their ability to bind strongly to the Y2 receptor combined with the capacity to fully activate the receptor compared to hPYY(1-36) and hPYY(3-36).

Also or alternatively, in a second functional aspect, the invention relates to PYY compounds displaying selectivity towards the Y receptor subtype Y2 as compared to Y receptor subtypes Y1, Y4 and Y5.

Also, or alternatively, in a third functional aspect, the PYY compounds of the invention have improved pharmacokinetic properties. Also, or alternatively, in a fourth functional aspect, the PYY compounds of the invention have increased half-life and/or a decreased clearance. Also, or alternatively, in a fifth functional aspect, they have the effect in vivo of decreasing the blood glucose. Also, or alternatively, in a sixth functional aspect, they have the effect in vivo of decreasing food intake. Also, or alternatively, in a seventh functional aspect, they have the effect in vivo of decreasing body weight.

Biological Activity—In Vitro Potency

According to the first functional aspect, the PYY compounds of the invention are biologically active, or potent.

In a particular embodiment, potency and/or activity refers to in vitro potency, i.e. performance in a functional Y2 receptor assay, more in particular to the capability of activating the human Y2 receptor.

The term half maximal effective concentration ($EC_{50}$) generally refers to the concentration which induces a response halfway between the baseline and maximum, by reference to the dose response curve. $EC_{50}$ is used as a measure of the potency of a compound and represents the concentration where 50% of its maximal effect is observed.

The in vitro potency of the derivatives of the invention may be determined as described in Example 39, and the $EC_{50}$ of the derivative in question determined. The lower the $EC_{50}$ value, the better the potency.

In one aspect of the invention, the derivative of the invention has an in vitro potency determined using the method of Example 39 corresponding to an $EC_{50}$ at or below 100 nM. In one aspect, the derivative of the invention has an in vitro potency determined using the method of Example 39 corresponding to an $EC_{50}$ at or below 50 nM. In one aspect, the derivative of the invention has an in vitro potency determined using the method of Example 39 corresponding to an $EC_{50}$ at or below 25 nM.

Biological Activity—In Vitro Receptor Binding

According to the second functional aspect, the PYY compounds of the invention bind very well to the Y2 receptor. This may be determined as described in Example 40.

Generally, the binding to the Y2 receptor should be as good as possible, corresponding to a low Ki value. The Ki value is determined by the Cheng-Prusoff equation Ki=IC50/(1+[L]/Kd), wherein IC50 is the half maximal inhibitory concentration of the agonist, [L] is the concentration of the radioligand and Kd is the dissociation constant for binding.

As an example, in a particular aspect, the Y2 receptor binding affinity (Ki) is below 100 nM. In one aspect of the invention, the Y2 receptor binding affinity (Ki) is below 50 nM. In one aspect of the invention, the Y2 receptor binding affinity (Ki) is below 10 nM.

Biological Activity—In Vivo Pharmacology

In another particular embodiment the PYY compounds of the invention are potent in vivo, which may be determined as is known in the art in any suitable animal model, as well as in clinical trials.

The diabetic db/db mouse is one example of a suitable animal model, and the blood glucose lowering effect may be determined in such mice in vivo, e.g. as described in Example 42.

In addition, inhibition of food intake in the db/db mice is a suitable model for determination of effect on food intake and body weight as also described in Example 42.

Generally, the glucose lowering effect of a 1 μmol/kg dose should be as good as possible corresponding to a low relative % glucose level.

As an example, in a particular aspect of the invention, 16 hours after dosing (1 μmol/kg) the relative % glucose level is below 80%. In one aspect of the invention, 16 hours after dosing (1 μmol/kg) the relative % glucose level is below 70%. In one aspect of the invention, 16 hours after dosing (1 μmol/kg) the relative % glucose level is below 60%.

As an example, in a particular aspect of the invention, 16 hours after dosing (1 μmol/kg) the % relative food intake is below 40%. In one aspect of the invention, 16 hours after dosing (1 μmol/kg) the % relative food intake is below 30%. In one aspect of the invention, 16 hours after dosing (1 μmol/kg) the % relative food intake is below 20%.

As an example, in a particular aspect of the invention, 4 hours after dosing (1 μmol/kg) the relative % glucose level is below 80%. In one aspect of the invention, 4 hours after dosing (1 μmol/kg) the relative % glucose level is below 70%. In one aspect of the invention, 4 hours after dosing (1 μmol/kg) the relative % glucose level is below 60%.

As an example, in a particular aspect of the invention, 4 hours after dosing (1 μmol/kg) the % relative food intake is below 40%. In one aspect of the invention, 4 hours after dosing (1 μmol/kg) the % relative food intake is below 30%. In one aspect of the invention, 4 hours after dosing (1 μmol/kg) the % relative food intake is below 20%.

Pharmacokinetics Profile

According to the third functional aspect, the PYY compounds of the invention have improved pharmacokinetic properties such as increased terminal half-life and/or decreased clearance.

Increasing terminal half-life and/or decreasing of the clearance means that the compound in question is eliminated slower from the body. For the compounds of the invention this entails an extended duration of pharmacological effect.

The pharmacokinetic properties of the derivatives of the invention may suitably be determined in-vivo in pharmacokinetic (PK) studies. Such studies are conducted to evaluate how pharmaceutical compounds are absorbed, distributed, and eliminated in the body, and how these processes affect the concentration of the compound in the body, over the course of time.

In the discovery and preclinical phase of pharmaceutical drug development, animal models such as the mouse, rat, monkey, dog, or pig, may be used to perform this characterisation. Any of these models can be used to test the pharmacokinetic properties of the derivatives of the invention.

The estimate of terminal half-life and/or clearance is relevant for evaluation of dosing regimens and an important parameter in drug development, in the evaluation of new drug compounds.

Pharmacokinetics Profile—Half Life In Vivo in Minipigs

According to the third functional aspect, the derivatives of the invention have improved pharmacokinetic properties.

In a particular embodiment, the pharmacokinetic properties may be determined as terminal half-life ($T_{1/2}$) in vivo in minipigs after i.v. administration, e.g. as described in Example 41 herein.

In one aspect of the invention, the terminal half-life in minipigs is at least 10 hours. In one aspect of the invention, the terminal half-life in minipigs is at least 20 hours. In yet another aspect of the invention, the terminal half-life in minipigs is at least 40 hours.

Production of PYY Compounds

The production of peptides like the PYY compounds of the present invention is well known in the art.

The PYY moiety of the derivatives of the invention may for instance be produced by classical peptide synthesis, e.g., solid phase peptide synthesis using t-Boc or Fmoc chemistry or other well established techniques, see, e.g., Greene and Wuts, "Protective Groups in Organic Synthesis", John Wiley & Sons, 1999, Florencio Zaragoza Dörwald, "Organic Synthesis on solid Phase", Wiley-VCH Verlag GmbH, 2000, and "Fmoc Solid Phase Peptide Synthesis", Edited by W. C. Chan and P. D. White, Oxford University Press, 2000.

Also, or alternatively, they may be produced by recombinant methods, viz. by culturing a host cell containing a DNA sequence encoding the analogue and capable of expressing the peptide in a suitable nutrient medium under conditions permitting the expression of the peptide. Non-limiting examples of host cells suitable for expression of these peptides are: *Escherichia coli, Saccharomyces cerevisiae*, as well as mammalian BHK or CHO cell lines.

The PYY compounds of the invention which include non-natural amino acids and/or covalently attached substituents may e.g. be produced as described in the experimental part.

Specific examples of methods of preparing a number of the PYY compounds of the invention are included in the experimental part.

Protein Purification

The PYY compounds of the present invention may be purified by a variety of procedures known in the art including, but not limited to, chromatography (e.g., ion exchange, affinity, hydrophobic, and reverse-phase high performance liquid chromatography (RP-HPLC)), electrophoretic procedures, or extraction (see, e.g., Protein Purification, J.-C. Janson and Lars Ryden, editors, VCH Publishers, New York, 1989).

Mode of Administration

The term "treatment" is meant to include both the prevention and minimization of the referenced disease, disorder, or condition (i.e., "treatment" refers to both prophylactic and therapeutic administration of the PYY compounds of the invention or composition comprising the PYY compounds of the invention) unless otherwise indicated or clearly contradicted by context.

The route of administration may be any route which effectively transports a compound of this invention to the desired or appropriate place in the body, such as parenterally, for example, subcutaneously, intramuscularly or intravenously. Alternatively, a compound of this invention can be administered orally, pulmonary, rectally, transdermally, buccally, sublingually, or nasally.

Pharmaceutical Compositions

Injectable compositions comprising PYY compounds of the present invention can be prepared using the conventional techniques of the pharmaceutical industry which involve dissolving and mixing the ingredients as appropriate to give the desired end product. Thus, according to one procedure, a PYY compound of this invention is dissolved in a suitable buffer at a suitable pH so precipitation is minimised or avoided. The injectable composition is made sterile, for example, by sterile filtration.

A composition may be a stabilised formulation. The term "stabilised formulation" refers to a formulation with increased physical and/or chemical stability, preferably both. In general, a formulation must be stable during use and storage (in compliance with recommended use and storage conditions) until the expiration date is reached.

The term "physical stability" refers to the tendency of the polypeptide to form biologically inactive and/or insoluble aggregates as a result of exposure to thermo-mechanical stress, and/or interaction with destabilising interfaces and surfaces (such as hydrophobic surfaces). The physical stability of an aqueous polypeptide formulation may be evaluated by means of visual inspection, and/or by turbidity measurements after exposure to mechanical/physical stress (e.g. agitation) at different temperatures for various time periods. Alternatively, the physical stability may be evaluated using a spectroscopic agent or probe of the conformational status of the polypeptide such as e.g. Thioflavin T or "hydrophobic patch" probes.

The term "chemical stability" refers to chemical (in particular covalent) changes in the polypeptide structure leading to formation of chemical degradation products potentially having a reduced biological potency, and/or increased immunogenic effect as compared to the intact polypeptide. The chemical stability can be evaluated by measuring the amount of chemical degradation products at various time-points after exposure to different environmental conditions, e.g. by SEC-HPLC, and/or RP-HPLC.

In one aspect, the invention provides PYY compounds with improved physical stability. In one aspect, the invention provides PYY compounds with improved chemical stability.

Combination Treatment

The treatment with a PYY compound according to the present invention may also be combined with one or more additional pharmacologically active substances, e.g. selected from antidiabetic agents, antiobesity agents, appetite regulating agents, antihypertensive agents, agents for the treatment and/or prevention of complications resulting from or associated with diabetes and agents for the treatment and/or prevention of complications and disorders resulting from or associated with obesity.

Examples of these pharmacologically active substances are: GLP-1 receptor agonists, insulin, DPP-IV (dipeptidyl peptidase-IV) inhibitors, amylin agonists and leptin receptor agonists.

In one aspect of the invention, a PYY compound according to the present invention is combined with a GLP-1 agonist. The compounds may be supplied in a single-dosage form wherein the single-dosage form contains both compounds, or in the form of a kit-of-parts comprising a preparation of the PYY compound as a first unit dosage form and a preparation of the GLP-1 agonist as a second unit dosage form.

Non-limiting examples of GLP-1 agonists to be combined with the PYY compounds of the present invention are liraglutide, semaglutide, exenatide, dulaglutide, lixisenatide, taspoglutide, and albiglutide.

Liraglutide, a mono-acylated GLP-1 derivative for once daily administration which is marketed as of 2009 by Novo Nordisk A/S, is disclosed in WO 98/08871, Example 37.

WO 2006/097537 discloses additional GLP-1 derivatives including semaglutide (Example 4), a mono-acylated GLP-1 derivative for once weekly administration which is under development by Novo Nordisk A/S.

Exenatide is a synthetic version of exendin-4, a hormone found in the saliva of the Gila monster. It displays biological properties similar to GLP-1.

Dulaglutide is a GLP-1-Fc construct (GLP-1-linker-Fc from IgG4).

Lixisenatide is based on exendin-4(1-39) modified C-terminally with six Lys residues.

Taspoglutide is the 8-(2-methylalanine)-35-(2-methylalanine)-36-L-argininamide derivative of the amino acid sequence 7-36 of human GLP-1.

Albiglutide is a recombinant human serum albumin (HSA)-GLP-1 hybrid protein, likely a GLP-1 dimer fused to HSA. The constituent GLP-1 peptide is an analogue, in which Ala at position 8 has been substituted by Gly.

Pharmaceutical Indications

The present invention also relates to a PYY compound of the invention for use as a medicament.

In particular aspects of the invention, the PYY compounds of the invention may be used for the following medical treatments:

(i) prevention and/or treatment of all forms of diabetes, such as hyperglycemia, type 2 diabetes, impaired glucose tolerance, type 1 diabetes, non-insulin dependent diabetes, MODY (maturity onset diabetes of the young), gestational diabetes, and/or for reduction of HbA1C;

(ii) delaying or preventing diabetic disease progression, such as progression in type 2 diabetes, delaying the progression of impaired glucose tolerance (IGT) to insulin requiring type 2 diabetes, delaying or preventing insulin resistance, and/or delaying the progression of non-insulin requiring type 2 diabetes to insulin requiring type 2 diabetes;

(iii) improving β-cell function, such as decreasing β-cell apoptosis, increasing β-cell function and/or β-cell mass, and/or for restoring glucose sensitivity to β-cells;

(iv) prevention and/or treatment of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence;

(v) prevention and/or treatment of diabetic complications, such as angiopathy; neuropathy, including peripheral neuropathy; nephropathy; and/or retinopathy;

(vi) improving lipid parameters, such as prevention and/or treatment of dyslipidemia, lowering total serum lipids; increasing HDL; lowering small, dense LDL; lowering VLDL; lowering triglycerides; lowering cholesterol; lowering plasma levels of lipoprotein a (Lp(a)) in a human; inhibiting generation of apolipoprotein a (apo(a)) in vitro and/or in vivo;

(vii) prevention and/or treatment of cardiovascular diseases; and/or (viii) prevention and/or treatment of sleep apnoea.

The following indications are particularly preferred: Type 2 diabetes, and/or obesity.

In one aspect, a method is disclosed herein for altering energy metabolism in a subject. The method includes administering a therapeutically effective amount of a PYY compound of the invention to the subject, thereby altering energy expenditure. Energy is burned in all physiological processes. The body can alter the rate of energy expenditure directly, by modulating the efficiency of those processes, or changing the number and nature of processes that are occurring. For example, during digestion the body expends energy moving food through the bowel, and digesting food, and within cells, the efficiency of cellular metabolism can be altered to produce more or less heat.

In one aspect a method is disclosed herein for any and all manipulations of the accurate circuitry described in this application, which alter food intake co-ordinately and reciprocally alter energy expenditure. Energy expenditure is a result of cellular metabolism, protein synthesis, metabolic rate, and calorie utilization. Thus, in this embodiment, peripheral administration results in increased energy expenditure, and decreased efficiency of calorie utilization. In one aspect, a therapeutically effective amount of a PYY compound according to the invention is administered to a subject, thereby increasing energy expenditure.

While "obesity" is generally defined as a body mass index over 30, for purposes of this disclosure, any subject, including those with a body mass index of less than 30, who needs or wishes to reduce body weight is included in the scope of "obese." Without intending to be limited by theory, it is believed that the effects of peripherally administered PYY compounds of the present invention in the reduction of food intake, in the delay of gastric emptying, in the reduction of nutrient availability, and in the causation of weight loss are determined by interactions with one or more unique receptor classes in, or similar to, those in the PP family. More particularly, it appears that a receptor or receptors similar to the PYY-preferring (or Y2) receptors are involved.

PARTICULAR EMBODIMENTS

The invention is further described by the following non-limiting embodiments of the invention:

1. A PYY compound comprising a tryptophan at a position corresponding to position 30 of hPYY(1-36) (SEQ ID NO:1), and a maximum of 10 amino acid modifications as compared to hPYY(3-36), and a pharmaceutically acceptable salt thereof.

2. A PYY compound comprising tryptophan at the position corresponding to position 30 of hPYY(1-36) (SEQ ID NO:1), and a maximum of 10 amino acid modifications as compared to hPYY(3-36), or a pharmaceutically acceptable salt thereof.

3. A PYY compound according to any one of the preceding embodiments, further comprising N(alpha)-methyl-L-arginine at a position corresponding to position 35 of hPYY(1-36) (SEQ ID NO:1).

4. A PYY compound according to any one of the preceding embodiments, wherein the PYY compound comprises N(alpha)-methyl-L-arginine at a position corresponding to position 35 of hPYY(1-36) (SEQ ID NO:1).

5. A PYY compound according to any one of the preceding embodiments, further comprising glutamine at a position corresponding to position 18 of hPYY(1-36) (SEQ ID NO:1).

6. A PYY compound according to any one of the preceding embodiments, wherein the PYY compound comprises glutamine at a position corresponding to position 18 of hPYY (1-36) (SEQ ID NO:1).

7. A PYY compound according to any one of the preceding embodiments, further comprising arginine at a position corresponding to position 4 of hPYY(1-36) (SEQ ID NO:1).

8. A PYY compound according to any one of the preceding embodiments, wherein the PYY compound comprises arginine at a position corresponding to position 4 of hPYY(1-36) (SEQ ID NO:1).

9. A PYY compound according to any one of the preceding embodiments, further comprising Aib at a position corresponding to position 28 of hPYY(1-36) (SEQ ID NO:1).

10. A PYY compound according to any one of the preceding embodiments, wherein the PYY compound comprises Aib at a position corresponding to position 28 of hPYY(1-36) (SEQ ID NO:1).

11. A PYY compound according to any one of the preceding embodiments, wherein the positions corresponding to positions 1 and 2 of hPYY(1-36) (SEQ ID NO:1) are absent.

12. A PYY compound according to any one of the preceding embodiments, wherein the positions corresponding to position 1-3 of hPYY(1-36) (SEQ ID NO:1) are absent.

13. A PYY compound according to any one of the preceding embodiments, wherein the positions corresponding to positions 1-3 of hPYY(1-36) (SEQ ID NO:1) are absent, and wherein the PYY compound further comprises an N-terminal substituent, wherein the N-terminal substituent is an alkoxy group comprising up to 12 carbon atoms.

14. A PYY compound according to embodiment 13, wherein the N-terminal substituent is an alkoxy group comprising up to 10 carbon atoms.

15. A PYY compound according to embodiment 13, wherein the N-terminal substituent is an alkoxy group comprising up to 8 carbon atoms.

16. A PYY compound according to embodiment 13, wherein the N-terminal substituent is an alkoxy group comprising up to 6 carbon atoms.

17. A PYY compound according to embodiment 13, wherein the N-terminal substituent is an alkoxy group comprising 6 carbon atoms.

18. A PYY compound according to embodiment 13, wherein the N-terminal substituent is selected from 3-methylbutanoyl, 3-methylpentanoyl or hexanoyl.

19. A PYY compound according to embodiment 13, wherein the N-terminal substituent is 3-methylbutanoyl.

20. A PYY compound according to embodiment 13, wherein the N-terminal substituent is 3-methylpentanoyl.

21. A PYY compound according to embodiment 13, wherein the N-terminal substituent is hexanoyl.

22. A PYY compound according to any one of the preceding embodiments, wherein the PYY compound has a maximum of 8 amino acid modifications as compared to hPYY(3-36).

23. A PYY compound according to any one of the preceding embodiments, wherein the PYY compound has a maximum of 6 amino acid modifications as compared to hPYY(3-36).

24. A PYY compound according to any one of the preceding embodiments, wherein the PYY compound has a minimum of 4 amino acid modifications as compared to hPYY(3-36).

25. A PYY compound according to any one of the preceding embodiments, wherein the PYY compound has a minimum of 6 amino acid modifications as compared to hPYY(3-36).

26. A PYY compound according to any one of the preceding embodiments, wherein the PYY compound has a minimum of 8 amino acid modifications as compared to hPYY(3-36).

27. A PYY compound according to any one of the preceding embodiments, wherein the PYY compound has in the range of 4 to 10 amino acid modifications as compared to hPYY(3-36).

28. A PYY compound according to any one of the preceding embodiments, wherein the PYY compound has in the range of 6 to 8 amino acid modifications as compared to hPYY(3-36).

29. A PYY compound according to any one of the preceding embodiments, wherein the PYY compound has in the range of 4 to 6 amino acid modifications as compared to hPYY(3-36).

30. A PYY compound according to any one of the preceding embodiments, wherein the PYY compound has 4 amino acid modifications as compared to hPYY(3-36).

31. A PYY compound according to any one of the preceding embodiments, wherein the PYY compound has 6 amino acid modifications as compared to hPYY(3-36).

32. A PYY compound according to any one of the preceding embodiments, wherein the PYY compound has 8 amino acid modifications as compared to hPYY(3-36).

33. A PYY compound according to any one of the preceding embodiments, wherein the PYY compound exhibit at least 70% sequence identity to hPYY(3-36).

34. A PYY compound according to any one of the preceding embodiments, wherein the PYY compound exhibit at least 75% sequence identity to hPYY(3-36).

35. A PYY compound according to any one of the preceding embodiments, wherein the PYY compound exhibit at least 80% sequence identity to hPYY(3-36).

36. A PYY compound according to any one of the preceding embodiments, further comprising a Lysine at a position corresponding to position 7 of hPYY(1-36) (SEQ ID NO:1) and a modifying group attached to the epsilon amino group of the Lysine residue in position 7, wherein said modifying group is defined by A-B-C-, wherein A- comprises a carboxylic acid, a tetrazole or a sulfonic acid.

37. A PYY compound according to any one of the preceding embodiments, wherein the PYY compound comprises lysine at a position corresponding to position 7 of hPYY(1-36) (SEQ ID NO:1) and a modifying group attached to the epsilon amino group of said lysine, wherein said modifying group is defined by A-B-C-.

38. A PYY compound according to any one of embodiments 36-37, wherein A- is selected from

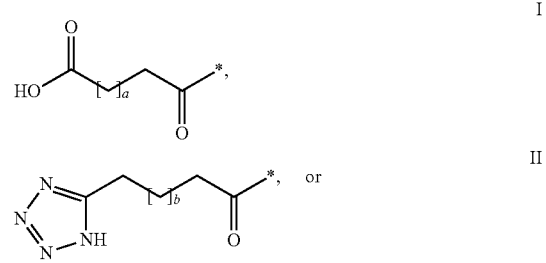

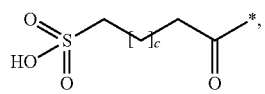

wherein a is an integer from 12 to 19, b is an integer from 10 to 16, and c is an integer from 10 to 16, and wherein * denotes the attachment point to -B-.

39. A PYY compound according to embodiment 38, wherein a is 15, b is 13, or c is 13.

40. A PYY compound according to any one of embodiments 36-37, wherein A- is selected from

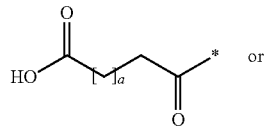

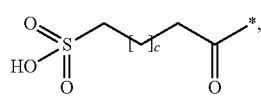

wherein a is an integer from 12 to 19, c is an integer from 10 to 16, and wherein * denotes the attachment point to -B-.

41. A PYY compound according to embodiment 40, wherein a is 15, or c is 13.

42. A PYY compound according to any one of embodiments 36-37, wherein A- is

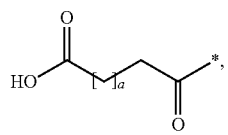

wherein a is an integer from 12 to 19, and wherein * denotes the attachment point to -B-.

43. A PYY compound according to embodiment 42, wherein a is 15.

44. A PYY compound according to any one of embodiments 36-37, wherein A- is

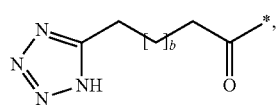

wherein b is an integer from 10 to 16, and wherein * denotes the attachment point to -B-.

45. A PYY compound according to embodiment 44, wherein b is 13.

46. A PYY compound according to any one of embodiments 36-37, wherein A- is

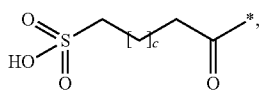

wherein c is an integer from 10 to 16, and wherein * denotes the attachment point to -B-.

47. A PYY compound according to embodiment 46, wherein c is 13.

48. A PYY compound according to any one of embodiments 36-47, wherein B- is selected from

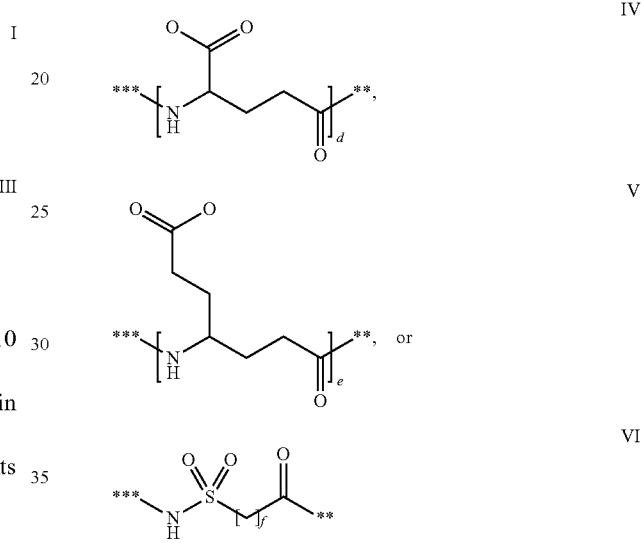

wherein d is 1 or 2; e is 1 or 2; and f is 2, 3 or 4; and wherein * denotes the attachment point to A-, and  denotes the attachment point to -C-.

49. A PYY compound according to embodiment 48, wherein B- is selected from

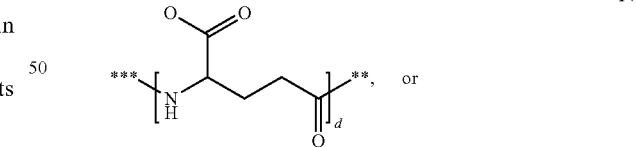

wherein d is 1 or 2; and f is 2, 3 or 4; and wherein * denotes the attachment point to A-, and  denotes the attachment point to -C-.

50. A PYY compound according to embodiment 49, wherein d is 1 or 2; and f is 3.

51. A PYY compound according to embodiment 48, wherein B- is

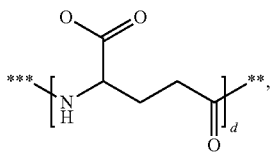

IV wherein d is 1 or 2; and wherein * denotes the attachment point to A-, and  denotes the attachment point to -C-.

52. A PYY compound according to embodiment 48, wherein B- is

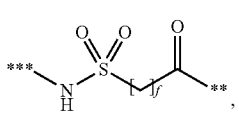

VI wherein f is 2, 3 or 4; and wherein * denotes the attachment point to A-, and  denotes the attachment point to -C-.

53. A PYY compound according to embodiment 52, wherein f is 3.

54. A PYY compound according to any one of embodiments 36-53, wherein -C- is

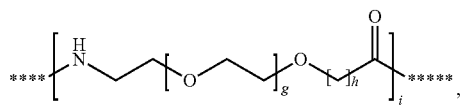

VII or

VIII wherein g is an integer in the range of 1-5, h is an integer in the range of 1-5, i is an integer in the range of 2 to 6, j is an integer in the range of 2 to 6, and wherein ** denotes the attachment point to -B-, and *** denotes the attachment point to the epsilon amino group of the Lysine residue in the position corresponding to position 7 of hPYY(1-36).

55. A PYY compound according to any one of embodiments 36-53, wherein -C- is ment point to -B-, and ***** denotes the attachment point to the epsilon amino group of the Lysine residue in the position corresponding to position 7 of hPYY(1-36).

56. A PYY compound according to any one of embodiments 54-55, wherein g and h are each 1.

57. A PYY compound according to any one of embodiments 54-56, wherein i is selected from 2, 3, 4 or 5 and j is selected from 1, 2 or 3.

58. A PYY compound according to any one of embodiments 36-53, wherein -C- is

VII wherein g is an integer in the range of 1-5, h is an integer in the range of 1-5, i is an integer in the range of 2 to 6, and wherein ** denotes the attachment point to -B-, and *** denotes the attachment point to the epsilon amino group of the Lysine residue in the position corresponding to position 7 of hPYY (1-36).

59. A PYY compound according to embodiment 58, wherein g and h are each 1.

60. A PYY compound according to any one of embodiments 58-59, wherein i is selected from 2, 4 or 6.

61. A PYY compound according to embodiment 60, wherein i is 2.

62. A PYY compound according to embodiment 60, wherein i is 4.

63. A PYY compound according to embodiment 60, wherein i is 6.

64. A PYY compound according to embodiment 58, wherein g and h are each 1, and i is 2.

65. A PYY compound, wherein the PYY compound has a maximum of 10 amino acid modifications as compared to hPYY(3-36), and wherein the PYY compound comprises (i) tryptophan at the position corresponding to position 30 of hPYY(1-36) (SEQ ID NO:1);

(ii) N(alpha)-methyl-L-arginine at a position corresponding to position 35 of hPYY(1-36) (SEQ ID NO:1);

(iii) glutamine at a position corresponding to position 18 of hPYY(1-36) (SEQ ID NO:1);

(iv) lysine at a position corresponding to position 7 of hPYY (1-36) (SEQ ID NO:1); and

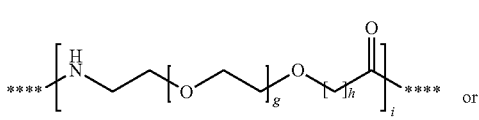

VII or

VIII

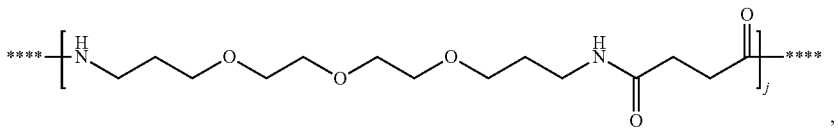

(v) a modifying group attached to the epsilon amino group of said lysine, wherein said modifying group is defined by A-B-C-, wherein wherein g is an integer in the range of 1-5, h is an integer in the range of 1-5, i is an integer in the range of 2 to 6, j is an integer in the range of 1 to 6, and wherein **** denotes the attach- A- is selected from or wherein a is 15, c is 13, and wherein * denotes the attachment point to -B-;

B- is wherein d is 1 or 2; and wherein * denotes the attachment point to A-, and  denotes the attachment point to -C-; and -C- is wherein g and h is each 1, i is selected from 2 or 4, and wherein ** denotes the attachment point to -B-, and *** denotes the attachment point to the epsilon amino group of the Lysine residue in the position corresponding to position 7 of hPYY(1-36); or a pharmaceutically acceptable salt thereof.

66. A PYY compound according embodiment 65, wherein the PYY compound comprises arginine at a position corresponding to position 4 of hPYY(1-36) (SEQ ID NO:1).

67. A PYY compound according to any one of embodiments 65-66, wherein the positions corresponding to positions 1 and 2 of hPYY(1-36) (SEQ ID NO:1) are absent.

68. A PYY compound according to any one of embodiments 65-67, wherein the positions corresponding to positions 1-3 of hPYY(1-36) (SEQ ID NO:1) are absent, and wherein the PYY compound further comprises an N-terminal substituent, wherein the N-terminal substituent is selected from 3-methylbutanoyl, 3-methylpentanoyl or hexanoyl.

69. A PYY compound according to any one of embodiments 65-68, wherein the PYY compound has a maximum of 8 amino acid modifications as compared to hPYY(3-36).

70. A PYY compound, wherein the PYY compound has a maximum of 10 amino acid modifications as compared to hPYY(3-36), wherein the positions corresponding to positions 1-3 of hPYY(1-36) (SEQ ID NO:1) are absent, and wherein the PYY compound comprises (i) tryptophan at the position corresponding to position 30 of hPYY(1-36) (SEQ ID NO:1);

(ii) N(alpha)-methyl-L-arginine at a position corresponding to position 35 of hPYY(1-36) (SEQ ID NO:1);

(iii) glutamine at a position corresponding to position 18 of hPYY(1-36) (SEQ ID NO:1);

(iv) lysine at a position corresponding to position 7 of hPYY (1-36) (SEQ ID NO:1);

(v) a modifying group attached to the epsilon amino group of said lysine, wherein said modifying group is defined by A-B-C-, wherein A- is wherein c is 13, and wherein * denotes the attachment point to -B-;

B- is wherein d is 1; and wherein * denotes the attachment point to A-, and  denotes the attachment point to -C-; and -C- is wherein g and h is each 1, i is 2, and wherein ** denotes the attachment point to -B-, and *** denotes the attachment point to the epsilon amino group of the Lysine residue in the position corresponding to position 7 of hPYY(1-36);

(vi) arginine at a position corresponding to position 4 of hPYY(1-36) (SEQ ID NO:1); and (vii) an N-terminal substituent, wherein the N-terminal substituent is selected from 3-methylbutanoyl, 3-methylpentanoyl or hexanoyl;

or a pharmaceutically acceptable salt thereof.

71. A PYY compound according to embodiment 70, wherein the PYY compound has a maximum of 8 amino acid modifications as compared to hPYY(3-36).

71a. A PYY compound according to embodiment 70, wherein the PYY compound has 6 amino acid modifications as compared to hPYY(3-36).

72. A PYY compound according to any one of the preceding embodiments, wherein the PYY compound is not a salt.

73. A PYY compound according to any one of the preceding embodiments selected from the following: [Trp30]hPYY(3-36) (SEQ ID NO: 3)

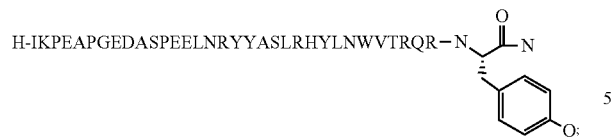

[Trp30, NMeArg35]hPYY3-36 (SEQ ID NO:4)

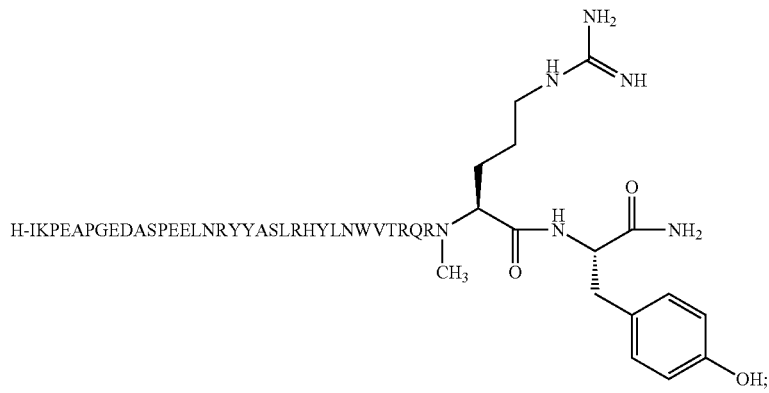

7-N{Epsilon}-[2-[2-[2-[[2-[2-[2-[[(4S)-4-carboxy-4-(17-carboxyheptadecanoylamino)-butanoyl]amino]ethoxy]ethoxy]acetyl]amino]ethoxy]ethoxy]acetyl]-[Lys7, Gln18, Trp30, NMeArg35]hPYY(3-36) (SEQ ID NO:5)

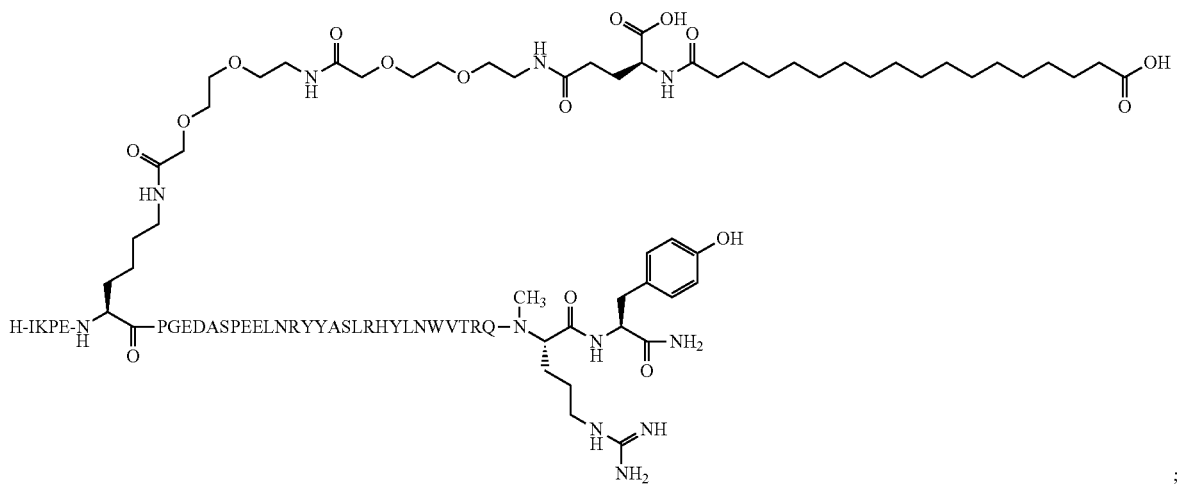

7-N{Epsilon}-[2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]amino]ethoxy]ethoxy]acetyl]amino]-ethoxy]ethoxy]acetyl]-[Lys7, Gln18, Trp30, NMeArg35]hPYY(3-36) (SEQ ID NO:6)

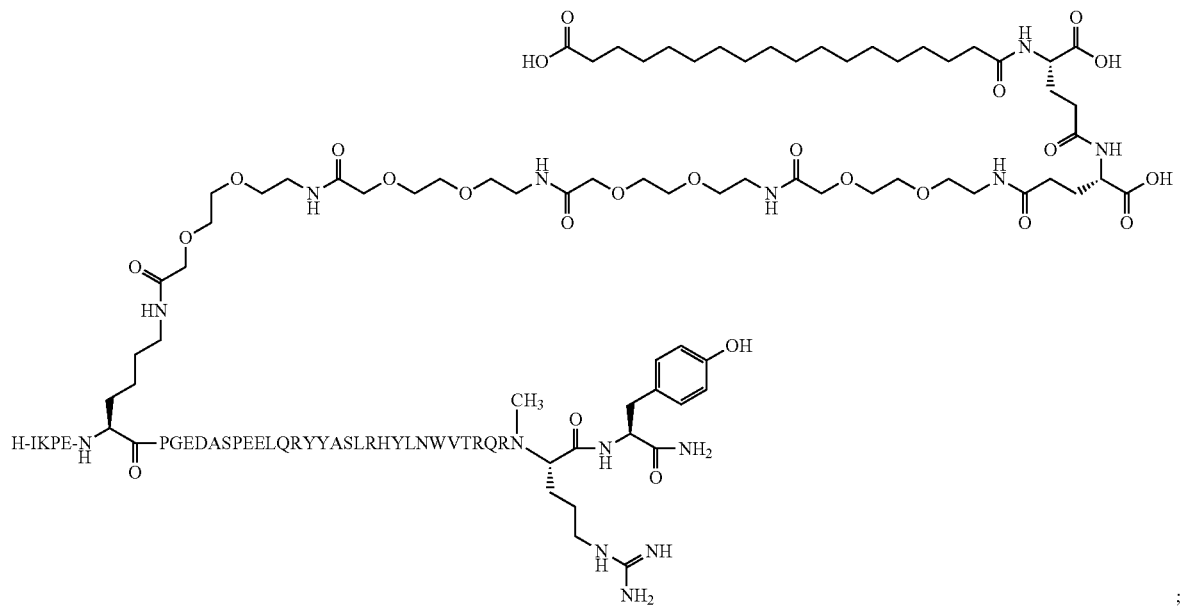
7-N{Epsilon}-[2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]amino]ethoxy]ethoxy]acetyl]amino]ethoxy]ethoxy]acetyl]-[Lys7, Gln18, Trp30, NMeArg35]hPYY(3-36) (SEQ ID NO:7)
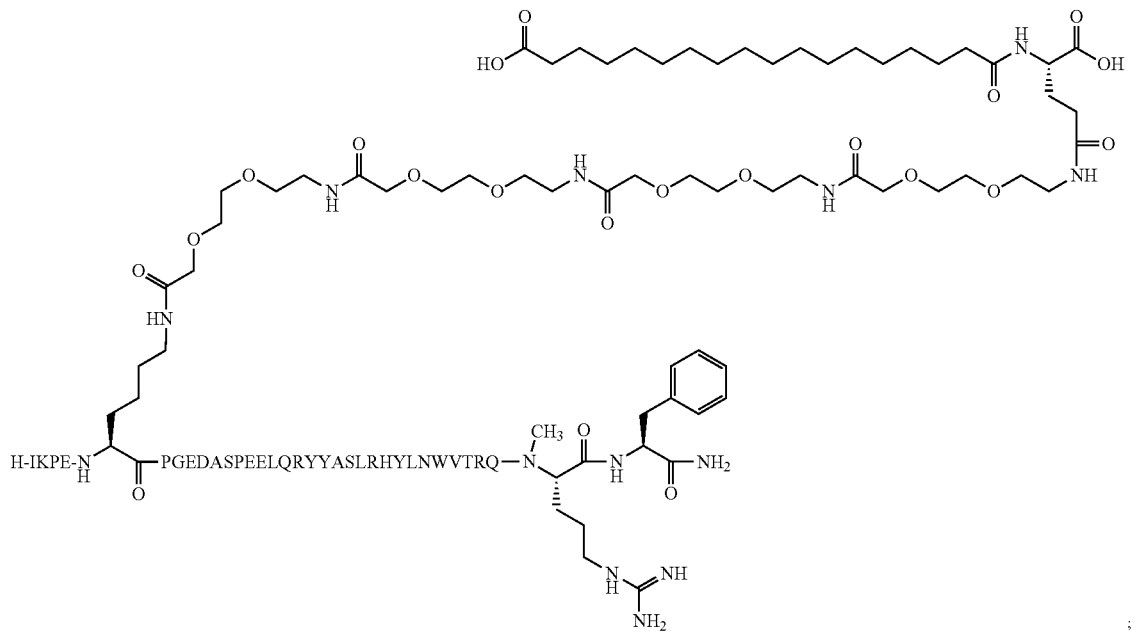
7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]ethoxy]acetyl]-[Lys7, Gln18, Trp30, NMeArg35]hPYY(3-36) (SEQ ID NO:8)

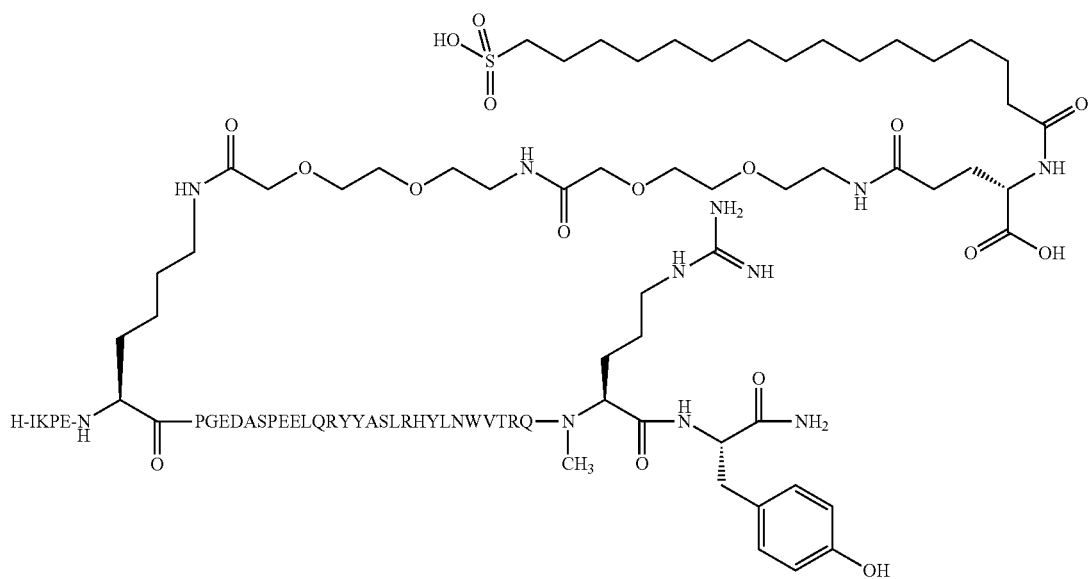

7-N{Epsilon}-[2-[2-[2-[[2-[2-[2-[[2-[2-[2-[[2-[2-[4-[16-(1H-tetrazol-5-yl)-hexadecanoylsulfamoyl]butanoylamino]ethoxy]ethoxy]acetyl]amino]ethoxy]-ethoxy]acetyl]amino]ethoxy]ethoxy]acetyl]amino]ethoxy]ethoxy]acetyl]-[Lys7, Gln18, Trp30, NMeArg35]hPYY(3-36) (SEQ ID NO:9)

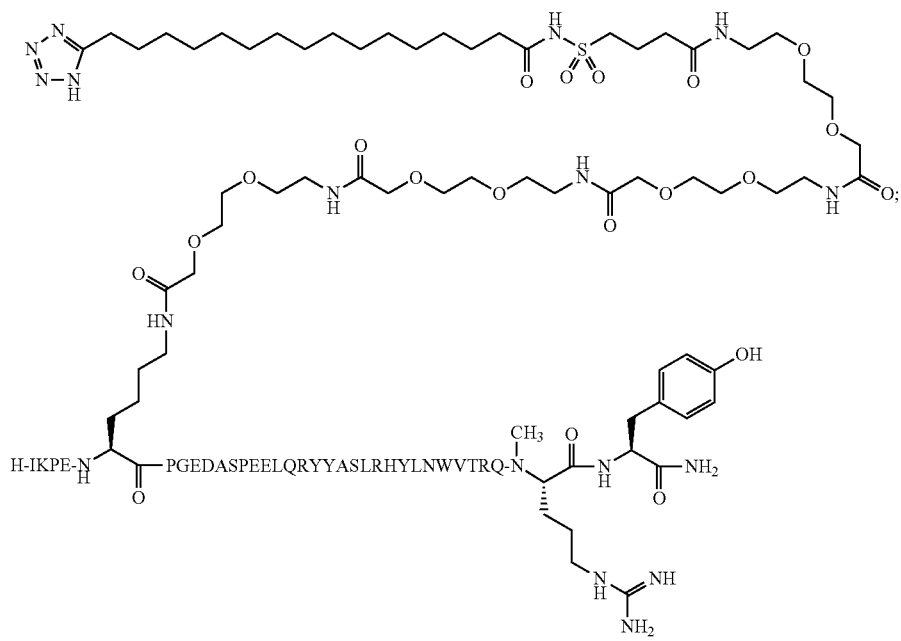

7-N{Epsilon}-[2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]-amino]ethoxy]ethoxy]acetyl]amino]ethoxy]ethoxy]acetyl]amino]ethoxy]-ethoxy]acetyl]amino]ethoxy]ethoxy]acetyl]-[Lys7, Gln18, Aib28, Trp30, NMeArg35]hPYY(3-36) (SEQ ID NO:10)

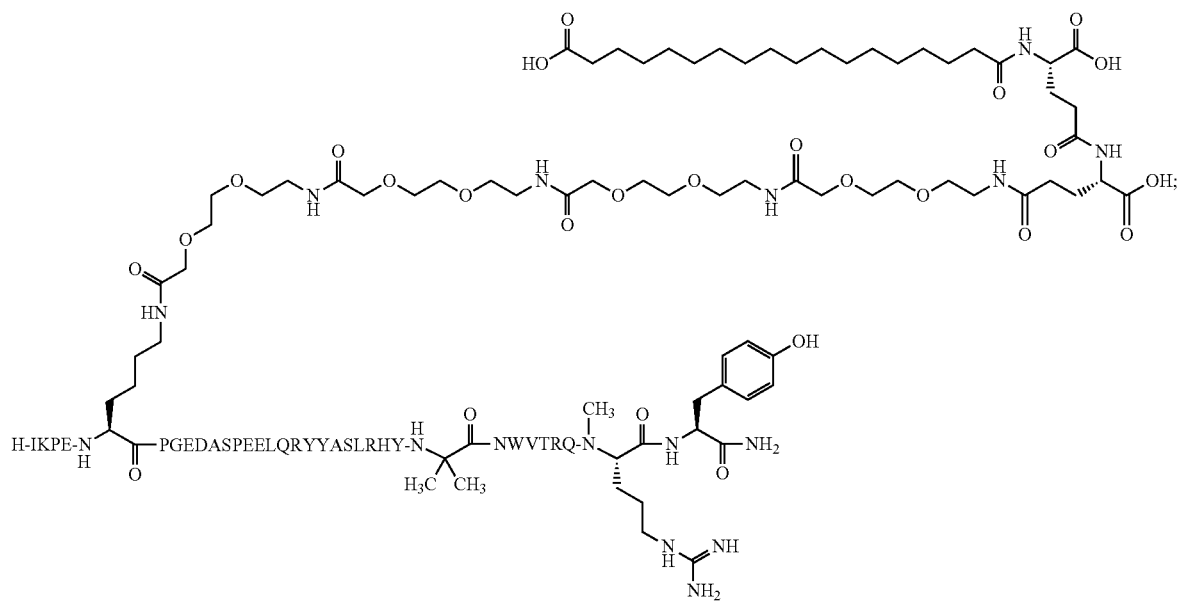
7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]ethoxy]acetyl]-[Arg4, Lys7, Gln18, Trp30, NMeArg35]hPYY(3-36) (SEQ ID NO:11)
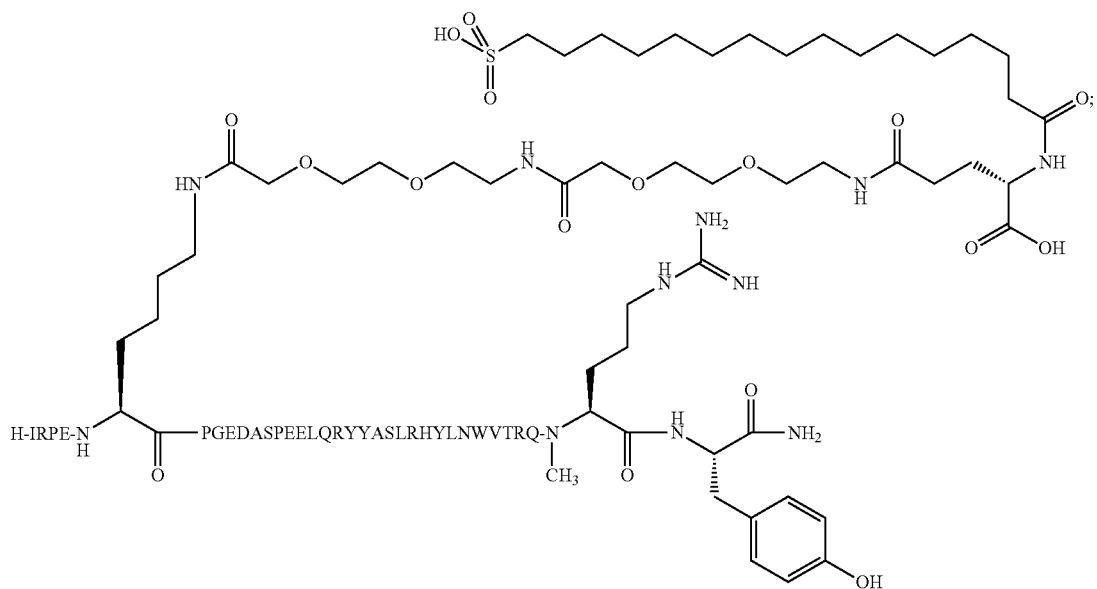
4-N{alpha}-(hexanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:12)

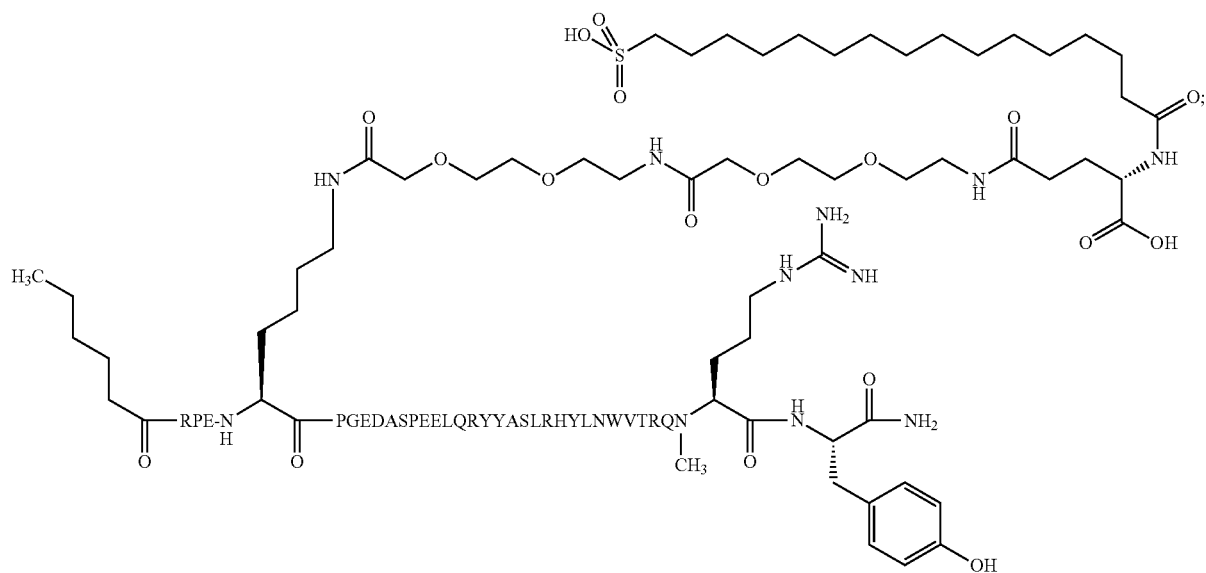
4-N{alpha}-(3-methyl-pentanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Lys7, Gln18, Trp30, NMeArg35] hPYY(4-36) (SEQ ID NO:13)
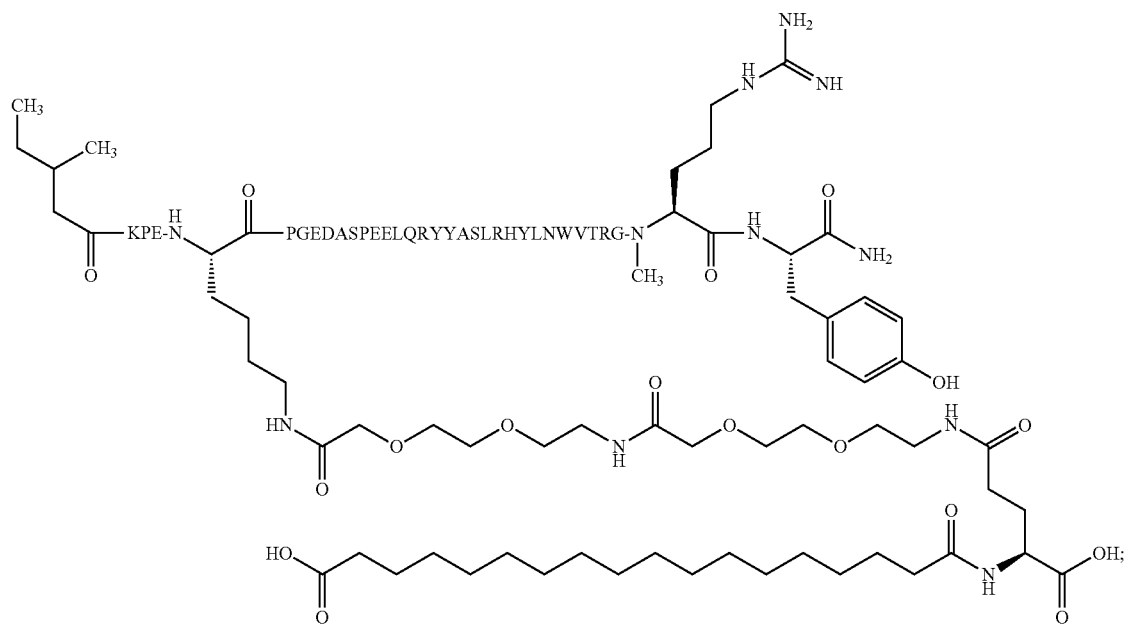
4-N{alpha}-(3-methyl-pentanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:14)

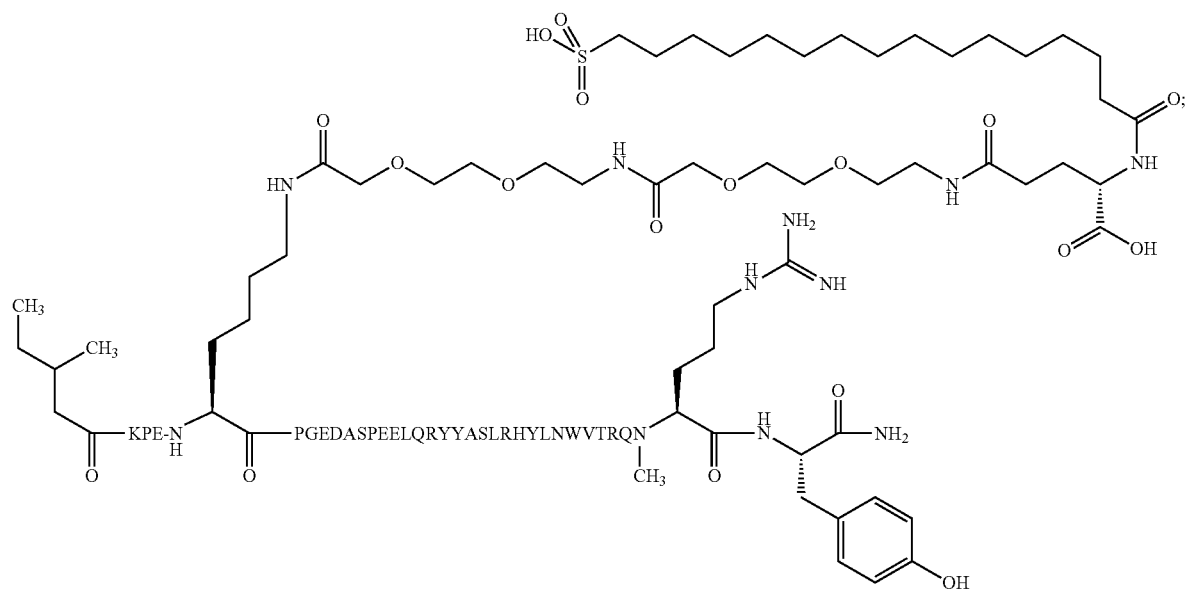
4-N{alpha}-(3-Methylbutanoyl)-7-N{Epsilon}-[2-[2-[2-[[2-[2-[2-[[(4S)-4-carboxy-4-[[(4S)-4-carboxy-4-(16-sulfo-hexadecanoylamino)butanoyl]amino]butanoyl]amino]-ethoxy]ethoxy]acetyl]amino]ethoxy]ethoxy]acetyl]-[Lys7, Gln18, Trp30, NMeArg35]hPYY(4-36) (SEQ ID NO:15)
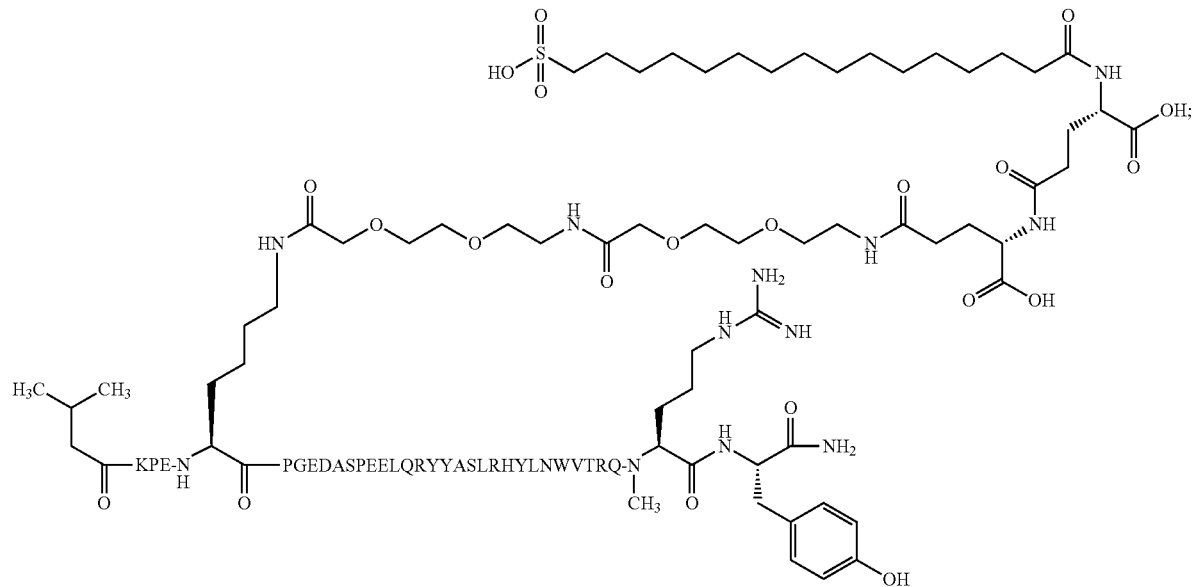
4-N{alpha}-(3-Methylbutanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:16)

33
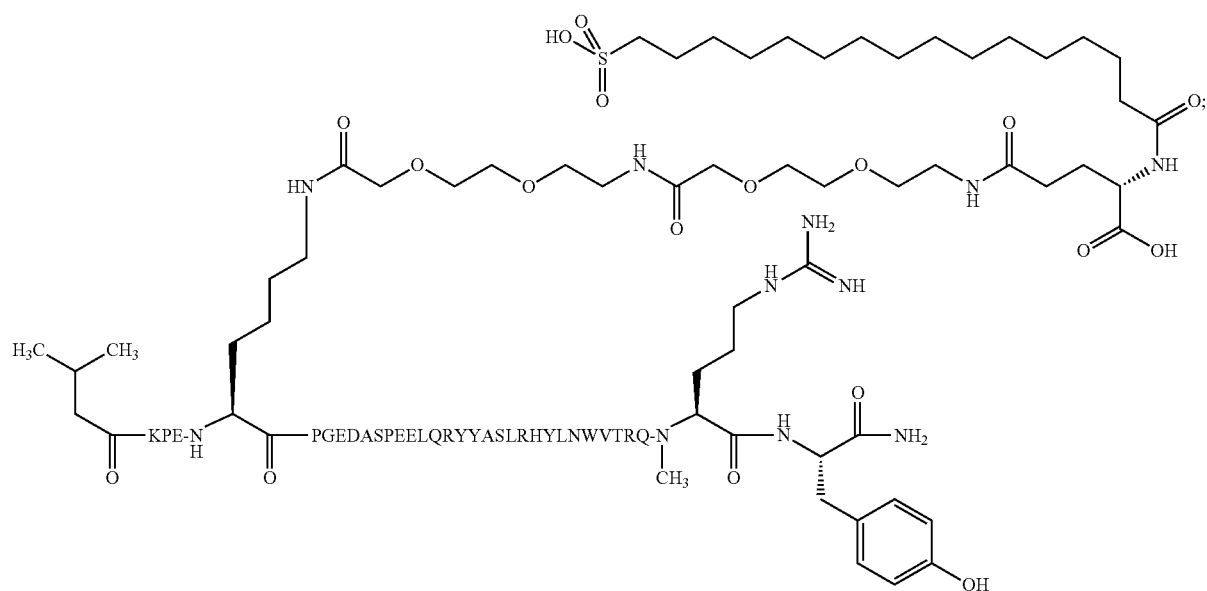
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]-amino]ethoxy]ethoxy]acetyl]-[Arg4, Lys7, Gln18, Trp30]hPYY(4-36) (SEQ ID NO:17)
34
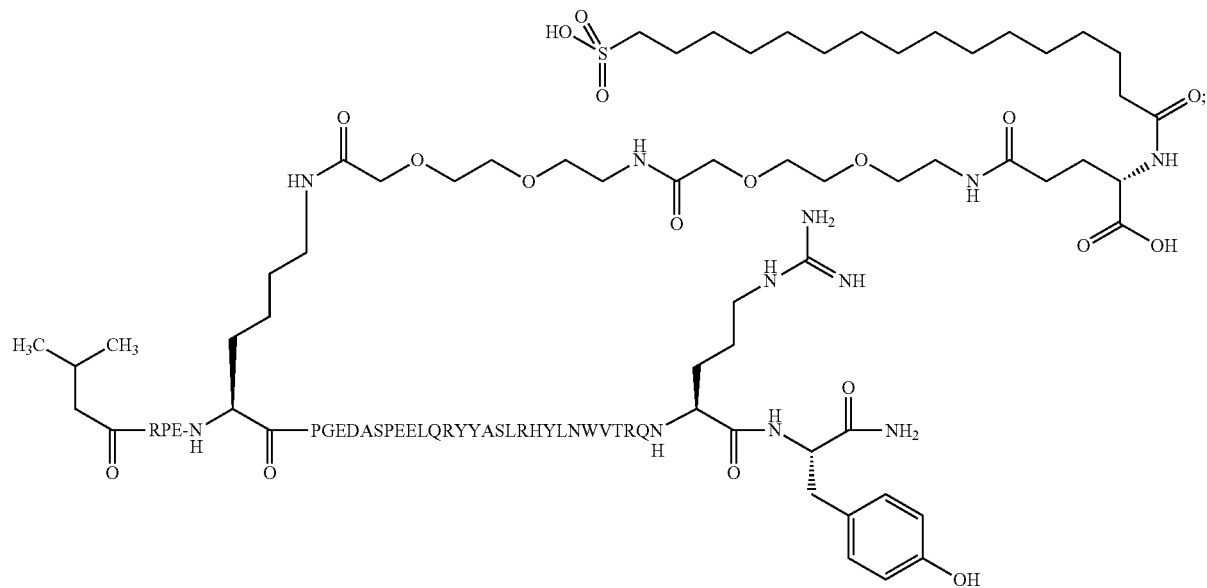
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)

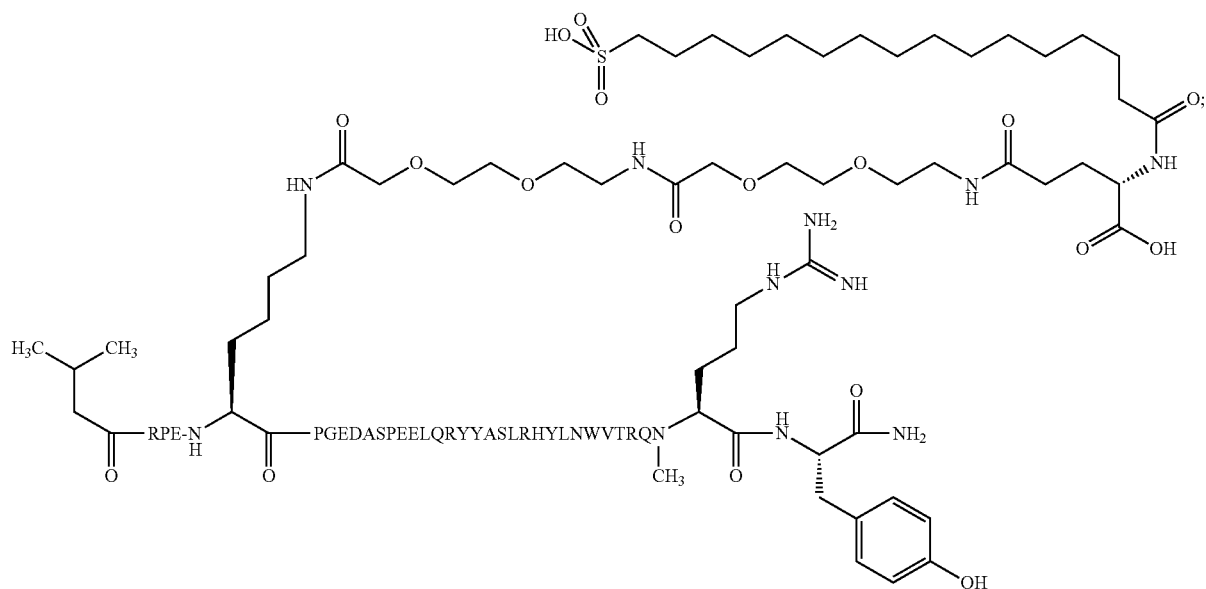
4-N{alpha}-(3-Methylbutanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:19)
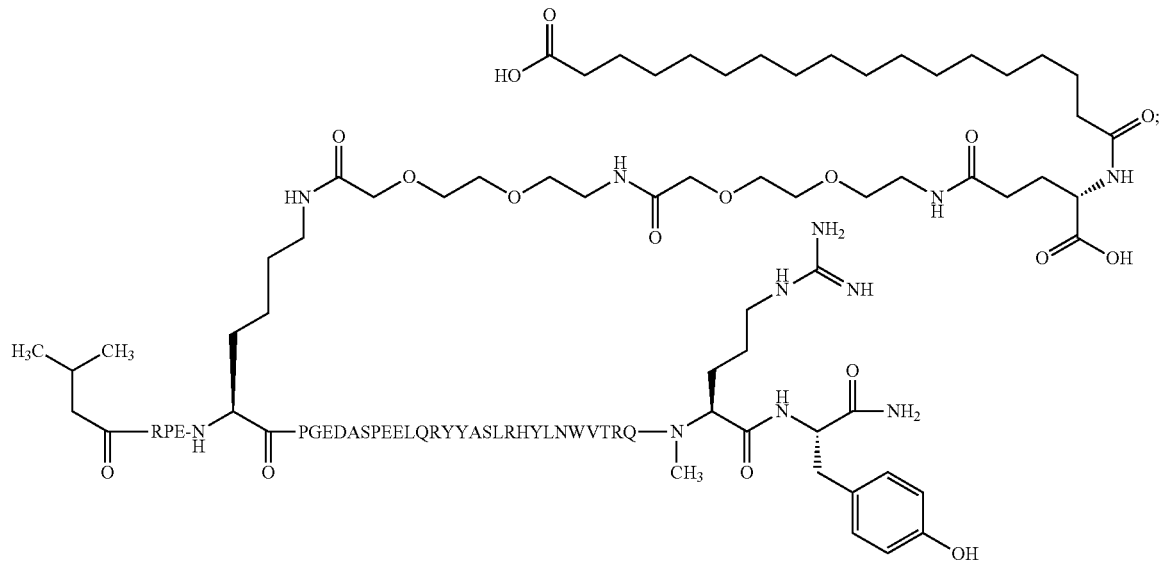
4-N{alpha}-(3-Methylbutanoyl)-7-N{Epsilon}-[2-[2-[2-[[2-[2-[2-[[(4S)-4-carboxy-4-(14-sulfotetradecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:20)

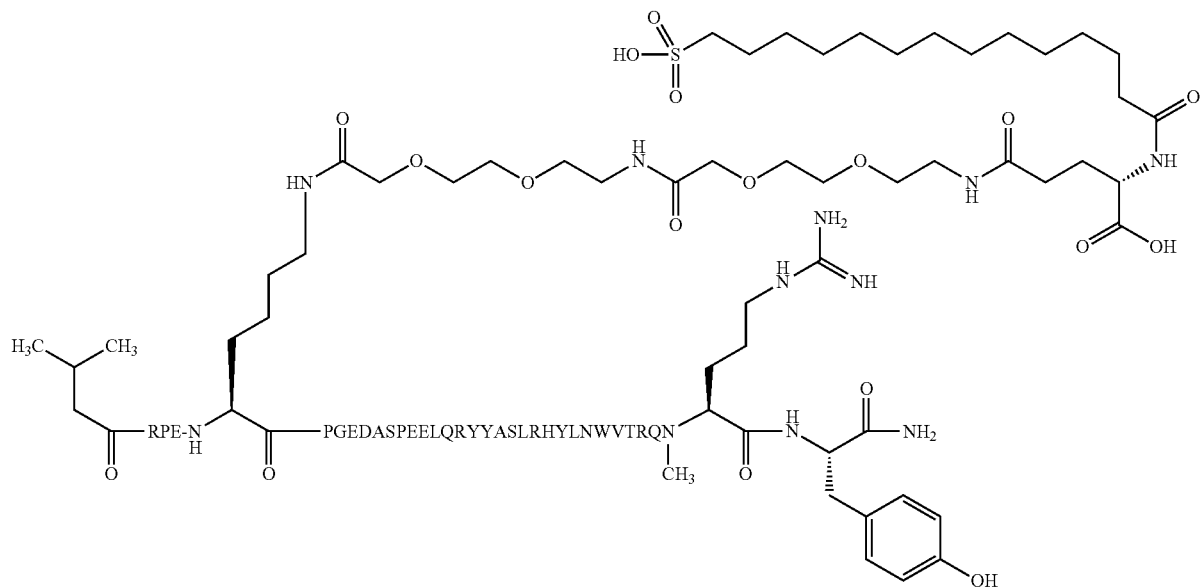
74. A PYY compound according to any one of the preceding embodiments selected from the following:
[Trp30]hPYY(3-36) (SEQ ID NO:3)
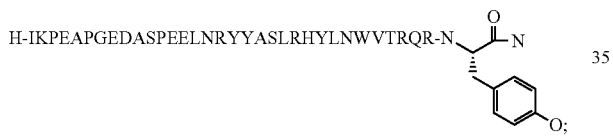
[Trp30, NMeArg35]hPYY3-36 (SEQ ID NO:4)
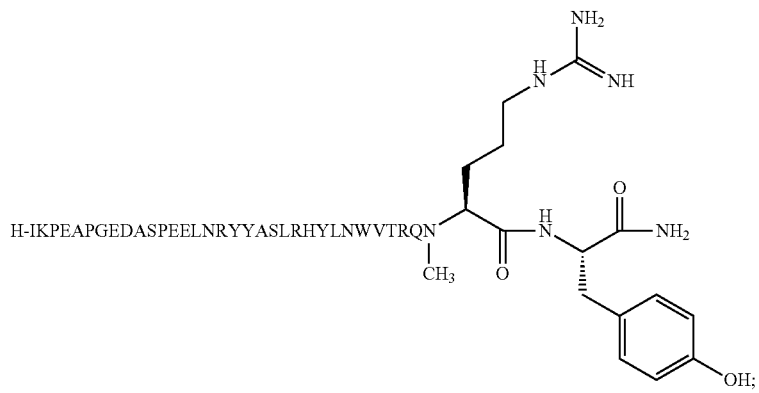
7-N{Epsilon}-[2-[2-[2-[[2-[2-[2-[[(4S)-4-carboxy-4-(17-carboxyheptadecanoylamino)-butanoyl]amino]ethoxy]ethoxy]acetyl]amino]ethoxy]ethoxy]acetyl]-[Lys7, Gln18, Trp30, NMeArg35]hPYY(3-36) (SEQ ID NO:5)

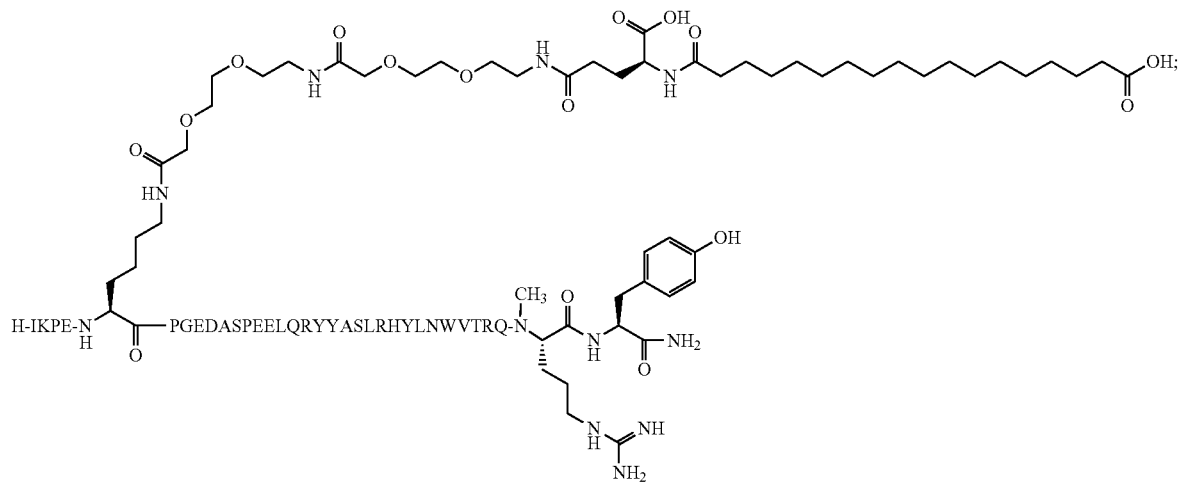

7-N{Epsilon}-[2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]amino]ethoxy]ethoxy]acetyl]amino]-ethoxy]ethoxy]acetyl]-[Lys7, Gln18, Trp30, NMeArg35]hPYY(3-36) (SEQ ID NO:6)

7-N{Epsilon}-[2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]amino]ethoxy]ethoxy]acetyl]amino]ethoxy]ethoxy]acetyl]-[Lys7, Gln18, Trp30, NMeArg35]hPYY(3-36) (SEQ ID NO:7)

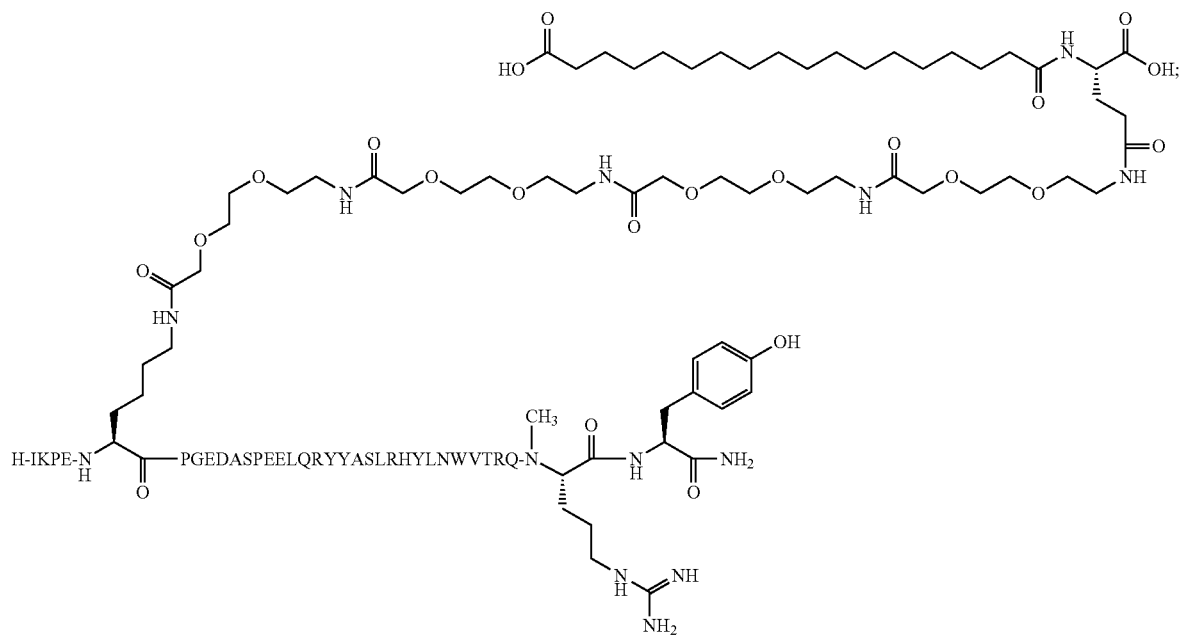
7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]ethoxy]acetyl]-[Lys7, Gln18, Trp30, NMeArg35]hPYY(3-36) (SEQ ID NO:8)
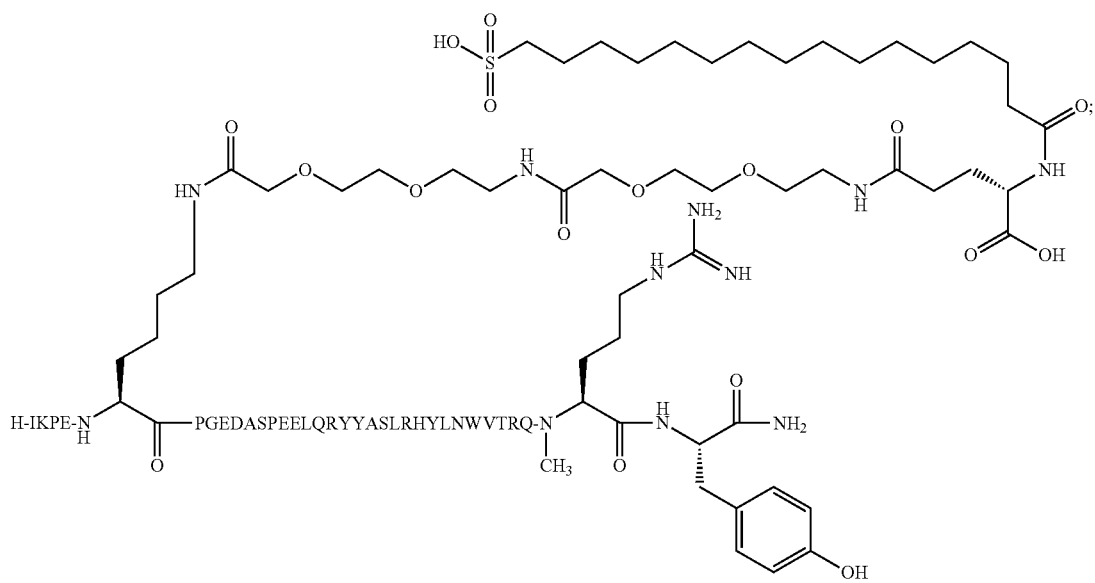
7-N{Epsilon}-[2-[2-[2-[[2-[2-[2-[[2-[2-[2-[[2-[2-[2-[4-[16-(1H-tetrazol-5-yl)-hexadecanoylsulfamoyl]butanoylamino]ethoxy]ethoxy]acetyl]amino]ethoxy]-ethoxy]acetyl]amino]ethoxy]ethoxy]acetyl]amino]ethoxy]ethoxy]acetyl]-[Lys7, Gln18, Trp30, NMeArg35]hPYY(3-36) (SEQ ID NO:9)

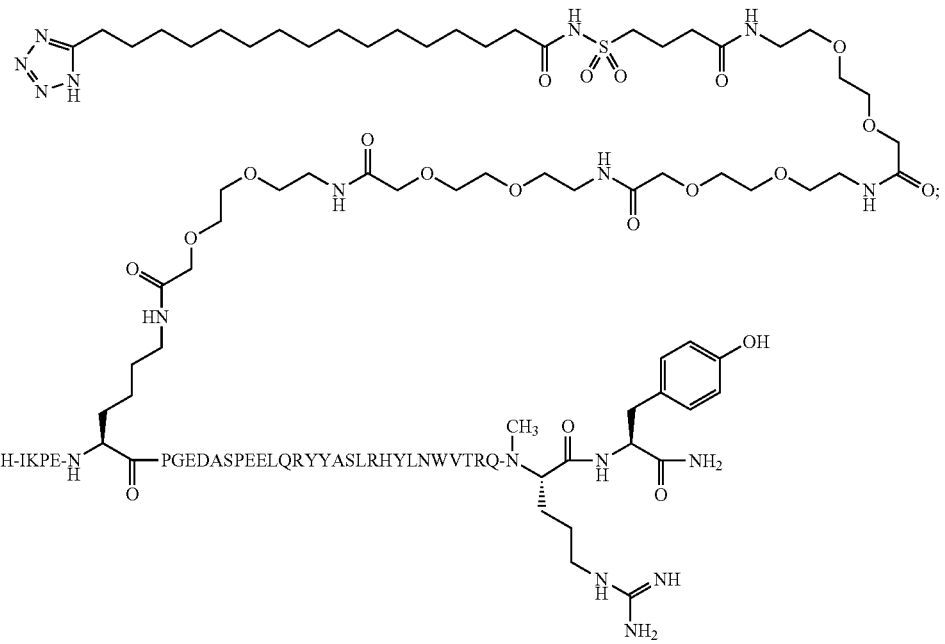
7-N{Epsilon}-[2-[2-[2-[[2-[2-[2-[[2-[2-[2-[[2-[2-[2-[[(4S)-4-carboxy-4-[[(4S)-4-carboxy-4-(17-carboxyheptadecanoy-lamino)butanoyl]amino]butanoyl]-amino]ethoxy]ethoxy] acetyl]amino]ethoxy]ethoxy]acetyl]amino]ethoxy]-ethoxy] acetyl]amino]ethoxy]ethoxy]acetyl]-[Lys7, Gln18, Aib28, Trp30, NMeArg35]hPYY(3-36) (SEQ ID NO:10)

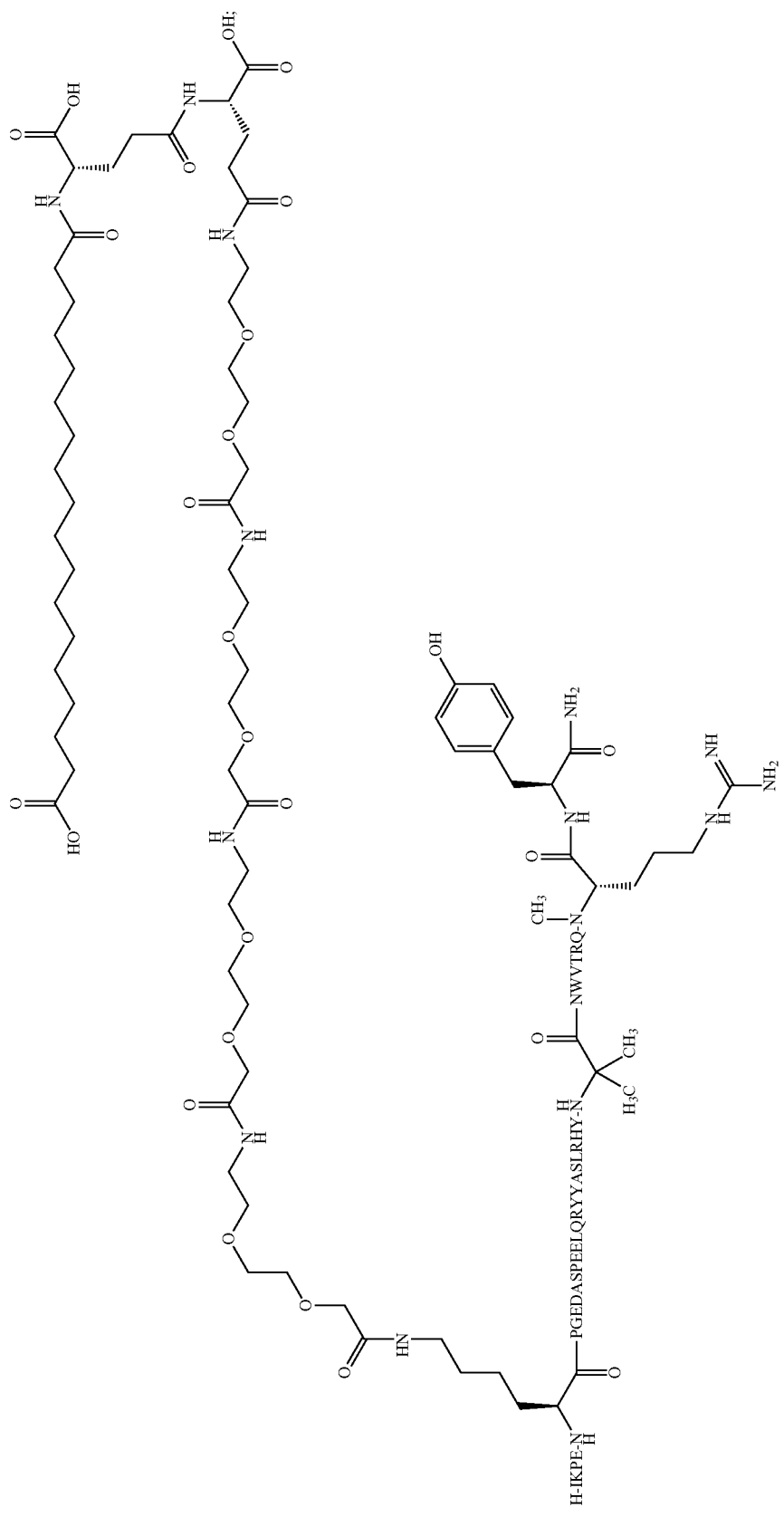

7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]ethoxy]acetyl]-[Arg4, Lys7, Gln18, Trp30, NMeArg35]hPYY(3-36) (SEQ ID NO:11)

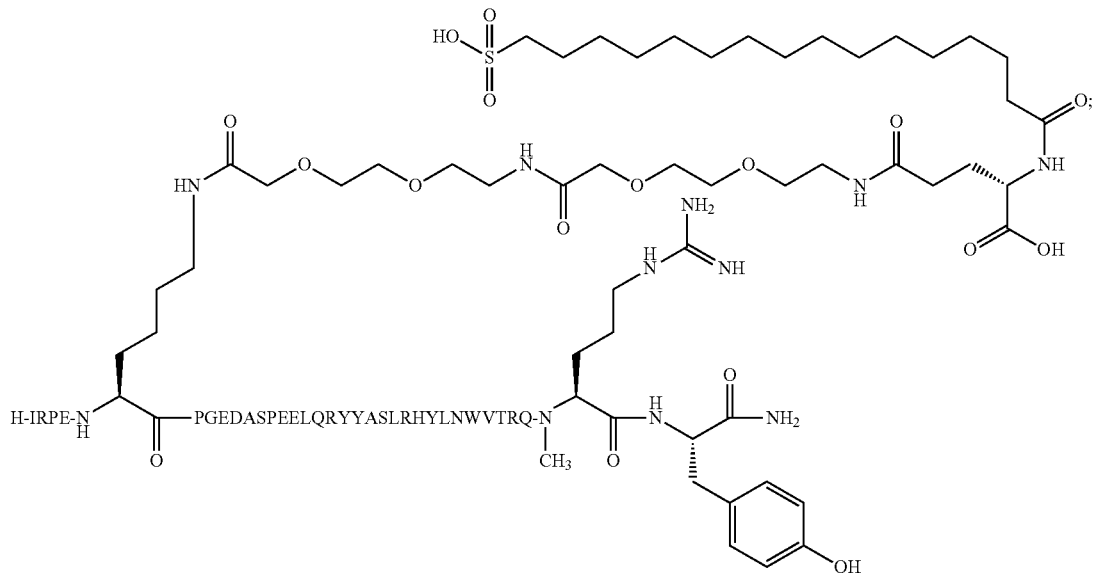

4-N{alpha}-(hexanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:12)

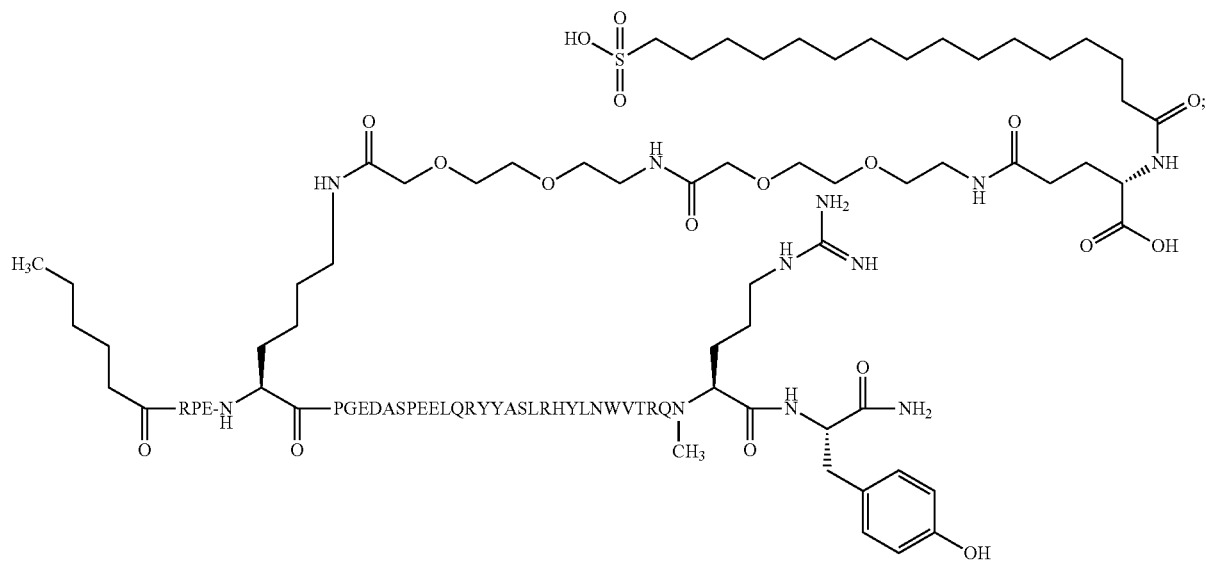

4-N{alpha}-(3-methyl-pentanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:13)

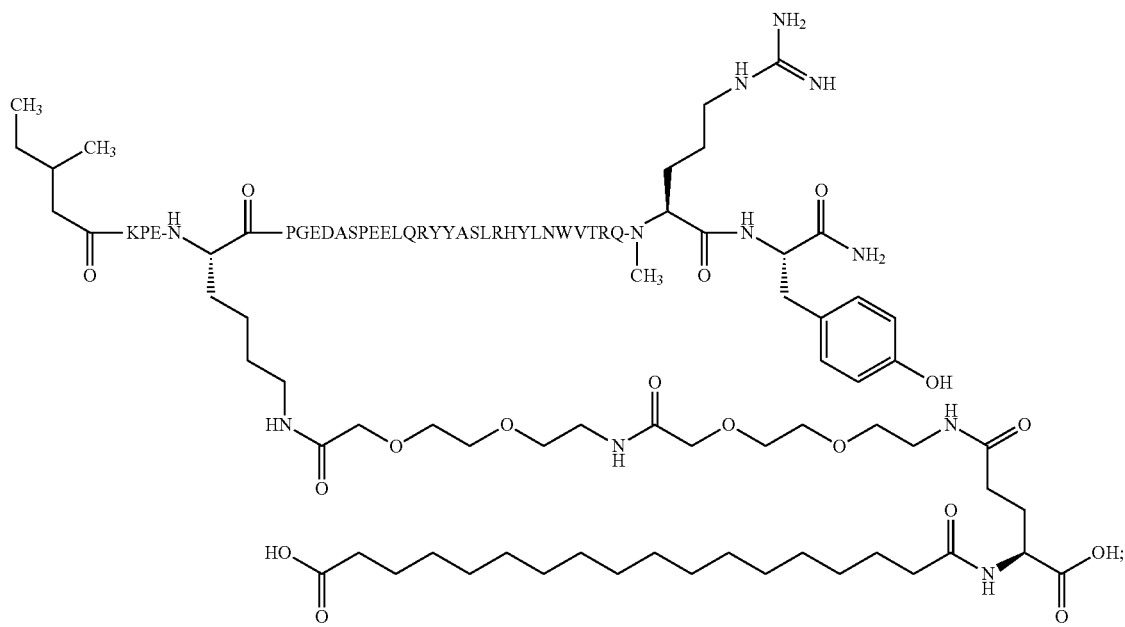
4-N{alpha}-(3-methyl-pentanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:14)
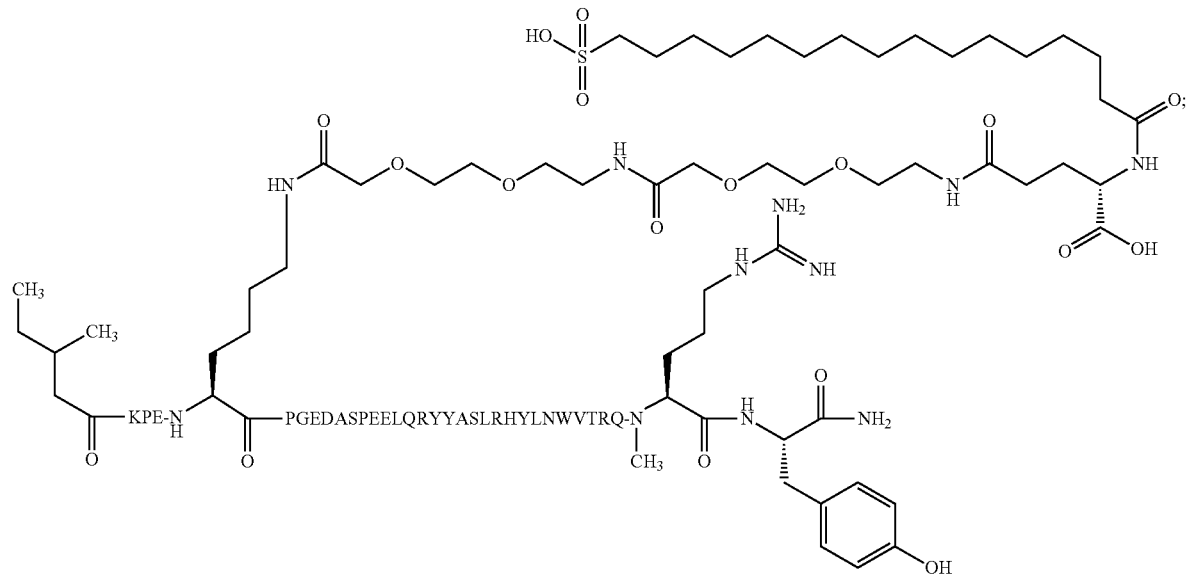
4-N{alpha}-(3-Methylbutanoyl)-7-N{Epsilon}-[2-[2-[2-[[2-[2-[2-[[(4S)-4-carboxy-4-[[(4S)-4-carboxy-4-(16-sulfo-hexadecanoylamino)butanoyl]amino]butanoyl]amino]-ethoxy]ethoxy]acetyl]amino]ethoxy]ethoxy]acetyl]-[Lys7, Gln18, Trp30, NMeArg35]hPYY(4-36) (SEQ ID NO:15)

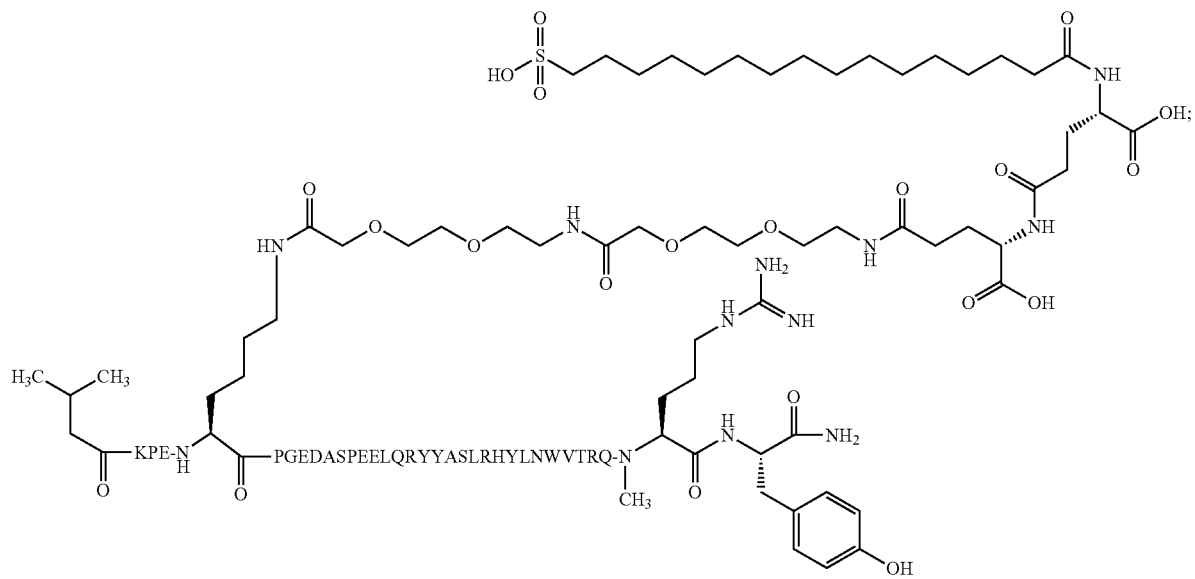
4-N{alpha}-(3-Methylbutanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:16)
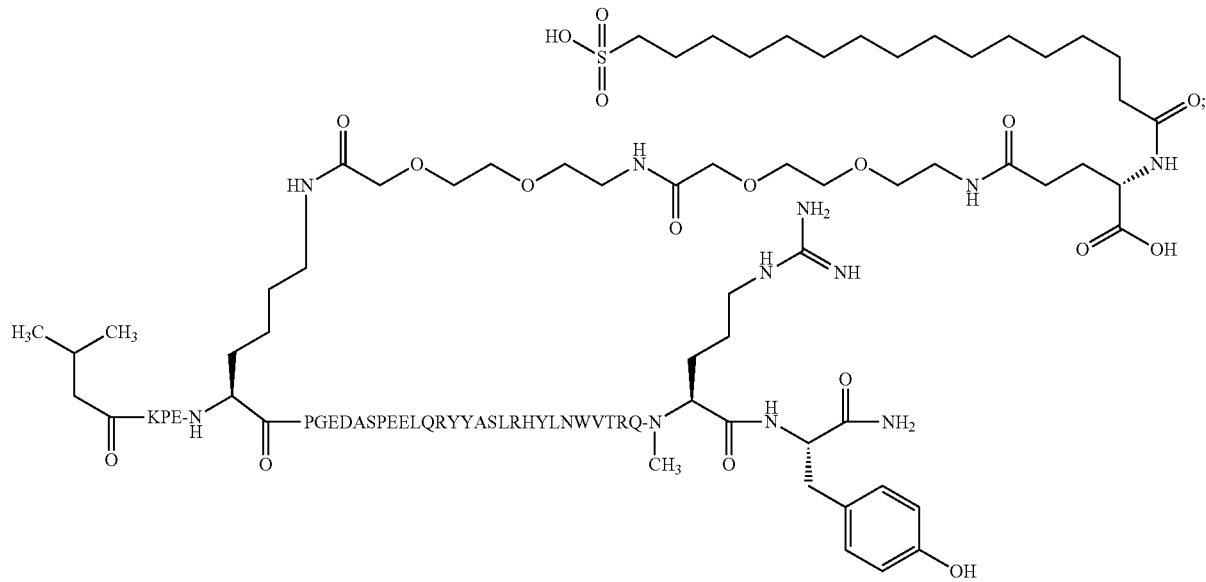
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]-amino]ethoxy]ethoxy]acetyl]-[Arg4, Lys7, Gln18, Trp30]hPYY(4-36) (SEQ ID NO:17)

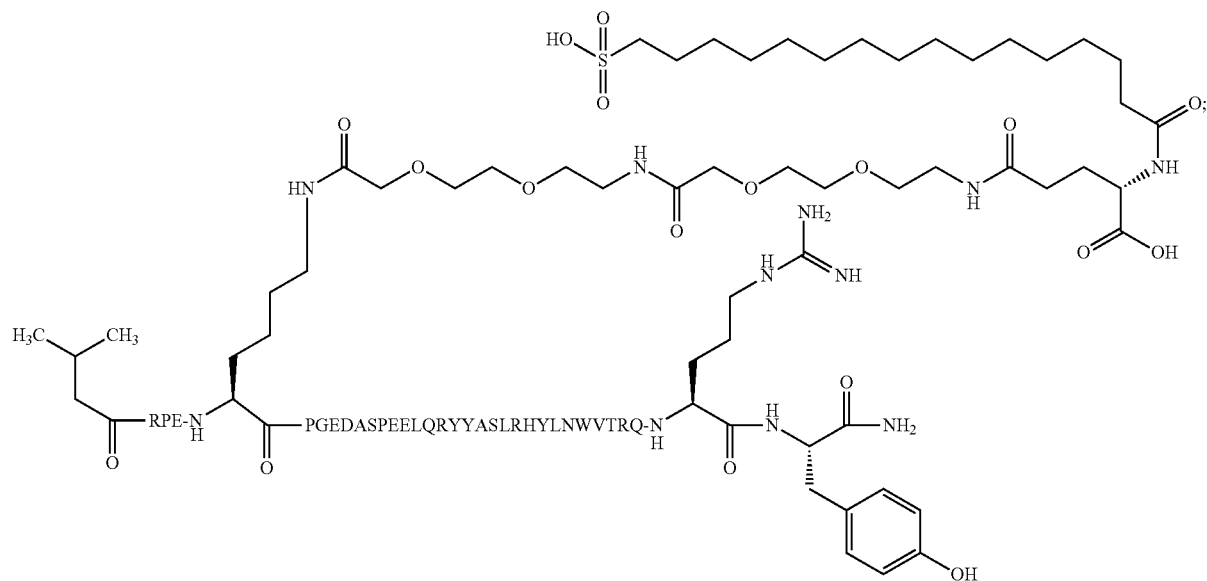
4-N{alpha}-(3-Methylbutanoyl)-7-N{Epsilon}-[2-[2-[2-[[2-[2-[2-[[(4S)-4-carboxy-4-(16-sulfohexadecanoy-lamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)
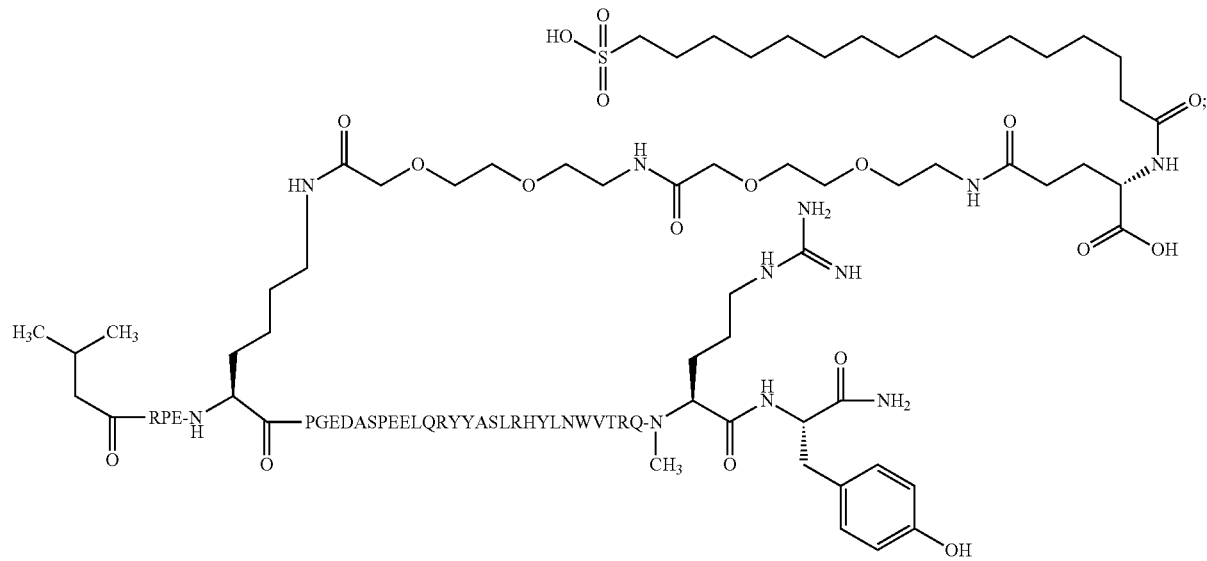
4-N{alpha}-(3-Methylbutanoyl)-7-N{Epsilon}-[2-[2-[2-[[2-[2-[2-[[(4S)-4-carboxy-4-(17-carboxyheptadecanoy-lamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:19)

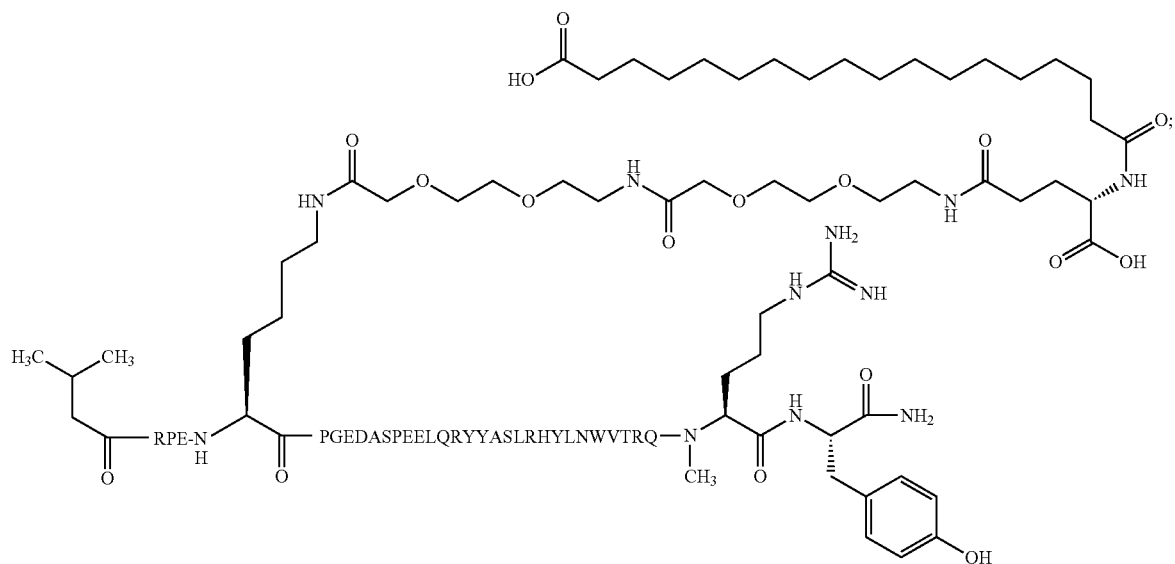
4-N{alpha}-(3-Methylbutanoyl)-7-N{Epsilon}-[2-[2-[2-[[2-[2-[2-[[(4S)-4-carboxy-4-(14-sulfotetradecanoylamino)butanoyl]amino]ethoxy]ethoxy]acetyl]]amino]ethoxy]-ethoxy]acetyl]-[Arg4, Lys7, Gln18, Trp30, NMeArg35] hPYY(4-36) (SEQ ID NO:20)
4-N{alpha}-(3-Methylbutanoyl)-7-N{Epsilon}-[2-[2-[2-[[2-[2-[2-[[(4S)-4-carboxy-4-(16-carboxy-hexadecanoylamino)butanoyl]amino]ethoxy]ethoxy]acetyl]]amino]ethoxy]-ethoxy]acetyl]-[Arg4, Lys7, Gln18, Trp30, NMeArg35]hPYY(4-36) (SEQ ID NO:21)

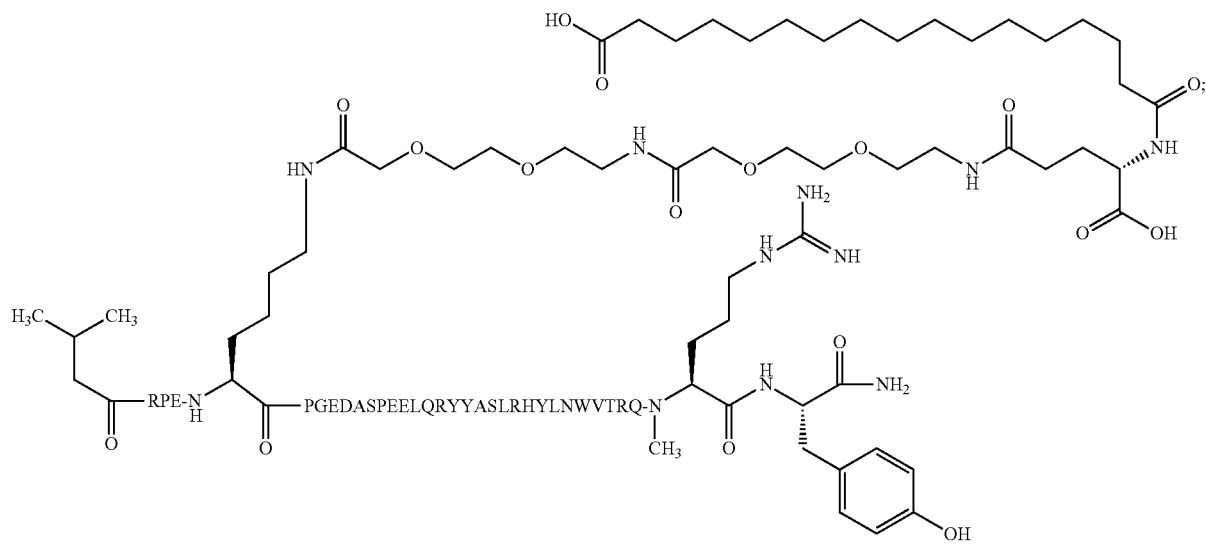
4-N{alpha}-(3-Methylbutanoyl)-7-N{Epsilon}-[2-[2-[2-[[2-[2-[2-[[(4S)-4-carboxy-4-(14-carboxy-tetracanoy-lamino)butanoyl]amino]ethoxy]ethoxy]acetyl]]amino]ethoxy]-ethoxy]acetyl]-[Arg4, Lys7, Gln18, Trp30, NMeArg35]hPYY(4-36) (SEQ ID NO:22)
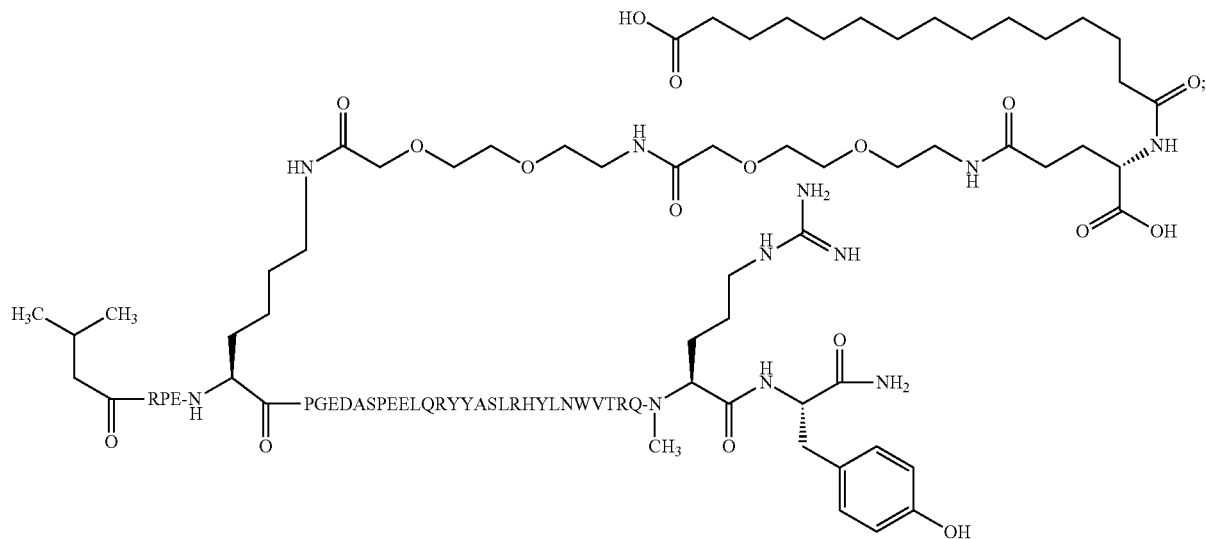
4-N{alpha}-(3-Methylbutanoyl)-7-N{Epsilon}-[2-[2-[2-[[2-[2-[2-[[(4S)-4-carboxy-4-(16-sulfohexadecanoy-lamino)-butanoyl]amino]ethoxy]ethoxy]acetyl]amino]ethoxy]-ethoxy]acetyl]-[Arg4, Lys7, Gln18, Ile28, Trp30, NMeArg35]hPYY(4-36) (SEQ ID NO:23)

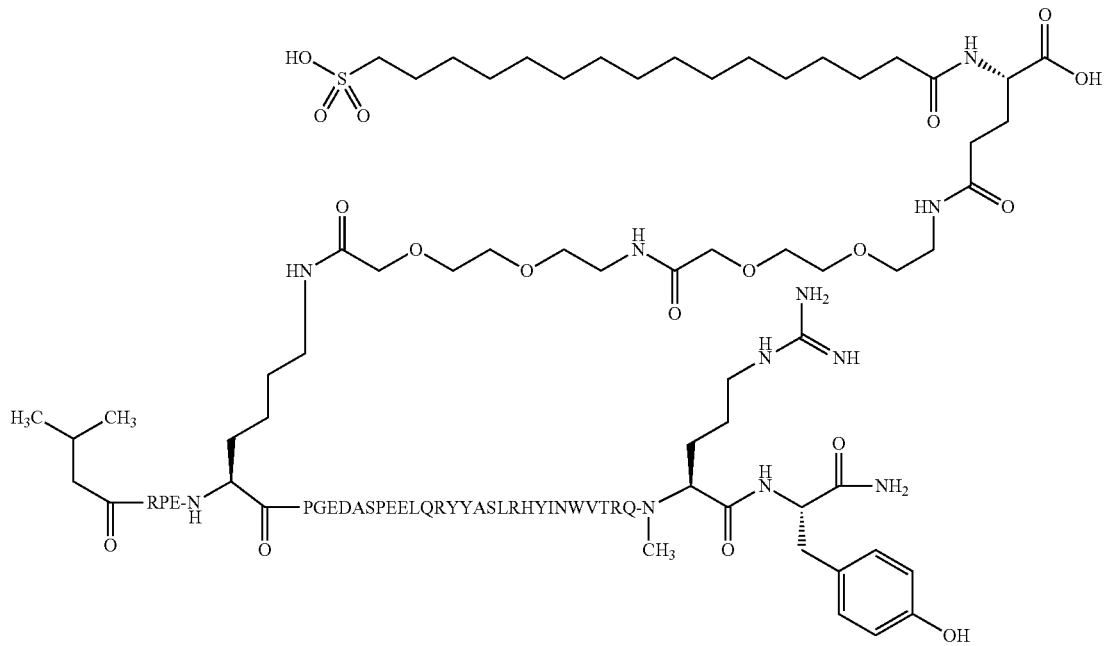

4-N{alpha}-(3-Methylbutanoyl)-7-N{Epsilon}-[2-[2-[2-[[2-[2-[2-[[2-[2-[2-[[(4S)-4-carboxy-4-(16-sulfohexadecanoylamino)butanoyl]amino]ethoxy]ethoxy]acetyl]amino]ethoxy]ethoxy]acetyl]amino]ethoxy]ethoxy]acetyl]-[Arg4, Lys7, Gln18, Trp30, NMeArg35]hPYY(4-36) (SEQ ID NO:24)

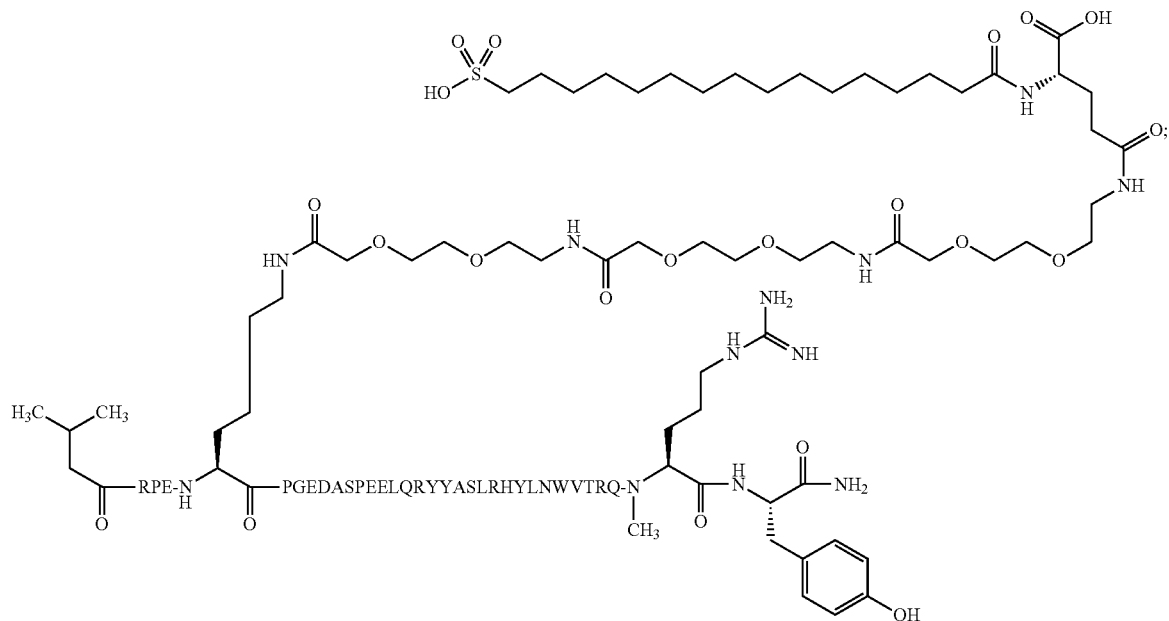

4-N{alpha}-(3-Methylbutanoyl)-7-N{Epsilon}-[2-[2-[2-[[2-[2-[2-[[2-[2-[2-[[(4S)-4-carboxy-4-(16-sulfo-hexadecanoylamino)butanoyl]amino]ethoxy]-ethoxy]acetyl]amino]ethoxy]ethoxy]acetyl]amino]ethoxy]ethoxy]acetyl]-[Arg4, Lys7, Gln18, Trp30, NMeArg35]hPYY(4-36) (SEQ ID NO:25)

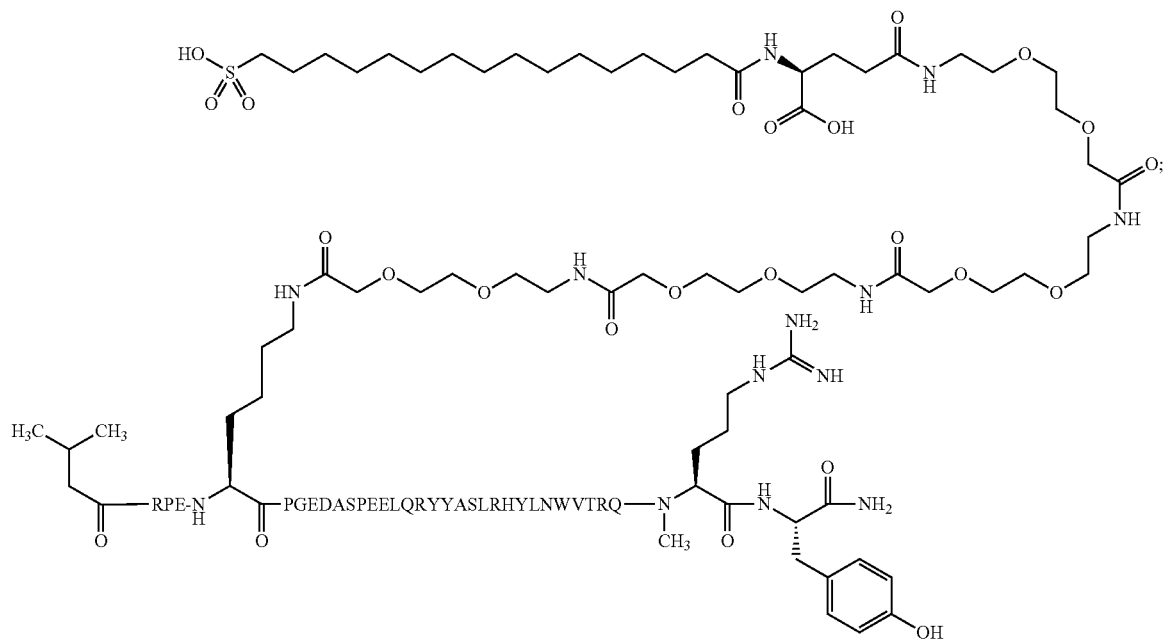

4-N{alpha}-(3-Methylbutanoyl)-7-N{Epsilon}-[2-[2-[2-[[2-[2-[2-[[2-[2-[2-[[2-[2-[2-[[(4S)-4-carboxy-4-(16-sulfohexadecanoylamino)butanoyl]amino]-ethoxy]ethoxy]acetyl]amino]ethoxy]ethoxy]acetyl]amino]ethoxy]ethoxy]acetyl]amino]-ethoxy]ethoxy]acetyl]amino]ethoxy]ethoxy]acetyl]-[Arg4, Lys7, Gln18, Trp30, NMeArg35] hPYY(4-36) (SEQ ID NO:26)

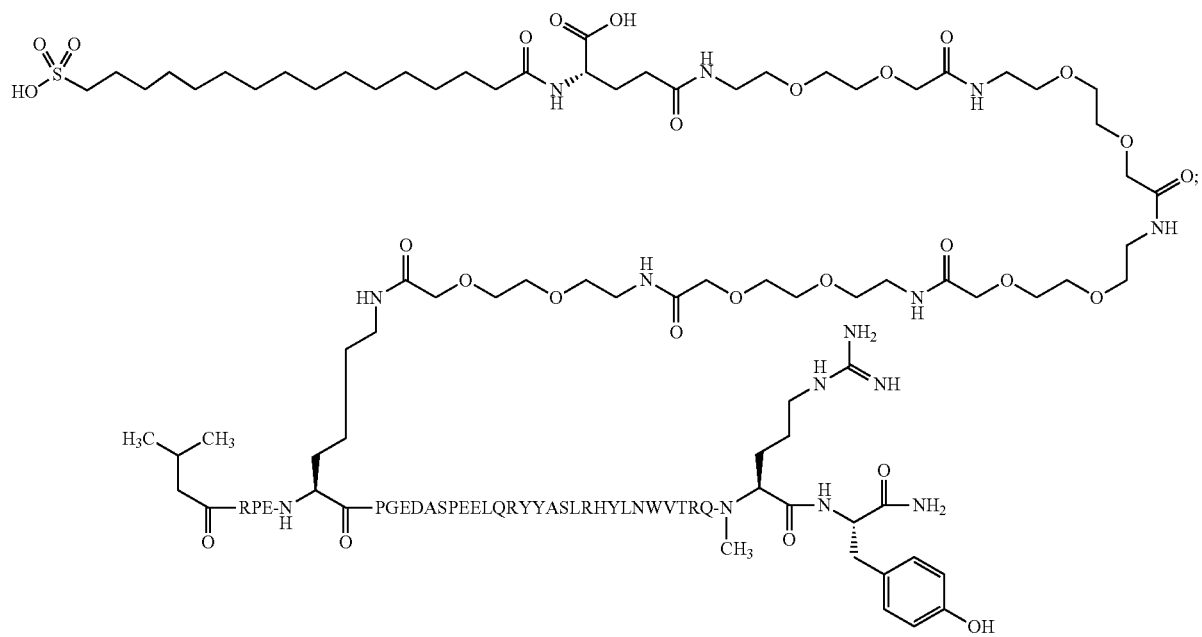

4-N{alpha}-(3-Methylbutanoyl)-7-N{Epsilon}-[4-[3-[2-[2-[3-[[(4S)-4-carboxy-4-(16-sulfohexadecanoylamino)butanoyl]amino]propoxy]ethoxy]ethoxy]propylamino]-4-oxobutanoyl]-[Arg4, Lys7, Gln18, Trp30, NMeArg35]hPYY(4-36) (SEQ ID NO:27)

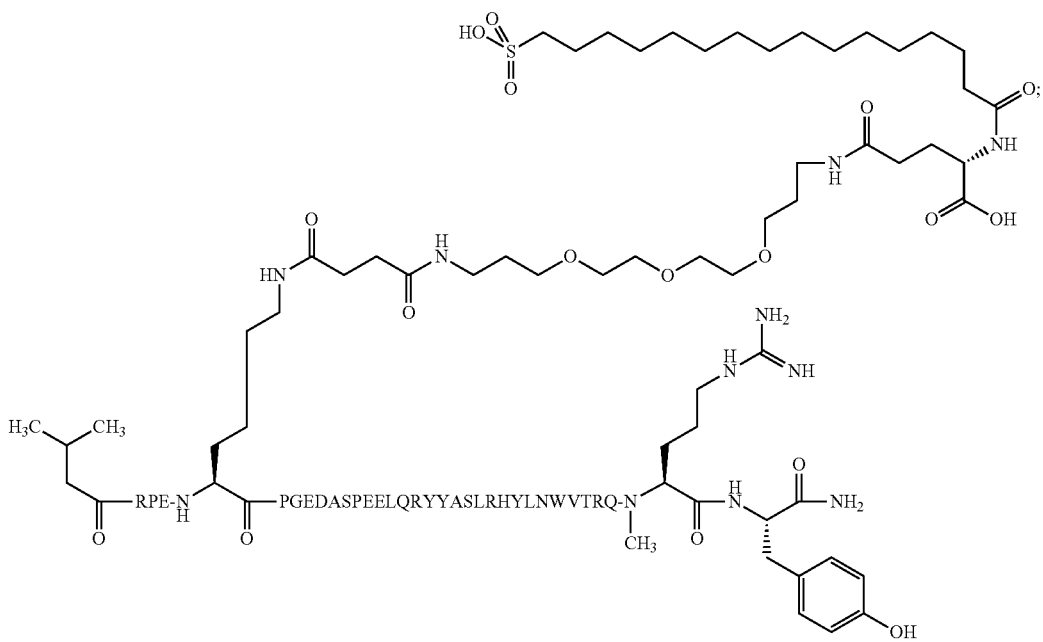

4-N{alpha}-(3-Methylbutanoyl)-7-N{Epsilon}-[4-[3-[2-[2-[3-[[4-[3-[2-[2-[3-[[(4S)-4-carboxy-4-(16-sulfohexadecanoylamino)butanoyl]amino]propoxy]ethoxy]-ethoxy]propylamino]-4-oxobutanoyl]amino]propoxy]ethoxy]ethoxy]propylamino]-4-oxobutanoyl]-[Arg4, Lys7, Gln18, Trp30, NMeArg35]hPYY(4-36) (SEQ ID NO:28)

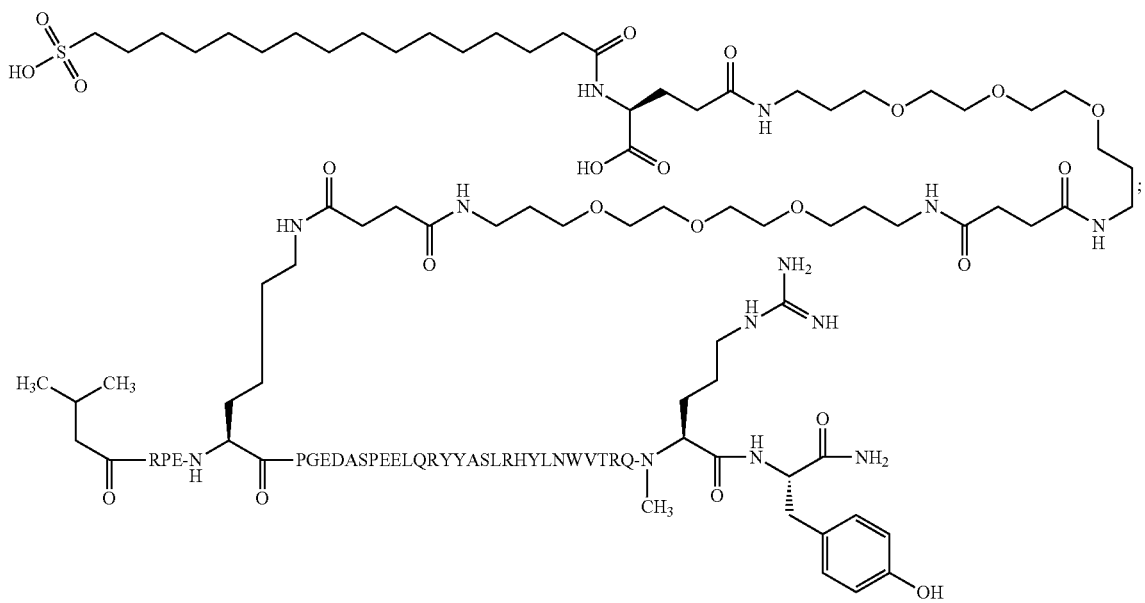

4-N{alpha}-(3-Methylbutanoyl)-7-N{Epsilon}-[4-[3-[2-[2-[3-[[4-[3-[2-[2-[3-[[4-[3-[2-[2-[3-[[(4S)-4-carboxy-4-(16-sulfohexadecanoylamino)butanoyl]amino]propoxy]-ethoxy]ethoxy]propylamino]-4-oxobutanoyl]amino]propoxy]ethoxy]-ethoxy]propylamino]-4-oxobutanoyl]amino]propoxy]ethoxy]ethoxy]propylamino]-4-oxobutanoyl]-[Arg4, Lys7, Gln18, Trp30, NMeArg35]hPYY(4-36) (SEQ ID NO:29)

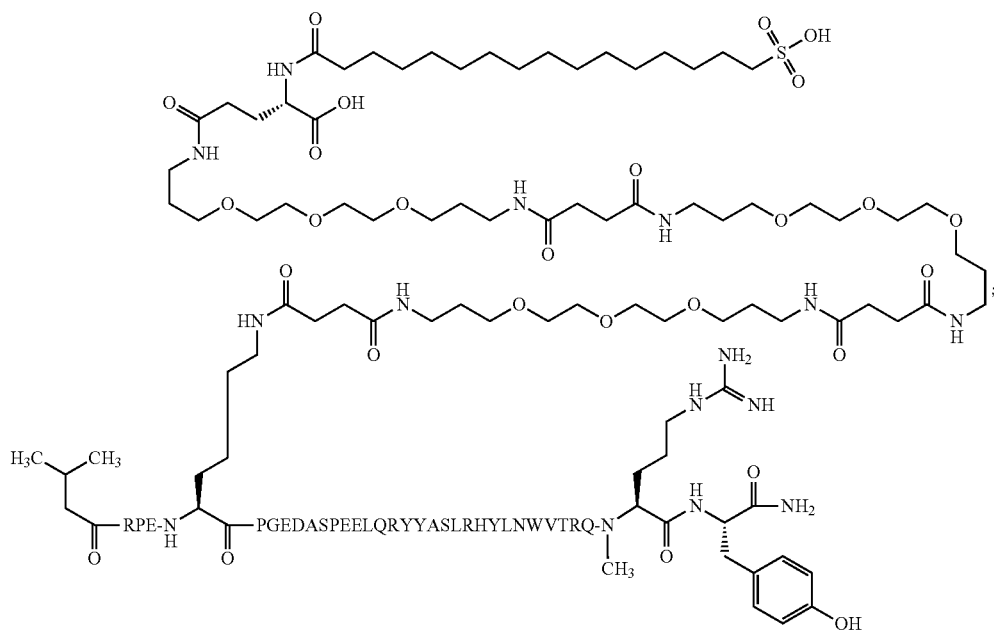
4-N{alpha}-(3-Methylbutanoyl)-7-N{Epsilon}-[(2S)-2-amino-6-[[2-[2-[2-[[(4S)-4-carboxy-4-(16-sulfohexadecanoylamino)butanoyl]amino]ethoxy]ethoxy]acetyl]-amino]hexanoyl]]-[Arg4, Lys7, Gln18, Trp30, NMeArg35] hPYY(4-36) (SEQ ID NO:30)
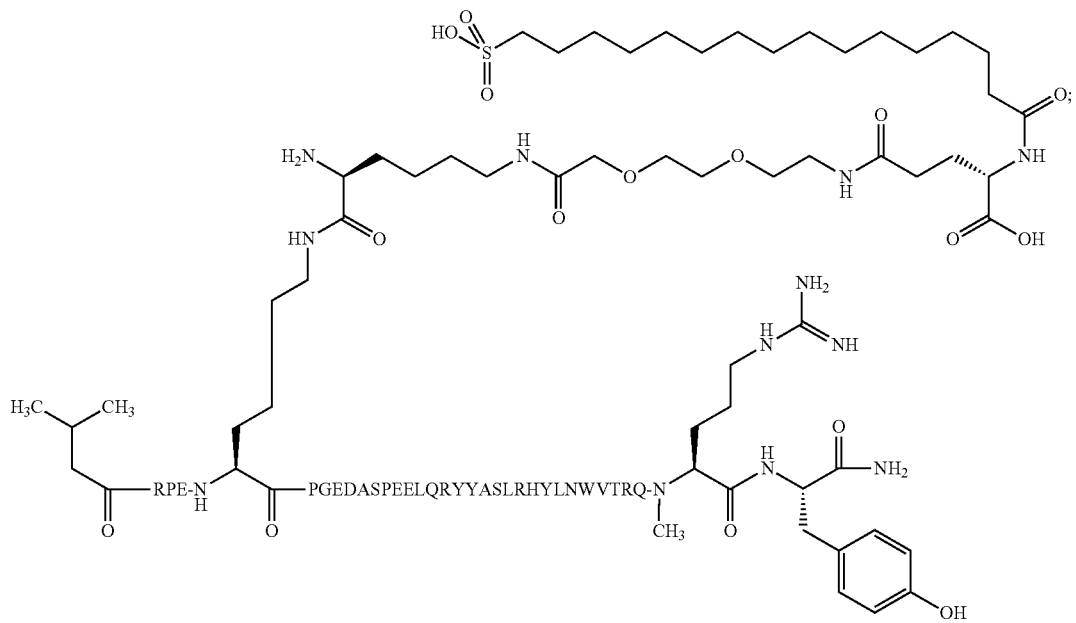
4-N{alpha}-(3-Methylbutanoyl)-7-N{Epsilon}-[2-[2-[2-[[2-[2-[2-[[(4S)-4-carboxy-4-(15-carboxypentadecanoylamino)butanoyl]amino]ethoxy]ethoxy]acetyl]amino]-ethoxy]ethoxy]acetyl]-[Arg4, Lys7, Gln18, Trp30, NMeArg35]hPYY(4-36) (SEQ ID NO:31)

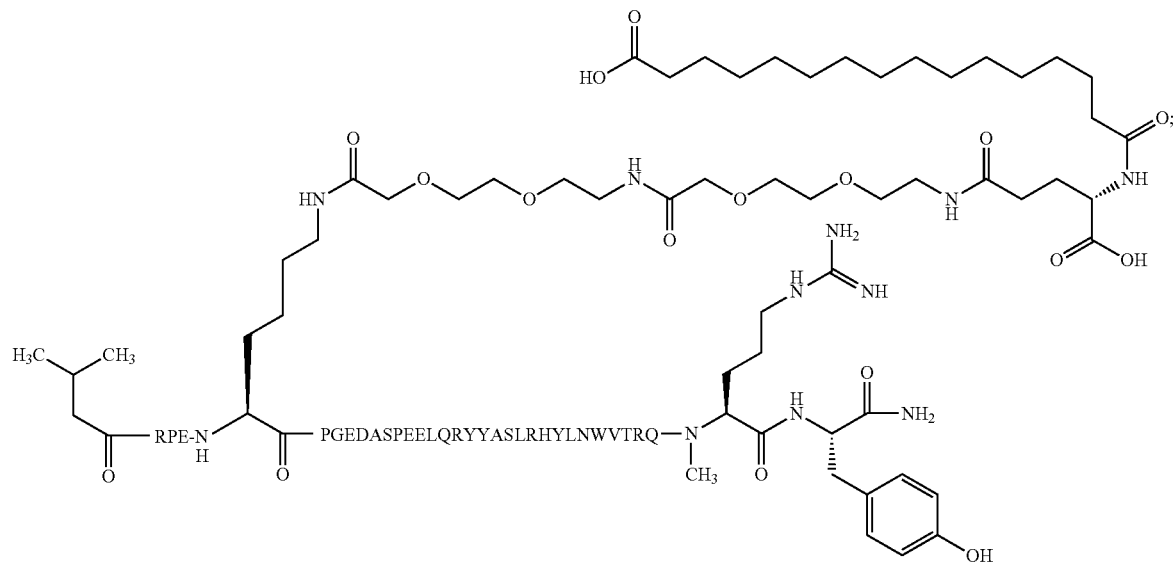
7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Val3, Arg4, Lys7, Gln18, Trp30, NMeArg35]hPYY(3-36) (SEQ ID NO:32)
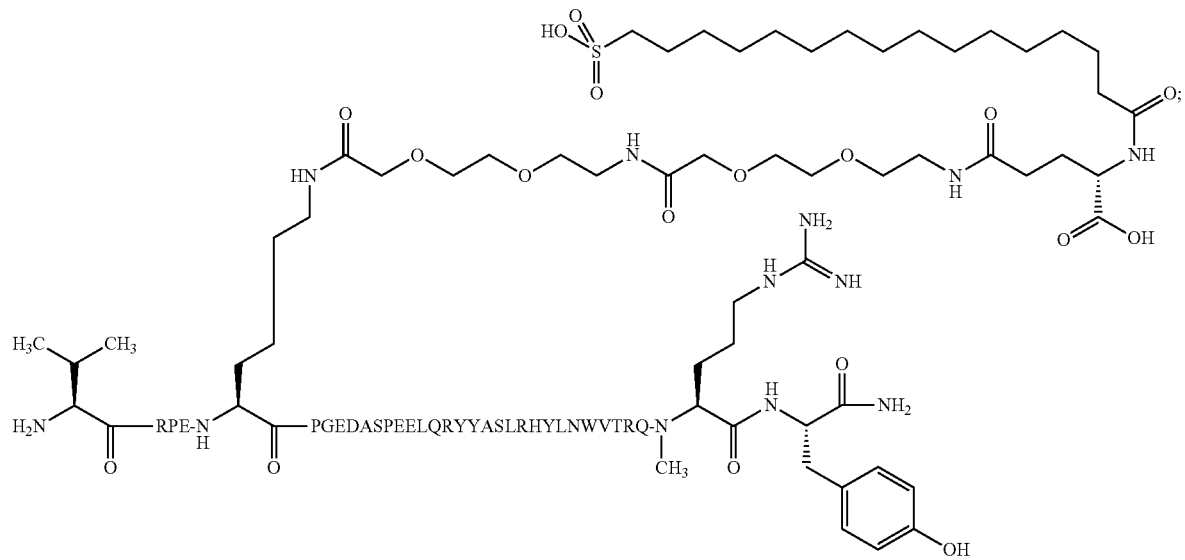
4-N{alpha}-(3-Methylbutanoyl)-7-N{Epsilon}-[2-[2-[2-[[2-[2-[2-[[(4S)-4-carboxy-4-(16-sulfohexadecanoy-lamino)-butanoyl]amino]ethoxy]ethoxy]acetyl]amino]ethoxy]-ethoxy]acetyl]-[Arg4, Lys7, D-Asp11, Gln18, Trp30, NMeArg35]hPYY(4-36) (SEQ ID NO:33)

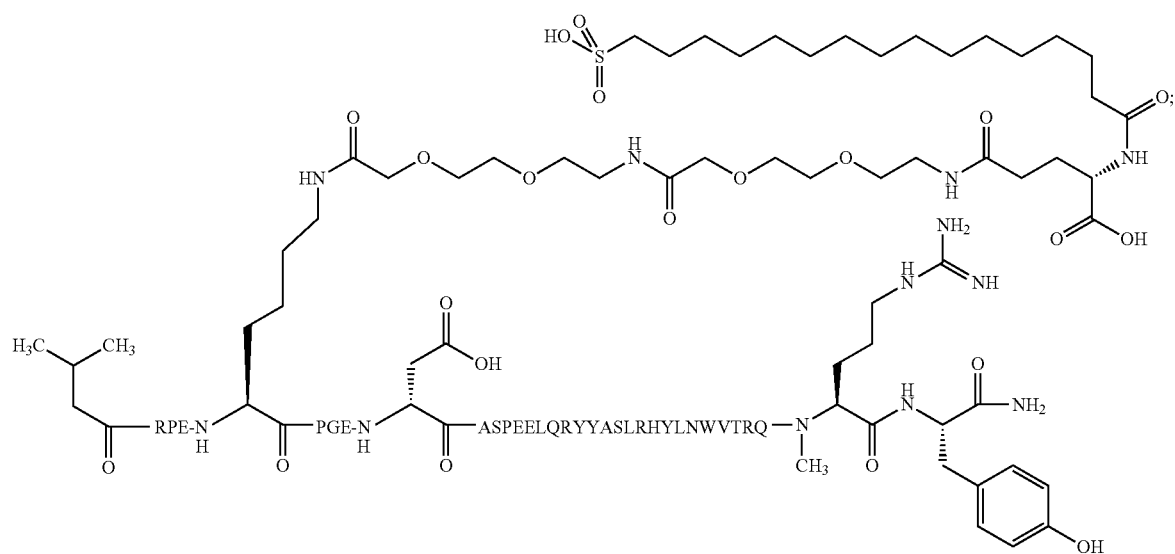
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, isoAsp11, Gln18, Trp30, NMeArg35]hPYY(4-36) (SEQ ID NO:34)
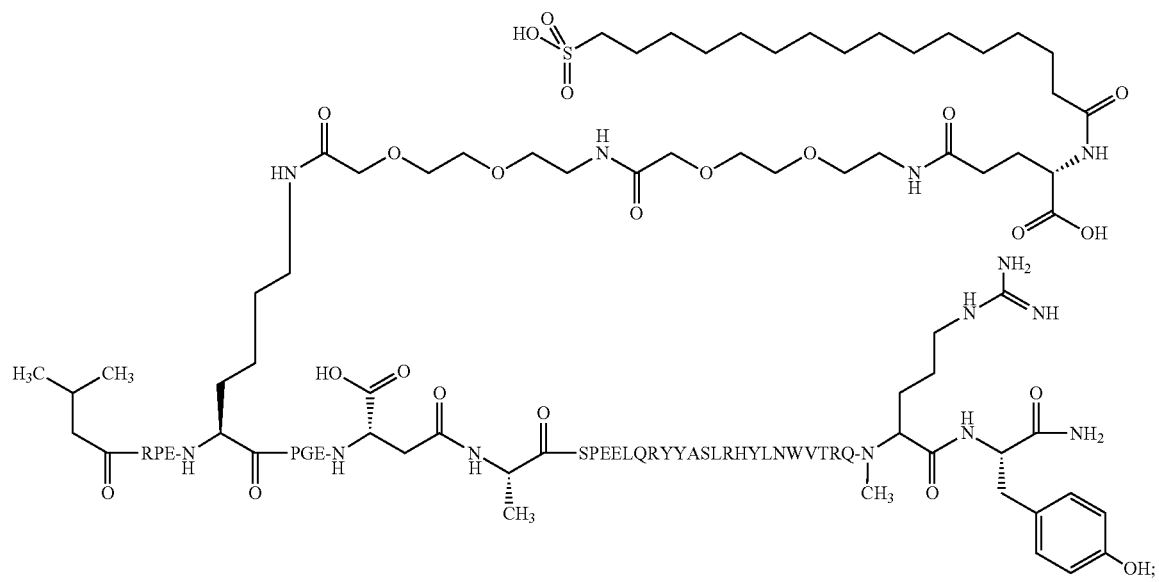
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, D-isoAsp11, Gln18, Trp30, NMeArg35]hPYY(4-36) (SEQ ID NO:35)

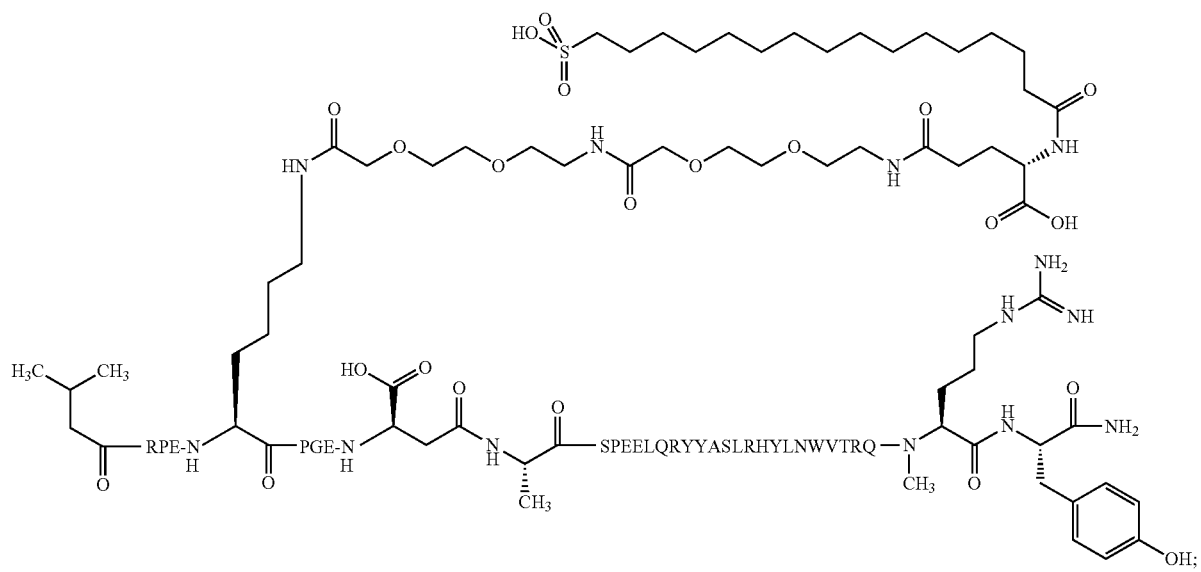
4-N{alpha}-(3-Methylbutanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]ethoxy]-ethoxy]acetyl]-[Arg4, Lys7, Gln18, Trp30]hPYY(4-36) (SEQ ID NO:36)
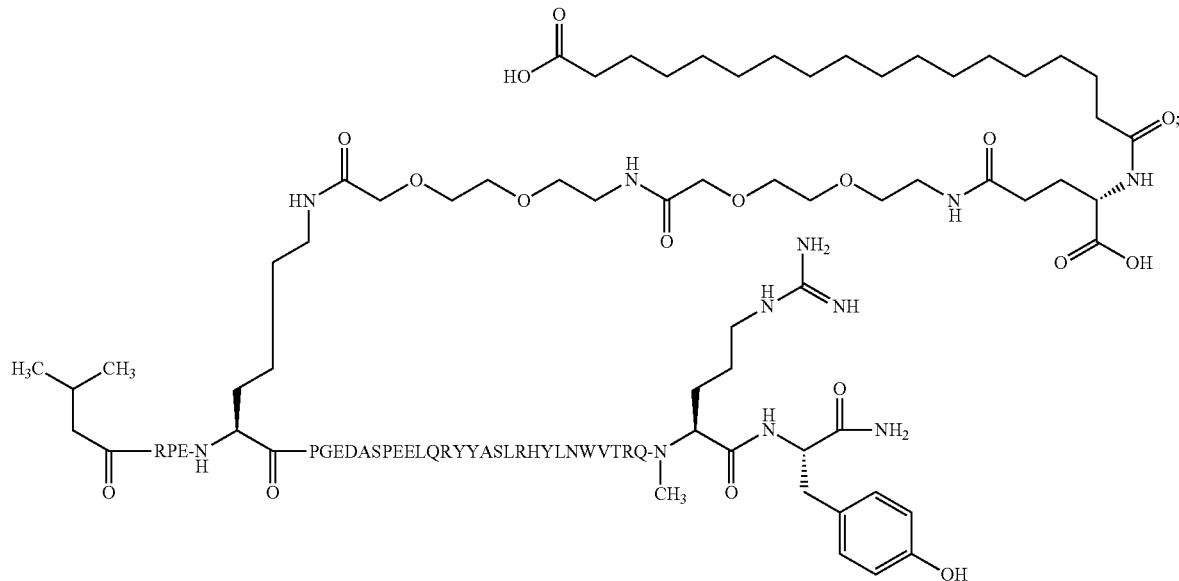
7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30]hPYY(3-36) (SEQ ID NO:37)

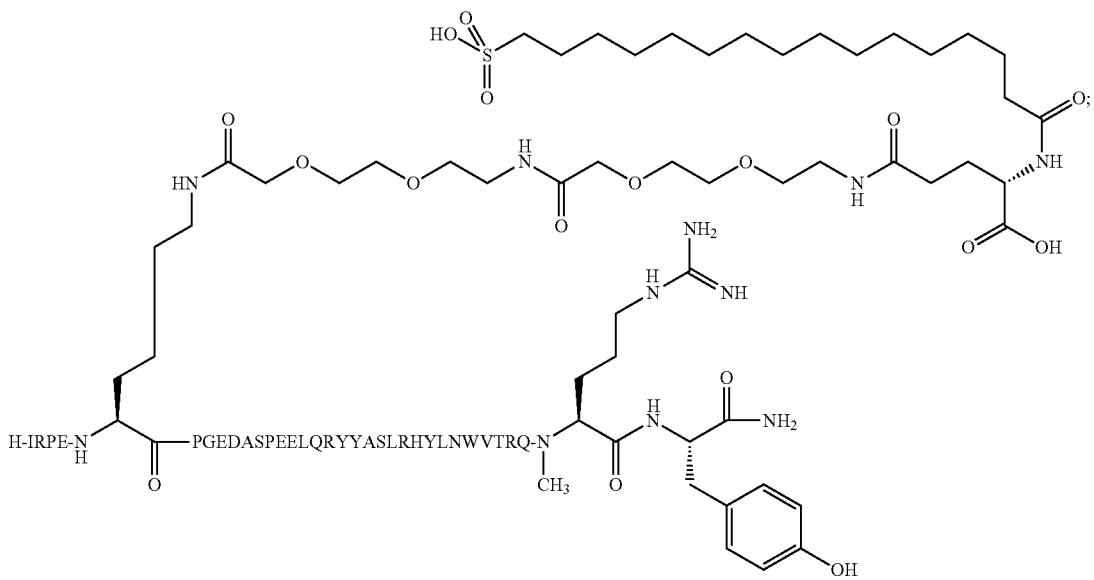

75. A PYY compound according to any one of embodiments 1-2, wherein the PYY compound is SEQ ID NO:3.
76. A PYY compound according to any one of embodiments 1-2, wherein the PYY compound is SEQ ID NO:4.
77. A PYY compound according to any one of embodiments 1-2, wherein the PYY compound is SEQ ID NO:5.
78. A PYY compound according to any one of embodiments 1-2, wherein the PYY compound is SEQ ID NO:6.
79. A PYY compound according to any one of embodiments 1-2, wherein the PYY compound is SEQ ID NO:7.
80. A PYY compound according to any one of embodiments 1-2, wherein the PYY compound is SEQ ID NO:8.
81. A PYY compound according to any one of embodiments 1-2, wherein the PYY compound is SEQ ID NO:9.
82. A PYY compound according to any one of embodiments 1-2, wherein the PYY compound is SEQ ID NO:10.
83. A PYY compound according to any one of embodiments 1-2, wherein the PYY compound is SEQ ID NO:11.
84. A PYY compound according to any one of embodiments 1-2, wherein the PYY compound is SEQ ID NO:12.
85. A PYY compound according to any one of embodiments 1-2, wherein the PYY compound is SEQ ID NO:13.
86. A PYY compound according to any one of embodiments 1-2, wherein the PYY compound is SEQ ID NO:14.
87. A PYY compound according to any one of embodiments 1-2, wherein the PYY compound is SEQ ID NO:15.
88. A PYY compound according to any one of embodiments 1-2, wherein the PYY compound is SEQ ID NO:16.
89. A PYY compound according to any one of embodiments 1-2, wherein the PYY compound is SEQ ID NO:17.
90. A PYY compound according to any one of embodiments 1-2, wherein the PYY compound is SEQ ID NO:18.
91. A PYY compound according to any one of embodiments 1-2, wherein the PYY compound is SEQ ID NO:19.
92. A PYY compound according to any one of embodiments 1-2, wherein the PYY compound is SEQ ID NO:20.
93. A PYY compound according to any one of embodiments 1-2, wherein the PYY compound is SEQ ID NO:21.
94. A PYY compound according to any one of embodiments 1-2, wherein the PYY compound is SEQ ID NO:22.
95. A PYY compound according to any one of embodiments 1-2, wherein the PYY compound is SEQ ID NO:23.
96. A PYY compound according to any one of embodiments 1-2, wherein the PYY compound is SEQ ID NO:24.
97. A PYY compound according to any one of embodiments 1-2, wherein the PYY compound is SEQ ID NO:25.
98. A PYY compound according to any one of embodiments 1-2, wherein the PYY compound is SEQ ID NO:26.
99. A PYY compound according to any one of embodiments 1-2, wherein the PYY compound is SEQ ID NO:27.
100. A PYY compound according to any one of embodiments 1-2, wherein the PYY compound is SEQ ID NO:28.
101. A PYY compound according to any one of embodiments 1-2, wherein the PYY compound is SEQ ID NO:29.
102. A PYY compound according to any one of embodiments 1-2, wherein the PYY compound is SEQ ID NO:30.
103. A PYY compound according to any one of embodiments 1-2, wherein the PYY compound is SEQ ID NO:31.
104. A PYY compound according to any one of embodiments 1-2, wherein the PYY compound is SEQ ID NO:32.
105. A PYY compound according to any one of embodiments 1-2, wherein the PYY compound is SEQ ID NO:33.
106. A PYY compound according to any one of embodiments 1-2, wherein the PYY compound is SEQ ID NO:34.
107. A PYY compound according to any one of embodiments 1-2, wherein the PYY compound is SEQ ID NO:35.
108. A PYY compound according to any one of embodiments 1-2, wherein the PYY compound is SEQ ID NO:36.
109. A PYY compound according to any one of embodiments 1-2, wherein the PYY compound is SEQ ID NO:37.
110. A PYY compound according to any one of the preceding embodiments which is a human Y2 receptor agonist.
111. A PYY compound according to any one of the preceding embodiments which is a full human Y2 receptor agonist.
112. A PYY compound according to any one of the preceding embodiments which is a selective human Y2 receptor agonist.
113. A PYY compound according to any one of the preceding embodiments which is a selective full human Y2 receptor agonist.
114. A PYY compound according to any one of the preceding embodiments which is capable of activating the human Y2 receptor.
115. A PYY compound according to any one of the preceding embodiments which is capable of activating the human Y2 receptor in an assay with whole cells expressing the human Y2 receptor.

116. A PYY compound according to any one of the preceding embodiments which is capable of activating the human Y2 receptor in the Actone functional potency assay of example 39.

117. A PYY compound according to any one of the preceding embodiments which is capable of binding to the human Y2 receptor.

118. A PYY compound according to any one of the preceding embodiments which is capable of binding to the human Y2 receptor, wherein the binding to the human Y2 receptor is measured in a competitive binding assay, such as the assay of example 40.

119. A PYY compound according to any one of the preceding embodiments which has improved pharmacokinetic properties.

120. A PYY compound according to any one of the preceding embodiments which has an increased half-life and/or a decreased clearance.

121. A PYY compound according to any one of the preceding embodiments which has the effect in vivo of decreasing the blood glucose determined in a single-dose study in a db/db mouse model.

122. A PYY compound according to any one of the preceding embodiments which has the effect in vivo of decreasing food intake determined in a single-dose study in a db/db mouse model.

123. A pharmaceutical composition comprising a PYY compound according to any one of embodiments 1-122, and at least one pharmaceutically acceptable excipient.

124. A PYY compound according to any one of embodiments 1-122, for use as a medicament.

125. A PYY compound according to any one of embodiments 1-122, for use in the treatment and/or prevention of all forms of diabetes and related diseases, such as eating disorders, diabetic complications, cardiovascular diseases and/or sleep apnoea; and/or for improving lipid parameters, improving β-cell function, and/or for delaying or preventing diabetic disease progression.

126. A PYY compound according to any one of embodiments 1-122, for use in the treatment and/or prevention of diabetes.

127. A PYY compound according to any one of embodiments 1-122, for use in the treatment and/or prevention of type 2 diabetes.

128. Use of a PYY compound according to any one of embodiments 1-122, for the manufacture of a medicament for the treatment and/or prevention of all forms of diabetes and related diseases, such as eating disorders, diabetic complications, cardiovascular diseases and/or sleep apnoea; and/or for improving lipid parameters, improving β-cell function, and/or for delaying or preventing diabetic disease progression.

129. Use of a PYY compound according to any one of embodiments 1-122, for the manufacture of a medicament for the treatment and/or prevention of diabetes.

130. Use of a PYY compound according to any one of embodiments 1-122, for the manufacture of a medicament for the treatment and/or prevention of type 2 diabetes.

131. A method of treatment and/or prevention of all forms of diabetes and related diseases, such as eating disorders, diabetic complications, cardiovascular diseases and/or sleep apnoea; and/or for improving lipid parameters, improving β-cell function, and/or for delaying or preventing diabetic disease progression by administering a pharmaceutically active amount of a PYY compound according to any one of embodiments 1-122.

132. A method of treatment and/or prevention of diabetes by administering a pharmaceutically active amount of a PYY compound according to any one of embodiments 1-122.

133. A method of treatment and/or prevention of type 2 diabetes by administering a pharmaceutically active amount of a PYY compound according to any one of embodiments 1-122.

134. A PYY compound according to any one of embodiments 1-122, for use in the treatment and/or prevention of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence.

135. A PYY compound according to any one of embodiments 1-122, for use in the treatment and/or prevention of obesity.

136. Use of a PYY compound according to any one of embodiments 1-122, in the manufacture of a medicament for the treatment and/or prevention of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence.

137. Use of a PYY compound according to any one of embodiments 1-122, in the manufacture of a medicament for the treatment and/or prevention of obesity.

138. A method of treatment and/or prevention of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence by administering a pharmaceutically active amount of a PYY compound according to any one of embodiments 1-122.

139. A method of treatment and/or prevention of obesity, by administering a pharmaceutically active amount of a PYY compound according to any one of embodiments 1-122.

140. A pharmaceutical composition comprising a PYY compound according to any one of embodiments 1-122, a GLP-1 agonist, and at least one pharmaceutically acceptable excipient.

141. A pharmaceutical composition according to embodiment 140, wherein the GLP-1 agonist is liraglutide.

142. A pharmaceutical composition according to embodiment 140, wherein the GLP-1 agonist is semaglutide.

143. A pharmaceutical composition according to any one of embodiments 140-142, wherein the PYY compound is SEQ ID NO.18.

144. A pharmaceutical composition according to any one of embodiments 140-143 for use as a medicament.

145. A pharmaceutical composition according to any one of embodiments 140-143, for use in the treatment and/or prevention of all forms of diabetes and related diseases, such as eating disorders, diabetic complications, cardiovascular diseases and/or sleep apnoea; and/or for improving lipid parameters, improving β-cell function, and/or for delaying or preventing diabetic disease progression and/or eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence.

146. A pharmaceutical composition according to any one of embodiments 140-143, for use in the treatment and/or prevention of diabetes.

147. A pharmaceutical composition according to any one of embodiments 140-143, for use in the treatment and/or prevention of type 2 diabetes.

148. A pharmaceutical composition according to any one of embodiments 140-143, for use in the treatment and/or prevention of obesity.

149. Use of a pharmaceutical composition according to any one of embodiments 140-143, for the manufacture of a medicament for the treatment and/or prevention diabetes and/or obesity.

150. A method of treatment and/or prevention of all forms of diabetes and related diseases, such as eating disorders, diabetic complications, cardiovascular diseases and/or sleep apnoea; and/or for improving lipid parameters, improving β-cell function, and/or for delaying or preventing diabetic disease progression by administering a pharmaceutically active amount of the pharmaceutical composition according to any one of embodiments 140-143.

151. A method of treatment and/or prevention of eating disorders, such as obesity, e.g. by decreasing food intake, reducing body weight, suppressing appetite, inducing satiety; treating or preventing binge eating disorder, bulimia nervosa, and/or obesity induced by administration of an antipsychotic or a steroid; reduction of gastric motility; delaying gastric emptying; increasing physical mobility; and/or prevention and/or treatment of comorbidities to obesity, such as osteoarthritis and/or urine incontinence by administering a pharmaceutically active amount the pharmaceutical composition according to any one of embodiments 140-143.

EXAMPLES

This experimental part starts with a list of abbreviations, and is followed by a section including general methods for synthesising and characterising compounds of the invention. Then follows a number of examples which relate to the preparation of specific PYY compounds, and at the end a number of examples have been included relating to the activity and properties of these compounds (section headed pharmacological methods).

The examples serve to illustrate the invention.

LIST OF ABBREVIATIONS

ACN: acetonitrile
Aib: α-aminoisobutanoic acid
Boc: tert butyloxycarbonyl
$CH_3CN$: acetonitrile
cpm: counts per minute
DCM: dichloromethane
DIC: Diisopropylcarbodiimide
DIPEA: diisopropylethylamine
DMF: N,N-dimethylformamide
Et2O: diethyl ether
Fmoc: 9H-fluoren-9-ylmethoxycarbonyl
HFIP: Hexafluoroisopropanol
HMWP: High molecular weight proteins
h: hours
$H_2O$: water
HOAc: acetic acid
HOAt: 1-Hydroxy-7-azabenzotriazole
HOBt: 1-Hydroxybenzotriazole
Min: minutes
Mtt: 4-methyltrityl
MW: Molecular weight
NMeArg: N(alpha)-methyl-L-arginine
NMF: 1-Methyl-formamide
NMP: 1-Methyl-pyrrolidin-2-one
OtBu: tert butyl ester
Pbf: 2,2,4,6,7-pentamethyldihydrobenzofuran-5-sulfonyl
PyBOP: benzotriazol-1-yl-oxytripyrrolidinophosphonium hexafluorophosphate
rpm: rounds per minute
r.t: Room temperature
tBu: tert butyl
TFA: trifluoroacetic acid
TIPS: triisopropylsilane
Trt: triphenylmethyl
Materials and Methods
General Methods of Preparation This section relates to methods for solid phase synthesis of peptide backbone and synthesis of side chain attached to backbone (SPPS methods, including methods for the coupling of amino acids, the de-protection of Fmoc-amino acids, methods for cleaving the peptide from the resin, and for its purification).

1. Synthesis of Resin Bound Protected Peptide Backbone

Procedure for the Automatic Step-Wise Assembly of Peptide Backbone.

The protected peptidyl resin was synthesized according to the Fmoc strategy on a solid phase peptide synthesiser Prelude (Protein Technologies, Tucson, USA) either 0.25 mmol scale or 0.4 mmol scale using the manufacturer supplied machine protocols. The Fmoc-protected amino acid derivatives used were the standard recommended: Fmoc-Ala-OH, Fmoc-Arg(Pbf)-OH, Fmoc-Asn(Trt)-OH, Fmoc-Asp(OtBu)-OH, Fmoc-Cys(Trt)-OH, Fmoc-Gln(Trt)-OH, Fmoc-Glu(OtBu)-OH, Fmoc-Gly-OH, Fmoc-His(Trt)-OH, Fmoc-Ile-OH, Fmoc-Leu-OH, Fmoc-Lys(Boc)-OH, Fmoc-Lys(Mtt)-OH, Fmoc-Met-OH, Fmoc-Phe-OH, Fmoc-Pro-OH, Fmoc-Ser(tBu)-OH, Fmoc-Thr(tBu)-OH, Fmoc-Trp(Boc)-OH, Fmoc-Tyr(tBu)-OH, or, Fmoc-Val-OH etc. supplied from e.g., Bachem, Iris Biotech, Protein Technologies or Novabiochem. If nothing else is specified the natural L-form of the amino acids are used. Coupling was done by the use of DIC (dicyclohexylcarbodiimide) and Ozyma Pure (ethyl 2-cyano-2-(hydroxyimino)-acetate, Merck, Novabiochem, Switzerland) mediated couplings in NMP (N-methyl pyrrolidone). The coupling of the Fmoc-amino acid was done as described above using 4-8 time excess of amino acid relative to resin substitution (4-8 eq). Coupling time ranged from 1 hour up to 4 hours. The Fmoc-Arg(pbf)-OH was coupled using a double coupling procedure (1 hour+1 hour). The resin used for the synthesis of the peptide amides can be Tentagel RAM (Rapp Polymere, Germany), Rink amid ChemMatrix resin (Matrix Innovation, Canada) Rink-Amide resin (Merck/Novabiochem). The protected amino acid derivatives used were standard Fmoc-amino acids (supplied from e.g. Protein Technologies, or Novabiochem. The epsilon amino group of lysine to be derivatised was protected with Mtt. The N-terminal amino acid or building was coupled as a Boc-protected amino acid, e.g., Boc-Ile. Alternatively isovaleric acid was coupled according to the above described coupling procedure for the Fmoc-amino acids. The step-wise solid phase assembly on the Prelude was done using the following steps: 1) deprotection (removal of Fmoc) by the use of 25% piperidine in NMP for 2×4 min., step 2) Wash (removal of piperidine)

with NMP and DCM, step 3) Coupling of Fmoc-amino acid (0.3M Fmoc-amino acid in 0.3M Oxyma Pure in NMP) 4-8 eq excess for 1-4 hours coupling initiated by adding 1/10 volume of 3M DIC in NMP and 1/10 volume collidine in NMP. Mixing was done by occasional bubbling with nitrogen, step 4) Wash (removal of excess amino acid and reagents by the use of NMP and DCM). Last step included washing with DCM which made the resin ready for attachment of albumin binding moiety on lysine side chain.

2. Attachment of Modifying Groups to Resin Bound Protected Peptide Backbone

Procedure for Manual Removal of Mtt-Protection (Lysine (Mtt)):

Before synthesis of the modifying group, the Mtt group on the site of attachment (lysine) must be removed. The resin was placed in a syringe or reaction flask and treated with 75% hexafluroisopropanol (HFIP)+25% DCM for 2×30 minutes to remove the Mtt group. The resin was then washed with DCM and NMP as described above and neutralized with 5% DIPEA (neutralisation step) in NMP or 25% piperidine in NMP followed by NMP washing before coupling the albumin moiety. Alternatively, the neutralisation step was omitted.

Procedure for Prelude Removal of Mtt-Protection (Lysine (Mtt)):

On the Prelude the resin was treated with 75% hexafluoroisopropanol (HFIP)+25% DCM for 2×2 minutes followed 2×30 minutes to remove the Mtt group on the lysine. The resin was then washed with DCM and NMP followed by a neutralisation step using 25% piperidine in NMP by 4 minutes, and was then ready for the synthesis of the modifying group.

Procedure for Manual Synthesis of Modifying Groups onto a Lysine Residue:

The building blocks Fmoc-8-amino-3,6-dioxaoctanoic acid (CAS No. 166108-71-0), Fmoc-TTDS-OH (CAS No. 172089-14-4, IRIS Biotech GmbH), Fmoc-L-Glu-OtBu (84793-07-7), and eicosanedioic acid mono-tert-butyl ester (CAS No. 843666-40-0) were coupled using DIC and Oxyma Pure in 4-8 eq relative to resin substitution. The coupling time was 2-16 hours usually followed by a capping step using 1 M acetic anhydride for 15-60 min. The Fmoc-group was removed by 25% piperidine in NMP for 10-30 min. followed by washing. The 16-sulfonic hexadecanoic acid was solubilised in NMP or N-methylformamid (NMF) at 60 degree Celsius or above and activated by PyBOP 1 eq relative to the sulfonic hexadecanoic acid and 2 eq of diisopropylethylamine (DIPEA) relative to sulfonic hexadecanoic acid was also added. The peptidyl resin was washed with hot NMP or NMF just prior to the addition of activated sulfonic hexadecanoic acid. An excess of 3-4 of the sulfonic building block was used and coupling allowed to proceed >16 hours.

Procedure for Automated Synthesis of Modifying Groups onto a Lysine Residue:

For the synthesis of the modifying groups the following building blocks were used: Fmoc-8-amino-3,6-dioxaoctanoic acid, Fmoc-TTDS-OH, Fmoc-Glu-OtBu, and eicosanedioic acid mono-tert-butyl ester (CAS No. 843666-40-0). Modifying groups were coupled using DIC and Oxyma Pure in 4-8 eq relative to resin substitution. The coupling time was 2-16 hours usually followed by a capping step using 1 M acetic anhydride for 20 min. The Fmoc-group was removed by 25% piperidine in NMP for 2×4 min. followed by washing as described in the SPPS of the peptide backbone. All other synthesis steps were also the same as described above with the backbone synthesis. The coupling of 16-sulfonic hexadecanoic acid was done by the manual procedure as described above using pyBOP as coupling reagent.

3. Cleavage of Resin Bound Peptide with or without Attached Modifying Groups and Purification Prior to TFA deprotection the peptidyl resin was washed with DCM or diethyl ether and dried. The peptide and side chain protection groups were removed by addition of 20-40 ml (0.25 mmol scale) 30-60 (0.4 mmol scale) ml 92% TFA, 5% TIPS and 3% $H_2O$ for 2-4 hours. Then TFA was filtered and in some cases concentrated by a stream of argon and diethyl ether was added to precipitate the peptide. The peptide was washed three-five times with diethyl ether and dried.

General Methods of Detection and Characterisation

This section relates to methods for detection and characterisation of the resulting peptides, including LCMS, MALDI and UPLC methods.

1. LC-MS method (LCMS1)

Agilent Technologies LC/MSD TOF (G1969A) mass spectrometer was used to identify the molecular weight of the peptide after elution from an Agilent 1200 series HPLC system. The de-convolution of the mass data was calculated using the Agilents software.

Eluents:
Buffer A: 0.1% TFA in water
Buffer B: 0.1% TFA in $CH_3CN$
LC-MS Waters Acquity (LCMS2)
LC-system: Waters Acquity UPLC
Column: Waters Acquity UPLC BEH, C-18, 1.7 μm, 2.1 mm×50 mm
Detector: Waters (Micromass) LCT Premier XE
Linear gradient: 5% to 95% B
Gradient run-time: 4.0 minutes
Total run-time: 7.0 minutes
Flow rate: 0.4 ml/minutes
Column temperature: 40° C.
Solvent A: 99.90% MQ-water, 0.1% formic acid
Solvent B: 99.90% acetonitrile, 0.1% formic acid 2. UPLC Methods Method UPLC2
Buffer A: 0.05% TFA
Buffer B: CH3CN+0.05% TFA
Flow: 0.4 ml/min
Gradient: 5-95% B, (16 min),
Column: Acquity UPLC BEH C18, 1.7 um, 2.1×150 mm column
Column temp: 40° C.
Method UPLC26v01
Buffer A: 0.05% TFA
Buffer B: CH3CN+0.05% TFA
Flow: 0.45 ml/min
Gradient: 5-60% Buffer B (0.5-4 min.)
Column: Acquity UPLC BEH C18 1.7 um, 2.1×50 mm
Column temperature: 40° C.
Method UPLC29v01
Buffer A: 0.05% TFA
Buffer B CH3CN+0.05% TFA
Flow: 0.45 ml/min
Gradient: 15-35% Buffer B (0.5-4 min.)
Column: Acquity UPLC BEH C18 1.7 um, 2.1×50 mm
Column temperature: 40° C.
Method UPLC30v01
Buffer A: 0.05% TFA
Buffer B: CH3CN+0.05% TFA
Flow: 0.45 ml/min
Gradient: 20-40% Buffer B (0.5-4 min.)
Column: Acquity UPLC BEH C18 1.7 um, 2.1×50 mm
Column temperature: 40° C.
Method UPLC31v01
Buffer A: 0.05% TFA Buffer B: CH3CN+0.05% TFA
Flow: 0.45 ml/min
Gradient: 25-45% Buffer B (0.5-4 min.)
Column: Acquity UPLC BEH C18 1.7 um, 2.1×50 mm
Column temperature: 40° C.
Method UPLC02v01
System: Waters Acquity UPLC system
Buffer A: 0.05% TFA in $H_2O$
Buffer B: CH3CN+0.05% TFA
Flow: 0.40 ml/min
Gradient: 5-95% Buffer B (16 min.)
Column: Acquity UPLC BEH C18 1.7 um, 2.1×150 mm
Column temperature: 40° C.
Method UPLC07v01
System: Waters Acquity UPLC system
Buffer A: 0.09 M di-Ammonium Hydrogen Phosphate (aq) and 10% Acetonitrile, pH 3.6
Buffer B: 20% Isopropanole, 20% Water and 60% Acetonitrile
Flow: 0.50 ml/min
Gradient: 35-65% Buffer B (2-17 min.)
Column: Phenomenex Kinetex C18, 1.7 um, 2.1 mm×150 mm column
Column temperature: 60° C.
Method UPLC16v01
System: Waters Acquity UPLC system
Buffer A: 0.2 M Sodium Sulfate, 0.02 M di-Sodium Hydrogen Phosphate, 0.02 M Sodium di-Hydrogen Phosphate, 90% Water and 10% Acetonitrile, pH 7.2
Buffer B: 70% Acetonitrile, 30% Water
Flow: 0.40 ml/min
Gradient: 20-50% Buffer B (3-20 min.)
Column: ACQUITY UPLC BEH Shield RP18, 1.7 um, 2.1 mm×150 mm column
Column temperature: 60° C.
Method UPLC60
System: Waters Acquity UPLC system
Buffer A: 0.02 M Sodium Sulfate, 0.02 M di-Sodium Hydrogen Phosphate, 0.02 M Sodium di-Hydrogen Phosphate, 90% Water and 10% Acetonitrile, pH 7.2
Buffer B: 70% Acetonitrile, 30% Water
Flow: 0.40 ml/min
Gradient: 20-50% Buffer B (3-20 min.)
Column: ACQUITY UPLC BEH Shield RP18, 1.7 um, 2.1 mm×150 mm column
Column temperature: 60° C.
Method UPLC17
System: Waters Acquity UPLC system
Buffer A: 0.2 M Sodium Sulfate, 0.02 M di-Sodium Hydrogen Phosphate, 0.02 M Sodium di-Hydrogen Phosphate, 90% Water and 10% Acetonitrile, pH 7.2
Buffer B: 70% Acetonitrile, 30% Water
Flow: 0.40 ml/min
Step gradient: 10-20% B over 3 minutes, then 20-80% B over 17 minutes, then 80-90% B over 1 minute
Column: ACQUITY UPLC BEH Shield RP18, 1.7 um, 2.1 mm×150 mm column
Column temperature: 60° C.
Method UPLC61
System: Waters Acquity UPLC system
Buffer A: 0.02 M Sodium Sulfate, 0.02 M di-Sodium Hydrogen Phosphate, 0.02 M Sodium di-Hydrogen Phosphate, 90% Water and 10% Acetonitrile, pH 7.2
Buffer B: 70% Acetonitrile, 30% Water
Flow: 0.40 ml/min
Gradient: 10-20% buffer B (0-3 min) 20-80% Buffer B (3-20 min.)
Column: ACQUITY UPLC BEH Shield RP18, 1.7 um, 2.1 mm×150 mm column
Column temperature: 60° C.
Method UPLC- ΔP-01
Buffer A: 0.1% TFA in $H_2O$
Buffer B: CH3CN+0.1% TFA
Flow: 0.40 ml/min
Gradient: 5-95% Buffer B (16 min.)
Column; Acquity UPLC BEH130; 150× 2.1; 1.7 um
Column temperature: 40° C.
Method UPLC-AP-02
Buffer A: 20 mM Na2HPO4, 20 mM NaH2PO4, 200 mM Na2SO4 in 90% water/10% acetonitrile, pH 7.20
Buffer B: 70% acetonitrile/30% water
Flow: 0.40 ml/min
Gradient: 10-20% Buffer B (0-3 min.); 20-50% buffer B (3-20 min); 50-80% (20-21 min)
Column; Acquity UPLC BEH Shield, RP18 1.7 um, 2.1×150 mm
Column temperature: 40° C.
3. MALDI-MS Method Molecular weights of the peptides were determined using matrix-assisted laser desorption time of flight mass spectroscopy (MALDI-MS), recorded on a Microflex (Bruker). A matrix of alpha-cyano-4-hydroxy cinnamic acid was used. The molecular weight of the product was calculated based on the result of MALDI-MS analysis using the software supplied from the manufacturer.

Synthesis of Intermediates

Synthesis of 16-sulfo-hexadecanoic acid

16-Hexadecanolide (997 g, 3.92 mol) was dissolved in methanol (15.1 L) and toluene-4-sulfonic acid monohydrate (90.0 g, 0.473 mol) was added. Reaction mixture was heated in 50 L reactor at 55° C. for 16 hours. After cooling down sodium hydrogen carbonate (56.0 g, 0.67 mol) was added and the reaction mixture was stirred for 15 min. Solvent was evaporated on Heidolph 20 L rotary evaporator. Ethyl acetate (12 L) was added and the mixture was extracted with 5% solution of sodium hydrogen carbonate (10 L). Organic layer was separated; emulsion layer was extracted with ethyl acetate (3×3 L), white insoluble muddy material was separated and ethyl acetate layer was washed again with 5% solution of sodium hydrogen carbonate (5 L). Organic layers were combined and washed with saturated solution of sodium hydrogen carbonate (5 L) and brine (10 L). Solvent was evaporated on Heidolph 20 L rotary evaporator. Crude product was crystallized from hexanes (8 L). Hot solution in hexanes was decanted and then let to crystallize in ice bath. The material was filtered on large frit and washed with cold hexanes (2 L). Pure material was dried in vacuo.

Yield: 1062.2 g (95%). $R_F$ ($SiO_2$, dichloromethane/methanol 95:5): 0.65.

$^1$H NMR spectrum (300 MHz, $CDCl_3$, $\delta_H$): 3.67 (s, 3H); 3.67-3.60 (m, 2H); 2.30 (t, J=7.5 Hz, 2H); 1.67-1.53 (m, 4H); 1.25 (s, 22H).

The above ester (957 g, 3.34 mol) was dissolved in dichloromethane (7 L) on Heidolph 20 L rotary evaporator. Triethylamine (695 mL, 4.98 mol) was added, reaction mixture was cooled to 0° C. (by putting ice into evaporator bath) and methanesulfonyl chloride (325 mL, 4.19 mol) in dichloromethane (200 mL) was added slowly during 10 minutes by external tubing using small vacuum. Then the reaction mixture was heated to 35° C. for 1 hour. NMR analysis showed complete conversion. Water was added (690 mL) and solvents were evaporated. Ethyl acetate (8 L) was added and the mixture was washed with 1 M hydrochloric acid (4 L) and 5% solution of sodium carbonate (4 L). Since sodium carbonate extraction formed an emulsion this layer was extracted with ethyl acetate (4 L) and added to main portion. Combined ethyl acetate layer was washed with brine (4 L), dried over anhydrous sodium sulfate and filtered. Solvent was evaporated giving 16-methanesulfonyloxy-hexadecanoic acid methyl ester as white solid.

Yield: 1225.4 g (100%).

$^1$H NMR spectrum (300 MHz, CDCl$_3$, $\delta_H$): 4.22 (t, J=6.6 Hz, 2H); 3.66 (s, 3H); 3.00 (s, 3H); 2.30 (t, J=7.5 Hz, 2H) 1.82-1.67 (m, 2H); 1.68-1.54 (m, 2H); 1.36-1.17 (m, 22H).

The above mesylate (1.23 kg, 3.34 mol) was dissolved in acetone (8 L) and lithium bromide (585 g, 6.73 mol) was added and the reaction mixture was heated on Heidolph 20 L rotary evaporator at 50° C. for 12 hours. After cooling down solvent was evaporated, ethyl acetate (10 L) was added and the mixture was washed with 5% solution of sodium hydrogencarbonate (3×15 L) and brine (8 L). Solvent was evaporated to dryness to yield 16-bromo-hexadecanoic acid methyl ester as pale yellow oil which started to crystallize.

Yield: 1219 g (105%); contains acetone and product of acetone aldolization.

$R_F$ (SiO$_2$, hexanes/ethyl acetate 9:1): 0.90.

$^1$H NMR spectrum (300 MHz, CDCl$_3$, $\delta_H$): 3.65 (s, 3H); 3.42 (t, J=6.9 Hz, 2H); 2.32 (t, J=7.5 Hz, 2H); 1.92-1.77 (m, 2H) 1.69-1.53 (m, 2H); 1.50-1.35 (m, 2H); 1.25 (bs, 10H).

Solutions of sodium sulfite (327 g, 2.60 mol) in water (1.26 L) and 16-bromo-hexadecanoic acid methyl ester (728 g, 2.00 mol, 96% purity) in 1-propanol (945 mL) and methanol (420 mL) were heated to reflux in 6 L reactor equipped with mechanical stirrer for 48 hours. The reaction mixture was cooled to 27° C. and diluted with tetrahydrofuran (2 L). Reaction mixture was filtered and solid material was washed with tetrahydrofuran (3×700 mL). Filtrate was cooled to 0° C. and another portion of material was precipitated. This precipitate was filtered and washed with tetrahydrofuran (2×200 mL). Solids were combined and mixed with water (8.4 L) in 20 L pot. Solution of sodium hydroxide (120 g, 3.00 mol) was added. The mixture was heated to boiling for about 5 hours. Solution of sulfuric acid (430 mL, 8.00 mol) in water (500 mL) was slowly added into the reaction mixture (sulfur dioxide is formed). Reaction mixture was heated to boiling for 10 minutes and then let to cool to 15° C. (ice bath). The mixture was filtered on Büchner funnel through filter paper Seitz (several layers filter) applying vacuo. This procedure was very slow and took two days. Solid material was several times washed with distilled water until pH of filtrate was between 2 and 3. This procedure took about three days. Muddy white material was dried in oven at 80° C. giving desired product.

Yield: 510 g (76%).

$^1$H NMR spectrum (300 MHz, DMSO-d$_6$, $\delta_H$): 2.45-2.33 (m, 2H); 2.18 (t, J=7.3 Hz, 2H); 1.60-1.40 (m, 4H); 1.24 (s, 22H).

MS-ESI (neg, sample in H$_2$O/MeCN+NaHCO$_3$; m/z): 335.5 (M-H)$^-$, 357.5 (M-2H+Na)$^-$, 167.3 (M-2H)$^{2-}$ Synthesis of 14-sulfo-hexadecanoic acid 1 M Solution of borane-tetrahydrofuran complex in tetrahydrofuran (52 mL, 52.0 mmol) was added dropwise to a solution of tetradecanedioic acid mono-tert-butyl ester (10.0 g, 31.9 mmol) in dry tetrahydrofuran (75 mL) at 0 C under argon. The resulting solution was stirred at 0 C for 2 hrs, then the cooling bath was removed and the mixture stirred at room temperature overnight. Saturated aqueous solution of sodium hydrogencarbonate (150 mL) was added and the resulting mixture was extracted with dichloromethane (3×100 mL). Combined organic extracts were extracted with 5% aqueous solution of sodium carbonate (1×150 mL) and 10% aqueous solution citric acid (1×100 mL). Combined organic extracts were dried over anhydrous magnesium sulfate and evaporated to dryness. The residue was subjected to column chromatography (Silicagel 60A, 0.060-0.200 mm; eluent: dichloromethane/methanol 100:0-99:1) to give 14-hydroxy-tetradecanoic acid tert-butyl ester as yellowish oil.

Yield: 9.19 g (96%).

RF (SiO2, chloroform/methanol 9:1): 0.60.

1H NMR spectrum (300 MHz, CDCl3, dH): 3.60 (t, J=6.4 Hz, 2H); 2.18 (t, J=7.2 Hz, 2H); 1.61-1.48 (m, 4H); 1.42 (s, 9H); 1.24 (bs, 18H).

A solution of potassium hydroxide (8.60 g, 153 mmol) in water (100 mL) was added to a solution of the above ester (9.20 g, 30.6 mmol) in methanol (100 mL) and the resulting mixture was heated at 60 C for 2 days. The mixture was cooled to room temperature; then it was washed with hexanes (2×70 mL) and concentrated in vacuo. Concentrated hydrochloric acid (32%, 20 mL, 0.65 mol) was added dropwise and the mixture was extracted with ethyl acetate (2×150 mL). The combined organic layers were dried over anhydrous magnesium sulfate and evaporated to dryness to yield 14-hydroxytetradecanoic acid as white solid.

Yield: 7.10 g (95%).

RF (SiO2, chloroform/methanol 85:15): 0.50.

1H NMR spectrum (300 MHz, CDCl3, dH): 3.66 (t, J=6.6 Hz, 2H); 2.36 (t, J=7.4 Hz, 2H); 1.72-1.52 (m, 4H); 1.29 (bs, 18H).

p-Toluenesulfonic acid monohydrate (0.28 g, 1.45 mmol) was added to a solution of the above 14-hydroxy-tetradecanoic acid (7.10 g, 29.1 mmol) in methanol (150 mL) and the resulting solution was stirred at room temperature for 3 days. Methanol was removed under reduced pressure; the residue was dissolved in ethyl acetate (170 mL); washed with 5% aqueous solution of sodium carbonate (3×50 mL) and brine (25 mL); dried over anhydrous magnesium sulfate and evaporated in vacuo to give methyl 14-hydroxy-tetradecanoate as white solid.

Yield: 7.28 g (97%).

RF (SiO2, dichloromethane/methanol 95:5): 0.45.

1H NMR spectrum (300 MHz, CDCl3, dH): 3.61-3.71 (m, 5H); 2.32 (t, J=7.5 Hz, 2H); 1.70-1.52 (m, 4H); 1.44 (s, 1H); 1.28 (bs, 18H).

Above prepared ester (7.28 g, 28.2 mmol) was dissolved in DCM (60 mL). Triethylamine was added (5.30 mL, 52.3 mmol), reaction mixture was cooled to 0 C and mesylchloride (2.45 mL, 31.7 mmol) was added slowly during 10 minutes. After one hour the reaction mixture was allowed to warm to room temperature and has been stirred overnight. After 16 hrs water was added (1 mL) and the mixture was stirred 30 minutes. Solvents were evaporated, ethyl acetate was added (80 mL) and the mixture was extracted with 1M hydrochloric acid (2×30 mL), 5% solution of sodium carbonate (2×20 mL) and water (20 mL). After drying with anhydrous magnesium sulfate, filtration and evaporation of solvents 16-mesylhexadecanoic acid methyl ester was obtained as white solid.

Yield: 9.15 g (92%).

RF (SiO2, dichloromethane/methanol 95:5): 0.70.

1H NMR spectrum (300 MHz, CDCl3, dH): 4.24 (t, J=6.6 Hz, 2H); 3.68 (s, 3H); 3.01 (s, 3H); 2.32 (t, J=7.5 Hz, 2H) 1.83-1.70 (m, 2H); 1.70-1.56 (m, 2H); 1.47-1.20 (m, 22H).

Above prepared mesylate (9.15 g, 26.0 mmol) was dissolved in acetone (230 mL) and lithium bromide (4.50 g, 51.8 mmol) was added and the reaction mixture was refluxed overnight. After cooling down solvent was evaporated, ethyl acetate (530 mL) was added and the mixture was extracted with 5% solution of sodium hydrogencarbonate (3×230 mL). Combined organic extracts were dried over anhydrous magnesium sulfate and evaporated to dryness to yield 14-bromo-tetradecanoic acid methyl ester as orange oil.

Yield: 8.34 g (100%).

RF (SiO2, dichloromethane/methanol 95:5): 0.90.

1H NMR spectrum (300 MHz, CDCl3, dH): 3.66 (s, 3H); 3.42 (t, J=6.9 Hz, 2H); 2.32 (t, J=7.5 Hz, 2H); 1.93-1.80 (m, 2H) 1.69-1.56 (m, 2H); 1.50-1.38 (m, 2H); 1.28 (bs, 16H).

Above prepared 14-bromo-tetradecanoic acid (8.34 g, 26.0 mmol) was dissolved in n-propanol (10 mL), water (25 mL) and 1M aqueous solution of sodium hydroxide (32 mL) and sodium sulfite (5.00 g, 39.7 mmol) was added. Reaction mixture was heated to reflux for 22 hrs. After cooling down white precipitate was filtered off. Conc. hydrochloric acid was added to give acidic pH and precipitate was centrifuged and decanted two times with water (2×50 ml). After lyophilization 14-sulfo-tetradecanoic acid sodium salt was obtained as a white solid.

Yield: 7.3 g (85%).

RF (SiO2, dichloromethane/methanol 95:5): 0.60.

1H NMR spectrum (300 MHz, DMSO-d6, dH): 2.40 (m, 2H); 2.18 (t, J=7.2 Hz, 2H); 1.61-1.40 (m, 4H); 1.23 (bs, 18H).

IKPEAPGEDASPEELNRYYASLRHYLNLVTRQRY-NH2

Retention time HPLC method UPLC16v01: 3.37 minutes (91.4%)

Retention time HPLC method UPLC29v01: 10.07 minutes (85.6%)

MW calculated: 4049.6 g/mol

MALDI MS: 4048.2 g/mol

Example 3

SEQ ID NO:3
[Trp30]hPYY(3-36)

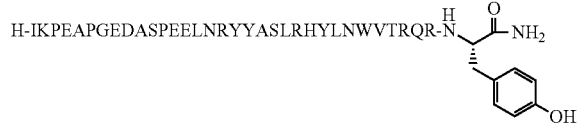

Retention time HPLC method UPLC-AP-01: (96.6%)

MW calculated: 4123.6 g/mol

LCMS1: ((M/3)+3) 1374.8; ((M/4)+4) 1031.3

Example 4

SEQ ID NO:4
[Trp30, NMeArg35]hPYY3-36

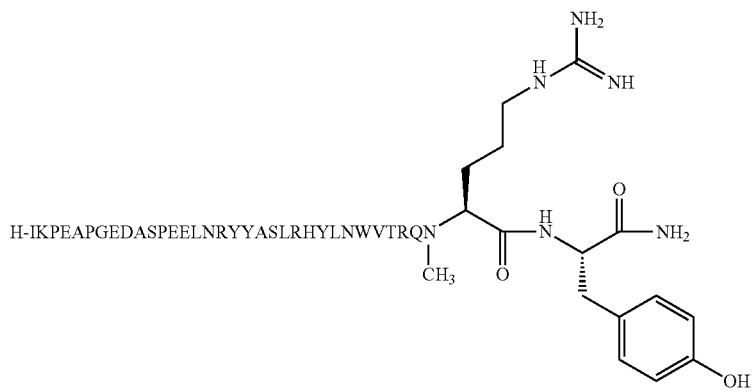

Retention time UPLC29v01: 3.43 minutes (100%)
Retention time UPLC16v01: 10.93 (90.9%)
MW calculated: 4136.6 g/mol
LCMS2: ((M/1)+1) 4136.03; ((M/2)+2) 2069.02 ((M/3)+3) 1379.68; ((M/4)+4) 1035.02

SYNTHESIS OF COMPOUNDS OF THE INVENTION

Example 1

SEQ ID NO:1
hPYY(1-36)
YPIKPEAPGEDASPEELNRYYASL-RHYLNLVTRQRY-NH2

Example 2

SEQ ID NO:2
hPYY(3-36)

Example 5

SEQ ID NO:5
7-N{Epsilon}-[2-[2-[2-[[2-[2-[2-[[(4S)-4-carboxy-4-(17-carboxyheptadecanoylamino)-butanoyl]amino]ethoxy]ethoxy]acetyl]amino]ethoxy]ethoxy]acetyl]-[Lys7, Gln18, Trp30, NMeArg35]hPYY(3-36)

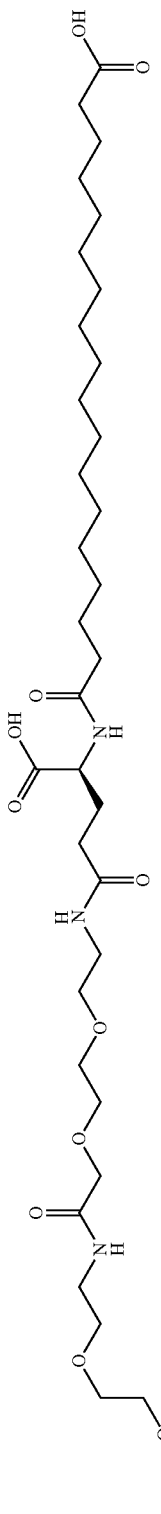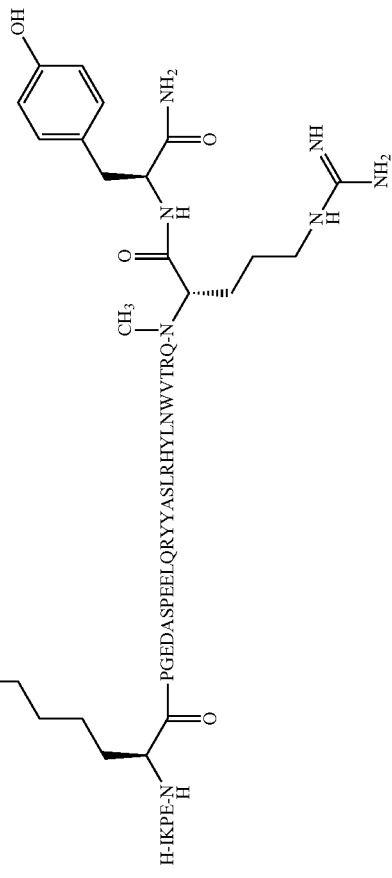

Retention time UPLC-AP-01: 7.44 minutes (95.7%)
MW calculated: 4923.6 g/mol
LCMS: ((M/3)+3) 1641.9; ((M/4)+4) 1231.5; ((M/5)+5) 985.6

Example 6

SEQ ID NO:6
7-N{Epsilon}-[2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]amino]-ethoxy]ethoxy]acetyl]amino]ethoxy]ethoxy]acetyl]amino]ethoxy]ethoxy]acetyl]amino]-ethoxy]ethoxy]acetyl]-[Lys7, Gln18, Trp30, NMeArg35]hPYY(3-36)

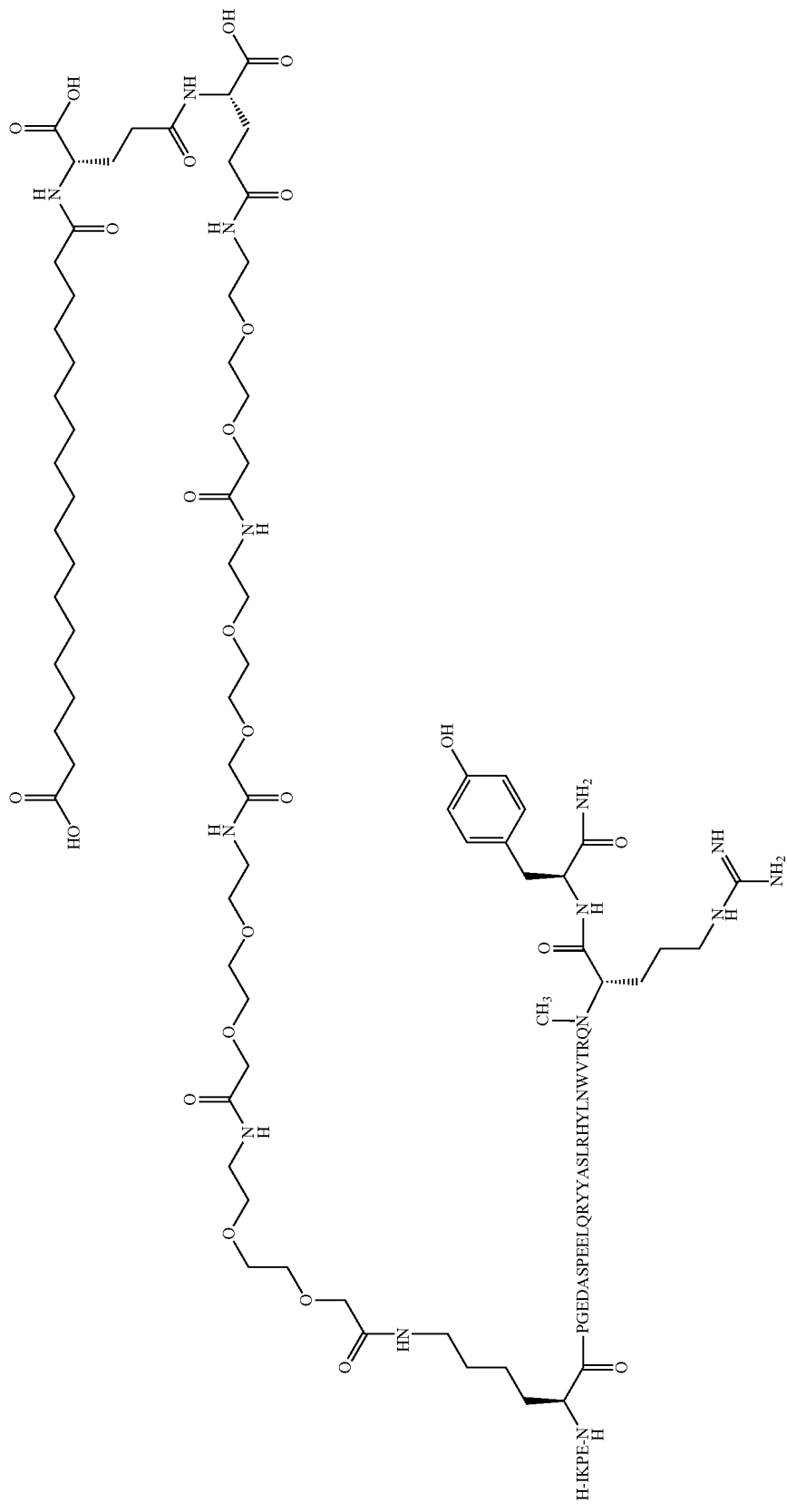

Retention time UPLC-AP-01: 7.46 minutes (93%)
MW calculated: 5343.1 g/mol
LCMS2: ((M/3+3) 1782.6; ((M/4)+4) 1336.6; ((M/5+5) 1069.6

Example 7

SEQ ID NO:7
7-N{Epsilon}-[2-[2-[2-[[2-[2-[2-[[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]amino]ethoxy]ethoxy]acetyl]amino]ethoxy]ethoxy]acetyl]-[Lys7, Gln18, Trp30, NMeArg35]hPYY(3-36)

MW calculated: 5213.97 g/mol
MALDI MS: 5215.8 g/mol

Example 8

SEQ ID NO:8
7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]ethoxy]acetyl]-[Lys7, Gln18, Trp30, NMeArg35]hPYY(3-36)

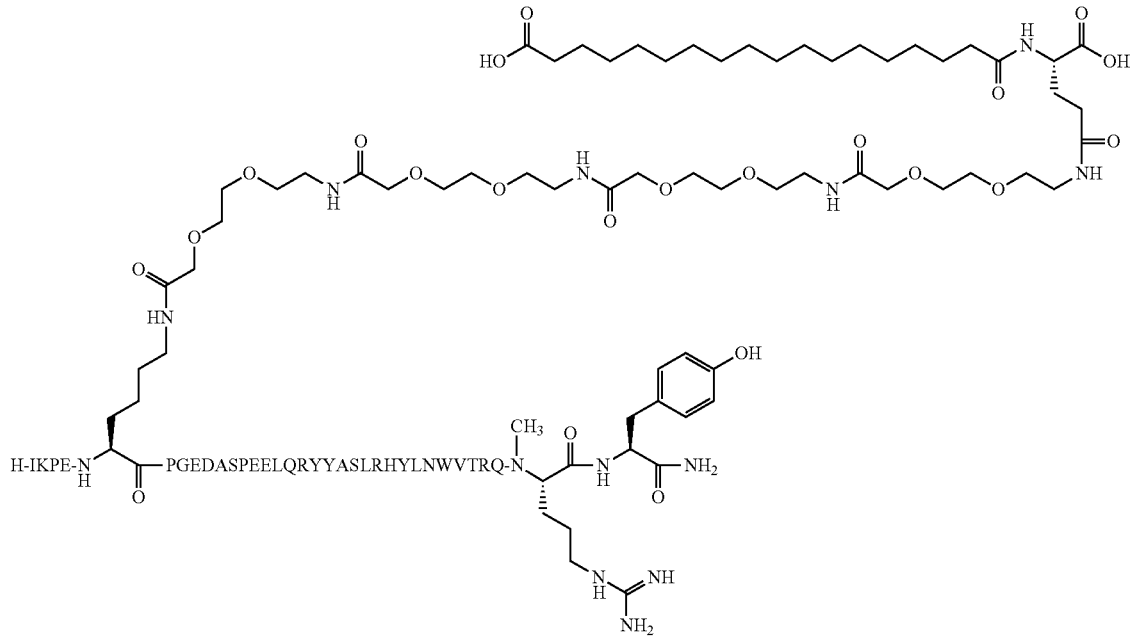

Retention time HPLC method UPLC30v01: 3.11 minutes (91.6%)

Retention time HPLC method UPLC16v01: 13.89 minutes (89.7%)

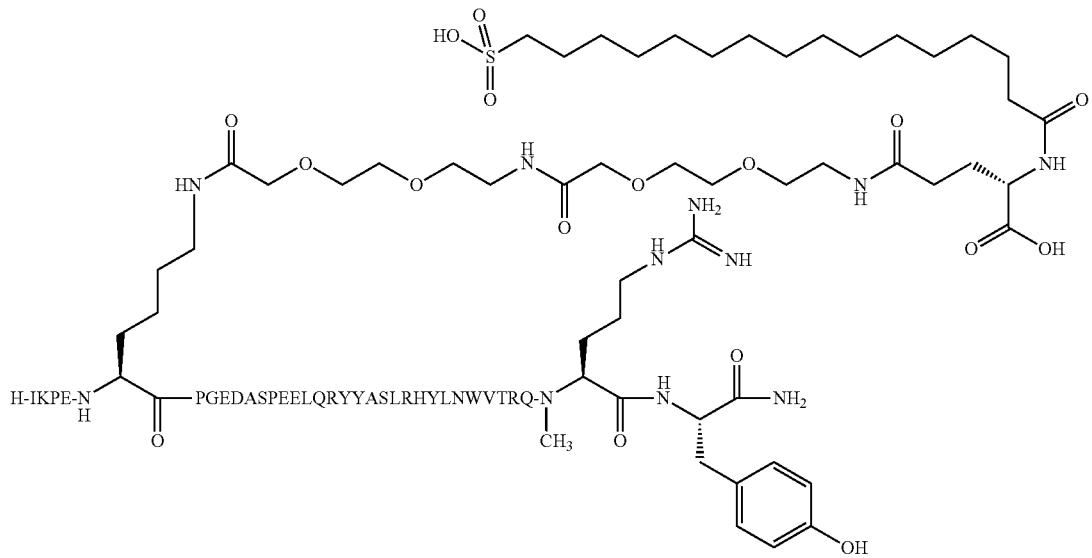

Retention time UPLC02v02: 6.63 minutes (97%)
Retention time UPLC16v01: 11.94 minutes (93.2%)
MW calculated: 4945.67 g/mol
LCMS2: ((M/4)+4) 1237.47; ((M/3)+3) 1649.61; ((M/2)+2) 2473.87

Example 9

SEQ ID NO:9
7-N{Epsilon}-[2-[2-[2-[[2-[2-[2-[[2-[2-[2-[[2-[2-[2-[4-[16-(1H-tetrazol-5-yl)-hexadecanoylsulfamoyl]butanoylamino]ethoxy]ethoxy]acetyl]amino]ethoxy]-ethoxy]acetyl]amino]ethoxy]ethoxy]acetyl]amino]ethoxy]ethoxy]acetyl]-[Lys7, Gln18, Trp30, NMeArg35]hPYY(3-36)

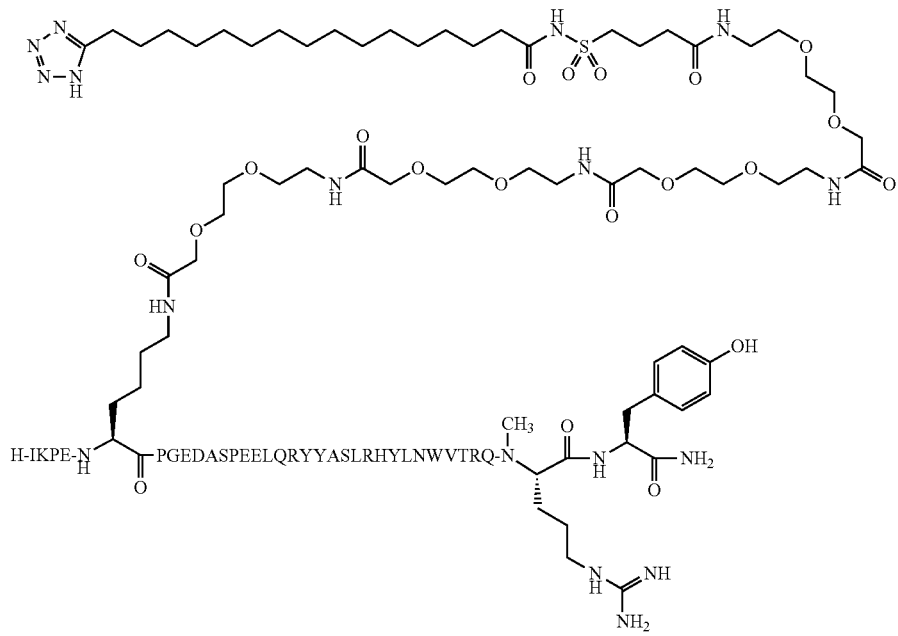

Retention time HPLC method UPLC30v01: 3.78 minutes (100%)

Retention time HPLC method UPLC16v01: 12.41 minutes (96.4%)

MW calculated: 5244.0 g/mol

LCMS (LCMS1): m/z 1748.9 ((M/3)+3); 1311.9 ((M/4)+4); 875 ((M/6)+6)

Example 10

SEQ ID NO:10
7-N{Epsilon}-[2-[2-[2-[[2-[2-[2-[[2-[2-[2-[[2-[2-[2-[[(4S)-4-carboxy-4-[[(4S)-4-carboxy-4-(17-carboxyheptadecanoylamino)butanoyl]amino]butanoyl]-amino]ethoxy]ethoxy]acetyl]amino]ethoxy]ethoxy]acetyl]amino]ethoxy]-ethoxy]acetyl]amino]ethoxy]ethoxy]acetyl]-[Lys7, Gln18, Aib28, Trp30, NMeArg35]hPYY(3-36)

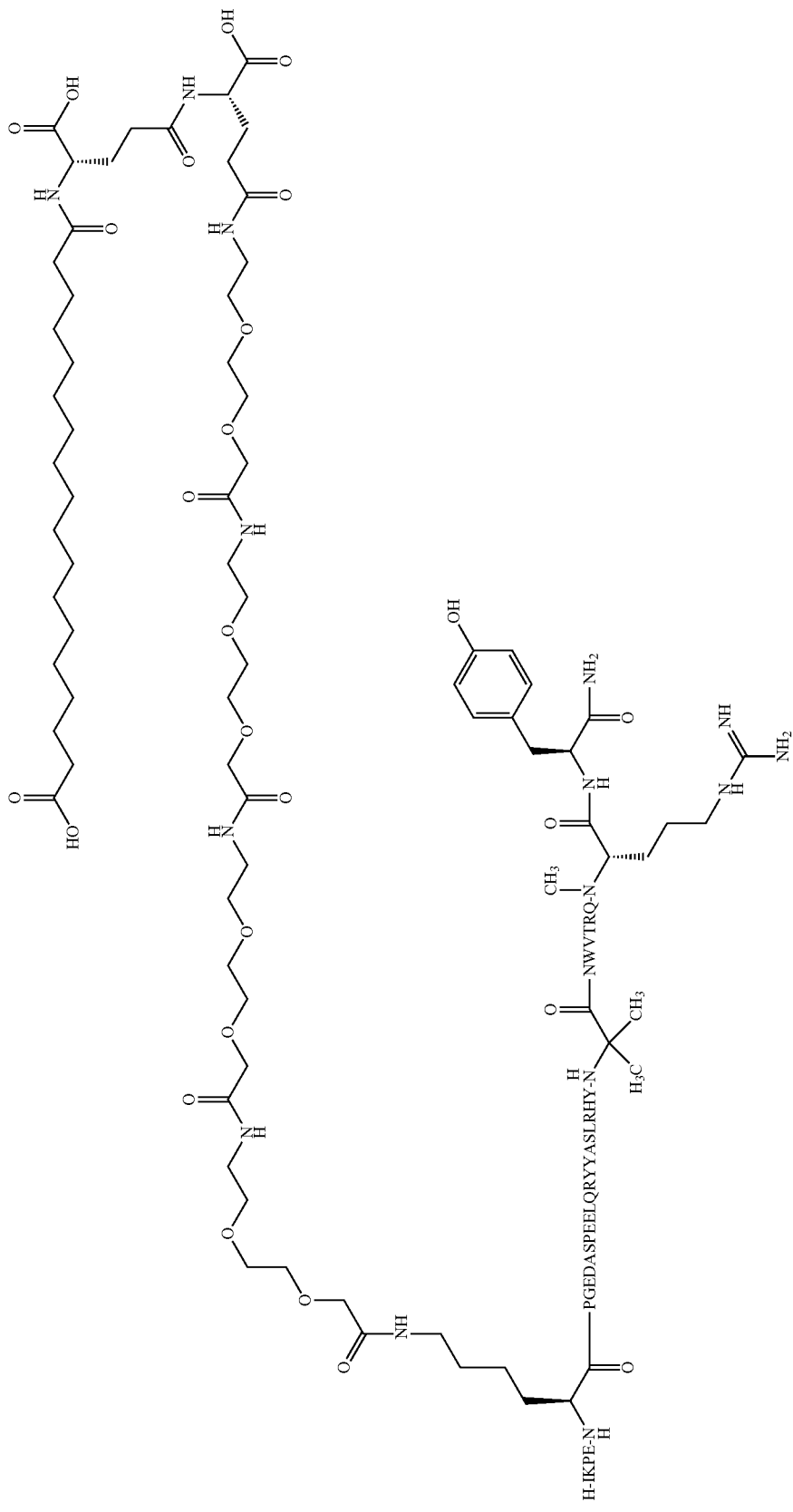

Retention time UPLC-AP-01: 7.26 (91.5%)
MW calculated: 5315.0 g/mol
LCMS: ((M/3)+3) 1772.6; ((M/4)+4) 1329.6; ((M/5)+5) 1063.5

Example 11

SEQ ID NO:11
7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]ethoxy]acetyl]-[Arg4, Lys7, Gln18, Trp30, NMeArg35]hPYY(3-36)

Mass (found): 4973.35 g/mol.
LCMS2: ((M/4)+4) 1244.22; ((M/3)+3) 1658.94

Example 12

SEQ ID NO:12
4-N{alpha}-(hexanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36)

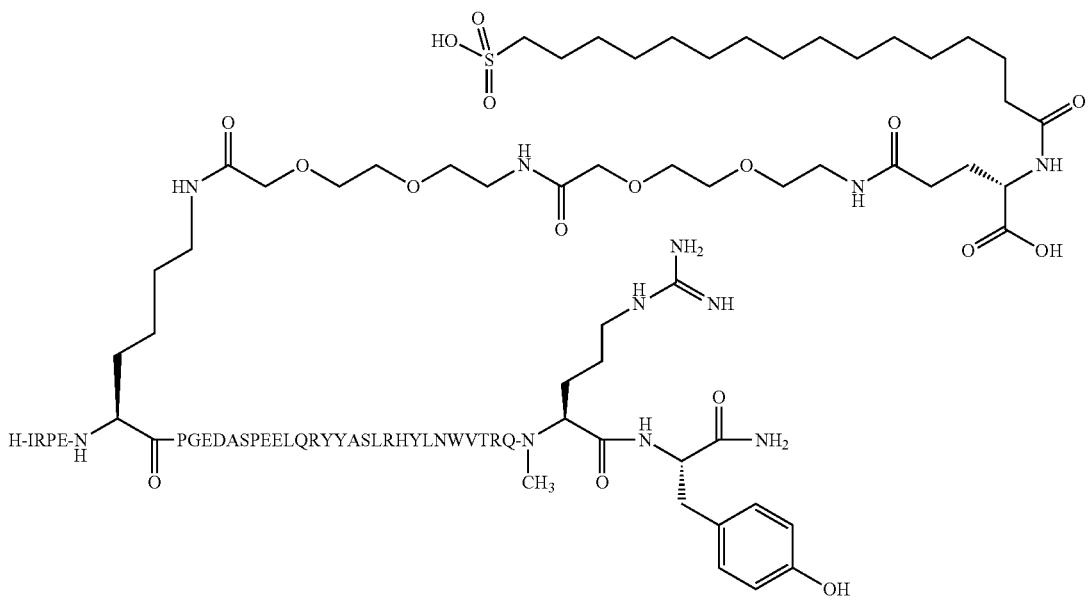

Retention time UPLC02v02: 6.64 minutes (94.7%)
Retention time UPLC16v01: 12.05 minutes (92%)
MW calculated: 4973.69 g/mol.

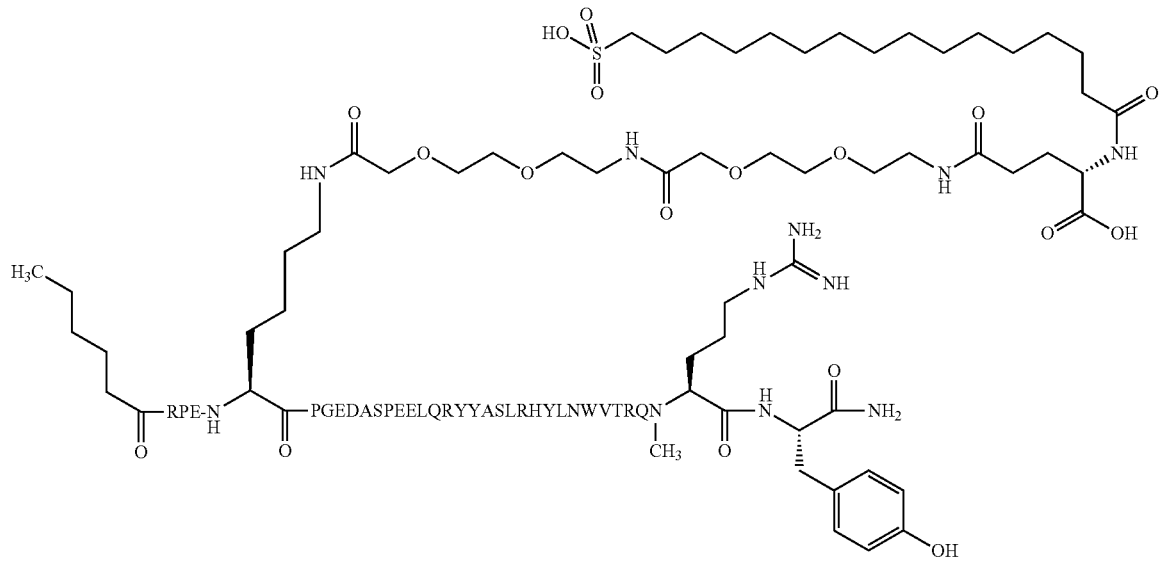

| | |
|---|---|
| 101 | 102 |
| Retention time UPLC16v01: 12.72 minutes (95.1%) | Retention time UPLC02v01: 7.76 minutes (98%) |
| MW calculated: 4958.67 g/mol. | Retention time UPLC16v01: 9.2 minutes (93.2%) |
| Mass found: 4959.22. | MW calculated: 4908.63 g/mol. |
| LCMS2: ((M/4)+4) 1240.64 | LCMS: not determined |

Example 13

SEQ ID NO:13
4-N{alpha}-(3-methyl-pentanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Lys7, Gln18, Trp30, NMeArg35] hPYY(4-36)

Example 14

SEQ ID NO:14
4-N{alpha}-(3-methyl-pentanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35] hPYY(4-36)

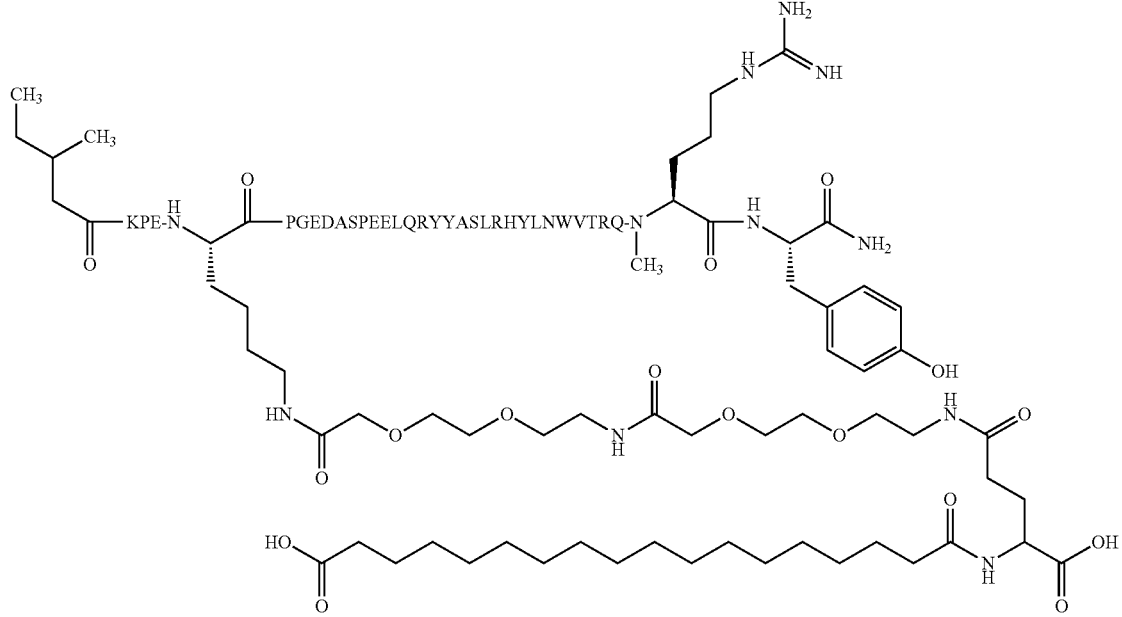

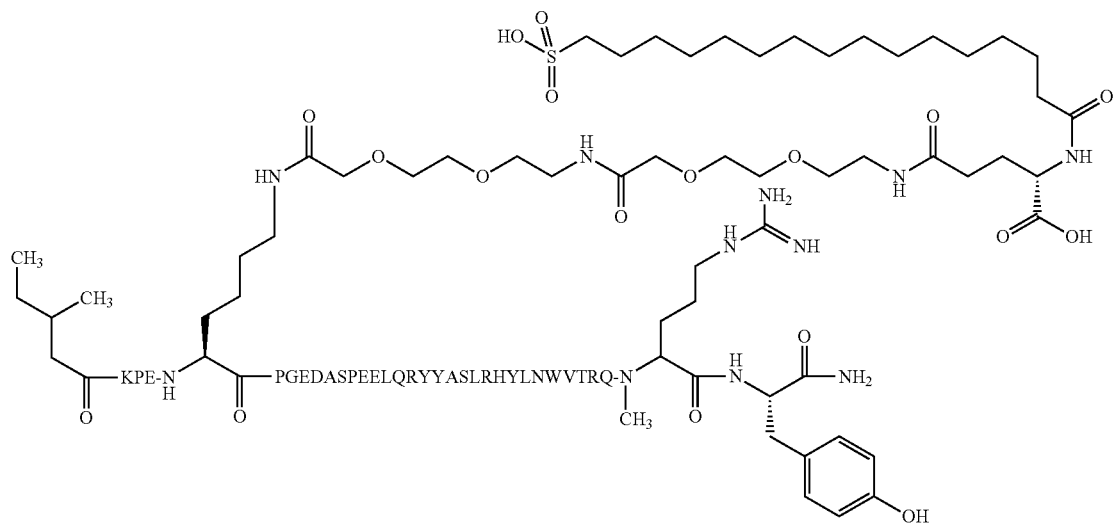

Retention time UPLC02v01: 6.96 minutes (99%)
Retention time UPLC07v01: 5.04 minutes (89%)
Retention time UPLC16v01: 13.01 minutes (89.6%)
MW calculated: 4930.65 g/mol.
LCMS2: ((M/1)+1) 4931.6; ((M/3)+3) 1644.5; ((M/4)+4) 1233.4

Example 15

SEQ ID NO:15
4-N{alpha}-(3-Methylbutanoyl)-7-N{Epsilon}-[2-[2-[2-[[2-[2-[2-[[(4S)-4-carboxy-4-[[(4S)-4-carboxy-4-(16-sulfo-hexadecanoylamino)butanoyl]amino]butanoyl]amino]-ethoxy]ethoxy]acetyl]amino]ethoxy]ethoxy]acetyl]-[Lys7, Gln18, Trp30, NMeArg35]hPYY(4-36)

Retention time UPLC30v01: 3.37 minutes (91.7%)
Retention time UPLC16v01: 12.18 minutes (91.35%)
MW calculated: 5045.7 g/mol.
MALDI (Found): 5045 g/mol.

Example 16

SEQ ID NO:16
4-N{alpha}-(3-Methylbutanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36)

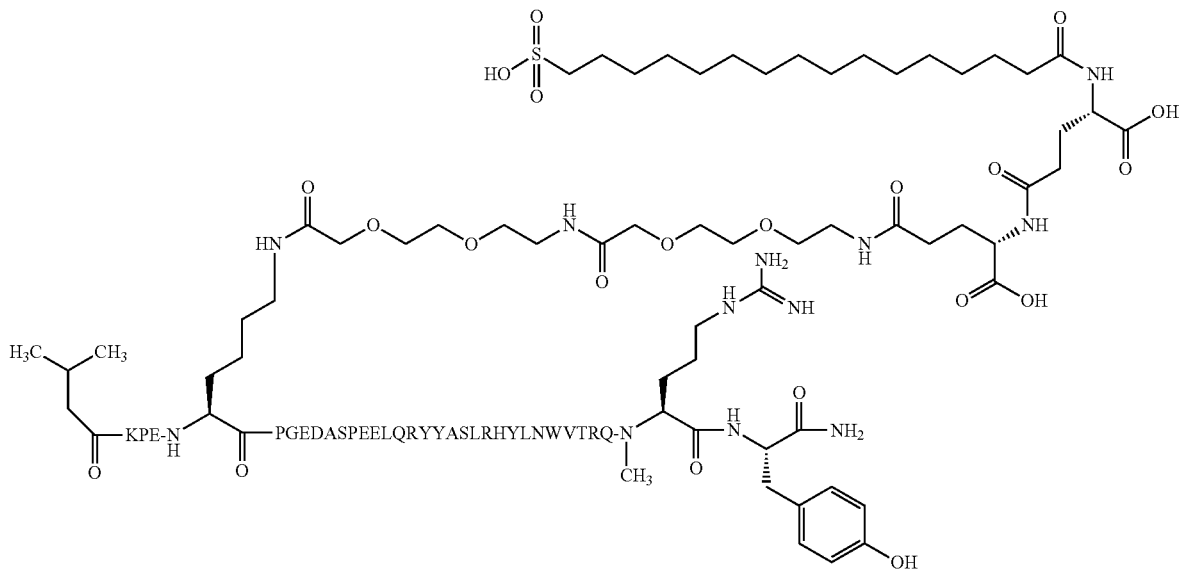

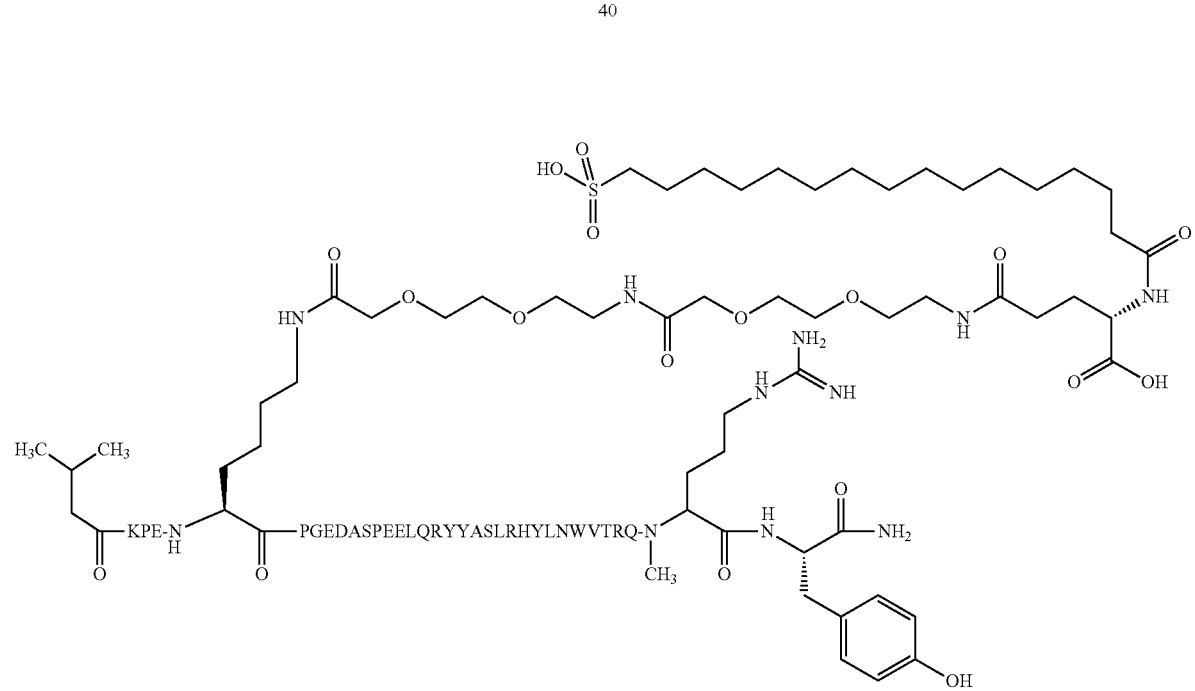

Retention time UPLC30v01: 3.43 minutes (94.5%)
Retention time UPLC16v01: 12.39 minutes (90.24%)
MW calculated: 4916.6 g/mol.
MALDI (Found): 4915 g/mol.

Example 17

SEQ ID NO:17
4-N{alpha}-(3-Methylbutanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]ethoxy]ethoxy]acetyl]-[Arg4, Lys7, Gln18, Trp30]hPYY(4-36)

Retention time UPLC30v01: 3.50 minutes (94%)
Retention time UPLC17v01: 8.56 (86.3%)
MW calculated: 4930.62 g/mol.
MALDI-MS (Found): 4929.8 g/mol.

Example 18

SEQ ID NO:18
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30, NMeArg35]hPYY(4-36)

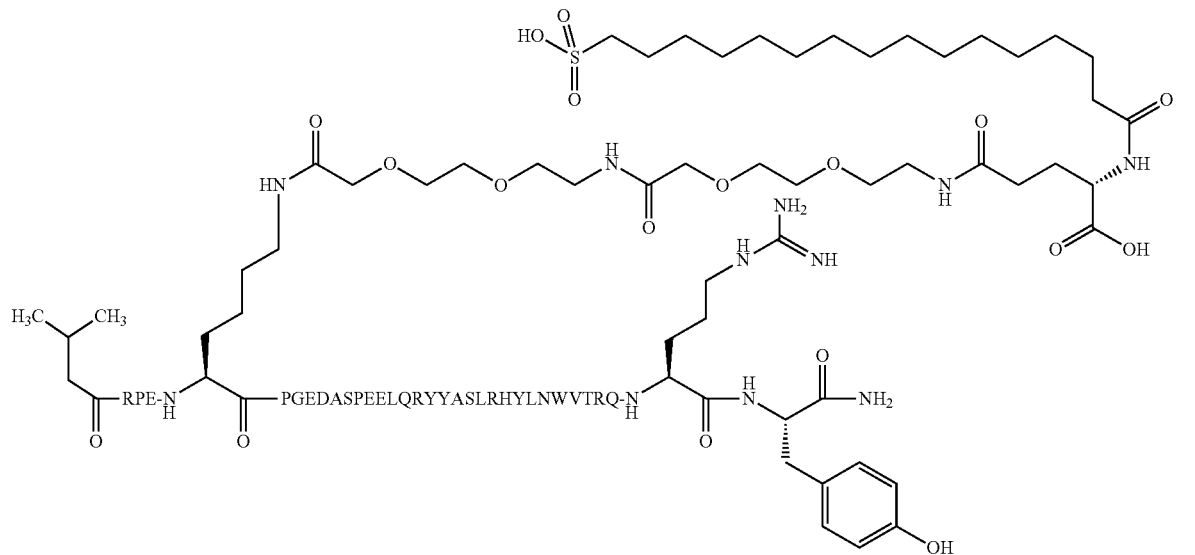

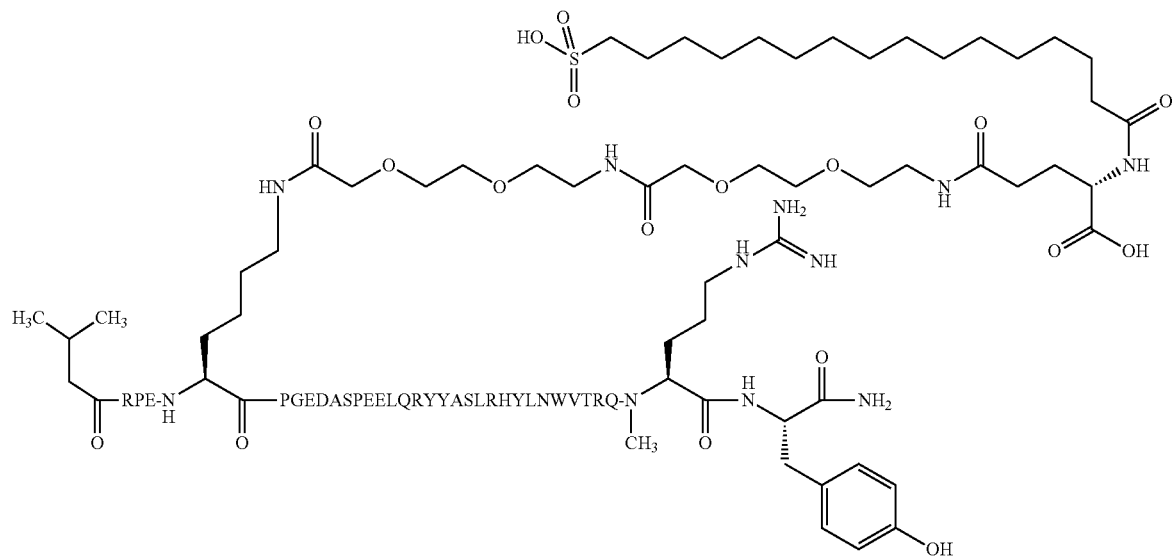

Retention time UPLC16v01: 12.23 minutes (95.2%)
MW calculated: 4944.6 g/mol.
Mass found 4945.34.
LCMS2: M((/4)+4) 1237.20

Example 19

SEQ ID NO:19
4-N{alpha}-(3-Methylbutanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36)

Retention time UPLC02v01: 7.69 minutes (96.7%)
Retention time UPLC17v01: 9.50 minutes (92.5%)
MW calculated: 4922.62 g/mol.
LCMS (LCMS1): m/z: 1231.7.0 ((M/4)+4); 985.3 ((M/5+5); 821.3 ((M/6+6)

Example 20

SEQ ID NO:20
4-N{alpha}-(3-Methylbutanoyl)-7-N{Epsilon}-[2-[2-[2-[[2-[2-[2-[[(4S)-4-carboxy-4-(14-sulfotetradecanoylamino)butanoyl]amino]ethoxy]ethoxy]acetyl]]amino]ethoxy]-ethoxy]acetyl]-[Arg4, Lys7, Gln18, Trp30, NMeArg35]hPYY(4-36)

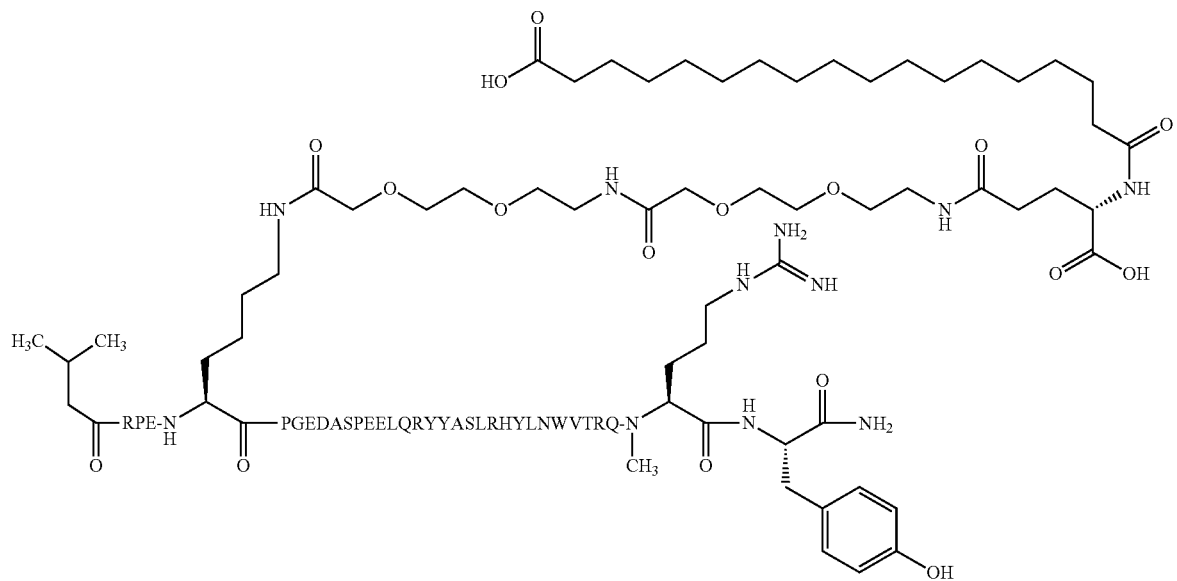

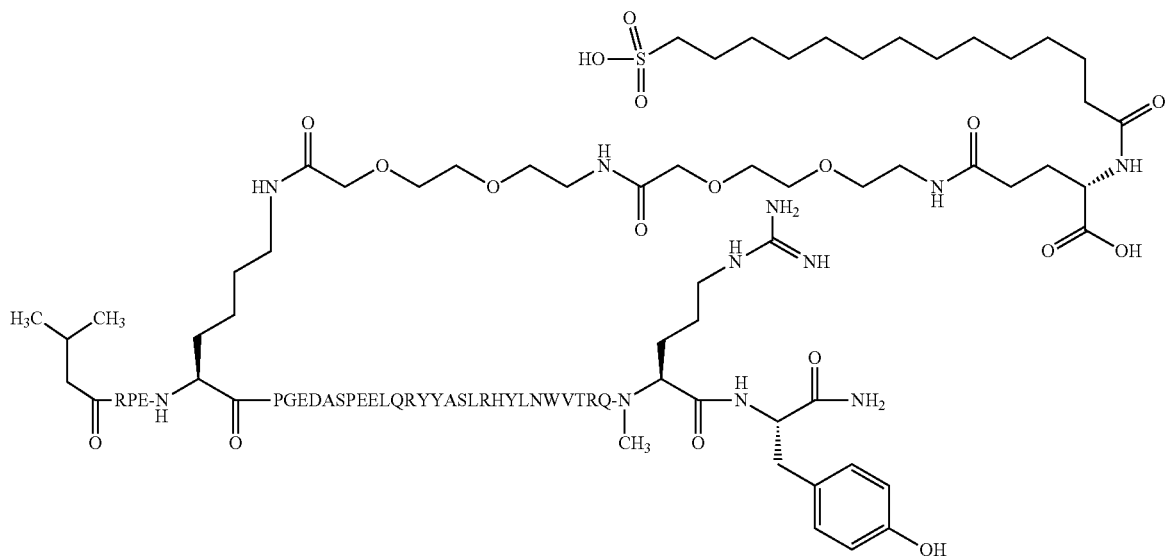

Retention time HPLC method UPLC30v01.3.32 minutes (90.4%)
Retention time HPLC method UPLC60: 17.1 minutes (85.2%)
MW calculated: 4916.48 g/mol.
LCMS (LCMS1): m/z: 1229.9 ((M/4)+4); 984.33 ((M/5+5)

Example 21

SEQ ID NO:21
4-N{alpha}-(3-Methylbutanoyl)-7-N{Epsilon}-[2-[2-[2-[[2-[2-[2-[[(4S)-4-carboxy-4-(16-carboxy-hexadecanoylamino)butanoyl]amino]ethoxy]ethoxy]acetyl]]amino]ethoxy]-ethoxy]acetyl]-[Arg4, Lys7, Gln18, Trp30, NMeArg35]hPYY(4-36)

MW calculated: 4908.6 g/mol.
LCMS (LCMS1): m/z: 1637.20 ((M/3)+3); 1227.91 ((M/4)+4); 982.52 ((M/5+5)

Example 22

SEQ ID NO:22:
4-N{alpha}-(3-Methylbutanoyl)-7-N{Epsilon}-[2-[2-[2-[[2-[2-[2-[[(4S)-4-carboxy-4-(14-carboxy-tetracanoylamino)butanoyl]amino]ethoxy]ethoxy]acetyl]]amino]ethoxy]-ethoxy]acetyl]-[Arg4, Lys7, Gln18, Trp30, NMeArg35]hPYY(4-36)

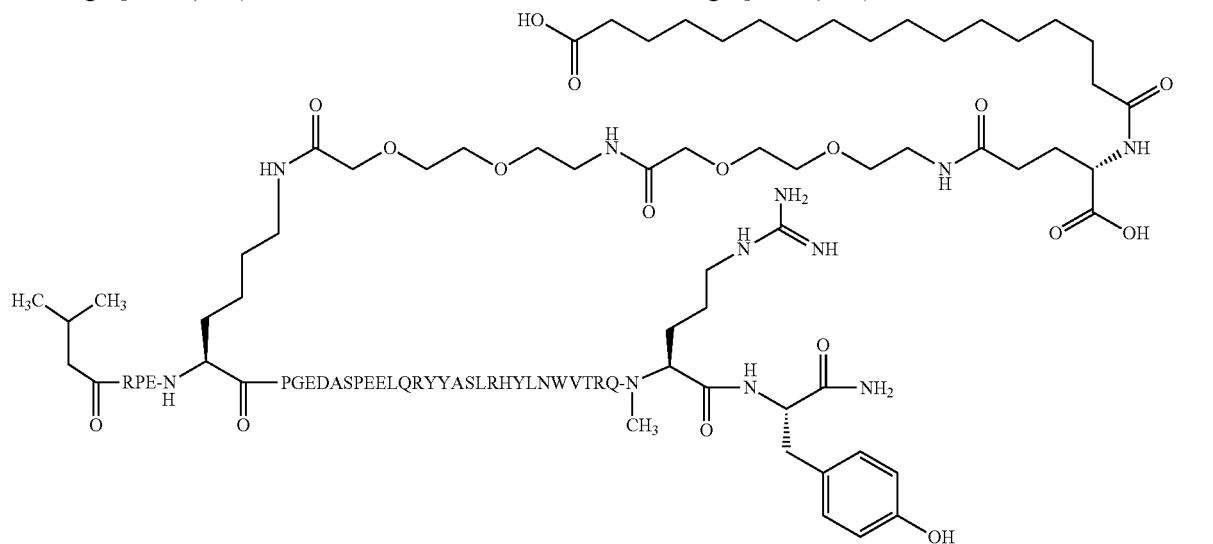

Retention time HPLC method UPLC31v01: 13.0 minutes (97.4%)
Retention time HPLC method UPLC16v01: 3.3 minutes (95.8%)

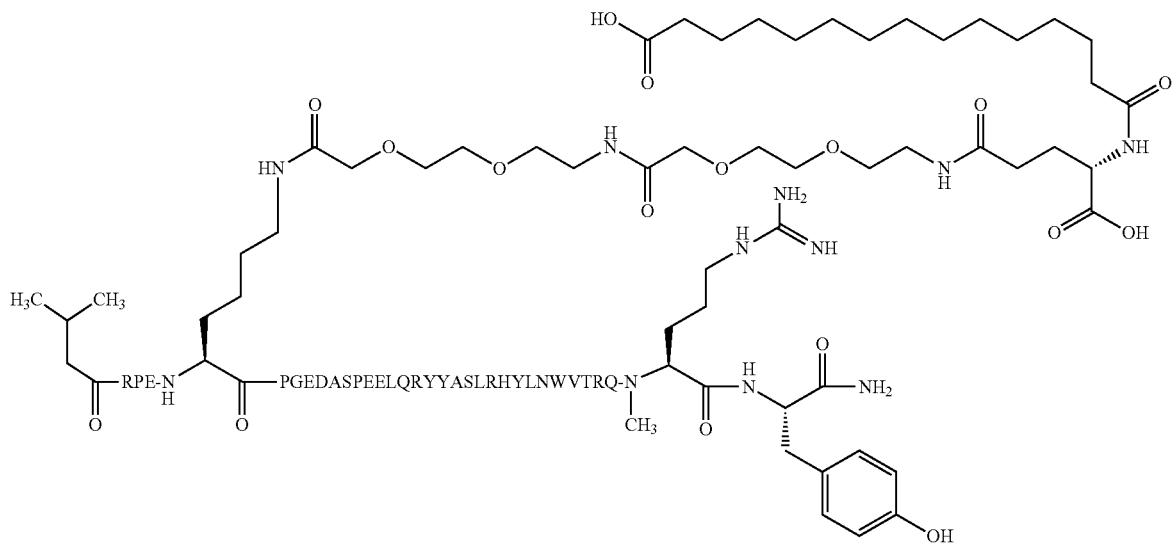

Retention time HPLC method UPLC30v01:3.8 minutes (97%)

Retention time HPLC method UPLC16v01: 10.7 minutes (100%)

MW calculated: 4880.43 g/mol.

LCMS (LCMS1): m/z: 1627.64 ((M/3)+3); 1220.98 ((M/4)+4); 977.19 ((M/5+5)

Example 23

SEQ ID NO:23:
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Ile28, Trp30, NMeArg35]hPYY(4-36)

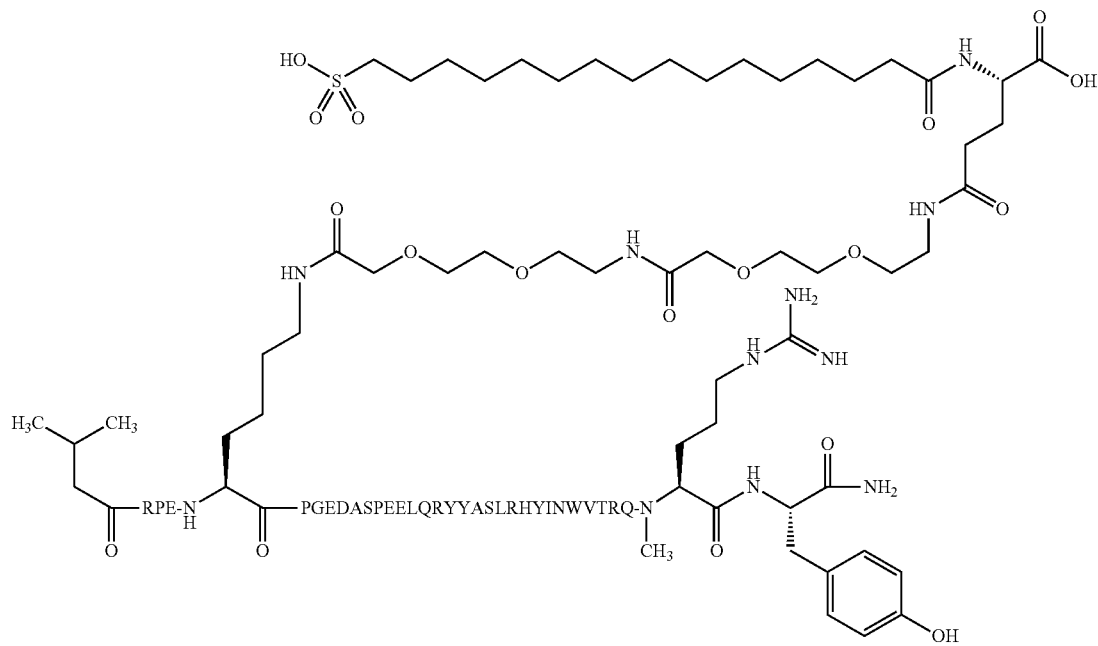

Retention time HPLC method UPLC2:6.8 minutes (100%)

Retention time HPLC method UPLC17: 8.4 minutes (91.8%)

MW calculated: 4944.53 g/mol.

LCMS (LCMS1): m/z: 1648.2 ((M/3)+3); 1236.2 ((M/4)+4); 988.7 ((M/5+5)

Example 24

SEQ ID NO:24
4-N{alpha}-(3-Methylbutanoyl)-7-N{Epsilon}-[2-[2-[2-[[2-[2-[2-[[2-[2-[2-[[(4S)-4-carboxy-4-(16-sulfohexadecanoylamino)butanoyl]amino]ethoxy]ethoxy]acetyl]-amino]ethoxy]ethoxy]acetyl]amino]ethoxy]ethoxy]acetyl]-[Arg4, Lys7, Gln18, Trp30, NMeArg35]hPYY(4-36)

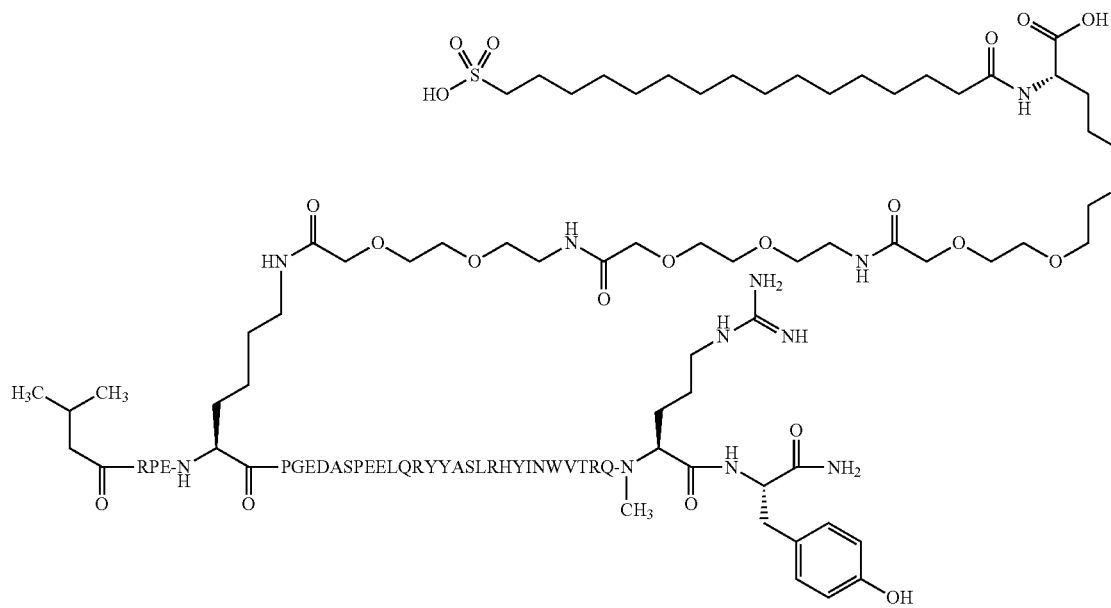
Retention time HPLC method UPLC2 6.76 minutes (100%):
Retention time HPLC method UPLC17 8.4 minutes (91.7%)
MW calculated: 5089.69 g/mol.
LCMS (LCMS1): m/z: 1696.8 ((M/3)+3); 1272.5 ((M/4)+4); 1017.7 ((M/5+5)
Example 25
SEQ ID NO:25
4-N{alpha}-(3-Methylbutanoyl)-7-N{Epsilon}-[2-[2-[2-[[2-[2-[2-[[2-[2-[2-[[2-[2-[2-[[(4S)-4-carboxy-4-(16-sulfo-hexadecanoylamino)butanoyl]amino]ethoxy]-ethoxy]acetyl]amino]ethoxy]ethoxy]acetyl]amino]ethoxy]ethoxy]acetyl]-[Arg4, Lys7, Gln18, Trp30, NMeArg35]hPYY(4-36)
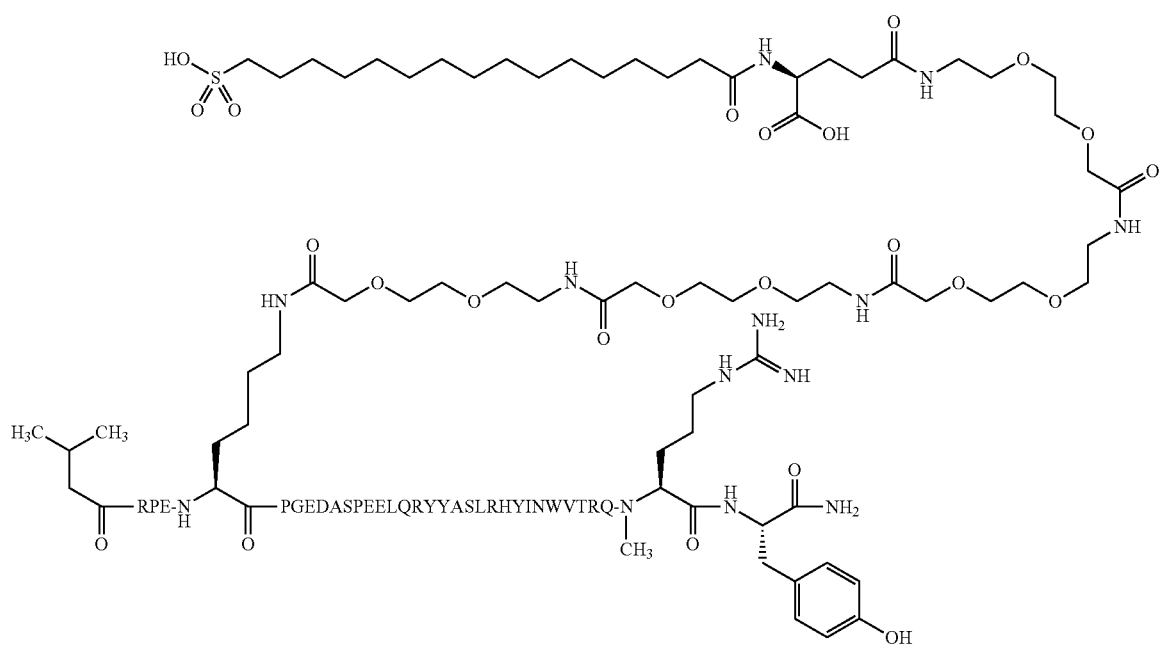

Retention time HPLC method UPLC30v01:
Retention time HPLC method UPLC16v01:
MW calculated: 5234.84 g/mol.
LCMS (LCMS1): m/z: 1745 ((M/3)+3); 1308.7 ((M/4)+4); 1046.7 ((M/5+5)

Example 26

SEQ ID NO:26

4-N{alpha}-(3-Methylbutanoyl)-7-N{Epsilon}-[2-[2-[2-[[2-[2-[2-[[2-[2-[2-[[2-[2-[2-[[(4S)-4-carboxy-4-(16-sulfohexadecanoylamino)butanoyl]amino]-ethoxy]ethoxy]acetyl]amino]ethoxy]ethoxy]acetyl]amino]ethoxy]ethoxy]acetyl]amino]-ethoxy]ethoxy]acetyl]amino]ethoxy]ethoxy]acetyl]-[Arg4, Lys7, Gln18, Trp30, NMeArg35] hPYY(4-36)

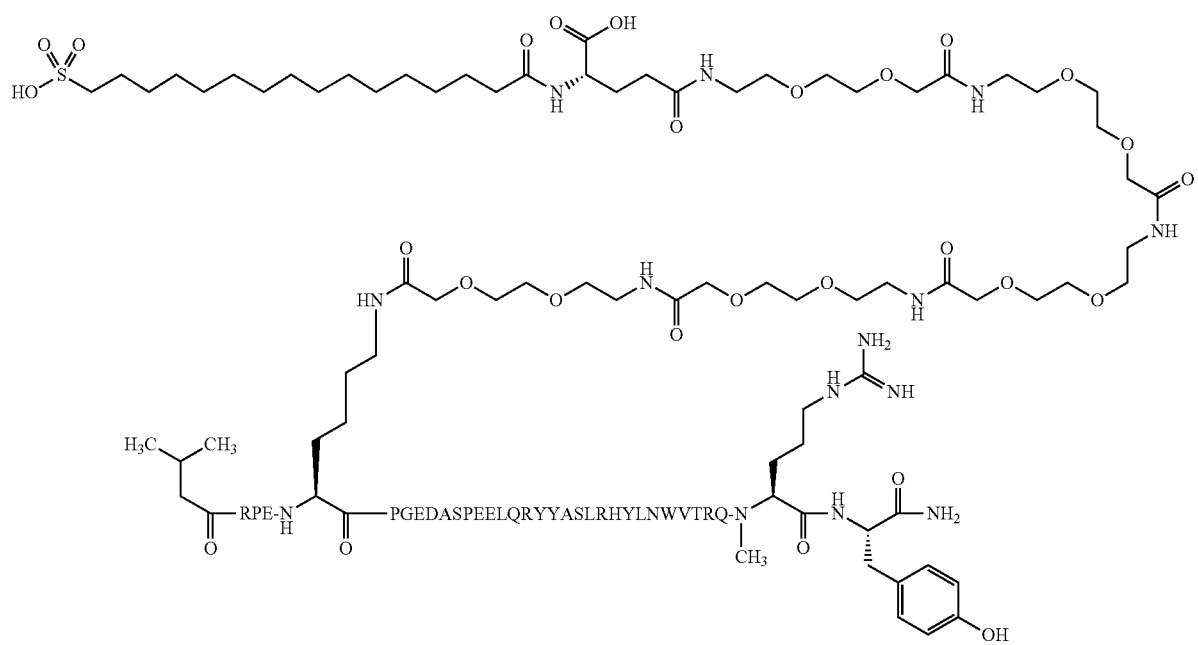

Retention time HPLC method UPLC2:6.7 minutes (100%)

Retention time HPLC method UPLC16v01: 8.5 minutes (88.9%)

MW calculated: 0.5380.00 g/mol.

LCMS (LCMS1): m/z: 1793 ((M/3)+3); 1344.9 ((M/4)+4); 1075.8 ((M/5+5)

Example 27

SEQ ID NO:27

4-N{alpha}-(3-Methylbutanoyl)-7-N{Epsilon}-[4-[3-[2-[2-[3-[[(4S)-4-carboxy-4-(16-sulfohexadecanoylamino)butanoyl]amino]propoxy]ethoxy]ethoxy]propylamino]-4-oxobutanoyl]-[Arg4, Lys7, Gln18, Trp30, NMeArg35]hPYY(4-36)

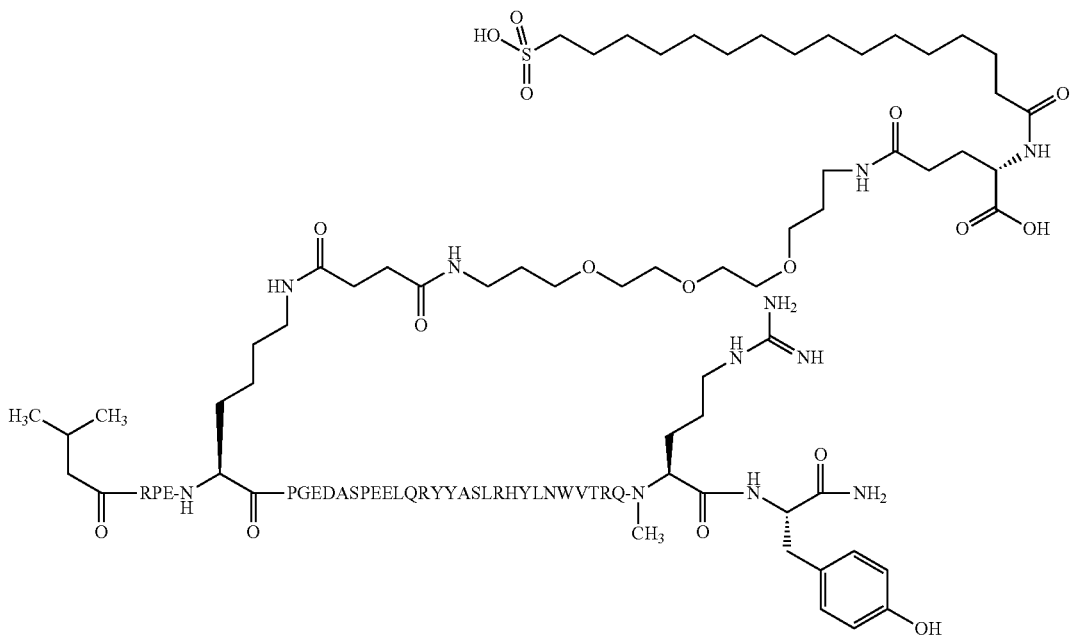

Retention time HPLC method UPLC30v01: 3.69 minutes (93.2%)
Retention time HPLC method UPLC16v01: 12.21 minutes (84.6%)
MW calculated: 4956.59·g/mol.
MW(found): 4957.4 g/mol.
LCMS (LCMS1): m/z: 1653.23 ((M/3)+3); 1240.19 ((M/4)+4); 992.36 ((M/5+5)

Example 28

SEQ ID NO:28
4-N{alpha}-(3-Methylbutanoyl)-7-N{Epsilon}-[4-[3-[2-[2-[3-[[4-[3-[2-[2-[3-[[(4S)-4-carboxy-4-(16-sulfohexadecanoylamino)butanoyl]amino]propoxy]ethoxy]-ethoxy]propylamino]-4-oxobutanoyl]amino]propoxy]ethoxy]ethoxy]propylamino]-4-oxobutanoyl]-[Arg4, Lys7, Gln18, Trp30, NMeArg35]hPYY(4-36)

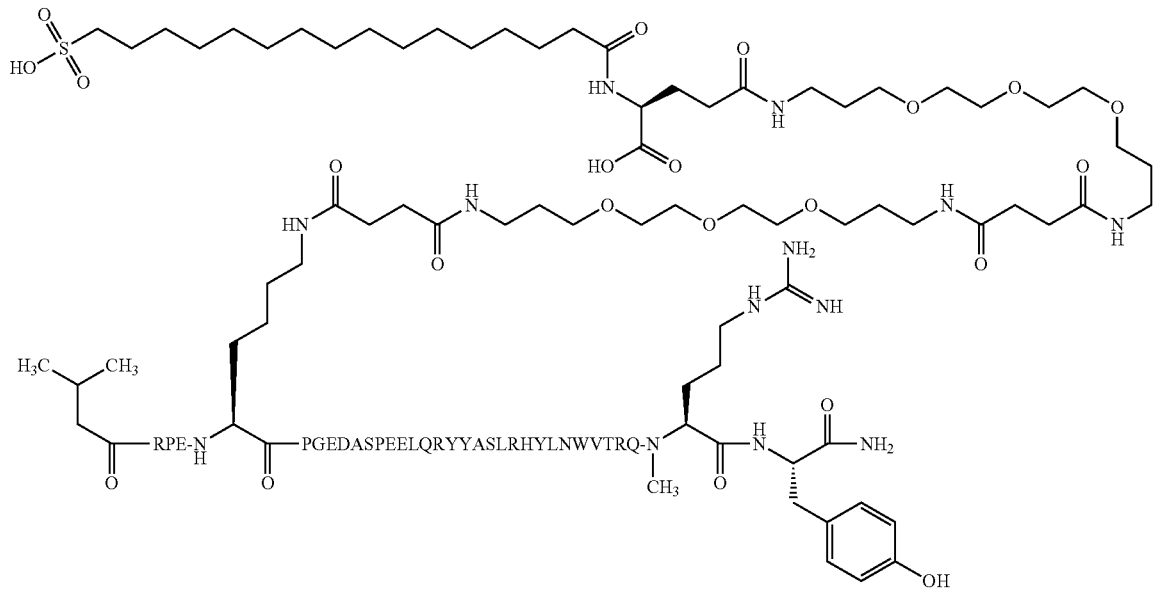

Retention time HPLC method UPLC30v01: 3.66 minutes (92.4%)
Retention time HPLC method UPLC16v01: 12.36 minutes (65.6%)
MW calculated: 5258.96·g/mol.
MW(found): 5258.96 g/mol.
LCMS (LCMS1): m/z: 1753.96 ((M/3)+3); 1315.80 ((M/4)+4); 1052.80 ((M/5+5)

Example 29

SEQ ID NO:29

4-N{alpha}-(3-Methylbutanoyl)-7-N{Epsilon}-[4-[3-[2-[2-[3-[[4-[3-[2-[2-[3-[[4-[3-[2-[2-[3-[[(4S)-4-carboxy-4-(16-sulfohexadecanoylamino)butanoyl]amino]propoxy]-ethoxy]ethoxy]propylamino]-4-oxobutanoyl]amino]propoxy]ethoxy]-ethoxy]propylamino]-4-oxobutanoyl]amino]propoxy]ethoxy]ethoxy]propylamino]-4-oxobutanoyl]-[Arg4, Lys7, Gln18, Trp30, NMeArg35]hPYY(4-36)

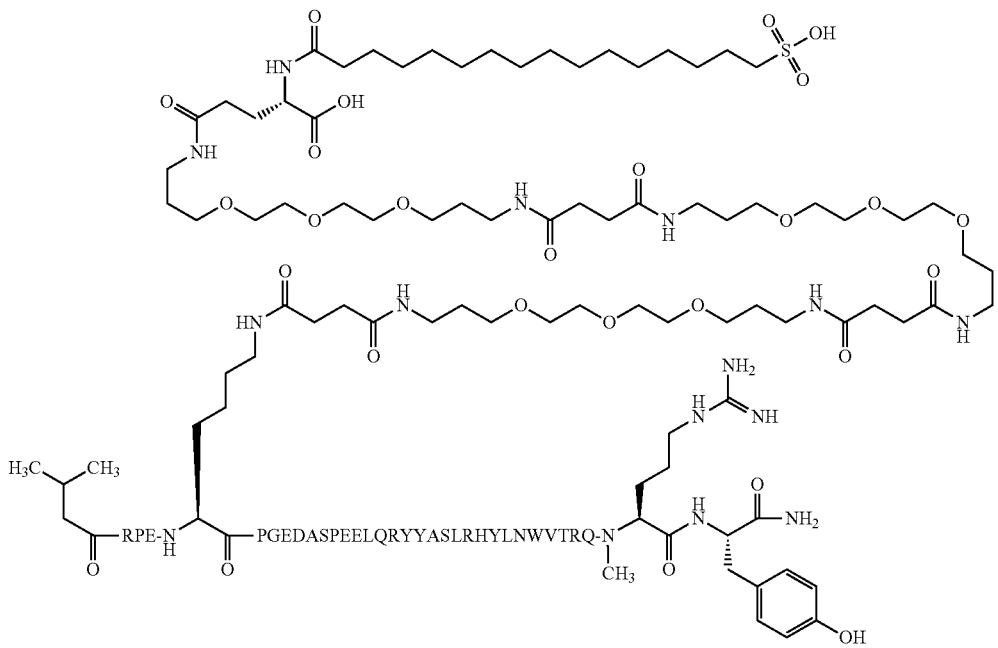

Retention time HPLC method UPLC30v01: 3.68 minutes (94.5%)

Retention time HPLC method UPLC16v01: 11.89 minutes (85.8%)

MW calculated: 5561.32·g/mol.

MW(found): 5562.1 g/mol.

LCMS (LCMS1): m/z: 1391.31 ((M/4)+4); 1113.26 ((M/5+5)

Example 30

SEQ ID NO:30

4-N{alpha}-(3-Methylbutanoyl)-7-N{Epsilon}-[(2S)-2-amino-6-[[2-[2-[2-[[(4S)-4-carboxy-4-(16-sulfohexadecanoylamino)butanoyl]amino]ethoxy]ethoxy]acetyl]-amino]hexanoyl]]-[Arg4, Lys7, Gln18, Trp30, NMeArg35]hPYY(4-36)

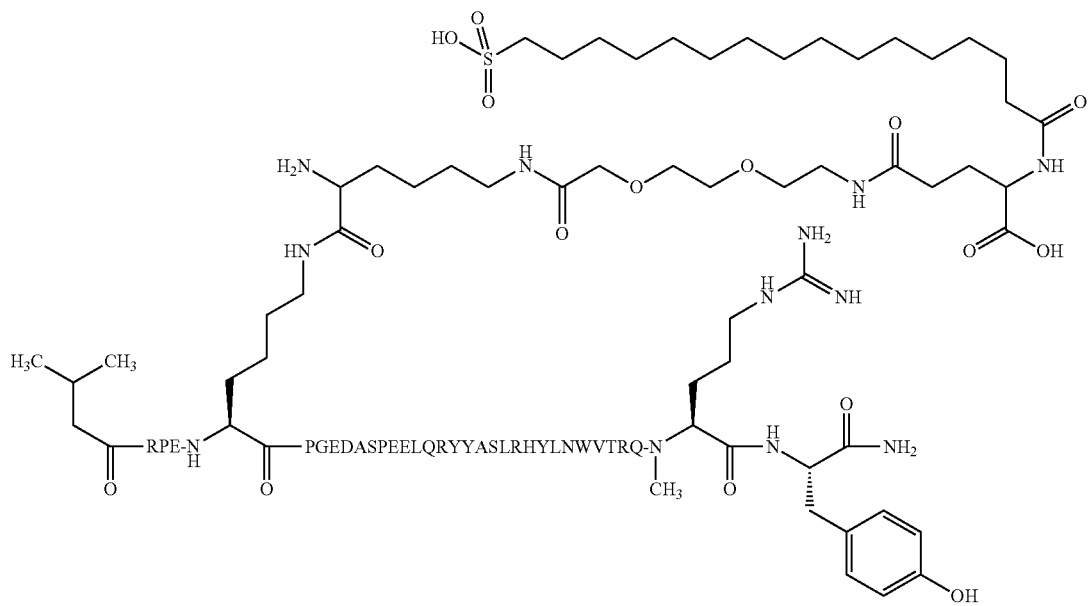

Retention time HPLC method UPLC16v01: 11.8 minutes (93.29%)
MW calculated: 4927.55·g/mol.
MW(found): 4928.36 g/mol.
LCMS (LCMS1): m/z: 1232.92 ((M/4)+4); 986.54 ((M/5+5)

Example 31

SEQ ID NO:31
4-N{alpha}-(3-Methylbutanoyl)-7-N{Epsilon}-[2-[2-[2-[[2-[2-[2-[[(4S)-4-carboxy-4-(15-carboxypentadecanoylamino)butanoyl]amino]ethoxy]ethoxy]acetyl]amino]-ethoxy]ethoxy]acetyl]-[Arg4, Lys7, Gln18, Trp30, NMeArg35]hPYY(4-36)

Retention time HPLC method UPLC31v01:3.21 minutes (95.8%)
Retention time HPLC method UPLC61v01: 12.36 minutes (85.9%)
MW calculated: 4894.46·g/mol.
MW(found): 4894.56 g/mol.
LCMS (LCMS1): m/z: 1632.52 ((M/3)+3); 1224.64 ((M/4+4)

Example 32

SEQ ID NO:32
7-N{Epsilon}-[2-[2-[2-[[2-[2-[2-[[(4S)-4-carboxy-4-(16-sulfohexadecanoylamino)-butanoyl]amino]ethoxy]ethoxy]

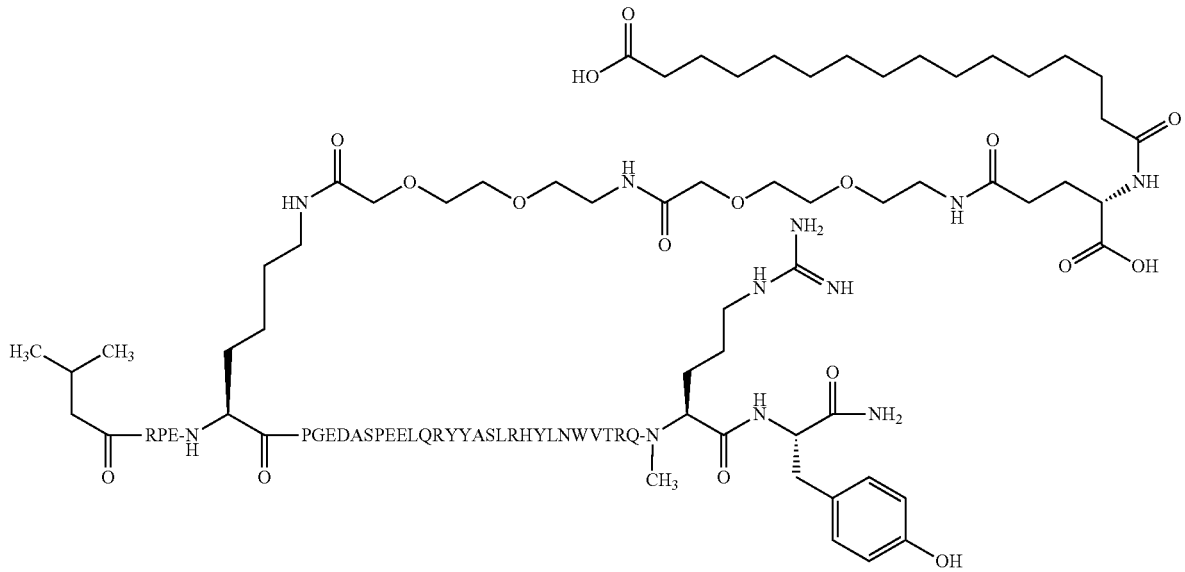

acetyl]amino]ethoxy]-ethoxy]acetyl]-[Val3, Arg4, Lys7, Gln18, Trp30, NMeArg35]hPYY(3-36)

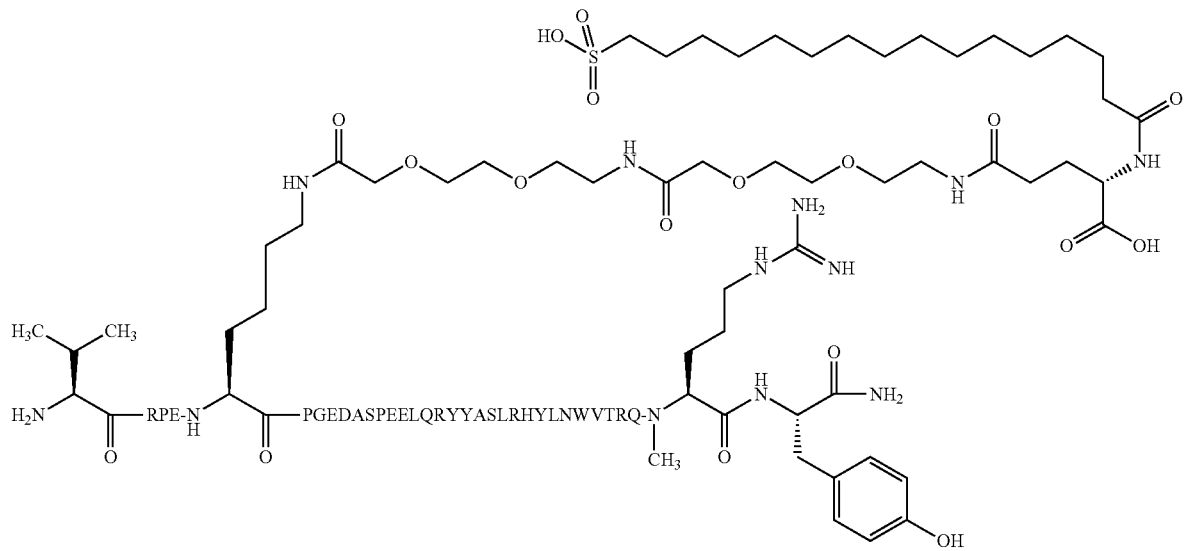

Retention time HPLC method UPLC16v01: 12.83 minutes (88.6%).
MW calculated: 4859.55·g/mol.
MW(found): 4960.21 g/mol.
LCMS (LCMS1): m/z: 1240-64 ((M/4)+4); 992.91 ((M/5+5)

Example 33

SEQ ID NO:33
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, D-Asp11, Gln18, Trp30, NMeArg35]hPYY(4-36)

Retention time HPLC method UPLC30v01:3.82 minutes (95.3%)

Retention time HPLC method UPLC17v01: 9.07 minutes (90.5%)
MW calculated: 4944.53·g/mol.
MW(found): 4944.60 g/mol.
LCMS (LCMS1): m/z: 1237.15 ((M/4)+4); 989.68 ((M/5+5)

Example 34

SEQ ID NO:34
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, isoAsp11, Gln18, Trp30, NMeArg35]hPYY(4-36)

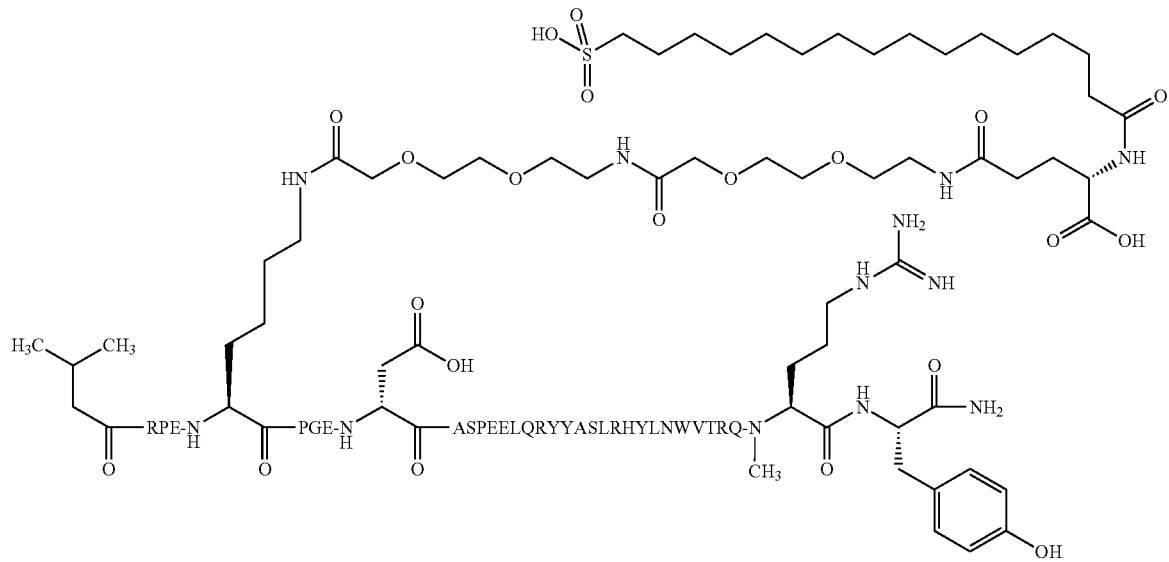

125

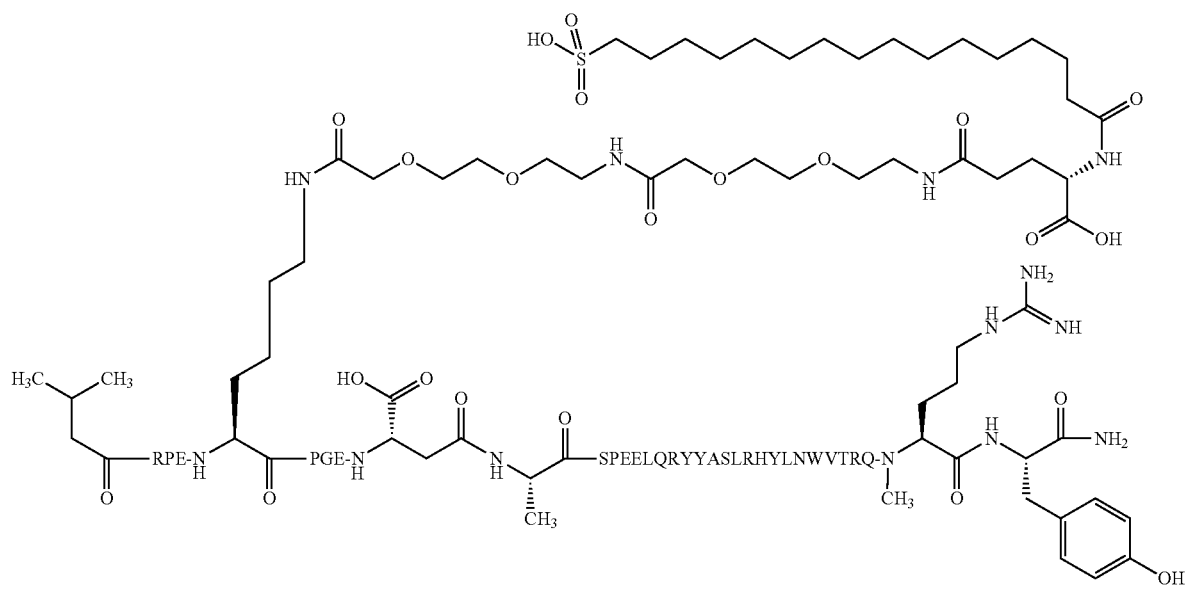

Retention time HPLC method UPLC30v01:1.87 minutes (89.0%)

126 ethoxy]-ethoxy]acetyl]-[Arg4, Lys7, D-isoAsp11, Gln18, Trp30, NMeArg35]hPYY(4-36)

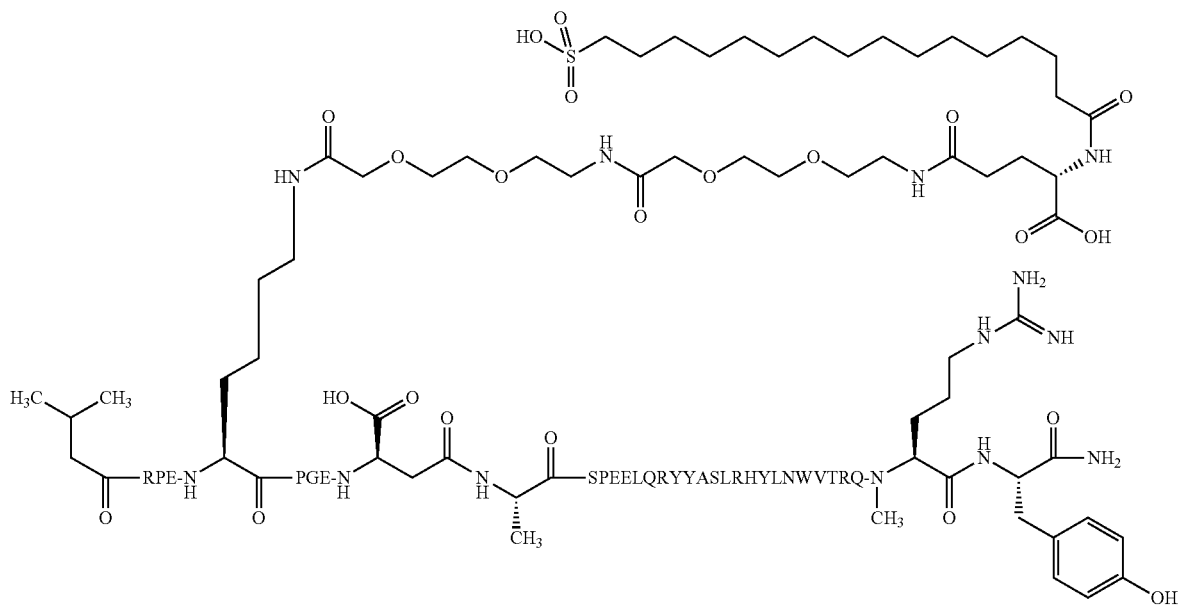

Retention time HPLC method UPLC17v01: 8.65 minutes (74.3%)
MW calculated: 4944.53·g/mol.
MW(found): 4943.36 g/mol.
LCMS (LCMS1): m/z: 1236.84 ((M/4)+4); 989.68 ((M/5+5)

Retention time HPLC method UPLC30v01:3.72 minutes (98.1%)
Retention time HPLC method UPLC61: 12.78 minutes (96.2%)
MW calculated: 4944.53·g/mol.

Example 35

SEQ ID NO:35
4-N{alpha}-(3-Methylbutanoyl)-7-N{Epsilon}-[2-[2-[2-[[2-[2-[2-[[(4S)-4-carboxy-4-(16-sulfohexadecanoy-lamino)-butanoyl]amino]ethoxy]ethoxy]acetyl]amino]

Example 36

SEQ ID NO:36
4-N{alpha}-(3-Methylbutanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]ethoxy]-ethoxy]acetyl]-[Arg4, Lys7, Gln18, Trp30]hPYY(4-36)

Retention time UPLC-AP-01: 6.51 minutes (95.3%)
MW calculated: 4960.7·g/mol.
MW(found): 4960.2 g/mol.

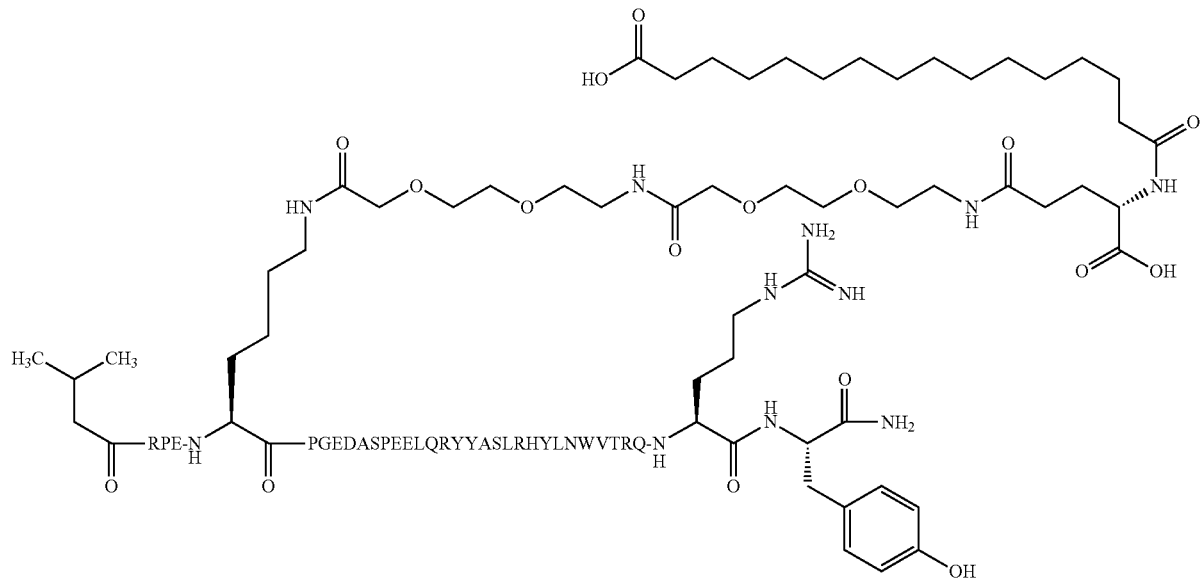

Retention time UPLC-AP-01: 7.78 minutes (96%)
MW calculated: 4909.48·g/mol.
MW(found): 4909.8 g/mol.
LCMS (LCMS1): m/z: 1637.6 ((M/3)+3); 1228.2 ((M/4)+4); 982.9 ((M/5+5)

LCMS (LCMS1): m/z: 1654.46 ((M/3)+3); 1241.1 ((M/4)+4); 992.7 ((M/5+5)

Example 37

SEQ ID NO:37
7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30]hPYY(3-36)

Example 38

SEQ ID NO:38

4-N{alpha}-(3-Methylbutanoyl)-[Arg4, Gln18, Trp30, NMeArg35]hPYY(4-36)

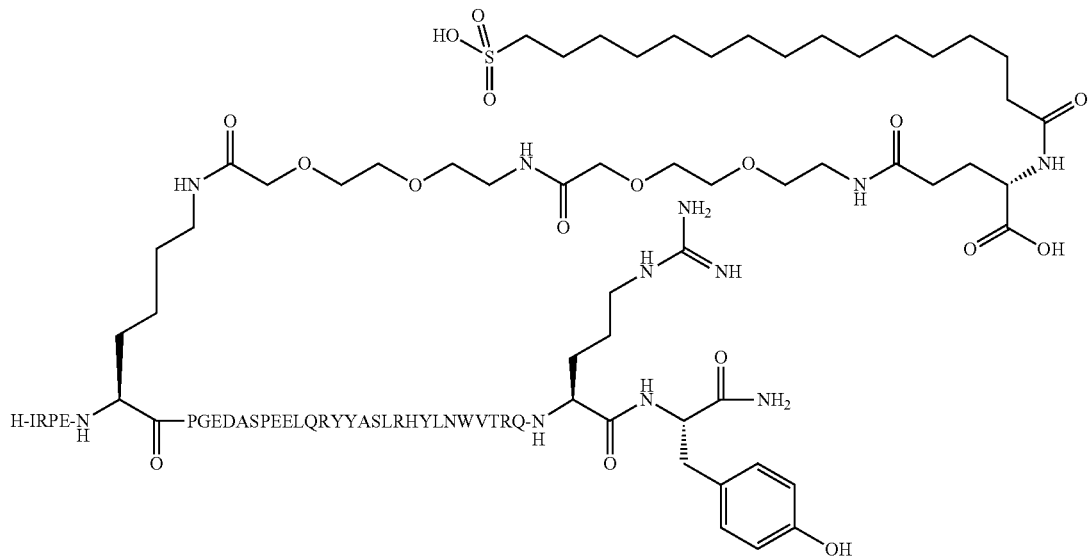

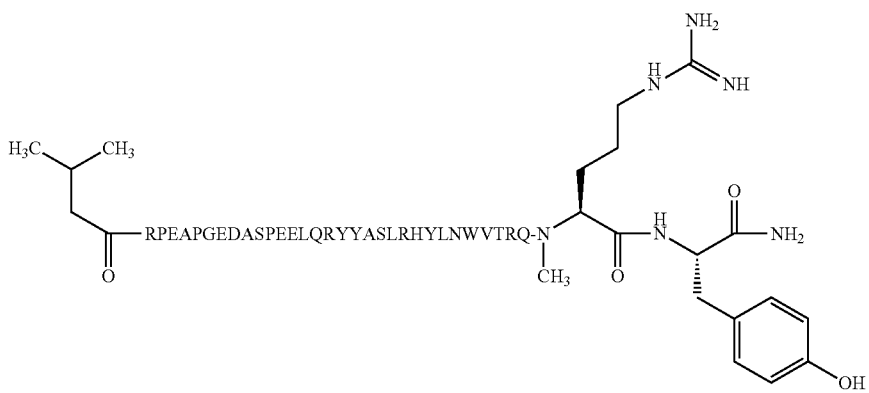

Retention time UPLC16: 13.18 minutes (62.5%)
Retention time UPLC29: 3.80 minutes (92.3%)
MW calculated: 4149.6 g/mol.
MW(found): 4149.9.2 g/mol.
LCMS (LCMSv27): m/z: 1384.04 ((M/3)+3); 1038.28 ((M/4)+4); 830.83 ((M/5+5)

Pharmacological Methods

The utility of PYY peptide derivatives or analogues thereof of the present invention as pharmaceutically active agents in the reduction of weight gain and treatment of obesity in mammals (such as humans), and for treatment of diabetes may be demonstrated by the activity of the agonists in conventional assays and in the in vitro and in vivo assays described below.

Such assays also provide a means whereby the activities of the PYY compounds of this invention can be compared with the activities of known compounds.

Example 39

Receptor Potency of PYY Compounds

The purpose of this example is to test the activity, or potency, of the PYY compounds in vitro. The in vitro potency is the measure of the activation of the human Y1, Y2, Y4 and Y5 receptor subtypes, respectively, in a whole cell assay.

The potencies of the PYY compounds of examples 3-38 were determined using the Actone functional potency assay as described below. hPYY(3-36) (Example 2, SEQ ID NO:2) was included as a reference.

Actone Functional Potency Assay

The Neuropeptide Y (NPY) receptors are $G_i$-coupled seven trans-membrane receptors that mainly signal through the cAMP dependent pathway by inhibiting adenylate cyclase activity which results in a decrease of cAMP production from ATP. The Actone assay is based on a modified calcium channel that has a selective binding for cAMP, resulting in cellular calcium influx, detected by a calcium responsive dye. In order to measure decreased levels of cAMP, as result of NPY receptor activation, the β1/β2-adrenoreceptor agonist, isoproterenol, is added to activate adenylate cyclase and increases cAMP levels in the cell. Decreased cellular calcium concentrations, reflecting a decrease of cAMP levels due to NPY receptor activation, is detected as a decrease in fluorescence from the calcium sensitive dye.

HEK-293 cells expressing the cAMP sensitive calcium channel and one of the human NPY receptors Y1, Y2, Y4 or Y5 (CodexBiosolution, Gaithersburg, Md., USA) were seeded into poly lysine coated 384 well plates at a density of 14.000 cells/well in a volume of 25 μl in DMEM medium containing 10% Fetal calf serum (FCS), 1% Penicillin-Streptomycin, 250 μg/ml aminoglycoside antibiotic G418 and 1 μg/ml aminonucleoside antibiotic puromycin. The cells were incubated over night at +37° C. in a humidified milieu in 5% $CO_2$ followed by addition of 25 μl calcium dye buffer containing: 1 vial Calcium 5 dye (Molecular Devices, Sunnyvale, Calif., USA) solved in 100 ml buffer containing 20 mM Hepes, 0.1% Ovalbumin, 0.005% Tween 20, 1.5 mM probenecid, 250 μM PDE-inhibitor 4-(3-Butoxy-4-methoxybenzyl)imidazolidin-2-one and 8 mM $CaCl_2$ and pH was adjusted to 7.40. Cells were incubated for 1 hour with the calcium dye buffer and then placed in a FLIPR Tetra System (Molecular Devices) where the liquid handling system added PYY compound (1000-1 nM final concentrations) and isoproterenol (0.05 μM final concentration) simultaneously directly followed by fluorescence signal measurement (Ex540/Em590) for 360 seconds with 30 seconds intervals. All measurements were performed in duplicates and $EC_{50}$ values were calculated by nonlinear regression analysis of sigmoidal dose response curves using the GraphPad Prism v 5.02 (Graph Pad software, La Jolla, Calif., USA). The EC50 values are shown in table 1.

TABLE 1

In vitro potency

| Example | Compound | Y2 EC50 (nM) | Y1 EC50 (nM) | Y4 EC50 (nM) | Y5 EC50 (nM) |
|---|---|---|---|---|---|
| 2 | hPYY(3-36) SEQ ID NO: 2 | 0.80 | 6.6 | 651 | 8.4 |
| 3 | SEQ ID NO: 3 | 0.57 | 335 | 403 | 16 |
| 4 | SEQ ID NO: 4 | 0.64 | >1000 | >1000 | 201 |
| 5 | SEQ ID NO: 5 | 2.2 | >1000 | >1000 | 260 |
| 6 | SEQ ID NO: 6 | 8.5 | 628 | >1000 | 280 |
| 7 | SEQ ID NO: 7 | 3.2 | 977 | >1000 | 540 |
| 8 | SEQ ID NO: 8 | 1.1 | >1000 | >1000 | 345 |
| 9 | SEQ ID NO: 9 | 2.9 | >1000 | >1000 | 219 |
| 10 | SEQ ID NO: 10 | 21 | >1000 | >1000 | >1000 |
| 11 | SEQ ID NO: 11 | 1.9 | >1000 | >1000 | 189 |
| 12 | SEQ ID NO: 12 | 3.1 | >1000 | 999 | 188 |
| 13 | SEQ ID NO: 13 | 3.6 | >1000 | >1000 | 235 |
| 14 | SEQ ID NO: 14 | 1.6 | >1000 | >1000 | 246 |
| 15 | SEQ ID NO: 15 | 4.2 | 599 | >1000 | 860 |
| 16 | SEQ ID NO: 16 | 1.9 | >1000 | >1000 | 389 |
| 17 | SEQ ID NO: 17 | 1.7 | >1000 | >1000 | 81 |
| 18 | SEQ ID NO: 18 | 1.9 | >1000 | 971 | 311 |
| 19 | SEQ ID NO: 19 | 4.5 | >1000 | >1000 | >1000 |
| 20 | SEQ ID NO: 20 | 7.8 | >1000 | >1000 | >1000 |
| 21 | SEQ ID NO: 21 | 5.6 | >1000 | >1000 | 876 |
| 22 | SEQ ID NO: 22 | 5.7 | >1000 | >1000 | >1000 |

TABLE 1-continued

In vitro potency

| Example | Compound | Y2 EC50 (nM) | Y1 EC50 (nM) | Y4 EC50 (nM) | Y5 EC50 (nM) |
|---|---|---|---|---|---|
| 23 | SEQ ID NO: 23 | 2.8 | >1000 | >1000 | 526 |
| 24 | SEQ ID NO: 24 | 5.0 | >1000 | >1000 | 803 |
| 25 | SEQ ID NO: 25 | 6.8 | >1000 | >1000 | >1000 |
| 26 | SEQ ID NO: 26 | 9.3 | >1000 | >1000 | >1000 |
| 27 | SEQ ID NO: 27 | 2.9 | >1000 | >1000 | >1000 |
| 28 | SEQ ID NO: 28 | 6.5 | >1000 | >1000 | >1000 |
| 29 | SEQ ID NO: 29 | 19 | >1000 | >1000 | >1000 |
| 30 | SEQ ID NO: 30 | 1.7 | >1000 | >1000 | 292 |
| 31 | SEQ ID NO: 31 | 3.5 | >1000 | >1000 | 976 |
| 32 | SEQ ID NO: 32 | 1.4 | >1000 | >1000 | 167 |
| 33 | SEQ ID NO: 33 | 3.2 | >1000 | >1000 | 923 |
| 34 | SEQ ID NO: 34 | 3.2 | >1000 | >1000 | 420 |
| 35 | SEQ ID NO: 35 | 12 | >1000 | >1000 | 626 |
| 36 | SEQ ID NO: 36 | 1.5 | >1000 | >1000 | 61 |
| 37 | SEQ ID NO: 37 | 1.0 | >1000 | >1000 | 27 |
| 38 | SEQ ID NO: 38 | 1.0 | >1000 | >1000 | >1000 |

The PYY compounds of the inventions all display good Y2 potency, whereas the potency on the receptors Y1, Y4 and Y5 is strongly reduced.

Example 40

Y1, Y2, Y4 and Y5 Receptor Subtype Binding

The purpose of this example is to test the in vitro binding of the PYY compounds to the Y1, Y2, Y4 and Y5 receptor subtypes, respectively. The receptor binding affinity is a measure of affinity of a compound for the human Y1, Y2, Y4 and Y5 receptor subtypes, respectively.

The in vitro binding of the PYY compounds of examples 3-38 were determined in a scintillation proximity assay (SPA) as described below. hPYY(3-36) (Example 2, SEQ ID NO:2) was included as a reference.

Scintillation Proximity Assay (SPA)

NPY-Receptor Expressing Cell Lines.

All cells were cultured at +37° C. in a humidified atmosphere with 5% $CO_2$. BHK-482-8 cells with inducible expression of the human Y1 receptor (P25929, NPY1R_HUMAN, Uniprot) were cultured in Dulbecco's Modified Eagle Medium (DMEM) with 10% Fetal bovine serum (FBS), 1% Penicillin-Streptomycin (P/S), 1 mg/ml G418 antibotic, 1 mg/ml Hygromycin B antibiotic and 1% Non-essential amino acids. 1 mM Isopropyl β-D-1-thiogalactopyranoside (IPTG) was added 24 hours prior to harvesting cells for induction of NPY-Y1 receptor expression. CHO-K1 cells stably expressing the human Y2 receptor (P49146, NPY2R_HUMAN, Uniprot) were cultured in DMEM F-12 with 10% FBS, 1% P/S, 150 µg/ml Hygromycin B and 10 µg/ml Puromycin antibiotic. CHO-K1 cells stably expressing the human Y4 receptor (P50391, NPY4R_HUMAN, Uniprot) were cultured in DMEM F-12 with 10% FBS, 1% P/S, 10 µg/ml Puromycin. HEK-293 cells stably expressing the human Y5 receptor (Q15761, NPY5R_HUMAN, Uniprot) were cultured in DMEM F-12 medium containing 10% FBS, 1% Penicillin-Streptomycin, 250 µg/ml G418 and 1 µg/ml puromycin.

Membrane Preparation.

Cultured cells were detached mechanically by scraping and washed in ice cold PBS (137 mM NaCl, 2.7 mM KCl, 4.3 mM $Na_2HPO_4$, 1.47 mM $KH_2PO_4$ pH adjusted to 7.4) and transferred to tubes and centrifuged for 5 minutes at 1000 g at +4° C. Pellets were resuspended in ice cold homogenization buffer; Y1: 20 mM Hepes, 10 mM EDTA, with 2 complete EDTA-free protease inhibitor cocktail tablets/50 ml (Roche, Mannheim, Germany) pH 7.4); Y2, Y4: 20 mM Hepes, 5 mM $MgCl_2$, 1 mg/ml Bacitracin, pH 7.1; Y5: 10 mM NaCl, 20 mM Hepes, 0.22 mM $KH_2PO_4$, 1.26 mM $CaCl_2$, 0.81 mM $MgSO_4$, pH 7.4 and then homogenized for 30 seconds using a tissue homogenizer at medium speed. The homogenate was centrifuged at 35000 g using an ultracentrifuge for 10 minutes at +4° C. and the supernatant was discarded and fresh homogenization buffer added. Homogenization of the pellet was repeated a total of three times. The final pellet was resuspended in a few milliliters of homogenization buffer and protein concentration was determined using the Bradford method and measured at 595 nm in a microplate reader. Protein concentration were adjusted to 1 mg/ml and transferred to cryotubes and stored at −80° C. 250 mM sucrose was added to Y5 membranes prior to freezing.

Assay.

Human Y receptor SPA binding assay were performed in white 96-well plates in a total volume of 200 µl per well. Wheat germ agglutinin coated beads containing scintillation liquid (PerkinElmer, Waltham, Mass., USA) were reconstituted in binding buffer; Y1, Y2: 50 mM Hepes, 1 mM $CaCl_2$, 5 mM $MgCl_2$, 0.02% tween 20, 0.25% ovalbumin pH 7.4; Y4, Y5: 20 mM Hepes, 10 mM NaCl, 0.22 mM $KH_2PO_4$, 1.26 mM $CaCl_2$, 0.81 mM $MgSO_4$, 0.1% bacitracin and 0.25% ovalbumin pH 7.4 and mixed with membrane preparation to give final concentration of 1 mg beads and 3 µg of Y1 membranes/well, 3 µg of Y2 membranes/well, 1 µg of Y4 membranes/well or 20 µg of Y5 membranes/well. 50000 cpm per well of radio ligand human [$^{125}$I]-PYY was added corresponding to a concentration of 100 pM in Y1, Y2 and Y5 binding assays. 50000 cpm per well of radio ligand human [$^{125}$I]-Pancreatic Polypeptide (PP) corresponding to a concentration of 100 pM was used in Y4 binding assay.

Freeze dried analogues were dissolved in 80% dimethyl sulfoxide (DMSO), 19% $H_2O$ and 1% acetic acid ($CH_3COOH$) to stock solutions of 2000 pM (Y1, Y4 and Y5) and 200 µM (Y2) and serial dilutions (1:10) were performed in binding buffer to final concentrations ranging from 10000 nM to 1 pM in the Y1, Y4 and Y5 assays and 1000 nM to 0.1 pM in the Y2 assay. Plates were sealed and incubated at +25° C. for 2 hours in a plate shaker set at 400 rpm and thereafter centrifuged at 1500 rpm for 10 minutes prior to reading of luminescence on a microplate scintillation and luminescence counter. Y1 SPA plates were let to stand in room temperature for 16 hours prior to reading. Displacement of radioligand was measured as reduction in luminescence and $IC_{50}$ values were calculated by nonlinear regression analysis of sigmoidal dose-response curves. Ki values for binding affinity were acquired by the Cheng-Prusoff equation ($K_i=IC_{50}/(1+[L]/K_d)$) including receptor specific Kd values (Y1=0.556 nM; Y2=0.275 nM; Y4=0.111 nM; Y5=0.345 nM), radioligand concentration and IC50 values.

TABLE 2

Y receptor binding affinity

| Example | Compound | Y2 Ki (nM) | Y1 Ki (nM) | Y4 Ki (nM) | Y5 Ki (nM) |
|---|---|---|---|---|---|
| 2 | hPYY(3-36) SEQ ID NO: 2 | 0.25 | 45.5 | 83 | 4.5 |
| 3 | SEQ ID NO: 3 | 0.21 | 443 | 51 | 15 |
| 4 | SEQ ID NO: 4 | 0.7 | 5089 | 788 | 379 |
| 5 | SEQ ID NO: 5 | 1.3 | 8021 | 9866 | 252 |
| 6 | SEQ ID NO: 6 | 5.7 | 6388 | >10000 | 894 |
| 7 | SEQ ID NO: 7 | 1.5 | 6370 | 7337 | 713 |

TABLE 2-continued

Y receptor binding affinity

| Example | Compound | Y2 Ki (nM) | Y1 Ki (nM) | Y4 Ki (nM) | Y5 Ki (nM) |
|---|---|---|---|---|---|
| 8 | SEQ ID NO: 8 | 0.87 | >10000 | 8881 | 427 |
| 9 | SEQ ID NO: 9 | 3.2 | >10000 | 9068 | 495 |
| 10 | SEQ ID NO: 10 | 48 | >10000 | >10000 | 5534 |
| 11 | SEQ ID NO: 11 | 1.1 | >10000 | 6077 | 246 |
| 12 | SEQ ID NO: 12 | 3.3 | >10000 | 9807 | 665 |
| 13 | SEQ ID NO: 13 | 1.4 | 1666 | 7984 | 275 |
| 14 | SEQ ID NO: 14 | 4.8 | >10000 | 9968 | 803 |
| 15 | SEQ ID NO: 15 | 6.1 | >10000 | >10000 | 2027 |
| 16 | SEQ ID NO: 16 | 3.0 | >10000 | >10000 | 1152 |
| 17 | SEQ ID NO: 17 | 0.93 | 8853 | 371 | 166 |
| 18 | SEQ ID NO: 18 | 4.0 | >10000 | 9584 | 621 |
| 19 | SEQ ID NO: 19 | 2.1 | >10000 | 6188 | 760 |
| 20 | SEQ ID NO: 20 | 7.0 | >10000 | 6730 | 2540 |
| 21 | SEQ ID NO: 21 | 3.3 | >10000 | 6587 | 1584 |
| 22 | SEQ ID NO: 22 | 5.0 | >10000 | 8601 | 2274 |
| 23 | SEQ ID NO: 23 | 3.7 | >10000 | 3115 | 1224 |
| 24 | SEQ ID NO: 24 | 4.8 | >10000 | 6276 | 1848 |
| 25 | SEQ ID NO: 25 | 5.6 | 9200 | 7196 | 1947 |
| 26 | SEQ ID NO: 26 | 6.1 | >10000 | 8852 | 3052 |
| 27 | SEQ ID NO: 27 | 2.7 | >10000 | 5411 | 1437 |
| 28 | SEQ ID NO: 28 | 6.5 | >10000 | 4912 | 2623 |
| 29 | SEQ ID NO: 29 | 8.3 | >10000 | 6427 | 2326 |
| 30 | SEQ ID NO: 30 | 1.2 | >10000 | 6826 | 690 |
| 31 | SEQ ID NO: 31 | 4.0 | >10000 | 3040 | 2000 |
| 32 | SEQ ID NO: 32 | 0.84 | >10000 | 4138 | 305 |
| 33 | SEQ ID NO: 33 | 2.6 | >10000 | 5182 | 1622 |
| 34 | SEQ ID NO: 34 | 4.3 | >10000 | 7692 | 1436 |
| 35 | SEQ ID NO: 35 | 7.5 | >10000 | >10000 | 1573 |
| 36 | SEQ ID NO: 36 | 1.5 | 6972 | 321 | 75 |
| 37 | SEQ ID NO: 37 | 0.37 | 2591 | 177 | 17 |
| 38 | SEQ ID NO: 38 | 0.87 | 3767 | 403 | 935 |

The PYY compounds of the invention all display good Y2 binding while the binding affinity on the receptors Y1, Y4 and Y5 is strongly reduced.

Example 41

Pharmacokinetic Study in Minipigs

The purpose of this study is to determine the half-life in vivo of the PYY compounds after i.v. administration to minipigs, i.e. the prolongation of their time in the body and thereby their time of action. This is done in a pharmacokinetic (PK) study, where the terminal half-life of the derivative in question is determined. By terminal half-life is generally meant the period of time it takes to halve a certain plasma concentration, measured after the initial distribution phase.

In Vivo Studies on Pharmacokinetic Evaluation in Göttingen Minipigs after Intravenous Administration.

Animals.

Göttingen minipigs female, 15-25 kg, purchased from Ellegaard Minipigs, Denmark. The animals were housed in the Animal Unit, Novo Nordisk A/S and were kept and handled according to normal procedure in the Animal Unit. After minimum 2 weeks of acclimatization two permanent central venous catheters were implemented in vena cava caudalis in each animal. After surgery the animals were in their normal individual pens during the pharmacokinetic experiments.

Body Weight.

The animals were weighed weekly. The animals were fasted on the morning prior to dosing but had ad libitum access to water; food was supplied during dosing.

Administration of Peptides and Dosing Solutions.

Intravenous injections were given through the central short catheter, which was flushed with minimum 10 ml of sterile saline post administration. The test substance was dosed at 15 nmol/kg, n=3, in a volume of 0.05 ml/kg. Buffer: 50 mM sodium phosphate, 70 mM sodium chloride, 0.05% tween 80, pH 7.4 or 20 mM HEPES, 2.2% glycerol, 0.05% Polysorbate 80, pH 6.5.

Blood Samples and Analysis.

Blood samples were taken through the central catheter according to the following schedule: Predose, 5, 15, 30, 45 min, 1 h, 1.5 h, 2 h, 3 h, 4 h, 6 h, 8 h, 10 h, 24 h, 48 h, 72 h, 96 h, 120 h, 168 h, 192 h, 216 h, 240 h, 264 h and 288 h. On day 1 the catheters are coupled to extension tubes, which will be removed at the end of day 1. Samples (0.8 ml) were taken through the catheter. Blood was collected in test tubes containing EDTA buffer (8 mM) and 50 µl Val-Pyr buffer (Stabilization buffer containing 3.097 g K3EDTA dissolved in 50 ml Trasylol and 0.5 ml 20 mM Val-Pyr was added. The pH was regulated to 7.4). After each blood sample the catheter was flushed with minimum 5 ml of sterile 0.9% NaCl and 10 IE/ml heparin. Aseptic technique was demanded to avoid bacterial growth in the catheter that increases the risk of clot formation in the catheter. Samples were kept on wet ice until centrifugation (10 min, 4° C., 1942 g). Afterwards, plasma (min. 200 µl) was transferred immediately to Micronic tubes and kept at −20° C. until analysis. The plasma samples were analysed by LC/MS as described below.

Data and Results.

Plasma concentration-time profiles was analysed by a non-compartmental pharmacokinetics analysis using Phoenix (Pharsight Inc., Mountain View, Calif., USA). Calculations were performed using individual concentration-time values from each animal.

Sample Analysis

Quantitative Assay for Plasma Samples.

The test substances were assayed in plasma by Turbulent Flow Chromatography coupled to Liquid Chromatography with subsequent Mass Spectrometric Detection (TFC/LC/MS). The selectivity of the method allowed various compounds to be quantitated in one sample, e.g. cassette dosing of four compounds per animal. The concentrations of the test substance in unknown samples were calculated using the peak area as a function of amount. Calibration graphs based on plasma samples spiked with the analyte were constructed by regression analysis. Typical dynamic range for the assay was 1-2,000 nmol/l. The method performance was assured by co-assaying quality control (QC) samples in duplicate at three concentration levels. Stock and working solutions of analytes were prepared in plasma and incubated by 37° C. for 1 hour.

Sample Preparation.

40.0 µl EDTA-plasma was added 160 µl 50% methanol, 1% formic acid, then vortexed and centrifuged at 14300 rpm (16457 g) at 4° C. for 20 minutes. The supernatant was transferred to a 96 well plate, (the plates have been preincubated with 0.4% BSA, 37° C. for ½ hour). Injection volume was 25 µl.

For sample clean up a TurboFlow Cyclone column (0.5×50 mm) both from Thermo Scientific, Franklin, Mass., USA, was used and the LC separation was done either on an Onyx C18 column (2.0×50 mm) from Phenomenex, Torrance, Calif., USA. Eluents were isocratic and gradient combinations of methanol, acetonitril, Milli-Q water and formic acid. Selective detection was done by mass spectrometry operated in positive mode ionisation.

Data Handling.

Plasma concentration-time profiles was analysed by a non-compartmental pharmacokinetics analysis using Phoenix (Pharsight Inc., Mountain View, Calif., USA). Calculations were performed using individual concentration-time values from each animal.

TABLE 3

Half-life (t½)

| Example | Compound | t½ (hours) |
|---|---|---|
| 2 | hPYY(3-36) SEQ ID NO: 2 | 0.33 |
| 7 | SEQ ID NO: 7 | 63 |
| 9 | SEQ ID NO: 9 | 72 |
| 11 | SEQ ID NO: 11 | 28 |
| 12 | SEQ ID NO: 12 | 65 |
| 13 | SEQ ID NO: 13 | 55 |
| 14 | SEQ ID NO: 14 | 52 |
| 15 | SEQ ID NO: 15 | 29 |
| 16 | SEQ ID NO: 16 | 50 |
| 17 | SEQ ID NO: 17 | 58 |
| 18 | SEQ ID NO: 18 | 66 |
| 19 | SEQ ID NO: 19 | 89 |
| 20 | SEQ ID NO: 20 | 14 |
| 21 | SEQ ID NO: 21 | 52 |
| 22 | SEQ ID NO: 22 | 11 |
| 25 | SEQ ID NO: 25 | 53 |
| 26 | SEQ ID NO: 26 | 52 |
| 27 | SEQ ID NO: 27 | 59 |
| 28 | SEQ ID NO: 28 | 50 |
| 30 | SEQ ID NO: 30 | 73 |
| 31 | SEQ ID NO: 31 | 30 |
| 33 | SEQ ID NO: 33 | 58 |
| 34 | SEQ ID NO: 34 | 62 |
| 35 | SEQ ID NO: 35 | 61 |
| 36 | SEQ ID NO: 36 | 83 |

The tested PYY compounds of the invention have very long half-lives as compared to the half-life of hPYY(3-36).

Example 42

Pharmacodynamic Studies in db/db Mice

In order to determine the in vivo effects of the PYY compounds on blood glucose and food intake in a diabetic setting, the compounds were tested in an obese, diabetic mouse model (db/db mice) as described below.

Male db/db mice are housed in a normal daily rhythm (6 μm to 6 am dark cycle) and provided ad libitum access to Altromin diet. At 11-13 weeks of age the mice are matched for blood glucose as well as body weight and divided into matching groups of 9 mice and housed 3 per cage. Mice are dosed subcutaneously with the indicated compound or vehicle (50 mM Na2HPO4, pH 7.4, 70 mM NaCl, 0.05% Tween 80) at a volume of 2.5 ml/kg at the indicated doses at 4 μm (time=0) and in some experiments a second injection was given at time=23 hours. Blood glucose and food intake are measured at the indicated time points post injection, e.g at 4 hours (4 h), 16 hours (16 h), 23 hours (23 h) and 40 hours (40 h) post injection. Blood samples for blood glucose are taken from the tail vein, into a 5 μl heparin coated capillary tube which is placed in an eppendorf tube with Biosen® system solution (250 μl). The samples are analysed on a Biosen® instrument immediately.

Blood glucose (BG) measurements are reported as mean±SEM of vehicle adjusted % BG relative to pre-treatment and calculated as follows:

100−[% BG(vehicle,average)−% BG]

where,
% BG=100*[BG(time=t)/BG(pre-treatment)]
and % BG(vehicle,average)=average of % BG values for the vehicle group at time=t relative to vehicle pre-treatment.

Food intake is reported as mean±SEM food intake per cage as a percentage of average food intake of the vehicle group for the indicated interval.

TABLE 4

Effect on blood glucose in db/db mice. Blood glucose (BG) measurements are reported as mean ± SEM of vehicle adjusted % BG relative to pre-treatment.

| Example | Compound | Dose (μmol/kg) | % relative change in blood glucose | | | |
|---|---|---|---|---|---|---|
| | | | 4 h | 16 h | 23 h | 40 h |
| 7 | SEQ ID NO: 7 | 0.3 | 77 | 88 | 83 | 86 |
| 8 | SEQ ID NO: 8 | 1 | nd | 68 | 55 | nd |
| 9 | SEQ ID NO: 9 | 1 | 73 | 70 | 66 | 66 |
| 11 | SEQ ID NO: 11 | 1 | nd | 62 | 48 | nd |
| 12 | SEQ ID NO: 12 | 1 | 70 | 68 | 73 | 67 |
| 14 | SEQ ID NO: 14 | 1 | 47 | 47 | 35 | 37 |
| 15 | SEQ ID NO: 15 | 1 | nd | 78 | 68 | nd |
| 16 | SEQ ID NO: 16 | 0.3 | 67 | 59 | 70 | 68 |
| 16 | SEQ ID NO: 16 | 1 | 64 | 47 | 44 | 40 |
| 17 | SEQ ID NO: 17 | 1 | nd | 58 | 42 | nd |
| 18 | SEQ ID NO: 18 | 0.3 | 66 | 53 | 56 | 64 |
| 18 | SEQ ID NO: 18 | 1 | 67 | 56 | 49 | 62 |
| 19 | SEQ ID NO: 19 | 1 | nd | 47 | 30 | nd |
| 20 | SEQ ID NO: 20 | 1 | 58 | 86 | 83 | nd |

TABLE 5

Effect on food intake in db/db mice. Food intake is reported as mean ± SEM foo dintake per cage as a percentage of average food intake of the vehicle group for the indicated interval.

| Example | Compound | Dose (μmol/kg) | % relative food intake | | | |
|---|---|---|---|---|---|---|
| | | | 4 h | 16 h | 23 h | 40 h |
| 7 | SEQ ID NO: 7 | 0.3 | 27 | 34 | 45 | 54 |
| 8 | SEQ ID NO: 8 | 1 | nd | 33 | 24 | nd |
| 9 | SEQ ID NO: 9 | 1 | 16 | 14 | 16 | 16 |
| 11 | SEQ ID NO: 11 | 1 | nd | 24 | 20 | nd |
| 12 | SEQ ID NO: 12 | 1 | 20 | 23 | 22 | 22 |
| 14 | SEQ ID NO: 14 | 1 | 11 | 14 | 13 | 15 |
| 15 | SEQ ID NO: 15 | 1 | nd | 13 | 26 | nd |
| 16 | SEQ ID NO: 16 | 0.3 | 6.5 | 12 | 19 | 27 |
| 16 | SEQ ID NO: 16 | 1 | 6.5 | 8.0 | 7.1 | 12 |
| 17 | SEQ ID NO: 17 | 1 | nd | 18 | 23 | nd |
| 18 | SEQ ID NO: 18 | 0.3 | 10 | 17 | 24 | 32 |
| 18 | SEQ ID NO: 18 | 1 | 12 | 12 | 20 | 21 |
| 19 | SEQ ID NO: 19 | 1 | nd | 7.6 | 6.7 | nd |
| 20 | SEQ ID NO: 20 | 1 | 0 | 56 | 61 | nd |

These data strongly support the blood glucose lowering effect and the inhibition of food intake of the PYY compounds of the invention.

Example 43

Physical Stability

The aim of this study is to determine the stability of peptide formulations in the presence and absence of phenol. As a measure of stability of the peptide formulation, the formation of high molecular weight peptide formation (% HMWP) as a function of time was analysed by size-exclusion HPLC (SE-HPLC).

Formulations:

The analogues were solubilised to 1 mM in 30 mM Na-phosphate buffer, 10 mM NaCl pH 8.2. If necessary the pH of the stock solution was adjusted with NaOH. These stock solutions were further diluted in in the above mentioned buffer or in a corresponding buffer containing phenol, giving the final formulations with the compositions as shown in table 6.

Incubation:

The samples were divided into UPLC vials with tight screw caps and stored incubated at 37° C. and 5° C., samples at 37° C. were moved to 5° C. or analysed after 1, 2 and 4 weeks. The 5° C. sample is used as start value.

Analysis Method:

The HMWP content was analysed using a dissociating SE-HPLC method with a Waters Insulin HMWP SEC column (7.8×300 mm) with a column temperature of 50° C. The samples were eluted by isocratic elution with an eluent of 500 mM NaCl, 10 mM NaH2PO4, 5 mM H3PO4, 50% (v/v) 2-propanol at a flow rate of 0.5 ml/min. Detection was carried out at 215 nm.

As can be seen from table 6, adding a N-terminal substituent such as 3-methylbutanoyl reduces the formation of aggregates (high molecular weight proteins—HMWP). Changing lysine in position 4 to an arginine also reduces the formation of aggregates. Combining the addition of a N-terminal substituent and the change of lysine in position 4 to an arginine reduces the formation of aggregates remarkably.

TABLE 6

HMWP formation

| Formu-lation No. | Compound (0.2 mM) of Example | Phosphate (mM) | NaCl (mM) | Phenol (mM) | pH | HMWP formation (%/month) |
|---|---|---|---|---|---|---|
| 1A | 18 | 30 | 10 | — | 8.2 | 0.5 |
| 1B | 18 | 27 | 9 | 58 | 8.2 | 1.6 |
| 2A | 16 | 30 | 10 | — | 8.2 | 1.0 |
| 2B | 16 | 27 | 9 | 58 | 8.2 | 13.0 |
| 3A | 8 | 29 | 10 | — | 8.2 | 1.9 |
| 3B | 8 | 26 | 8 | 55 | 8.2 | 19.1 |
| 4A | 11 | 29 | 10 | — | 8.2 | 0.7 |
| 4B | 11 | 26 | 8 | 55 | 8.2 | 7.5 |

Example 44

Pharmacodynamic Effect of Combination Treatment with a PYY Compound and a GLP-1 Agonist in Female Landrace Yorkshire Duroc (LYD) Pigs In order to determine the in vivo effects of the combination treatment with a PYY compound and a GLP-1 agonist on food intake in pigs, the effect of either the GLP-1 agonist liraglutide alone or a combination of liraglutide and the PYY compound of Example 18 (SEQ ID NO:18) were measured as described below.

Materials and Methods.

WO 98/08871 discloses liraglutide (example 37), including a method of preparation liraglutide.

Effect on food intake was studied in female Landrace Yorkshire Duroc (LYD) pigs (Askelygaard, Roskilde, Denmark), approximately 3 months of age, weighing 30-43 kg (n=4). The animals were acclimatised for 1-2 weeks before the study and were fed ad libitum with pig chow (Svine 5, Brogaarden, Denmark) at all times both during the acclimatisation and the experimental period. During the experimental period the animals were placed in individual pens for measurement of individual food intake using the system Mpigwin (Ellegaard Systems, Faaborg, Denmark). Any spillage of food (food waste) was collected and weighed, and the measured food intake was manually corrected for this amount (corrected food intake).

The PYY compound of example 18 (SEQ ID NO:18) was tested as a single s.c. administration of 2 different doses, 25 and 50 nmol/kg, in combination with 3 nmol/kg liraglutide. Liraglutide was dosed s.c. once daily from day −4 to day 3 (0.017 mL/kg corresponding to 2 nmol/kg the first 2 days, and then 0.025 mL/kg corresponding to 3 nmol/kg the remaining 6 days). The PYY analogue was dosed once in the morning of day 0 (dose volume was 0.025 mL/kg). The PYY analogue was formulated in the following buffer that also served as a vehicle for the PYY injections: 50 mM sodium phosphate 70 mM sodium chloride, 0.05% tween 80, pH 7.4. Liraglutide was formulated in the following buffer that also served as vehicle for the daily liraglutide injections: 8 mM phosphate, 184 mM propylenglycol, 58 mM phenol, pH 8.15.

The individual food intake in percent of mean vehicle food intake was calculated on day 0-4 and evaluated statistically with two-way ANOVA followed by Bonferroni's post test. Body weight change from day 0 to day 4 was calculated and evaluated statistically with one-way ANOVA followed by Bonferroni's post test.

TABLE 7

Percent food intake of vehicle on day 0-1 to day 3-4 after dosing of vehicle, liraglutide 3 nmol/kg, PYY analogue 25 nmol/kg in combination with liraglutide 3 nmol/kg and PYY analogue 50 nmol/kg in combination with liraglutide 3 nmol/kg in young, growing LYD pigs. Dosing of liraglutide was done once daily in the morning of day -4 to day 3, whereas the PYY compound of example 18 (SEQ ID NO: 18) was given as a single s.c. dose in the morning of day 0. N = 4. Data presented as mean. Two-way ANOVA followed by Bonferroni's post test.

| Day | Vehicle | Liraglutide 3 nmol/kg | Liraglutide 3 nmol/kg + SEQ ID NO: 18 25 nmol/kg | Liraglutide 3 nmol/kg + SEQ ID NO: 18 50 nmol/kg |
|---|---|---|---|---|
| 0-1 | 100.0 | 39.3 | 4.5 | 1.2 |
| 1-2 | 100.0 | 57.7 | 7.1 | 1.8 |
| 2-3 | 100.0 | 54.8 | 22.0 | 7.4 |
| 3-4 | 100.0 | 53.0 | 28.9 | 21.5 |

TABLE 8

Body weight change from day 0 to day 4 after dosing of vehicle, liraglutide 3 nmol/kg, the PYY compound of example 18 (SEQ ID NO: 18) 25 nmol/kg in combination with liraglutide 3 nmol/kg and the PYY compound of example 18 (SEQ ID NO: 18) 50 nmol/kg in combination with liraglutide 3 nmol/kg in young, growing LYD pigs. Dosing of liraglutide was done once daily in the morning of day -4 to day 3, whereas the PYY compound of example 18 (SEQ ID NO: 18) was given as a single s.c. dose in the morning of day 0. N = 4, data presented as mean. One-way ANOVA followed by Bonferroni's post test.

| | Vehicle | Liraglutide 3 nmol/kg | Liraglutide 3 nmol/kg + SEQ ID NO: 18 25 nmol/kg | Liraglutide 3 nmol/kg + SEQ ID NO: 18 50 nmol/kg |
|---|---|---|---|---|
| Delta BW day 0-4 (kg) | 4.5 | 3.1 | 0.4 | −2.3 |

In conclusion, these data strongly support the added benefits on inhibition of food intake and body weight lowering effect of combining PYY analogues with a GLP-1 analogue.

Example 45

Pharmacodynamic Effect of Combination Treatment with a PYY Analogue and a GLP-1 Analogue in db/db Mice In order to determine the in vivo effects of the combination treatment with a PYY compound and a GLP-1 agonist on blood glucose and body weight, the effect of either PYY compound, liraglutide alone or a combination were measured in an obese, diabetic mouse model (db/db mice) as described below.

Male db/db mice (9-10 weeks old) were used to measure the effect on blood glucose and body weight following treatment with varying doses of a PYY-derived analogue, the PYY compound of example 18 (SEQ ID NO:18), liraglutide (Lira), or both (combination). Prior to study mice were randomly assigned into groups that were matched for body weight, non-fasting blood glucose and HbA1c. Differences in blood glucose among groups were studied according to the dosing-schedule outlined in Table 9. Up-titration of SEQ ID NO:18 and liraglutide was used to prevent sudden appetite loss on days −9 to 0 prior the first dose (data not shown).

TABLE 9

Dosing-schedule outline

| 2 × daily treatment | Sample, n = | Dose given per injection days 1-8 (nmol/kg) | Dose given per injection days 9-16 | Dose given per injection days 17-24 |
|---|---|---|---|---|
| Vehicle + Vehicle | 9 | — | — | — |
| SEQ ID NO: 18 | 9 | 30 | 100 | 1000 |
| Liraglutide | 8 | 10 | 10 | 10 |
| SEQ ID NO: 18 + liraglutide | 9 | 15 + 5 | 50 + 5 | 1000 + 5 |
| SEQ ID NO: 18 + liraglutide | 8 | 30 + 10 | 100 + 10 | 1000 + 10 |

Briefly, compounds were administered subcutaneously (2.5 ml/kg) at 11:00 and 17:00 hour each day. The PYY compound of example 18 (SEQ ID NO:18) was given in 50 mM phosphate; 70 mM sodium chloride; 0.05% polysorbate 80 buffer (pH=8.0). Liraglutide was given in 50 mM phosphate; 70 mM sodium chloride; 0.05% polysorbate 80 buffer (pH=7.4). Blood glucose was measured at a single time point (9 am) after 3-5 days of treatment at each dose based on the glucose oxidase method, using a glucose analyzer (Biosen 5040). Body weight was measured the same day. The results are shown in table 10 below.

TABLE 10

The effect of varying doses of the PYY compound of example 18 (SEQ ID NO: 18) or liraglutide alone or, in combination, on blood glucose and body weight. Data presented as mean. Differences were analyzed via One-way ANOVA and Tukey's multiple comparisons test. Sample, n = 9.

| | 2 × daily treatment | Dose given per injection | Blood glucose (mmol/L) | Body weight (g) |
|---|---|---|---|---|
| Injection days 1-8 | vehicle + vehicle | Vehicle | 23.1 | 47.6 |
| | SEQ ID NO: 18 | 30 nmol/kg | 20.5 | 48.6 |
| | liraglutide | 10 nmol/kg | 15.4 | 47.6 |
| | SEQ ID NO: 18 + liraglutide | 15 + 5 nmol/kg | 9.9 | 46.4 |
| | SEQ ID NO: 18 + liraglutide | 30 + 10 nmol/kg | 6.6 | 44.0 |
| Injection days 9-16 | vehicle + vehicle | Vehicle | 25.3 | 46.8 |
| | SEQ ID NO: 18 | 100 nmol/kg | 20.2 | 47.7 |
| | liraglutide | 10 nmol/kg | 17.4 | 47.7 |
| | SEQ ID NO: 18 + liraglutide | 50 + 5 nmol/kg | 10.3 | 45.5 |
| | SEQ ID NO: 18 + liraglutide | 100 + 10 nmol/kg | 7.6 | 42.8 |
| Injection days 17-24 | vehicle + vehicle | Vehicle | 23.4 | 45.8 |
| | SEQ ID NO: 18 | 1000 nmol/kg | 13.7 | 45.3 |
| | liraglutide | 10 nmol/kg | 19.8 | 48.1 |
| | SEQ ID NO: 18 + liraglutide | 1000 + 5 nmol/kg | 6.2 | 41.9 |
| | SEQ ID NO: 18 + liraglutide | 1000 + 10 nmol/kg | 5.8 | 38.8 |

The glucose-lowering effect of the combination of the PYY compound of example 18 (SEQ ID NO:18) and liraglutide was significantly greater than the benefit produced by either compound in isolation. Glycemic levels were normalized in mice treated with the combination in the majority of the doses that were tested. Importantly, no instances of hypoglycemia were observed. The synergistic effect of the combination of the PYY compound of example 18 (SEQ ID NO:18) and liraglutide was also evident with respect to reductions in body weight. In conclusion, a combination of the PYY compound of example 18 (SEQ ID NO:18) and liraglutide synergistically lowers resting blood glucose and body weight, greatly reducing the amount of drug necessary to achieve the same, or similar, benefit produced by monotherapy.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A PYY compound, wherein the PYY compound has a maximum of 8 amino acid modifications as compared to hPYY(3-36), wherein the positions corresponding to positions 1-3 of hPYY(1-36) (SEQ ID NO:1) are absent, and wherein the PYY compound comprises (i) tryptophan at the position corresponding to position 30 of hPYY(1-36) (SEQ ID NO:1);

(ii) N(alpha)-methyl-L-arginine at a position corresponding to position 35 of hPYY(1-36) (SEQ ID NO:1);

(iii) glutamine at a position corresponding to position 18 of hPYY(1-36) (SEQ ID NO:1);

(iv) lysine at a position corresponding to position 7 of hPYY(1-36) (SEQ ID NO:1);

(v) a modifying group attached to the epsilon amino group of said lysine, wherein said modifying group is defined by A-B-C-, wherein A- is selected from

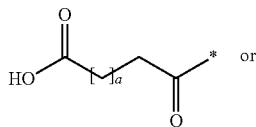

I

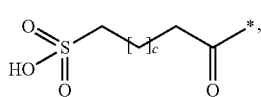

III wherein a is 15, c is 13, and wherein * denotes the attachment point to -B-;

B- is

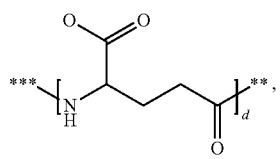

IV wherein d is 1; and wherein * denotes the attachment point to A-, and  denotes the attachment point to -C-;

-C- is

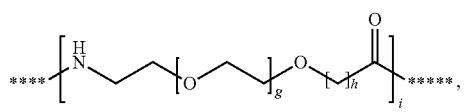

VII wherein g and h is each 1; i is 2; and wherein ** denotes the attachment point to -B-, and *** denotes the attachment point to the epsilon amino group of the Lysine residue in the position corresponding to position 7 of hPYY(1-36); and (vi) an N-terminal substituent, wherein the N-terminal substituent is selected from 3-methylbutanoyl, 3-methylpentanoyl or hexanoyl;

or a pharmaceutically acceptable salt thereof.

2. The PYY compound of claim 1, wherein the PYY compound has a maximum of 6 amino acid modifications as compared to hPYY(3-36).

3. The PYY compound of claim 2, wherein the PYY compound is selected from the following:

4-N{alpha}-(hexanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]ethoxy]- ethoxy]acetyl]-[Arg4, Lys7, Gln18, Trp30, NMeArg35] hPYY(4-36) (SEQ ID NO:12)

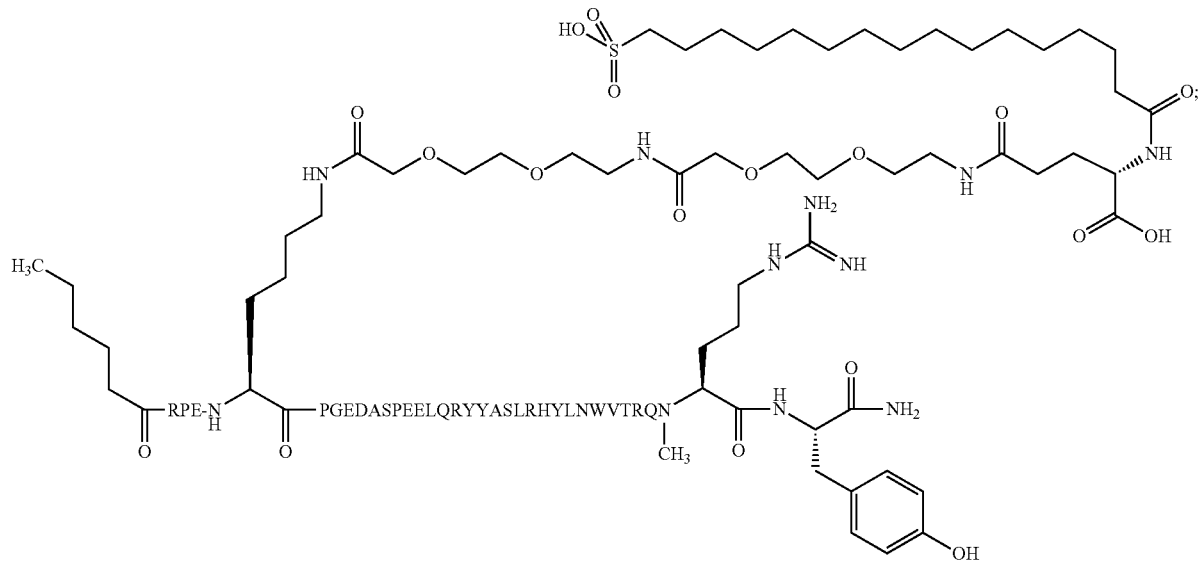

4-N{alpha}-(3-methyl-pentanoyl)-7-N{Epsilon}-[2-[2-[2-[[2-[2-[2-[[(4S)-4-carboxy-4-(17-carboxyheptade-canoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:13)

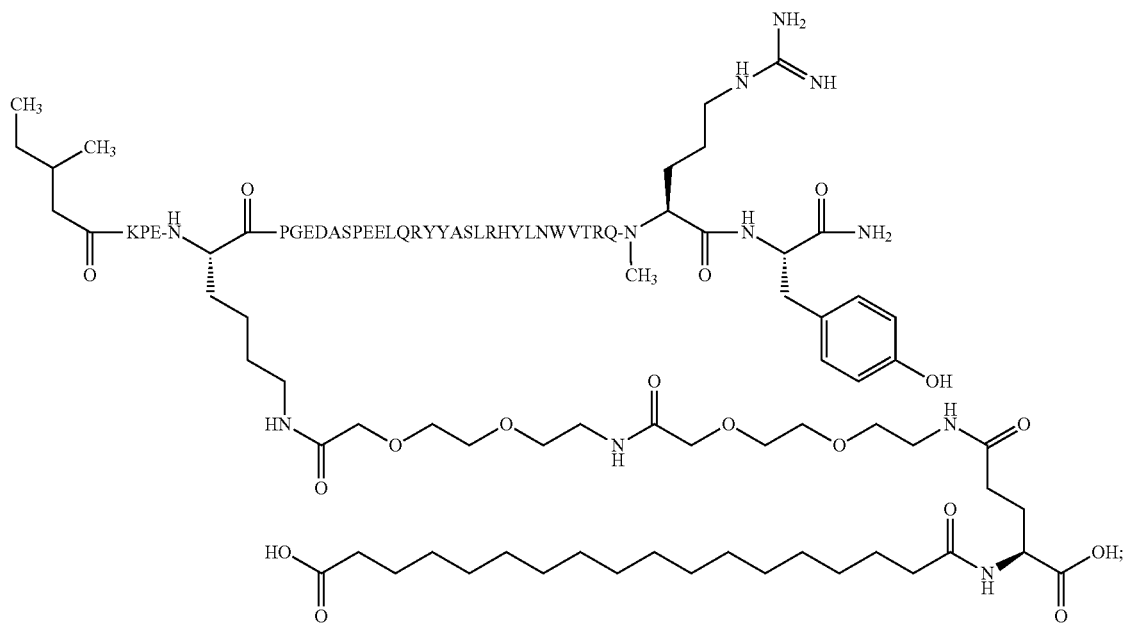

4-N{alpha}-(3-methyl-pentanoyl)-7-N{Epsilon}-[2-[2-[2-[[2-[2-[2-[[(4S)-4-carboxy-4-(16-sulfohexade-canoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:14)

181 182
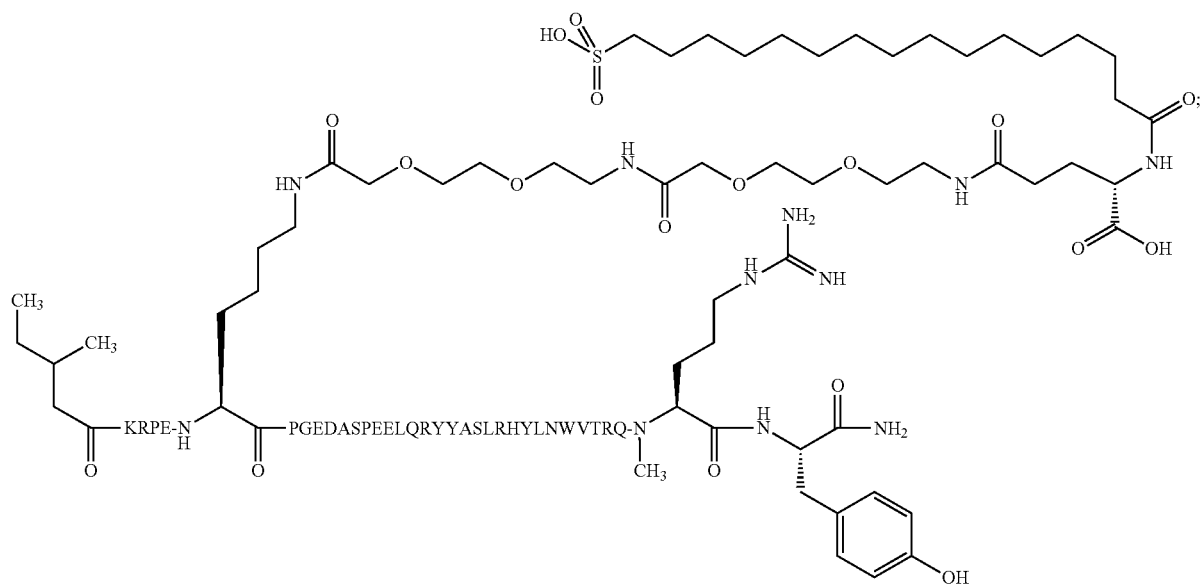
4-N{alpha}-(3-Methylbutanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:16)
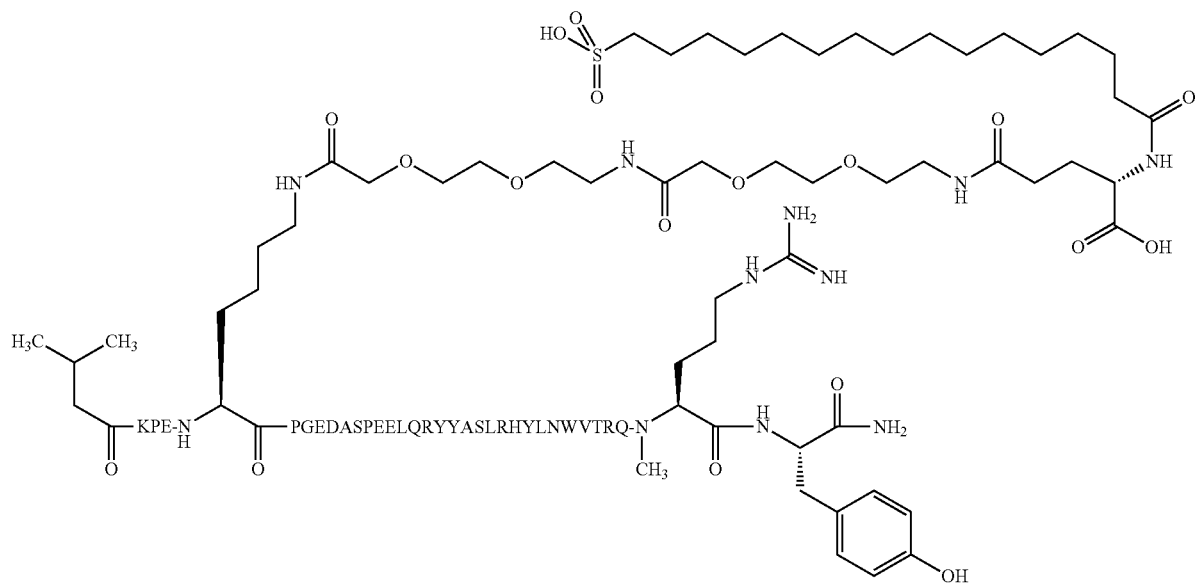
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)

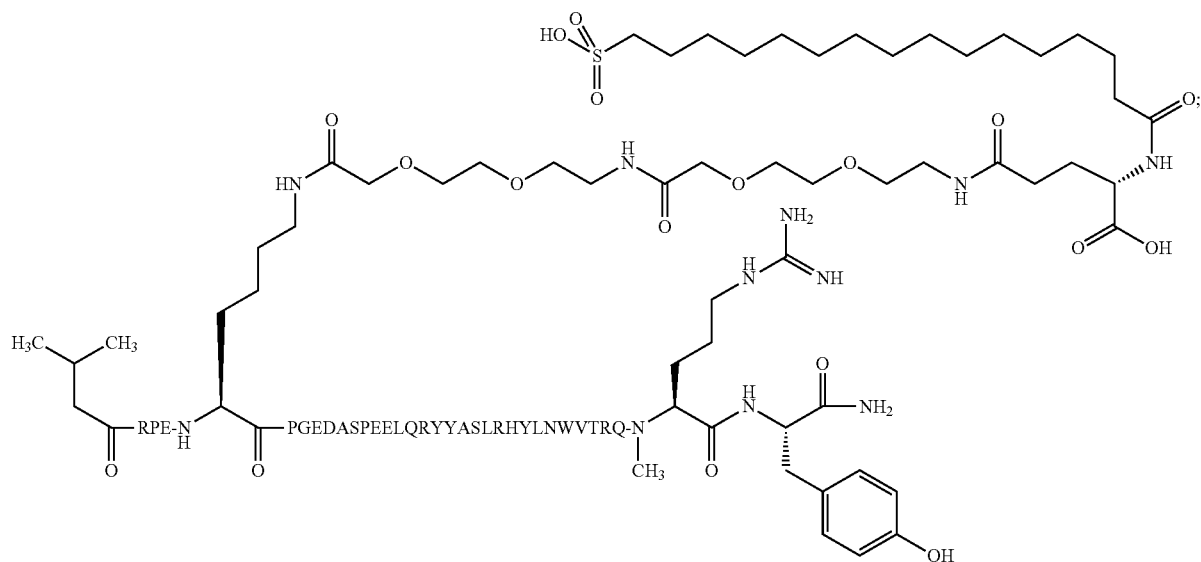

4-N{alpha}-(3-Methylbutanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:19)

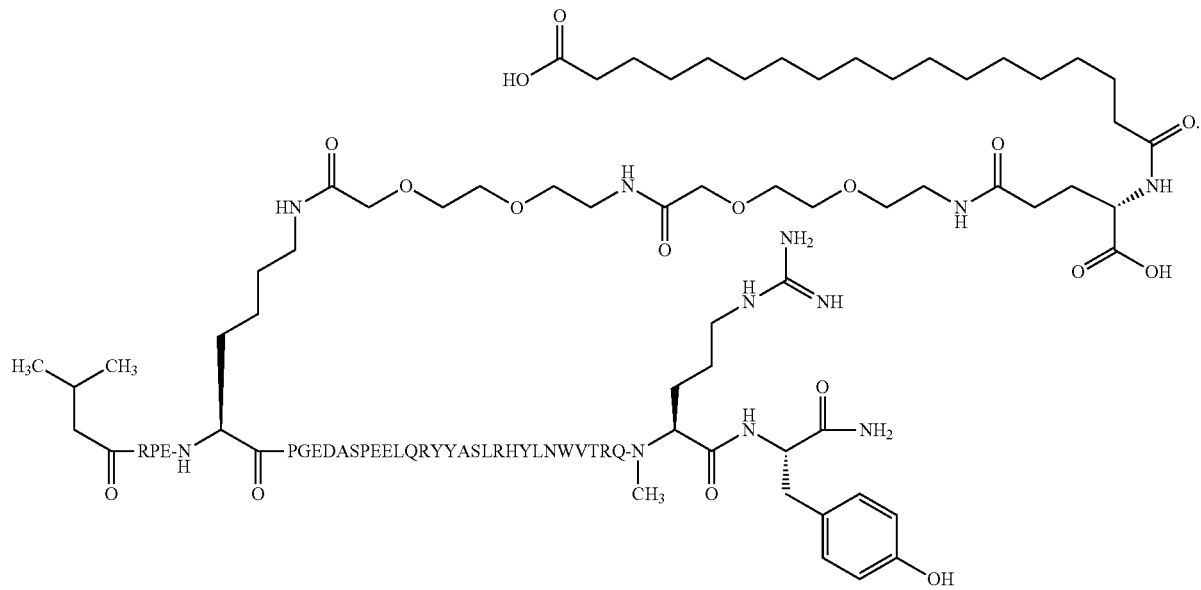

4. The PYY compound of claim 3, wherein the PYY compound is
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)

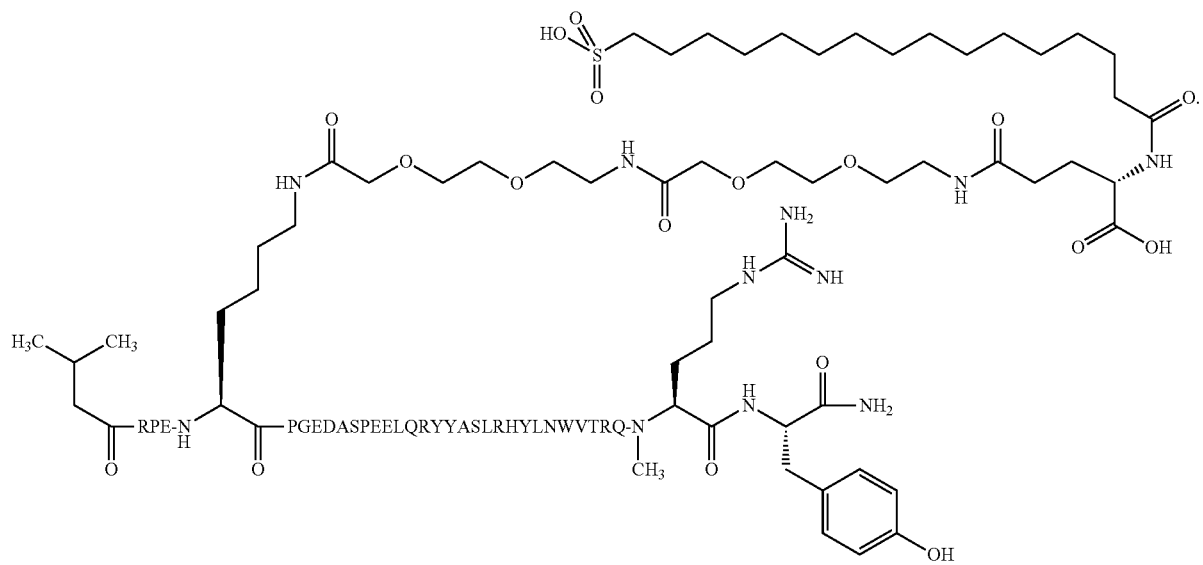

5. A pharmaceutical composition comprising the PYY compound of claim 1, and at least one pharmaceutically acceptable excipient.

6. The pharmaceutical composition of claim 5, wherein the PYY compound has a maximum of 6 amino acid modifications as compared to hPYY(3-36).

7. The pharmaceutical composition of claim 6, wherein the PYY compound is selected from the following:

4-N{alpha}-(hexanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]ethoxy]-ethoxy]acetyl]-[Arg4, Lys7, Gln18, Trp30, NMeArg35] hPYY(4-36) (SEQ ID NO:12)

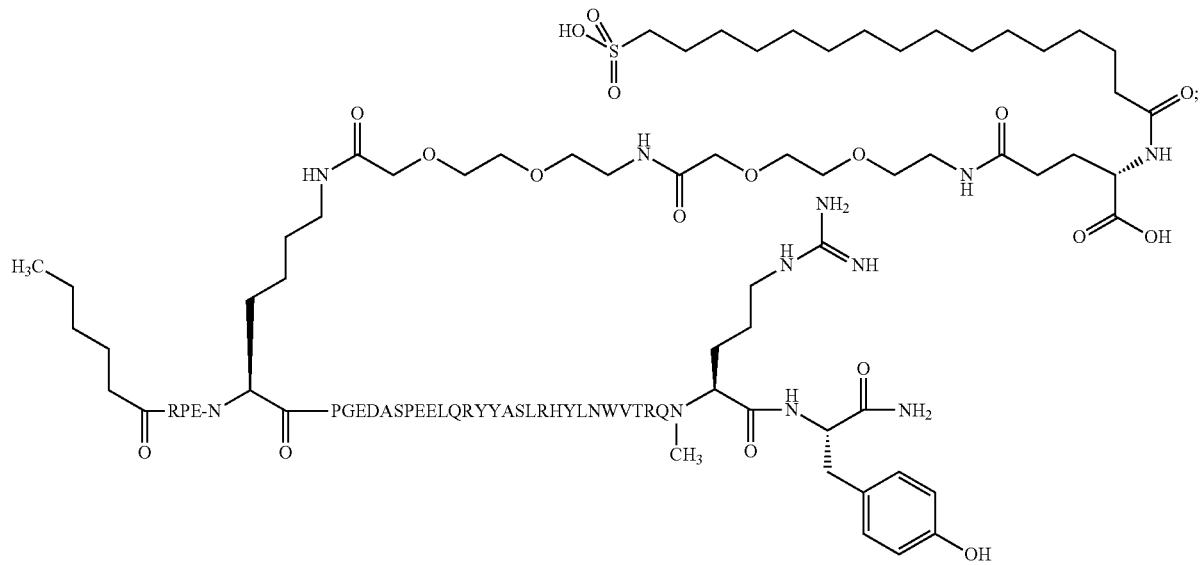

4-N{alpha}-(3-methyl-pentanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:13)

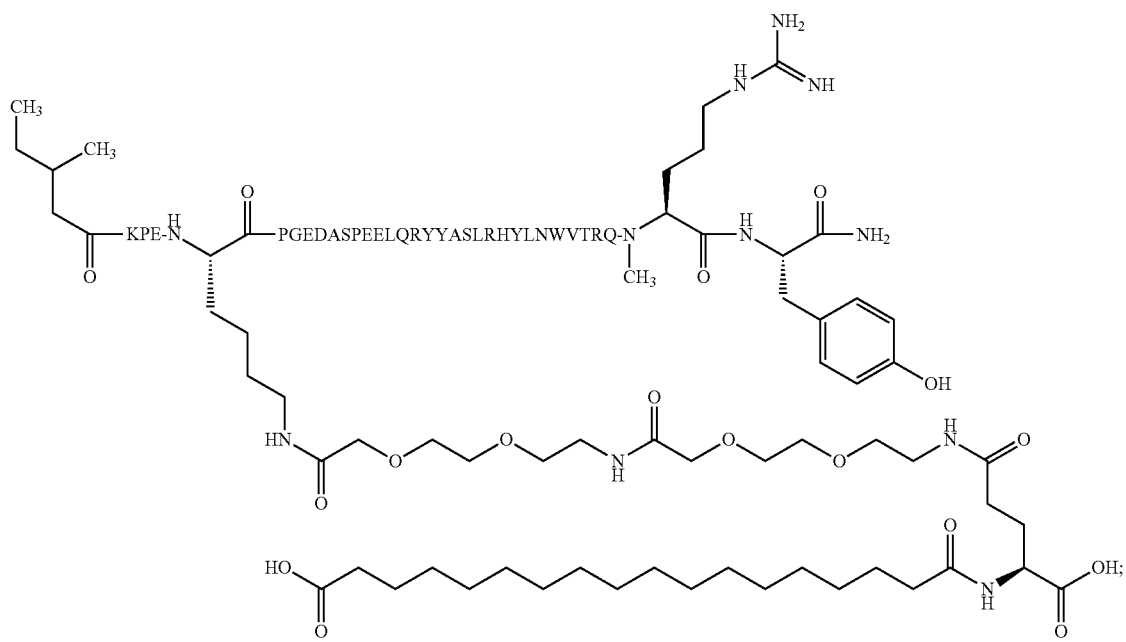
4-N{alpha}-(3-methyl-pentanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:14)
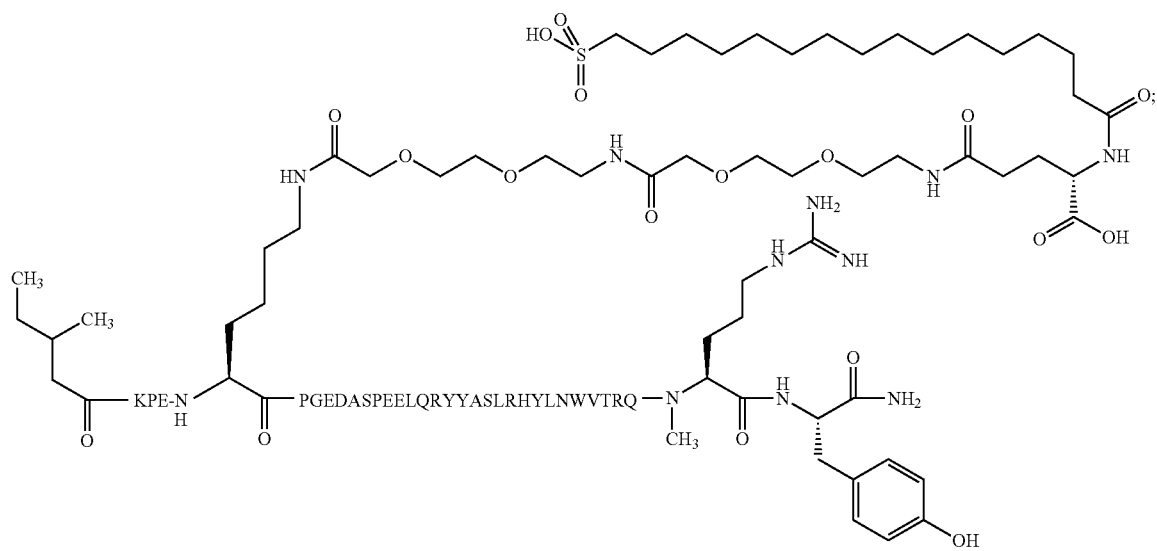
4-N{alpha}-(3-Methylbutanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:16)

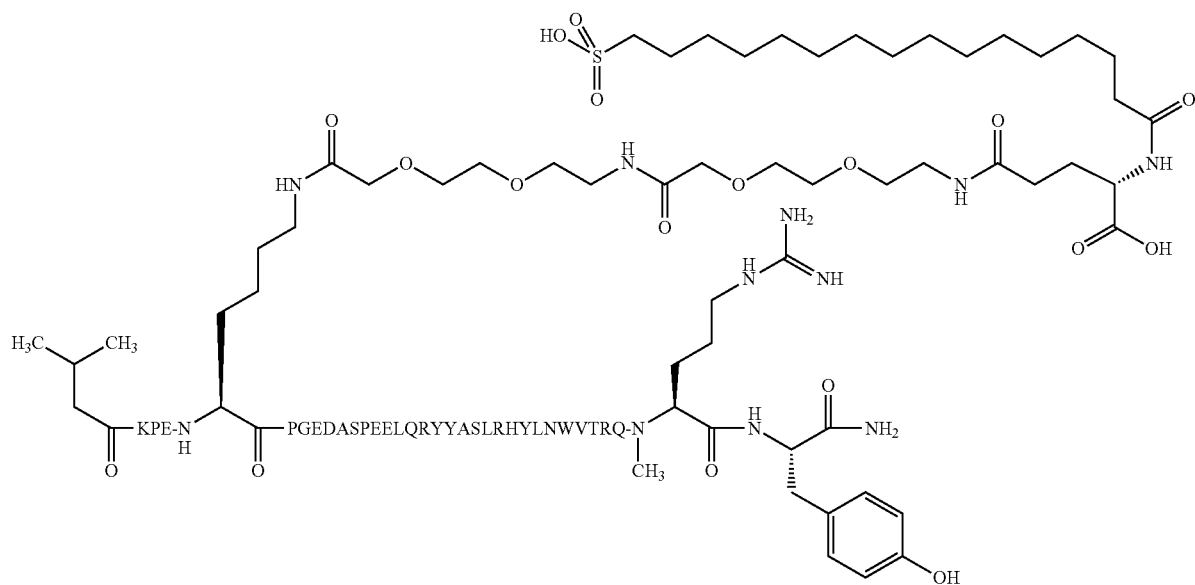
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)
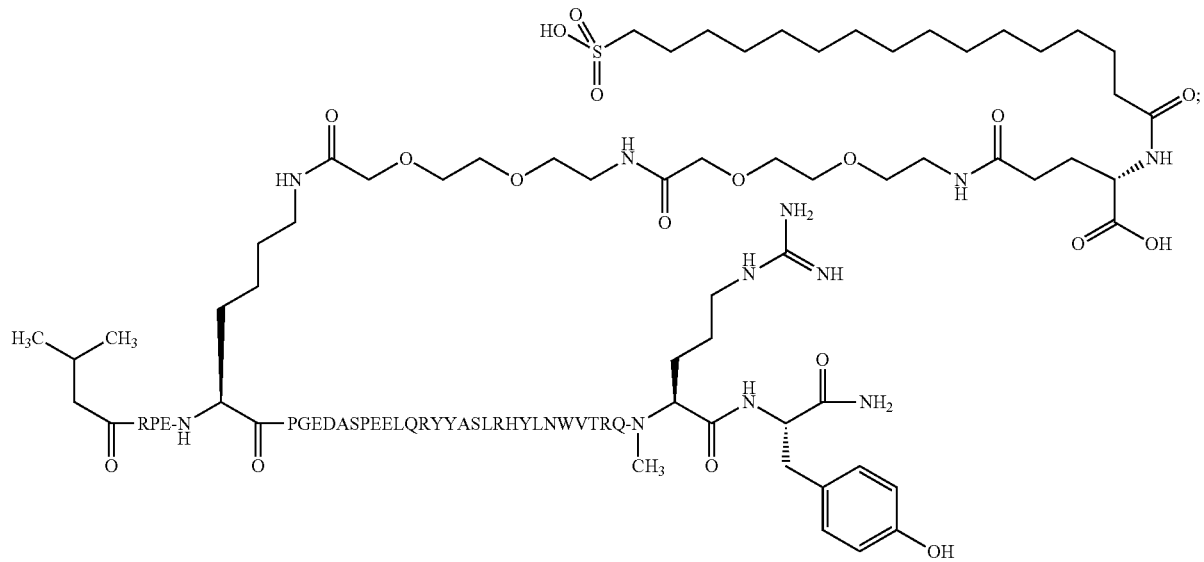
4-N{alpha}-(3-Methylbutanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:19)

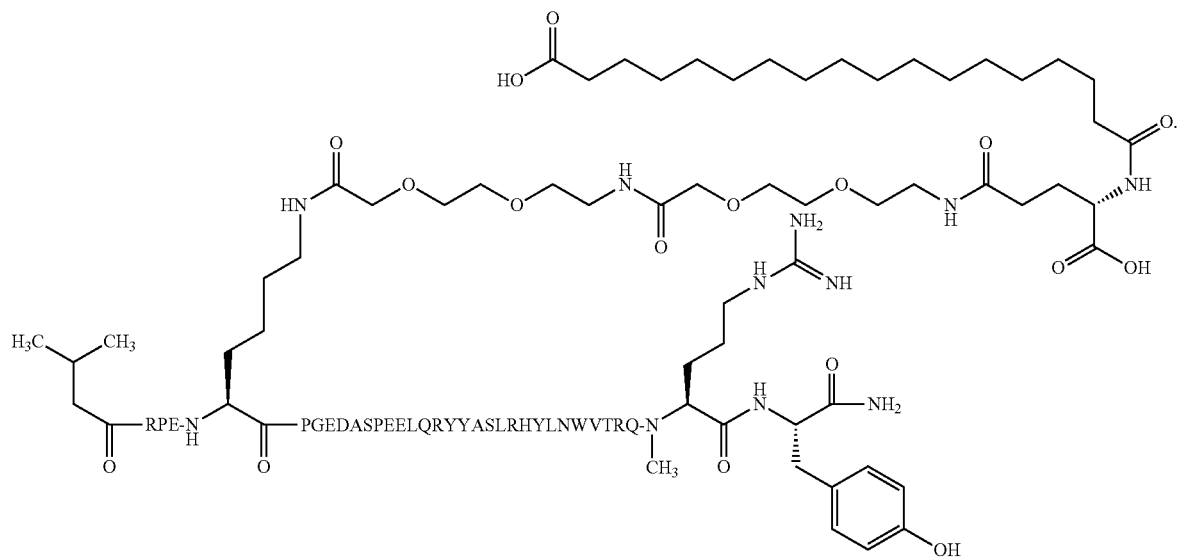

8. The pharmaceutical composition of claim 7, wherein the PYY compound is
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)

9. A pharmaceutical composition comprising the PYY compound of claim 1, a GLP-1 agonist, and at least one pharmaceutically acceptable excipient.

10. The pharmaceutical composition of claim 9, wherein the PYY compound has a maximum of 6 amino acid modifications as compared to hPYY(3-36).

11. The pharmaceutical composition of claim 10, wherein the PYY compound is selected from the following:
4-N{alpha}-(hexanoyl)-7-N{Epsilon}-[2-[2-[2-[[2-[2-[2-[[(4S)-4-carboxy-4-(16-sulfohexadecanoylamino)bu-tanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:12)

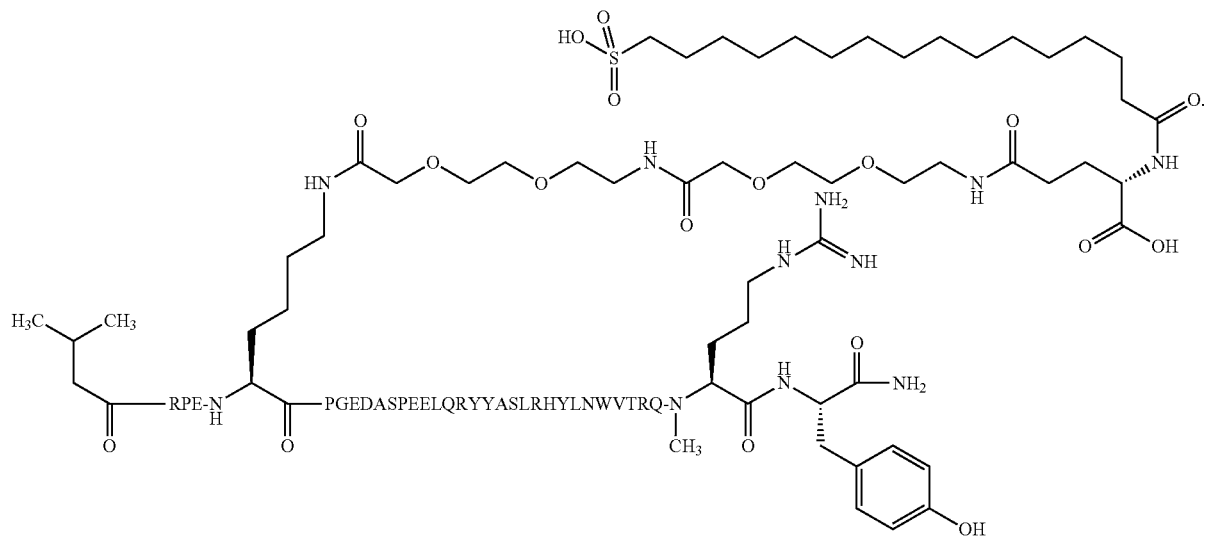

193
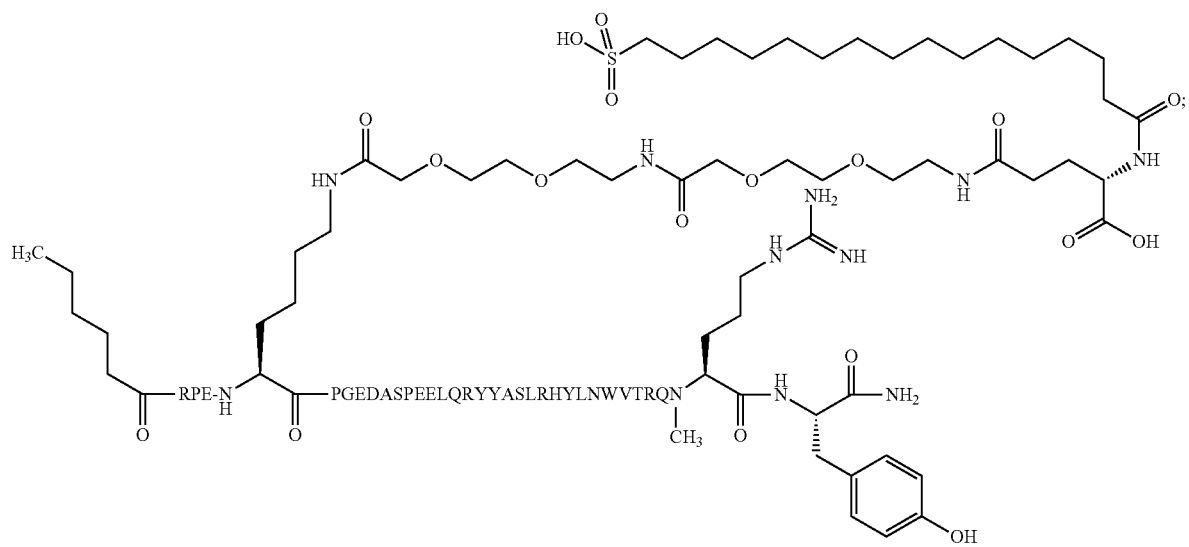
4-N{alpha}-(3-methyl-pentanoyl)-7-N{Epsilon}-[2-[2-[2-[[2-[2-[2-[[(4S)-4-carboxy-4-(17-carboxyheptade-canoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:13)
194
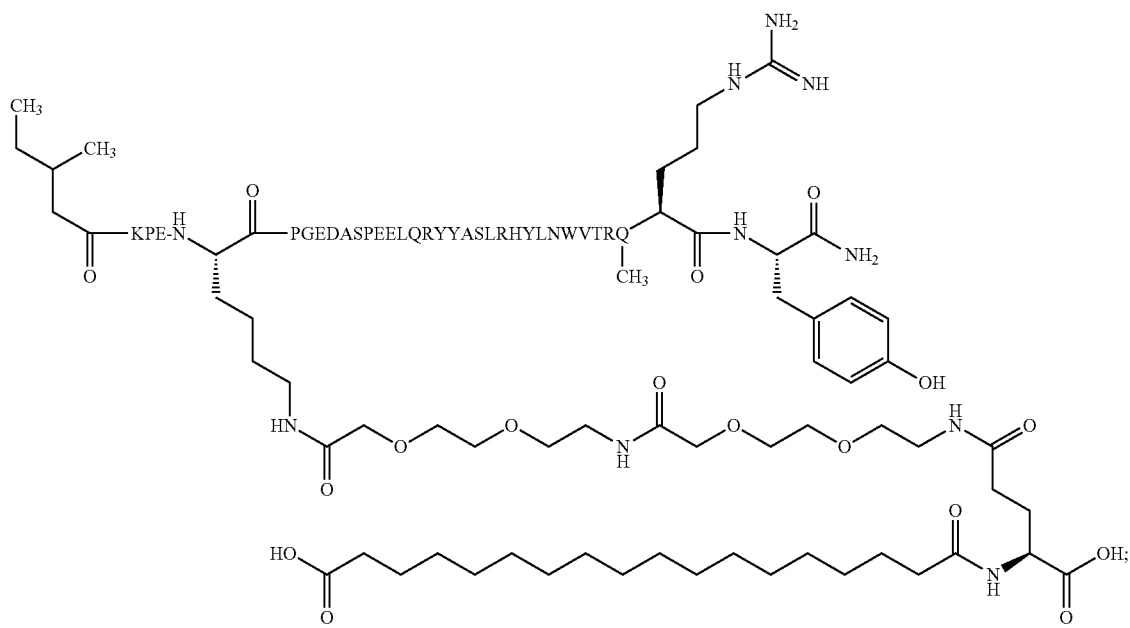
4-N{alpha}-(3-methyl-pentanoyl)-7-N{Epsilon}-[2-[2-[2-[[2-[2-[2-[[(4S)-4-carboxy-4-(16-sulfohexade-canoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:14)

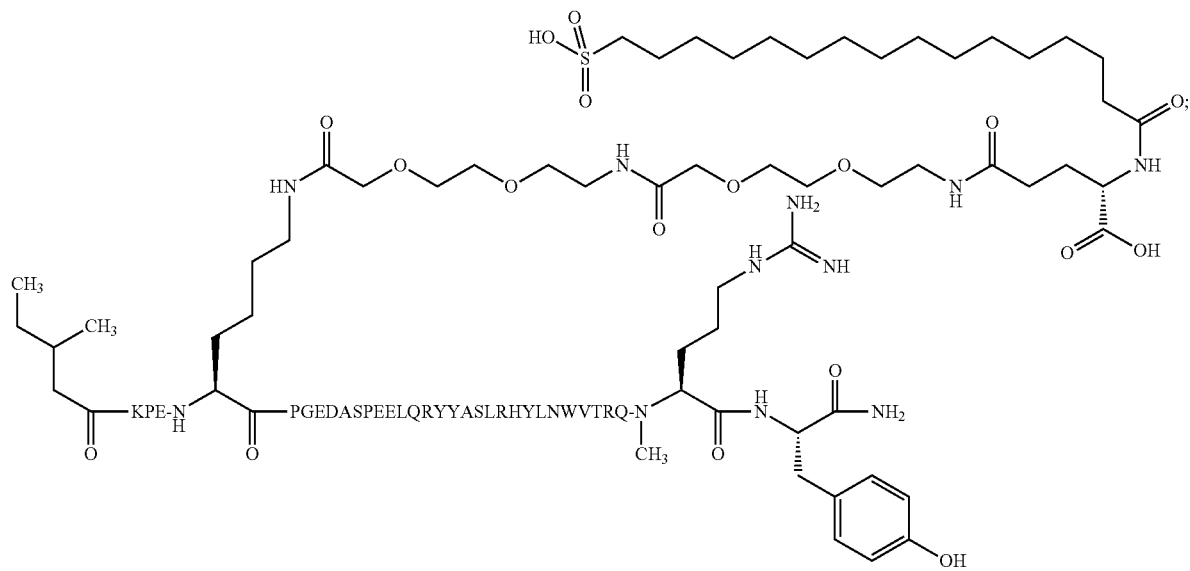
4-N{alpha}-(3-Methylbutanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]ethoxy]ethoxy]acetyl]-[Lys7, Gln18, Trp30, NMeArg35]hPYY(4-36) (SEQ ID NO:16)
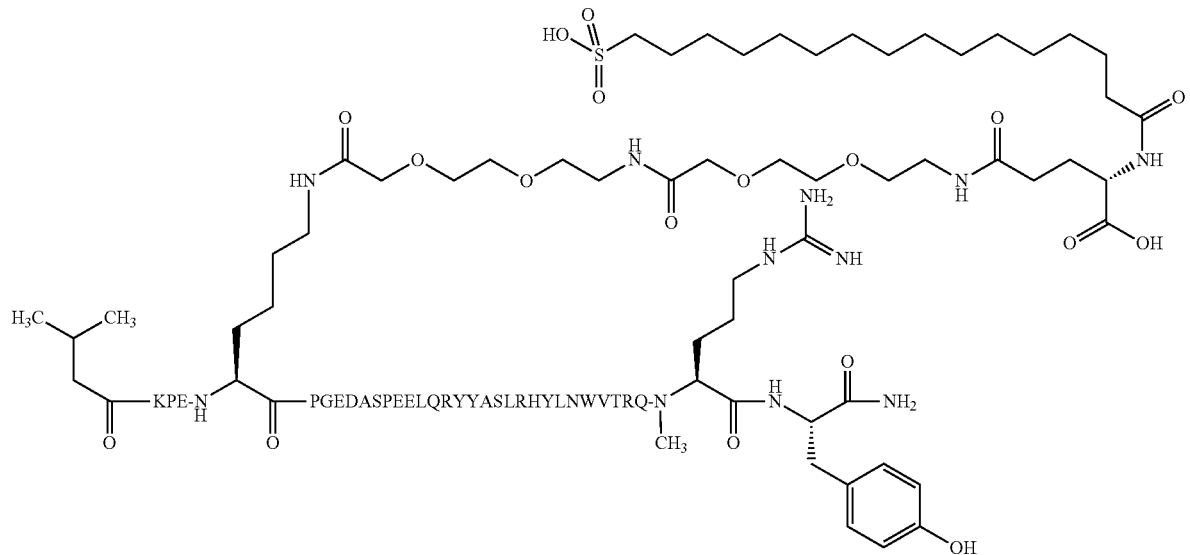
4-N{alpha}-(3-Methylbutanoyl)-7-N{Epsilon}-[2-[2-[2-[[2-[2-[2-[[(4S)-4-carboxy-4-(16-sulfohexadecanoylamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)

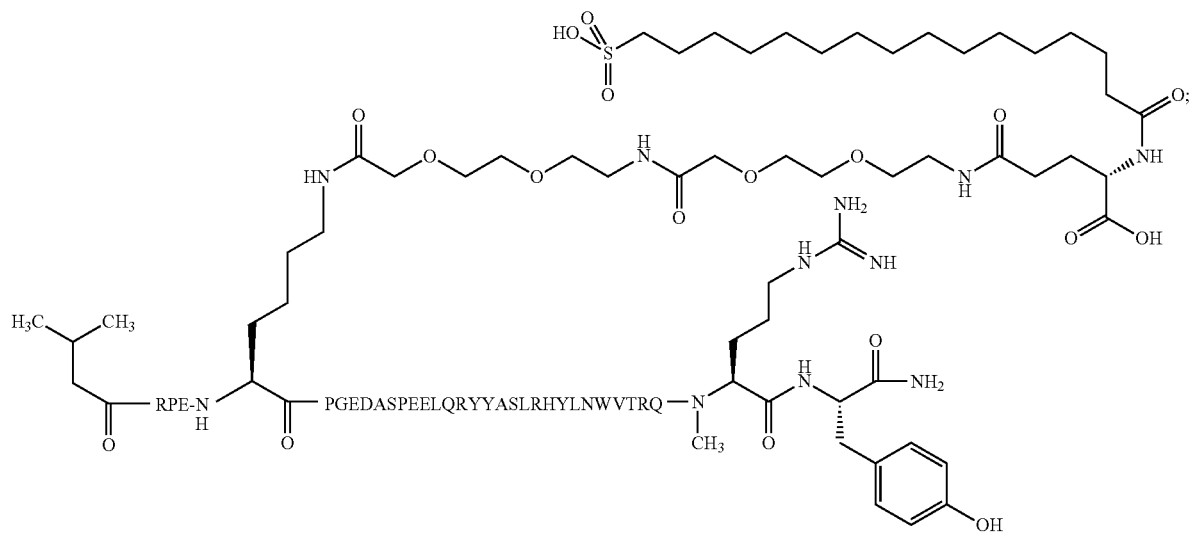

4-N{alpha}-(3-Methylbutanoyl)-7-N{Epsilon}-[2-[2-[2-[[2-[2-[2-[[(4S)-4-carboxy-4-(17-carboxyheptade-canoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:19)

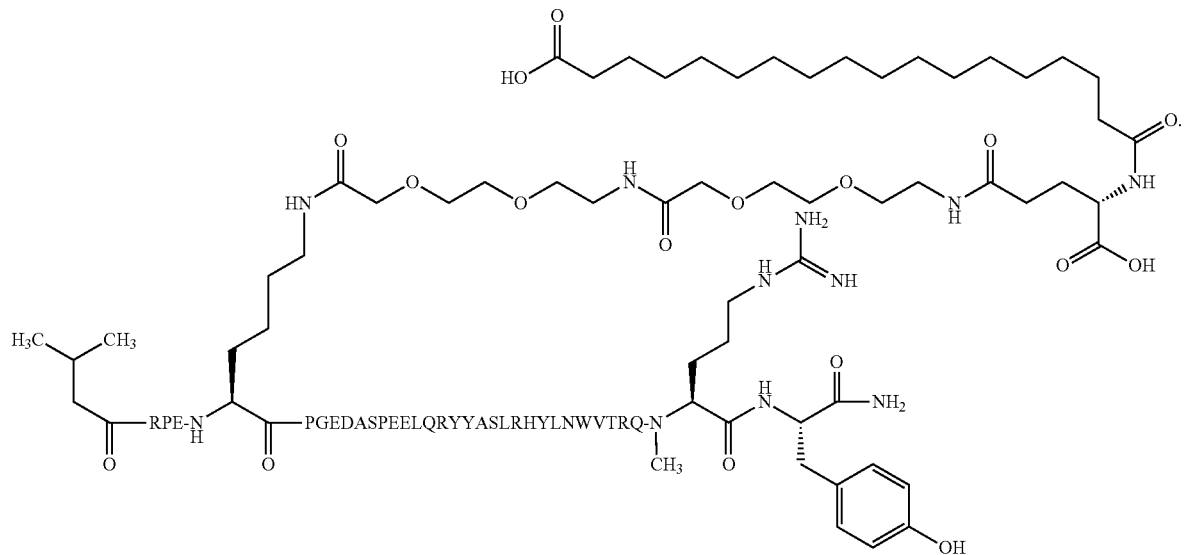

12. The pharmaceutical composition of claim 11, wherein the PYY compound is

4-N{alpha}-(3-Methylbutanoyl)-7-N{Epsilon}-[2-[2-[2-[[2-[2-[2-[[(4S)-4-carboxy-4-(16-sulfohexadecanoy-lamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)

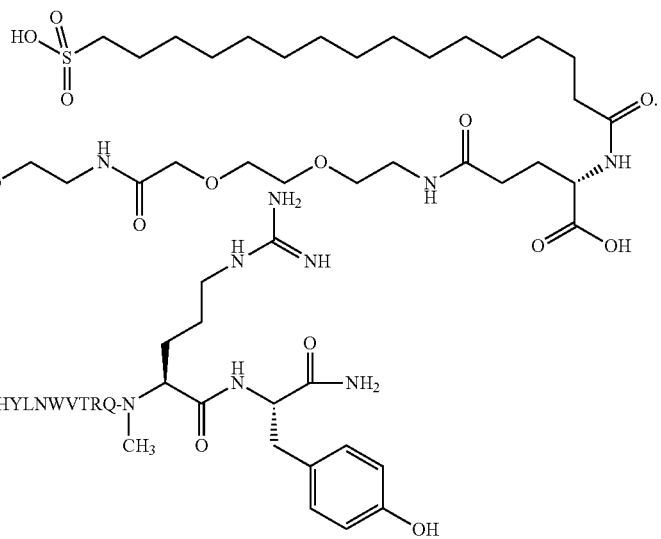

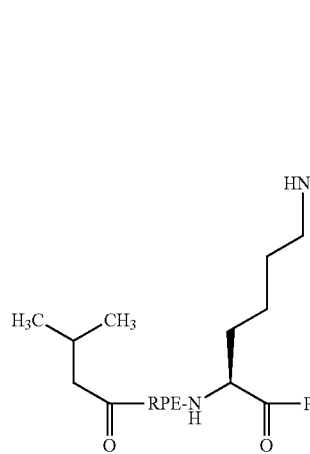

13. The pharmaceutical composition of claim 12, wherein the GLP-1 agonist is liraglutide.

14. The pharmaceutical composition of claim 12, wherein the GLP-1 agonist is semaglutide.

15. A method of treating of diabetes and/or obesity comprising administering to a patient in need thereof an effective amount of the PYY compound of claim 1.

16. The method of claim 15, wherein the PYY compound has a maximum of 6 amino acid modifications as compared to hPYY(3-36).

17. The method of claim 16, wherein the PYY compound is selected from the following:

4-N{alpha}-(hexanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:12)

4-N{alpha}-(3-methyl-pentanoyl)-7-N{Epsilon}-[2-[2-[2-[[2-[2-[2-[[(4S)-4-carboxy-4-(17-carboxyheptadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:13)

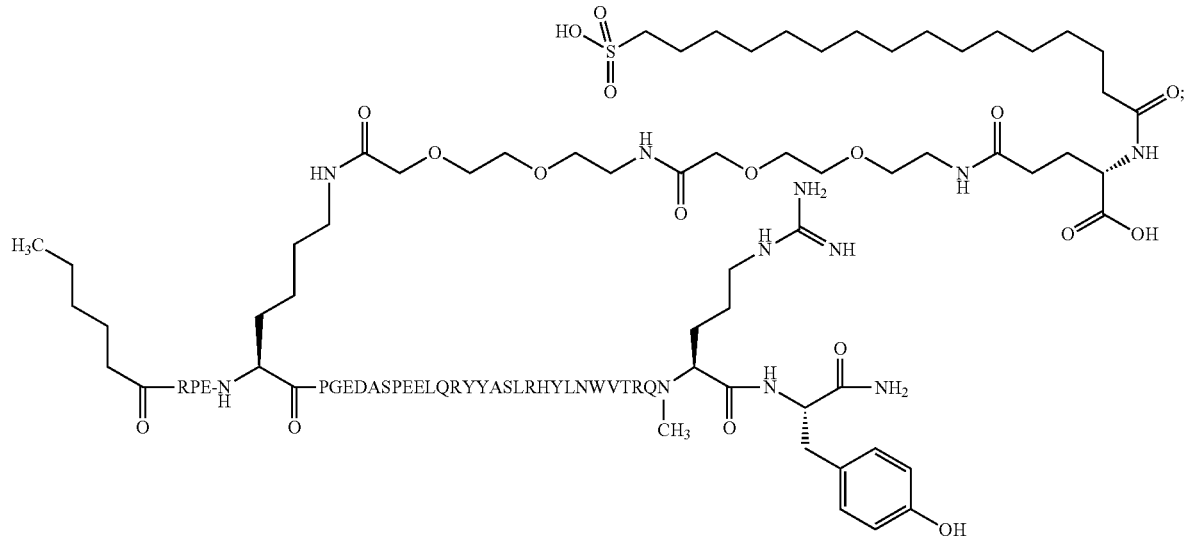

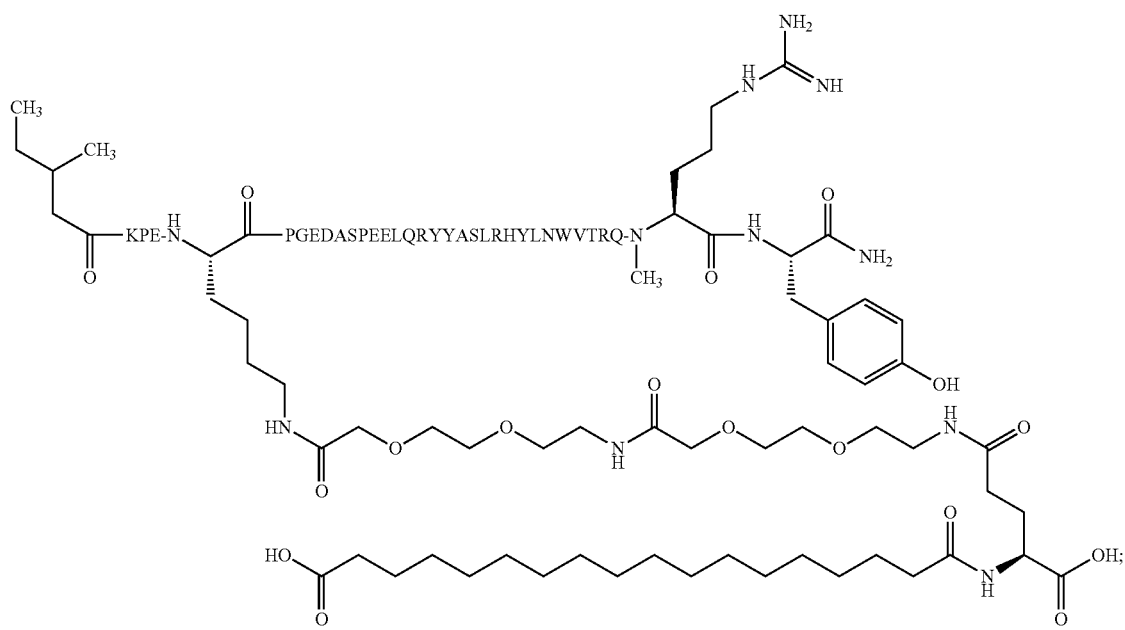
4-N{alpha}-(3-methyl-pentanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:14)
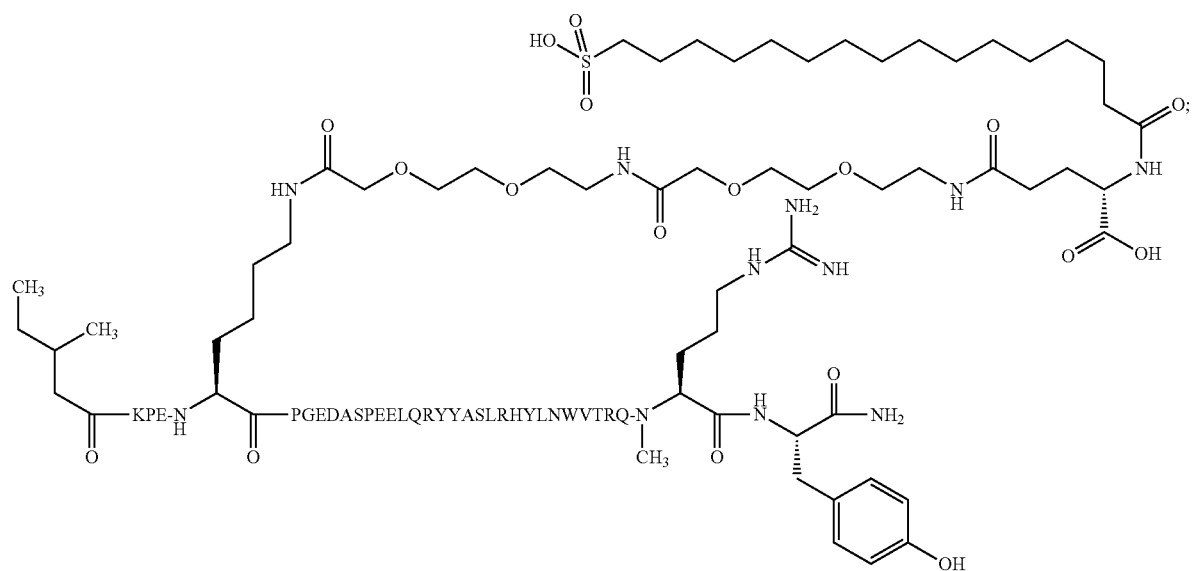
4-N{alpha}-(3-Methylbutanoyl)-7-N{Epsilon}-[2-[2-[2-[[2-[2-[2-[[(4S)-4-carboxy-4-(16-sulfohexadecanoylamino)butanoyl]amino]ethoxy]ethoxy]acetyl]amino]-ethoxy]ethoxy]acetyl]-[Lys7, Gln18, Trp30, NMeArg35]hPYY(4-36) (SEQ ID NO:16)

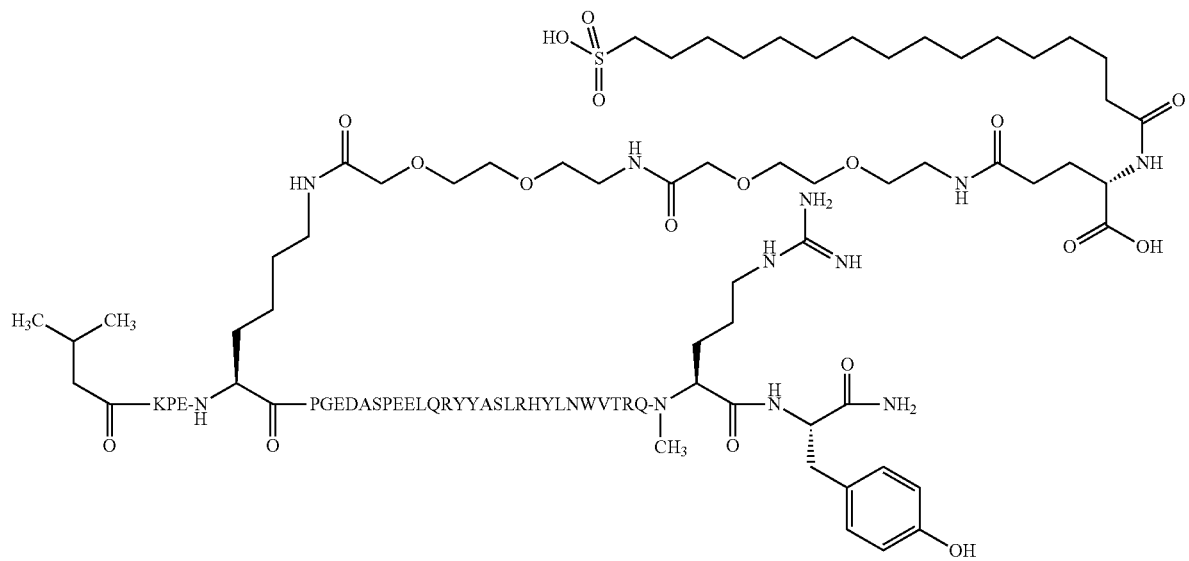
4-N{alpha}-(3-Methylbutanoyl)-7-N{Epsilon}-[2-[2-[2-[[2-[2-[2-[[(4S)-4-carboxy-4-(16-sulfohexadecanoy-lamino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)
; 4-N{alpha}-(3-Methylbutanoyl)-7-N{Epsilon}-[2-[2-[2-[[2-[2-[2-[[(4S)-4-carboxy-4-(17-carboxyheptade-canoylamino)butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:19)

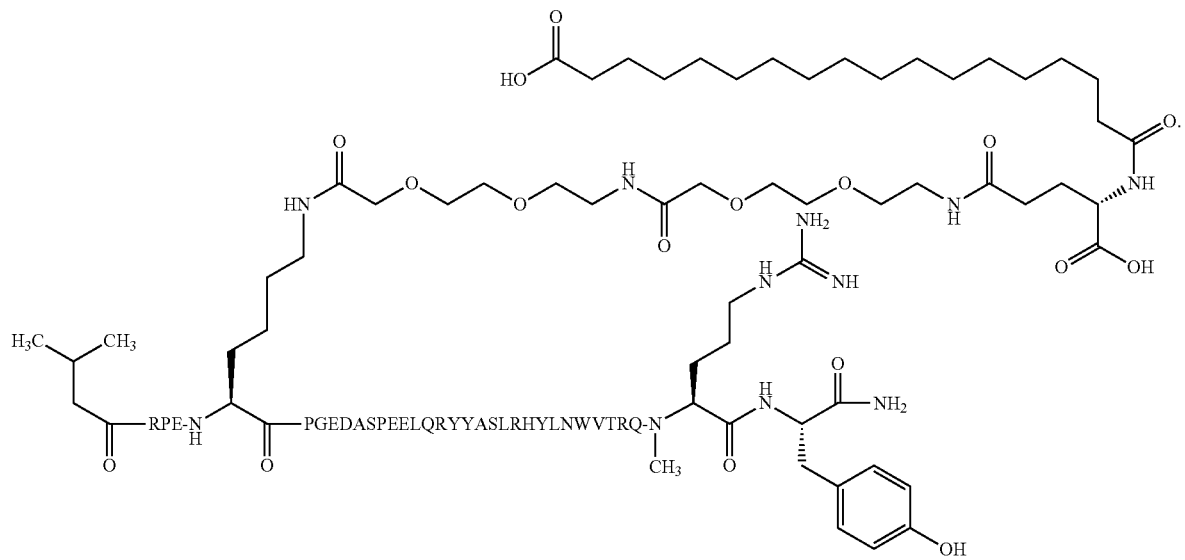

18. The method of claim 17, wherein the PYY compound is
   4-N{alpha}-(3-Methylbutanoyl)-7-N{Epsilon}-[2-[2-[2-[[2-[2-[2-[[(4S)-4-carboxy-4-(16-sulfohexadecanoyl-amino)-butanoyl]amino]ethoxy]ethoxy]acetyl]amino]ethoxy]-ethoxy]acetyl]-[Arg4, Lys7, Gln18, Trp30, NMeArg35]hPYY(4-36) (SEQ ID NO:18)

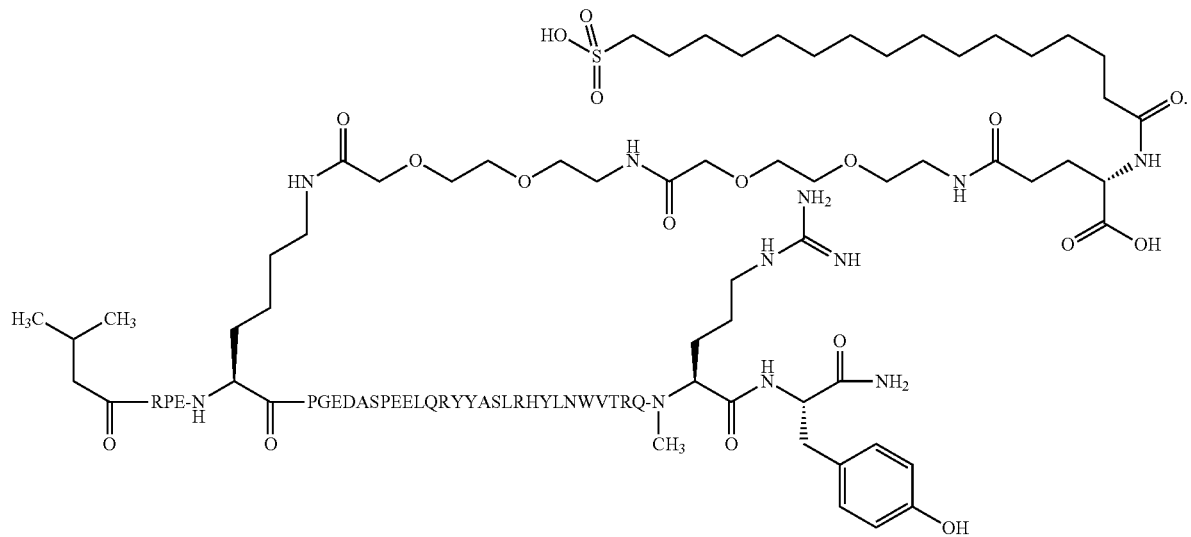

19. The method of claim 18, further comprising administering to the patient the GLP-1 agonist liraglutide.
20. The method of claim 18, further comprising administering to the patient the GLP-1 agonist semaglutide.

* * * * *

UNITED STATES PATENT AND TRADEMARK OFFICE
CERTIFICATE OF CORRECTION

PATENT NO. : 9,085,637 B2  
APPLICATION NO. : 14/540474  
DATED : July 21, 2015  
INVENTOR(S) : Soeren Oestergaard et al.

Page 1 of 1

It is certified that error appears in the above-identified patent and that said Letters Patent is hereby corrected as shown below:

In the Claims:

At column 185, claim number 7, at lines 38 to 61, enter the formula as follows:

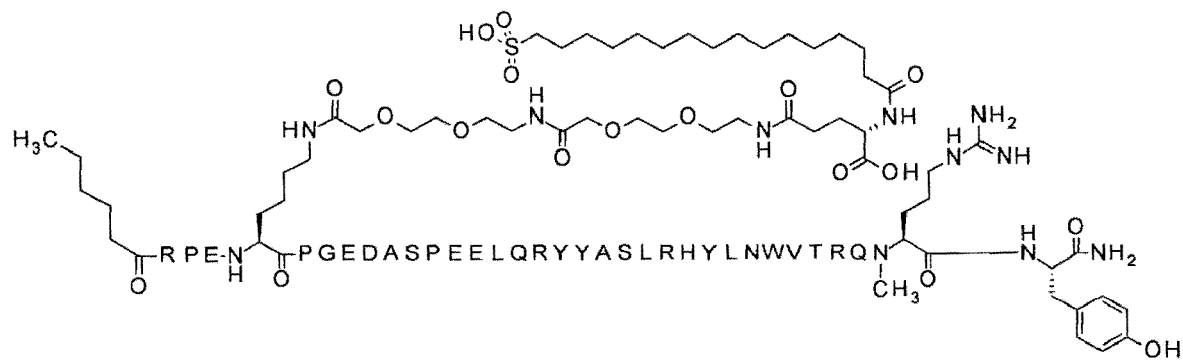

Signed and Sealed this  
Twelfth Day of January, 2016

Michelle K. Lee  
*Director of the United States Patent and Trademark Office*

SEQUENCE LISTING

<160> NUMBER OF SEQ ID NOS: 38

<210> SEQ ID NO 1
<211> LENGTH: 36
<212> TYPE: PRT
<213> ORGANISM: HOMO SAPIENS

<400> SEQUENCE: 1

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 2
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (34)..(34)
<223> OTHER INFORMATION: This position is amidated

<400> SEQUENCE: 2

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 3
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (34)..(34)
<223> OTHER INFORMATION: This position is amidated

<400> SEQUENCE: 3

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 4
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 4

Ile Lys Pro Glu Ala Pro Gly Glu Asp Ala Ser Pro Glu Glu Leu Asn
1               5                   10                  15

Arg Tyr Tyr Ala Ser Leu Arg His Tyr Leu Asn Trp Val Thr Arg Gln
            20                  25                  30

Arg Tyr

<210> SEQ ID NO 5
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (5)..(5)
<223> OTHER INFORMATION: A modifying group is attached to the epsilon
      amino group of Lys in this position
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 5

Ile Lys Pro Glu Lys Pro Gly Glu Asp Ala Ser Pro Glu Glu Leu Gln
1               5                   10                  15

Arg Tyr Tyr Ala Ser Leu Arg His Tyr Leu Asn Trp Val Thr Arg Gln
            20                  25                  30

Arg Tyr

<210> SEQ ID NO 6
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (5)..(5)
<223> OTHER INFORMATION: A modifying group is attached to the epsilon
      amino group of Lys in this position
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 6

Ile Lys Pro Glu Lys Pro Gly Glu Asp Ala Ser Pro Glu Glu Leu Gln
1               5                   10                  15

Arg Tyr Tyr Ala Ser Leu Arg His Tyr Leu Asn Trp Val Thr Arg Gln
            20                  25                  30

-continued

Arg Tyr

<210> SEQ ID NO 7
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (5)..(5)
<223> OTHER INFORMATION: A modifying group is attached to the epsilon
      amino group of Lys in this position
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 7

Ile Lys Pro Glu Lys Pro Gly Glu Asp Ala Ser Pro Glu Glu Leu Gln
1               5                   10                  15

Arg Tyr Tyr Ala Ser Leu Arg His Tyr Leu Asn Trp Val Thr Arg Gln
            20                  25                  30

Arg Tyr

<210> SEQ ID NO 8
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (5)..(5)
<223> OTHER INFORMATION: A modifying group is attached to the epsilon
      amino group of Lys in this position
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 8

Ile Lys Pro Glu Lys Pro Gly Glu Asp Ala Ser Pro Glu Glu Leu Gln
1               5                   10                  15

Arg Tyr Tyr Ala Ser Leu Arg His Tyr Leu Asn Trp Val Thr Arg Gln
            20                  25                  30

Arg Tyr

<210> SEQ ID NO 9
<211> LENGTH: 34
<212> TYPE: PRT

<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in the description
<220> FEATURE:
<221> NAME/KEY: MISC_FEATURE
<222> LOCATION: (5)..(5)
<223> OTHER INFORMATION: A modifying group is attached to the epsilon amino group of Lys in this position
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 9

Ile Lys Pro Glu Lys Pro Gly Glu Asp Ala Ser Pro Glu Glu Leu Gln
1               5                   10                  15

Arg Tyr Tyr Ala Ser Leu Arg His Tyr Leu Asn Trp Val Thr Arg Gln
            20                  25                  30

Arg Tyr

<210> SEQ ID NO 10
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in the description
<220> FEATURE:
<221> NAME/KEY: MISC_FEATURE
<222> LOCATION: (5)..(5)
<223> OTHER INFORMATION: A modifying group is attached to the epsilon amino group of Lys in this position
<220> FEATURE:
<221> NAME/KEY: MISC_FEATURE
<222> LOCATION: (26)..(26)
<223> OTHER INFORMATION: This position is Aib (2-aminoisobutyric acid)
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 10

Ile Lys Pro Glu Lys Pro Gly Glu Asp Ala Ser Pro Glu Glu Leu Gln
1               5                   10                  15

Arg Tyr Tyr Ala Ser Leu Arg His Tyr Xaa Asn Trp Val Thr Arg Gln
            20                  25                  30

Arg Tyr

<210> SEQ ID NO 11
<211> LENGTH: 34
<212> TYPE: PRT
<213> ORGANISM: ARTIFICIAL
<220> FEATURE:
<223> OTHER INFORMATION: Artificial protein based on human PYY

```
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (5)..(5)
<223> OTHER INFORMATION: A modifying group is attached to the epsilon
      amino group of Lys in this position
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 11

Ile Arg Pro Glu Lys Pro Gly Glu Asp Ala Ser Pro Glu Glu Leu Gln
 1               5                  10                  15

Arg Tyr Tyr Ala Ser Leu Arg His Tyr Leu Asn Trp Val Thr Arg Gln
                20                  25                  30

Arg Tyr

<210> SEQ ID NO 12
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: hexanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 12

Arg Pro Glu Lys Pro Gly Glu Asp Ala Ser Pro Glu Glu Leu Gln Arg
 1               5                  10                  15

Tyr Tyr Ala Ser Leu Arg His Tyr Leu Asn Trp Val Thr Arg Gln Arg
                20                  25                  30

Tyr

<210> SEQ ID NO 13
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
```

-continued

```
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Lys has the following
      substituent: 3-methylpentanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 13

Lys Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 14
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Lys has the following
      substituent: 3-methylpentanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 14

Lys Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 15
<211> LENGTH: 33
<212> TYPE: PRT
<213> ORGANISM: ARTIFICIAL
<220> FEATURE:
```

<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Lys has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 15

Lys Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 16
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Lys has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 16

Lys Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 17
<211> LENGTH: 33

```
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (33)..(33)
<223> OTHER INFORMATION: This position is amidated

<400> SEQUENCE: 17

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 18
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 18

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 19
<211> LENGTH: 33
<212> TYPE: PRT
```

```
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 19

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 20
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 20

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
```

Tyr

```
<210> SEQ ID NO 21
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 21

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
                20                  25                  30

Tyr

<210> SEQ ID NO 22
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 22
```

```
Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 23
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 23

Arg Pro Glu Lys Pro Gly Glu Asp Ala Ser Pro Glu Glu Leu Gln Arg
1               5                   10                  15

Tyr Tyr Ala Ser Leu Arg His Tyr Ile Asn Trp Val Thr Arg Gln Arg
            20                  25                  30

Tyr

<210> SEQ ID NO 24
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
```

-continued

<223> OTHER INFORMATION: This position is amidated

<400> SEQUENCE: 24

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 25
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 25

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 26
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg

```
<220> FEATURE:
<221> NAME/KEY: MISC_FEATURE
<222> LOCATION: (33)..(33)
<223> OTHER INFORMATION: This position is amidated

<400> SEQUENCE: 26

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 27
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 27

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 28
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
```

```
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 28

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 29
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 29

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 30
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
```

```
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 30

Arg Pro Glu Lys Pro Gly Glu Asp Ala Ser Pro Glu Glu Leu Gln Arg
 1               5                  10                  15

Tyr Tyr Ala Ser Leu Arg His Tyr Leu Asn Trp Val Thr Arg Gln Arg
            20                  25                  30

Tyr

<210> SEQ ID NO 31
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 31

Arg Pro Glu Lys Pro Gly Glu Asp Ala Ser Pro Glu Glu Leu Gln Arg
 1               5                  10                  15

Tyr Tyr Ala Ser Leu Arg His Tyr Leu Asn Trp Val Thr Arg Gln Arg
            20                  25                  30

Tyr

<210> SEQ ID NO 32
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (5)..(5)
<223> OTHER INFORMATION: A modifying group is attached to the epsilon
      amino group of Lys in this position
```

```
<220> FEATURE:
<221> NAME/KEY: MISC_FEATURE
<222> LOCATION: (33)..(33)
<223> OTHER INFORMATION: This position is N-Methyl Arg
<220> FEATURE:
<221> NAME/KEY: MISC_FEATURE
<222> LOCATION: (34)..(34)
<223> OTHER INFORMATION: This position is amidated

<400> SEQUENCE: 32

Val Arg Pro Glu Lys Pro Gly Glu Asp Ala Ser Pro Glu Glu Leu Gln
1               5                   10                  15

Arg Tyr Tyr Ala Ser Leu Arg His Tyr Leu Asn Trp Val Thr Arg Gln
            20                  25                  30

Arg Tyr

<210> SEQ ID NO 33
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (8)..(8)
<223> OTHER INFORMATION: This position is D-Asp
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 33

Arg Pro Glu Lys Pro Gly Glu Xaa Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 34
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
```

```
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (8)..(8)
<223> OTHER INFORMATION: This position is iso-Asp
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 34

Arg Pro Glu Lys Pro Gly Glu Xaa Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 35
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (8)..(8)
<223> OTHER INFORMATION: This position is D-iso-Asp
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 35

Arg Pro Glu Lys Pro Gly Glu Xaa Ala Ser Pro Glu Glu Leu Gln Arg
1               5                   10                  15
```

```
Tyr Tyr Ala Ser Leu Arg His Tyr Leu Asn Trp Val Thr Arg Gln Arg
            20                  25                  30

Tyr

<210> SEQ ID NO 36
<211> LENGTH: 33
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (4)..(4)
<223> OTHER INFORMATION: A modifying group is attached to the epsilon
      amino group of Lys in this position
<220> FEATURE:
<221> NAME/KEY: MISC_FEATURE
<222> LOCATION: (33)..(33)
<223> OTHER INFORMATION: This position is amidated

<400> SEQUENCE: 36

Arg Pro Glu Lys Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr

<210> SEQ ID NO 37
<211> LENGTH: 34
<212> TYPE: PRT
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 3 in
      the description
<220> FEATURE:
<221> NAME/KEY: MISC_FEATURE
<222> LOCATION: (5)..(5)
<223> OTHER INFORMATION: A modifying group is attached to the epsilon
      amino group of Lys in this position
<220> FEATURE:
<221> NAME/KEY: MISC_FEATURE
<222> LOCATION: (34)..(34)
<223> OTHER INFORMATION: This position is amidated

<400> SEQUENCE: 37

Ile Arg Pro Glu Lys Pro Gly Glu Asp Ala Ser Pro Glu Glu Leu Gln
1               5                   10                  15

Arg Tyr Tyr Ala Ser Leu Arg His Tyr Leu Asn Trp Val Thr Arg Gln
            20                  25                  30

Arg Tyr

<210> SEQ ID NO 38
<211> LENGTH: 33
<212> TYPE: PRT
```

```
<213> ORGANISM: ARTIFICIAL
<220> FEATURE:
<223> OTHER INFORMATION: Artificial protein based on human PYY
<220> FEATURE:
<221> NAME/KEY: MISC_FEATURE
<222> LOCATION: (1)..(1)
<223> OTHER INFORMATION: This position is referred to as position 4 in
      the description
<220> FEATURE:
<221> NAME/KEY: MISC_FEATURE
<222> LOCATION: (1)..(1)
<223> OTHER INFORMATION: The alpha amino group of Arg has the following
      substituent: 3-methylbutanoyl
<220> FEATURE:
<221> NAME/KEY: MISC_FEATURE
<222> LOCATION: (32)..(32)
<223> OTHER INFORMATION: This position is N-Methyl Arg
<220> FEATURE:
<221> NAME/KEY: MISC_FEATURE
<222> LOCATION: (33)..(33)
<223> OTHER INFORMATION: This position is amidated

<400> SEQUENCE: 38

Arg Pro Glu Ala Pro Gly Glu Asp Ala Ser Pro Glu Glu Leu Gln Arg
1               5                   10                  15

Tyr Tyr Ala Ser Leu Arg His Tyr Leu Asn Trp Val Thr Arg Gln Arg
            20                  25                  30

Tyr
```